(12) United States Patent
Romine et al.

(10) Patent No.: US 9,561,212 B2
(45) Date of Patent: *Feb. 7, 2017

(54) HEPATITIS C VIRUS INHIBITORS

(71) Applicant: BRISTOL-MYERS SQUIBB COMPANY, Princeton, NJ (US)

(72) Inventors: Jeffrey Lee Romine, Meriden, CT (US); Zhong Yang, Southington, CT (US); Gan Wang, Cheshire, CT (US); Van N. Nguyen, Auburn, MI (US); John A. Bender, Middletown, CT (US); Denis R. St. Laurent, Newington, CT (US); Makonen Belema, North Haven, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/227,709

(22) Filed: Aug. 3, 2016

(65) Prior Publication Data

US 2016/0338999 A1    Nov. 24, 2016

Related U.S. Application Data

(63) Continuation of application No. 14/434,049, filed as application No. PCT/US2012/061623 on Oct. 24, 2012.

(51) Int. Cl.
| | | |
|---|---|---|
| *C07D 405/14* | (2006.01) | |
| *A61K 45/06* | (2006.01) | |
| *A61K 31/4178* | (2006.01) | |
| *C07D 403/14* | (2006.01) | |

(52) U.S. Cl.
CPC .......... *A61K 31/4178* (2013.01); *A61K 45/06* (2013.01); *C07D 403/14* (2013.01); *C07D 405/14* (2013.01)

(58) Field of Classification Search
CPC ............................. C07D 405/14; A61K 45/06
See application file for complete search history.

(56) References Cited

U.S. PATENT DOCUMENTS 8,329,159 B2 * 12/2012 Belema ................ C07D 401/14
                                                                  424/85.2
9,340,520 B2 *  5/2016 Lopez .................. C07D 405/14

* cited by examiner

*Primary Examiner* — Sun Jae Yoo
(74) *Attorney, Agent, or Firm* — Pamela A. Mingo

(57) ABSTRACT

The present disclosure relates to compounds, compositions and methods for the treatment of Hepatitis C virus (HCV) infection. Also disclosed are pharmaceutical compositions containing such compounds and methods for using these compounds in the treatment of HCV infection.

16 Claims, No Drawings

HEPATITIS C VIRUS INHIBITORS

CROSS REFERENCE TO RELATED APPLICATIONS

This Continuation application claims the benefit of U.S. Ser. No. 14/434,049 filed Apr. 7, 2015, which is a US 371 of International Application PCT/US2012/061623 filed Oct. 24, 2012.

The present disclosure is generally directed to antiviral compounds, and more specifically directed to compounds which can inhibit the function of the NS5A protein encoded by Hepatitis C virus (HCV), compositions comprising such compounds, and methods for inhibiting the function of the NS5A protein.

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma.

The current standard of care for HCV, which employs a combination of pegylated-interferon and ribavirin, has a non-optimal success rate in achieving sustained viral response and causes numerous side effects. Thus, there is a clear and long-felt need to develop effective therapies to address this undermet medical need.

HCV is a positive-stranded RNA virus. Based on a comparison of the deduced amino acid sequence and the extensive similarity in the 5' untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome due to the high error rate of the encoded RNA dependent RNA polymerase which lacks a proof-reading capability. At least six major genotypes have been characterized, and more than 50 subtypes have been described with distribution worldwide. The clinical significance of the genetic heterogeneity of HCV has demonstrated a propensity for mutations to arise during monotherapy treatment, thus additional treatment options for use are desired. The possible modulator effect of genotypes on pathogenesis and therapy remains elusive.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to herein as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions by both acting as a cofactor for the NS3 protease and assisting in the membrane localization of NS3 and other viral replicase components. The formation of a NS3-NS4A complex is necessary for proper protease activity resulting in increased proteolytic efficiency of the cleavage events. The NS3 protein also exhibits nucleoside triphosphatase and RNA helicase activities. NS5B (also referred to herein as HCV polymerase) is a RNA-dependent RNA polymerase that is involved in the replication of HCV with other HCV proteins, including NS5A, in a replicase complex.

Compounds useful for treating HCV-infected patients are desired which selectively inhibit HCV viral replication. In particular, compounds which are effective to inhibit the function of the NS5A protein are desired. The HCV NS5A protein is described, for example, in the following references: S. L. Tan, et al., *Virology*, 284:1-12 (2001); K.-J. Park, et al., *J. Biol. Chem.*, 30711-30718 (2003); T. L. Tellinghuisen, et al., *Nature*, 435, 374 (2005); R. A. Love, et al., *J. Virol*, 83, 4395 (2009); N. Appel, et al., *J. Biol. Chem.*, 281, 9833 (2006); L. Huang, *J. Biol. Chem.*, 280, 36417 (2005); C. Rice, et al., WO2006093867.

In a first aspect the present disclosure provides a compound of Formula (I)

$$\underset{R}{\overset{O}{\|}}{-}X{-}A{-}L{-}A'{-}X'{-}\underset{R'}{\overset{O}{\|}},$$

(I)

or a pharmaceutically acceptable salt thereof, wherein

L is selected from a bond,

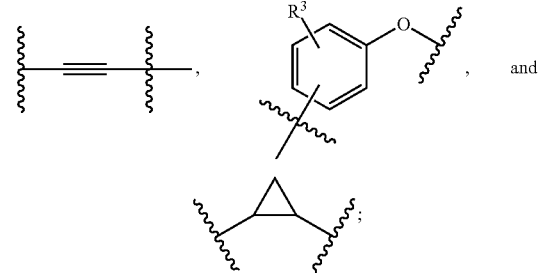

and

A and A' are independently selected from

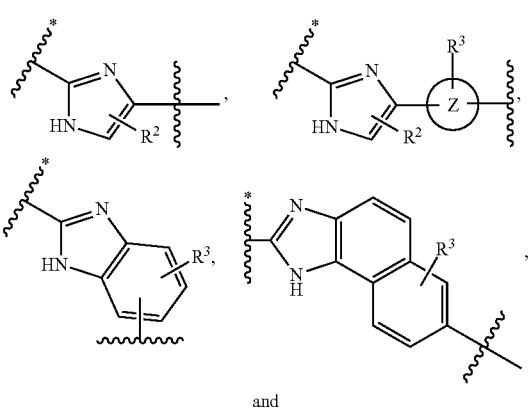

and

-continued

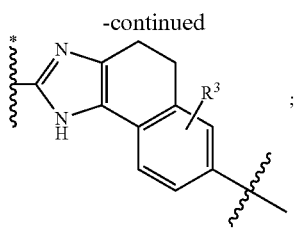

provided at least one of A and A' is other than

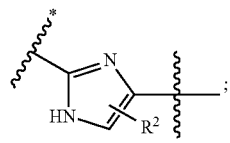

wherein "*" represents the point of attachment to X and X' and "⌇" represents the point of attachment to L; and wherein:

Z is a six-membered aromatic ring optionally containing one, two, or three nitrogen atoms;

$R^2$ is selected from hydrogen, alkyl, and halo; and $R^3$ is selected from hydrogen, alkoxy, alkyl, cyano, halo, and haloalkoxy;

X and X' are independently selected from

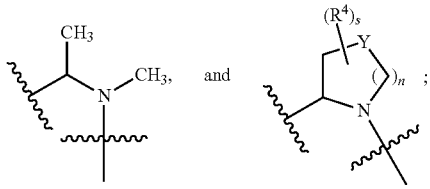

wherein each group is drawn with the carbon atom being attached to A or A' and with the nitrogen atom attached to the carbonyl group and wherein:

n is 0, 1, or 2;

s is 0, 1, 2, 3, or 4;

Y is selected from $Si(R^4)_2$, $NR^4$, O, S, S(O), $SO_2$, $CH_2$, $CHR^4$, and $C(R^4)_2$;

provided that when n is 0, Y is selected from $CH_2$, $CHR^4$, and $C(R^4)_2$; and each $R^4$ is independently selected from alkoxy, alkyl, aryl, cyano, halo, haloalkoxy, haloalkyl, hydroxy, —$NR^aR^b$, and thioalkyl, wherein the alkyl can optionally form a fused three- to six-membered ring or a bridged four- or five-membered ring with another carbon atom on the ring; or can optionally form a spirocyclic three- to six-membered ring with the carbon to which it is attached, wherein each formed ring system optionally contains one or two oxygen atoms, and wherein each formed ring system is optionally substituted with one or two groups independently selected from alkyl and halo; provided that when Y is $NR^4$, $R^4$ is other than halo, hydroxy, or —$NR^aR^b$;

R is ($NR^cR^d$)alkyl, wherein the alkyl part of the ($NR^cR^d$) alkyl is substituted with bicycloalkyl, fused bicycloheterocyclyl, cycloalkyl-substituted-heterocyclyl, ethenylcycloalkyl, heterocyclylethenyl, oxocycloalkyl, or spirocycloheterocyclyl, wherein the bicycloalkyl, bicycloheterocyclyl, oxocycloalkyl, and spirocycloheterocyclyl are optionally substituted with one or two groups independently selected from alkyl, halo, and haloalkyl;

R' is ($NR^cR^d$)alkyl, wherein the alkyl part of the ($NR^cR^d$) alkyl is optionally substituted with bicycloalkyl, fused bicycloheterocyclyl, cycloalkyl-substituted-heterocyclyl, ethenylcycloalkyl, heterocyclylethenyl, oxocycloalkyl, or spirocycloheterocyclyl, wherein the bicycloalkyl, bicycloheterocyclyl, oxocycloalkyl, and spirocycloheterocyclyl are optionally substituted with one or two groups independently selected from alkyl, halo, and haloalkyl;

$R^a$ and $R^b$ are independently selected from hydrogen and alkyl;

$R^c$ and $R^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkyloxycarbonyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, ($NR^eR^f$)alkyl, ($NR^eR^f$)alkylcarbonyl, ($NR^eR^f$)carbonyl, ($NR^eR^f$)sulfonyl, —C(NCN)OR", and —C(NCN)$NR^xR^y$, wherein R" is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro;

$R^e$ and $R^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, ($NR^xR^y$)alkyl, and ($NR^xR^y$)carbonyl; and $R^x$ and $R^y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and ($NR^{x'}R^{y'}$)carbonyl, wherein $R^{x'}$ and $R^{y'}$ are independently selected from hydrogen and alkyl.

In a first embodiment of the first aspect the present disclosure provides a compound of formula (I), or a pharmaceutically acceptable salt thereof, wherein L is ⌇=⌇.

In a second embodiment of the first aspect the present disclosure provides a compound of formula (I), or a pharmaceutically acceptable salt thereof, wherein L is selected from

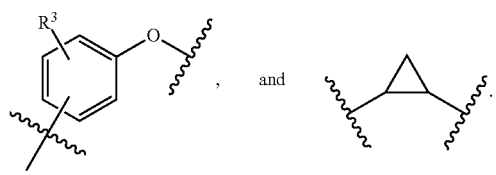

In a third embodiment of the first aspect the present disclosure provides a compound of formula (I), or a pharmaceutically acceptable salt thereof, wherein L is a bond.

In a fourth embodiment of the first aspect the present disclosure provides a compound of formula (I), or a pharmaceutically acceptable salt thereof, wherein L is a bond and A and A' are each

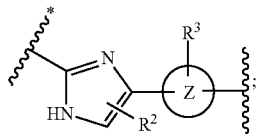

wherein Z is a six-membered aromatic ring optionally containing one nitrogen atom.

In a fifth embodiment of the first aspect the present disclosure provides a compound of formula (I), or a pharmaceutically acceptable salt thereof, wherein L is a bond; A and A' are each

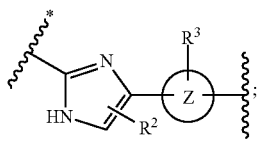

wherein Z is a six-membered aromatic ring optionally containing one nitrogen atom; and X and X' are each

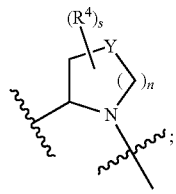

wherein n, s, and Y are as described for Formula (I).

In a sixth embodiment of the first aspect, the present disclosure provides a compound of formula (I), or a pharmaceutically acceptable salt thereof, wherein L is a bond; A and A' are each

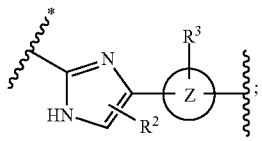

wherein Z is a six-membered aromatic ring optionally containing one nitrogen atom; and X and X' are each

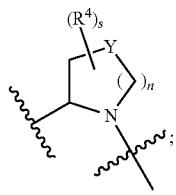

wherein n is 1 or 2; s is 1, 2, or 3; and Y is selected from O, $CH_2$, $CHR^4$, and $C(R^4)_2$.

In a seventh embodiment of the first aspect the present disclosure provides a compound of Formula (I), or a pharmaceutically acceptable salt thereof, wherein L is a bond; A and A' are each

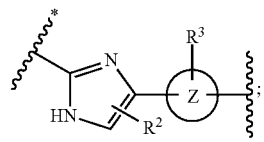

wherein Z is a six-membered aromatic ring optionally containing one nitrogen atom; and X and X' are each

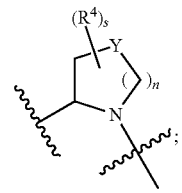

wherein n is 1; s is 1, 2, or 3; and Y is selected from $CH_2$, $CHR^4$, and $C(R^4)_2$. In an eighth embodiment of the first aspect, R and R' are each $(NR^cR^d)$alkyl, wherein the alkyl part of each $(NR^cR^d)$alkyl is substituted with bicycloalkyl, fused bicycloheterocyclyl, cycloalkyl-substituted-heterocyclyl, or spirocycloheterocyclyl, wherein the bicycloalkyl and the bicycloheterocyclyl are optionally substituted with one or two halo groups. In a ninth embodiment of the first aspect, the alkyl part of each $(NR^cR^d)$alkyl is substituted with spirocycloheterocyclyl, wherein spirocycloheterocyclyl is a six-membered saturated ring containing one oxygen atom adjoined to a three-membered saturated carbocyclic ring via one single carbon atom.

In a second aspect the present disclosure provides a compound of Formula (II):

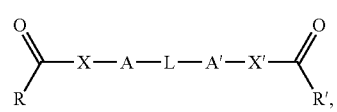

or a pharmaceutically acceptable salt thereof, wherein
L is selected from a bond,

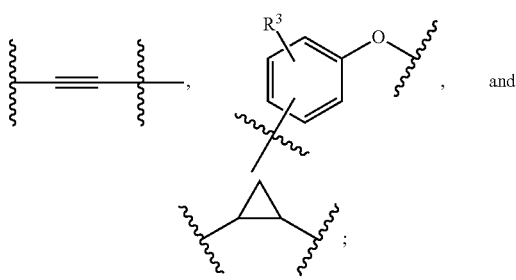

A and A' are independently selected from

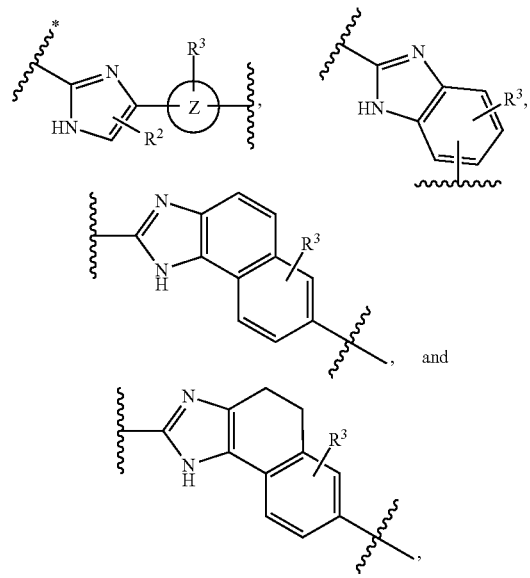

wherein each group is drawn with the imidazole ring being attached to X, and with the six-membered ring being attached to L, and wherein:

Z is a six-membered aromatic ring optionally containing one, two, or three nitrogen atoms;

$R^2$ is selected from hydrogen, alkyl, and halo; and $R^3$ is selected from hydrogen, alkoxy, alkyl, cyano, halo, and haloalkoxy;

X and X' are independently selected from

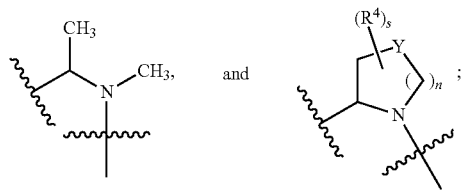

wherein each group is drawn with the carbon atom being attached to A or A' and with the nitrogen atom attached to the carbonyl group and wherein:

n is 0, 1, or 2;

s is 0, 1, 2, 3, or 4;

Y is selected from NH, $NR^4$, O, S, S(O), $SO_2$, $CH_2$, $CHR^4$, and $C(R^4)_2$; provided that when n is 0, Y is selected from $CH_2$, $CHR^4$, and $C(R^4)_2$; and each $R^4$ is independently selected from alkoxy, alkyl, aryl, cyano, halo, haloalkoxy, haloalkyl, hydroxy, and —$NR^aR^b$, wherein the alkyl can optionally form a fused three- to six-membered ring or a bridged four- or five-membered ring with another carbon atom on the ring; or can optionally form a spirocyclic three- to six-membered ring with the carbon to which it is attached, wherein the formed ring system is optionally substituted with one or two groups independently selected from alkyl and halo; provided that when Y is $NR^4$, $R^4$ is other than halo, hydroxy, or —$NR^aR^b$;

R is ($NR^cR^d$)alkyl, wherein the alkyl part of the ($NR^cR^d$) alkyl is substituted with bicycloalkyl, fused bicycloheterocyclyl, oxocycloalkyl, or spirocycloheterocyclyl, wherein the bicycloalkyl, bicycloheterocyclyl, oxocycloalkyl, and spirocycloheterocyclyl are optionally substituted with one or two groups independently selected from alkyl, halo, and haloalkyl;

R' is ($NR^cR^d$)alkyl, wherein the alkyl part of the ($NR^cR^d$) alkyl is optionally substituted with bicycloalkyl, fused bicycloheterocyclyl, oxocycloalkyl, or spirocycloheterocyclyl, wherein the bicycloalkyl, bicycloheterocyclyl, oxocycloalkyl, and spirocycloheterocyclyl are optionally substituted with one or two groups independently selected from alkyl, halo, and haloalkyl;

$R^a$ and $R^b$ are independently selected from hydrogen and alkyl;

$R^c$ and $R^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkyloxycarbonyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, ($NR^eR^f$)alkyl, ($NR^eR^f$)alkylcarbonyl, ($NR^eR^f$)carbonyl, ($NR^eR^f$)sulfonyl, —C(NCN)OR", and —C(NCN)$NR^xR^y$, wherein R" is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro;

$R^e$ and $R^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, ($NR^xR^y$) alkyl, and ($NR^xR^y$)carbonyl; and $R^x$ and $R^y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and ($NR^{x'}R^{y'}$)carbonyl, wherein $R^{x'}$ and $R^{y'}$ are independently selected from hydrogen and alkyl.

In a third aspect the present disclosure provides a composition comprising a compound of formula (I), or a pharmaceutically acceptable salt thereof, and a pharmaceutically acceptable carrier. In a first embodiment of the third aspect, the composition further comprises at least one additional compound having anti-HCV activity. In a second embodiment of the third aspect, at least one of the additional compounds is an interferon or a ribavirin. In a third embodiment of the third aspect, the interferon is selected from interferon alpha 2B, pegylated interferon alpha, pegylated interferon lambda, consensus interferon, interferon alpha 2A, and lymphoblastiod interferon tau.

In a fourth embodiment of the third aspect, the present disclosure provides a composition comprising comprising a compound of formula (I), or a pharmaceutically acceptable salt thereof, a pharmaceutically acceptable carrier, and at least one additional compound having anti-HCV activity, wherein at least one of the additional compounds is selected from interleukin 2, interleukin 6, interleukin 12, a compound that enhances the development of a type 1 helper T cell response, interfering RNA, anti-sense RNA, Imiquimod, ribavirin, an inosine 5'-monophosphate dehydrogenase inhibitor, amantadine, and rimantadine.

In a fifth embodiment of the third aspect, the present disclosure provides a composition comprising comprising a compound of formula (I), or a pharmaceutically acceptable salt thereof, a pharmaceutically acceptable carrier, and at least one additional compound having anti-HCV activity, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

In a fourth aspect the present disclosure provides a method of treating an HCV infection in a patient, comprising administering to the patient a therapeutically effective amount of a compound of formula (I), or a pharmaceutically acceptable salt thereof. In a first embodiment of the fourth aspect the method further comprises administering at least one additional compound having anti-HCV activity prior to, after or simultaneously with the compound of formula (I), or a pharmaceutically acceptable salt thereof. In a second embodiment of the fourth aspect, at least one of the additional compounds is an interferon or a ribavirin. In a third embodiment of the fourth aspect, the interferon is selected from interferon alpha 2B, pegylated interferon alpha, consensus interferon, interferon alpha 2A, and lymphoblastoid interferon tau.

In a fourth embodiment of the fourth aspect the present disclosure provides a method of treating an HCV infection in a patient, comprising administering to the patient a therapeutically effective amount of a compound of formula (I), or a pharmaceutically acceptable salt thereof and administering at least one additional compound having anti-HCV activity prior to, after or simultaneously with the compound of formula (I), or a pharmaceutically acceptable salt thereof, wherein at least one of the additional compounds is selected from interleukin 2, interleukin 6, interleukin 12, a compound that enhances the development of a type 1 helper T cell response, interfering RNA, anti-sense RNA, Imiquimod, ribavirin, an inosine 5'-monophosphate dehydrogenase inhibitor, amantadine, and rimantadine.

In a fifth embodiment of the fourth aspect the present disclosure provides a method of treating an HCV infection in a patient, comprising administering to the patient a therapeutically effective amount of a compound of formula (I), or a pharmaceutically acceptable salt thereof and administering at least one additional compound having anti-HCV activity prior to, after or simultaneously with the compound of formula (I), or a pharmaceutically acceptable salt thereof, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

Other aspects of the present disclosure may include suitable combinations of embodiments disclosed herein.

Yet other aspects and embodiments may be found in the description provided herein.

The description of the present disclosure herein should be construed in congruity with the laws and principals of chemical bonding. In some instances it may be necessary to remove a hydrogen atom in order to accommodate a substituent at any given location.

It should be understood that the compounds encompassed by the present disclosure are those that are suitably stable for use as pharmaceutical agent.

It is intended that the definition of any substituent or variable at a particular location in a molecule be independent of its definitions elsewhere in that molecule. For example, when s is 2, the two $R^4$ groups may be the same or different.

All patents, patent applications, and literature references cited in the specification are herein incorporated by reference in their entirety. In the case of inconsistencies, the present disclosure, including definitions, will prevail.

As used in the present specification, the following terms have the meanings indicated:

As used herein, the singular forms "a", "an", and "the" include plural reference unless the context clearly dictates otherwise.

Unless stated otherwise, all aryl, cycloalkyl, and heterocyclyl groups of the present disclosure may be substituted as described in each of their respective definitions. For example, the aryl part of an arylalkyl group may be substituted as described in the definition of the term "aryl".

The term "alkenyl," as used herein, refers to a straight or branched chain group of two to six carbon atoms containing at least one carbon-carbon double bond.

The term "alkenyloxy," as used herein, refers to an alkenyl group attached to the parent molecular moiety through an oxygen atom.

The term "alkenyloxycarbonyl," as used herein, refers to an alkenyloxy group attached to the parent molecular moiety through a carbonyl group.

The term "alkoxy," as used herein, refers to an alkyl group attached to the parent molecular moiety through an oxygen atom.

The term "alkoxyalkyl," as used herein, refers to an alkyl group substituted with one, two, or three alkoxy groups.

The term "alkoxyalkylcarbonyl," as used herein, refers to an alkoxyalkyl group attached to the parent molecular moiety through a carbonyl group.

The term "alkoxycarbonyl," as used herein, refers to an alkoxy group attached to the parent molecular moiety through a carbonyl group.

The term "alkyl," as used herein, refers to a group derived from a straight or branched chain saturated hydrocarbon containing from one to six carbon atoms. In the compounds of the present disclosure, when $R^4$ is alkyl, the alkyl can optionally form a fused three- to six-membered ring with an adjacent carbon atom to provide the structure shown below:

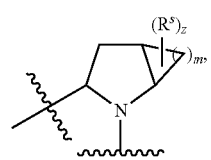

wherein m is selected from 1, 2, 3, and 4, wherein z is 0, 1, or 2, and wherein each $R^s$ is independently selected from alkyl, halo, and haloalkyl;

or wherein the alkyl can optionally form a bridged four- or five-membered ring with another carbon atom on the ring to provide the structure shown below:

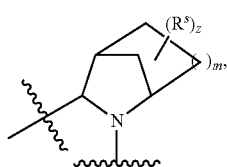

wherein m is selected from 0 or 1, wherein z is 0, 1, or 2, and wherein each $R^s$ is independently selected from alkyl, halo, and haloalkyl;

or wherein the alkyl can optionally form a a spirocyclic three- to six-membered ring with the carbon atom to which it is attached to provide the structure shown below:

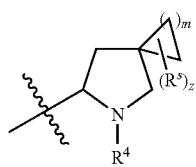

wherein m is selected from 1, 2, 3, and 4, wherein z is 0, 1, or 2, and wherein each $R^s$ is $R^s$ is independently selected from alkyl, halo, and haloalkyl.

The term "alkylcarbonyl," as used herein, refers to an alkyl group attached to the parent molecular moiety through a carbonyl group.

The term "alkylcarbonyloxy," as used herein, refers to an alkylcarbonyl group attached to the parent molecular moiety through an oxygen atom.

The term "alkylsulfanyl," as used herein, refers to an alkyl group attached to the parent molecular moiety through a sulfur atom.

The term "alkylsulfonyl," as used herein, refers to an alkyl group attached to the parent molecular moiety through a sulfonyl group.

The term "aryl," as used herein, refers to a phenyl group, or a bicyclic fused ring system wherein one or both of the rings is a phenyl group. Bicyclic fused ring systems consist of a phenyl group fused to a four- to six-membered aromatic or non-aromatic carbocyclic ring. The aryl groups of the present disclosure can be attached to the parent molecular moiety through any substitutable carbon atom in the group. Representative examples of aryl groups include, but are not limited to, indanyl, indenyl, naphthyl, phenyl, and tetrahydronaphthyl. The aryl groups of the present disclosure are optionally substituted with one, two, three, four, or five substituents independently selected from alkenyl, alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —$NR^xR^y$, ($NR^xR^y$)alkyl, oxo, and —$P(O)OR_2$, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro.

The term "arylalkoxy," as used herein, refers to an aryl group attached to the parent molecular moiety through an alkoxy group.

The term "arylalkoxycarbonyl," as used herein, refers to an arylalkoxy group attached to the parent molecular moiety through a carbonyl group.

The term "arylalkyl," as used herein, refers to an alkyl group substituted with one, two, or three aryl groups. The alkyl part of the arylalkyl is further optionally substituted with one or two additional groups independently selected from alkoxy, alkylcarbonyloxy, halo, haloalkoxy, haloalkyl, heterocyclyl, hydroxy, and —$NR^cR^d$, wherein the heterocyclyl is further optionally substituted with one or two substituents independently selected from alkoxy, alkyl, unsubstituted aryl, unsubstituted arylalkoxy, unsubstituted arylalkoxycarbonyl, halo, haloalkoxy, haloalkyl, hydroxy, —$NR^xR^y$, and oxo.

The term "arylalkylcarbonyl," as used herein, refers to an arylalkyl group attached to the parent molecular moiety through a carbonyl group.

The term "arylcarbonyl," as used herein, refers to an aryl group attached to the parent molecular moiety through a carbonyl group.

The term "aryloxy," as used herein, refers to an aryl group attached to the parent molecular moiety through an oxygen atom.

The term "aryloxycarbonyl," as used herein, refers to an aryloxy group attached to the parent molecular moiety through a carbonyl group.

The term "arylsulfonyl," as used herein, refers to an aryl group attached to the parent molecular moiety through a sulfonyl group.

The term "bicycloalkyl," as used herein, refers to a saturated, fused, bridged, or spirocyclic bicyclic hydrocarbon ring system having five to twelve carbon atoms and zero heteroatoms. The bicycloalkyl groups of the present disclosure are optionally substituted with one or two groups independently selected from alkyl, halo, and haloalkyl.

The term "carbonyl," as used herein, refers to —C(O)—.

The term "carboxy," as used herein, refers to —$CO_2H$.

The term "cyano," as used herein, refers to —CN.

The term "cycloalkyl," as used herein, refers to a saturated monocyclic, hydrocarbon ring system having three to seven carbon atoms and zero heteroatoms. Representative examples of cycloalkyl groups include, but are not limited to, cyclopropyl, cyclobutyl, cyclopentyl, and cyclohexyl. The cycloalkyl groups of the present disclosure are optionally substituted with one, two, three, four, or five substituents independently selected from alkoxy, alkyl, aryl, cyano, halo, haloalkoxy, haloalkyl, heterocyclyl, hydroxy, hydroxyalkyl, nitro, and —$NR^xR^y$, wherein the aryl and the heterocyclyl are further optionally substituted with one, two, or three substituents independently selected from alkoxy, alkyl, cyano, halo, haloalkoxy, haloalkyl, hydroxy, and nitro.

The term "(cycloalkyl)alkyl," as used herein, refers to an alkyl group substituted with one, two, or three cycloalkyl groups.

The term "cycloalkyloxy," as used herein, refers to a cycloalkyl group attached to the parent molecular moiety through an oxygen atom.

The term "cycloalkyloxycarbonyl," as used herein, refers to a cycloalkyloxy group attached to the parent molecular moiety through a carbonyl group.

The term "cycloalkylsulfonyl," as used herein, refers to a cycloalkyl group attached to the parent molecular moiety through a sulfonyl group.

The term "cycloalkyl-substituted-heterocyclyl," as used herein, refers to a saturated, monocyclic heterocyclyl group substituted with one or two cycloalkyl groups.

The term "ethenylcycloalkyl," as used herein, refers to:

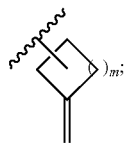

wherein m is 1, 2, or 3.

The term "formyl," as used herein, refers to —CHO.

The term "fused bicycloheterocyclyl," as used herein, refers to a four-, five-, six-, or seven-membered saturated or unsaturated ring containing one, two, or three heteroatoms independently selected from nitrogen, oxygen, and sulfur, fused to a three- to five-membered saturated carbocyclic ring. The heterocyclyl groups of the present disclosure can be attached to the parent molecular moiety through any carbon atom or nitrogen atom in the group. The bicycloheterocyclyl groups of the present disclosure are optionally substituted with one or two groups independently selected from alkyl, spicrocyclyl, halo, and haloalkyl.

The term "halo," as used herein, refers to Cl, Br, F, or I.

The term "haloalkoxy," as used herein, refers to a haloalkyl group attached to the parent molecular moiety through an oxygen atom.

The term "haloalkoxycarbonyl," as used herein, refers to a haloalkoxy group attached to the parent molecular moiety through a carbonyl group.

The term "haloalkyl," as used herein, refers to an alkyl group substituted with one, two, three, or four halogen atoms.

The term "heterocyclyl," as used herein, refers to a four-, five-, six-, or seven-membered ring containing one, two, three, or four heteroatoms independently selected from nitrogen, oxygen, and sulfur. The four-membered ring has zero double bonds, the five-membered ring has zero to two double bonds, and the six- and seven-membered rings have zero to three double bonds. The term "heterocyclyl" also includes bicyclic groups in which the heterocyclyl ring is fused to another monocyclic heterocyclyl group, or a four- to six-membered aromatic or non-aromatic carbocyclic ring; as well as bridged bicyclic groups such as 7-azabicyclo[2.2.1]hept-7-yl, 2-azabicyclo[2.2.2]oct-2-yl, 2,5-diazabicyclo[2.2.1]heptan-2-yl, and 2-azabicyclo[2.2.2]oct-3-yl. The heterocyclyl groups of the present disclosure can be attached to the parent molecular moiety through any carbon atom or nitrogen atom in the group. Examples of heterocyclyl groups include, but are not limited to, benzothienyl, furyl, imidazolyl, indolinyl, indolyl, isoquinolinyl, isothiazolyl, isoxazolyl, morpholinyl, oxazolyl, oxetanyl, piperazinyl, piperidinyl, pyrazolyl, pyridinyl, pyrrolidinyl, pyrrolopyridinyl, pyrrolyl, quinolinyl, tetrahydrofuranyl, tetrahydropyranyl, thiazolyl, thienyl, and thiomorpholinyl. The heterocyclyl groups of the present disclosure are optionally substituted with one, two, three, four, or five substituents independently selected from alkenyl, alkoxy, alkoxyalkyl, alkoxycarbonyl, alkyl, alkylcarbonyl, aryl, arylalkoxycarbonyl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —NR$^x$R$^y$, (NR$^x$R$^y$)alkyl, and oxo, wherein the alkyl part of the arylalkyl and the heterocyclylalkyl are unsubstituted and wherein the aryl, the aryl part of the arylalkyl, the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro.

The term "heterocyclylalkoxy," as used herein, refers to a heterocylyl group attached to the parent molecular moiety through an alkoxy group.

The term "heterocyclylalkoxycarbonyl," as used herein, refers to a heterocyclylalkoxy group attached to the parent molecular moiety through a carbonyl group.

The term "heterocyclylalkyl," as used herein, refers to an alkyl group substituted with one, two, or three heterocyclyl groups. The alkyl part of the heterocyclylalkyl is further optionally substituted with one or two additional groups independently selected from alkoxy, alkylcarbonyloxy, aryl, halo, haloalkoxy, haloalkyl, hydroxy, and —NR$^c$R$^d$, wherein the aryl is further optionally substituted with one or two substituents independently selected from alkoxy, alkyl, unsubstituted aryl, unsubstituted arylalkoxy, unsubstituted arylalkoxycarbonyl, halo, haloalkoxy, haloalkyl, hydroxy, and —NR$^x$R$^y$.

The term "heterocyclylalkylcarbonyl," as used herein, refers to a heterocyclylalkyl group attached to the parent molecular moiety through a carbonyl group.

The term "heterocyclylcarbonyl," as used herein, refers to a heterocyclyl group attached to the parent molecular moiety through a carbonyl group.

The term "heterocyclylethenyl," as used herein, refers to:

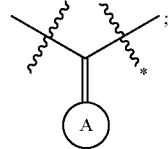

wherein A is a five- to seven-membered monocyclic heterocycle containing zero additional double bonds, and wherein "⌇" and "⌇" denote the point of attachment to the —NR$^c$R$^d$ group and the parent molecular moiety.

The term "heterocyclyloxy," as used herein, refers to a heterocyclyl group attached to the parent molecular moiety through an oxygen atom.

The term "heterocyclyloxycarbonyl," as used herein, refers to a heterocyclyloxy group attached to the parent molecular moiety through a carbonyl group.

The term "hydroxy," as used herein, refers to —OH.

The term "hydroxyalkyl," as used herein, refers to an alkyl group substituted with one, two, or three hydroxy groups.

The term "hydroxyalkylcarbonyl," as used herein, refers to a hydroxyalkyl group attached to the parent molecular moiety through a carbonyl group.

The term "nitro," as used herein, refers to —NO$_2$.

The term "—NR$^c$R$^d$," as used herein, refers to two groups, R$^c$ and R$^d$, which are attached to the parent molecular moiety through a nitrogen atom. R$^c$ and R$^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkyloxy, cycloalkyloxycarbonyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylalkyl, heterocyclyloxycarbonyl, hydroxyalkylcarbonyl, (NR$^e$R$^f$)alkyl, (NR$^e$R$^f$)alkylcarbonyl, (NR$^e$R$^f$)carbonyl, (NR$^e$R$^f$)sulfonyl, —C(NCN)OR', and —C(NCN)NR$^x$R$^y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —NR$^e$R$^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro.

The term "(NR$^c$R$^d$)alkenyl," as used herein, refers to

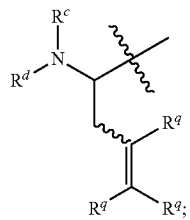

wherein R$^c$ and R$^d$ are as defined herein and each R$^q$ is independently hydrogen or C$_{1-3}$ alkyl.

The term "(NR$^c$R$^d$)alkyl," as used herein, refers to an alkyl group substituted with one, two, or three —NR$^c$R$^d$ groups. The alkyl part of the (NR$^c$R$^d$)alkyl is further optionally substituted with one or two additional groups selected from alkoxy, alkoxyalkylcarbonyl, alkoxycarbonyl, alkylsulfanyl, arylalkoxycarbonyl, carboxy, cycloalkyl, heterocyclyl, heterocyclylcarbonyl, hydroxy, and (NR$^e$R$^f$) carbonyl; wherein the heterocyclyl is further optionally substituted with one, two, three, four, or five substituents independently selected from alkoxy, alkyl, cyano, halo, haloalkoxy, haloalkyl, and nitro.

The term "—NR$^e$R$^f$," as used herein, refers to two groups, R$^e$ and R$^f$, which are attached to the parent molecular moiety through a nitrogen atom. R$^e$ and R$^f$ are independently selected from hydrogen, alkyl, unsubstituted aryl, unsubstituted arylalkyl, unsubstituted cycloalkyl, unsubstituted (cyclolalkyl)alkyl, unsubstituted heterocyclyl, unsubstituted heterocyclylalkyl, (NR$^x$R$^y$)alkyl, and (NR$^x$R$^y$)carbonyl.

The term "(NR$^e$R$^f$)alkyl," as used herein, refers to an alkyl group substituted with one, two, or three —NR$^e$R$^f$ groups.

The term "(NR$^e$R$^f$)alkylcarbonyl," as used herein, refers to an (NR$^e$R$^f$)alkyl group attached to the parent molecular moiety through a carbonyl group.

The term "(NR$^e$R$^f$)carbonyl," as used herein, refers to an —NR$^e$R$^f$ group attached to the parent molecular moiety through a carbonyl group.

The term "(NR$^e$R$^f$)sulfonyl," as used herein, refers to an —NR$^e$R$^f$ group attached to the parent molecular moiety through a sulfonyl group.

The term "—NR$^x$R$^y$," as used herein, refers to two groups, R$^x$ and R$^y$, which are attached to the parent molecular moiety through a nitrogen atom. R$^x$ and R$^y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{x'}$R$^{y'}$)carbonyl, wherein R$^{x'}$ and R$^{y'}$ are independently selected from hydrogen and alkyl.

The term "(NR$^x$R$^y$)alkyl," as used herein, refers to an alkyl group substituted with one, two, or three —NR$^x$R$^y$ groups.

The term "(NR$^x$R$^y$)carbonyl," as used herein, refers to an —NR$^x$R$^y$ group attached to the parent molecular moiety through a carbonyl group.

The term "(NR$^{x'}$R$^{y'}$)carbonyl," as used herein, refers to an —NR$^{x'}$R$^{y'}$ group attached to the parent molecular moiety through a carbonyl group.

The term "oxo," as used herein, refers to =O.

The term "oxocycloalkyl," as used herein, refers to a cycloalkyl group substituted with an oxo group.

The term "spirocycloheterocyclyl," as used herein, refers to a four-, five-, six-, or seven-membered saturated or unsaturated ring containing one, two, or three heteroatoms independently selected from nitrogen, oxygen, and sulfur, adjoined to one or two three- to five-membered saturated rings optionally containing one oxygen atom, via one or two single carbon atoms, respectively. The heterocyclyl groups of the present disclosure can be attached to the parent molecular moiety through any carbon atom or nitrogen atom in the group. The spirocycloheterocyclyl groups of the present disclosure are optionally substituted with one or two gropus independently selected from alkyl, halo, and haloalkyl.

The term "spirocyclyl," as used herein, refers to a three-, four-, or five-membered saturated ring adjoined to the parent molecular moiety through a single carbon atom.

The term "sulfonyl," as used herein, refers to —SO$_2$—.

The term "thioalkyl," as used herein, represents an alkyl group attached to the parent molecular moiety through a sulfur atom.

Asymmetric centers exist in the compounds of the present disclosure. These centers are designated by the symbols "R" or "S", depending on the configuration of substituents around the chiral carbon atom. It should be understood that the disclosure encompasses all stereochemical isomeric forms, or mixtures thereof, which possess the ability to inhibit NS5A. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

The compounds of the present disclosure also exist as tautomers; therefore the present disclosure also encompasses all tautomeric forms.

The term "compounds of the present disclosure", and equivalent expressions, are meant to embrace compounds of Formula (I), and pharmaceutically acceptable enantiomers, diastereomers, and salts thereof. Similarly, references to intermediates are meant to embrace their salts where the context so permits.

The present disclosure is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

When it is possible that, for use in therapy, therapeutically effective amounts of a compound of Formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of Formula (I) or pharmaceutically acceptable salts thereof, and one or more pharmaceutically acceptable carriers, diluents, or excipients. The term "therapeutically effective amount," as used herein, refers to the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially, or simultaneously. The compounds of Formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the present disclosure there is also provided a process for the preparation of a pharmaceutical formulation including admixing a compound of Formula (I), or a pharmaceutically acceptable salt thereof, with one or more pharmaceutically acceptable carriers, diluents, or excipients. The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

Pharmaceutical formulations may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the present disclosure are typical in a monotherapy for the prevention and treatment of HCV mediated disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this disclosure comprise a combination of a compound of the present disclosure and one or more additional therapeutic or prophylactic agent, both the compound and the additional agent are usually present at dosage levels of between about 10 to 150%, and more preferably between about 10 and 80% of the dosage normally administered in a monotherapy regimen.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection are preferred.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of Formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

The compounds of Formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research* 1986, 3(6), 318.

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

The term "patient" includes both human and other mammals.

The term "treating" refers to: (i) preventing a disease, disorder or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition.

The compounds of the present disclosure can also be administered with a cyclosporin, for example, cyclosporin A. Cyclosporin A has been shown to be active against HCV in clinical trials (*Hepatology* 2003, 38, 1282; *Biochem. Biophys. Res. Commun.* 2004, 313, 42; *J. Gastroenterol.* 2003, 38, 567).

Table 1 below lists some illustrative examples of compounds that can be administered with the compounds of this disclosure. The compounds of the disclosure can be administered with other anti-HCV activity compounds in combination therapy, either jointly or separately, or by combining the compounds into a composition.

TABLE 1

| Brand Name | Physiological Class | Type of Inhibitor or Target | Source Company |
|---|---|---|---|
| NIM811 | | Cyclophilin Inhibitor | Novartis |
| Zadaxin | | Immunomodulator | Sciclone |
| Suvus | | Methylene blue | Bioenvision |
| Actilon (CPG10101) | | TLR9 agonist | Coley |
| Batabulin (T67) | Anticancer | β-tubulin inhibitor | Tularik Inc., South San Francisco, CA |
| ISIS 14803 | Antiviral | antisense | ISIS Pharmaceuticals Inc, Carlsbad, CA/Elan Phamaceuticals Inc., New York, NY |
| Summetrel | Antiviral | antiviral | Endo Pharmaceuticals Holdings Inc., Chadds Ford, PA |
| GS-9132 (ACH-806) | Antiviral | HCV Inhibitor | Achillion/Gilead |
| Pyrazolopyrimidine compounds and salts From WO-2005047288 26 May 2005 | Antiviral | HCV Inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |

TABLE 1-continued

| Brand Name | Physiological Class | Type of Inhibitor or Target | Source Company |
|---|---|---|---|
| XTL-6865 (XTL-002) | Antiviral | monoclonal antibody | XTL Biopharmaceuticals Ltd., Rehovot, Isreal |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B Replicase Inhibitor | Wyeth/Viropharma |
| NM-283 | Antiviral | NS5B Replicase Inhibitor | Idenix/Novartis |
| GL-59728 | Antiviral | NS5B Replicase Inhibitor | Gene Labs/Novartis |
| GL-60667 | Antiviral | NS5B Replicase Inhibitor | Gene Labs/Novartis |
| 2'C MeA | Antiviral | NS5B Replicase Inhibitor | Gilead |
| PSI 6130 | Antiviral | NS5B Replicase Inhibitor | Roche |
| R1626 | Antiviral | NS5B Replicase Inhibitor | Roche |
| 2'C Methyl adenosine | Antiviral | NS5B Replicase Inhibitor | Merck |
| JTK-003 | Antiviral | RdRp inhibitor | Japan Tobacco Inc., Tokyo, Japan |
| Levovirin | Antiviral | ribavirin | ICN Pharmaceuticals, Costa Mesa, CA |
| Ribavirin | Antiviral | ribavirin | Schering-Plough Corporation, Kenilworth, NJ |
| Viramidine | Antiviral | Ribavirin Prodrug | Ribapharm Inc., Costa Mesa, CA |
| Heptazyme | Antiviral | ribozyme | Ribozyme Pharmaceuticals Inc., Boulder, CO |
| BILN-2061 | Antiviral | serine protease inhibitor | Boehringer Ingelheim Pharma KG, Ingelheim, Germany |
| SCH 503034 | Antiviral | serine protease inhibitor | Schering Plough |
| Zadazim | Immune modulator | Immune modulator | SciClone Pharmaceuticals Inc., San Mateo, CA |
| Ceplene | Immunomodulator | immune modulator | Maxim Pharmaceuticals Inc., San Diego, CA |
| CellCept | Immunosuppressant | HCV IgG immunosuppressant | F. Hoffmann-La Roche LTD, Basel, Switzerland |
| Civacir | Immunosuppressant | HCV IgG immunosuppressant | Nabi Biopharmaceuticals Inc., Boca Raton, FL |
| Albuferon-α | Interferon | albumin IFN-α2b | Human Genome Sciences Inc., Rockville, MD |

TABLE 1-continued

| Brand Name | Physiological Class | Type of Inhibitor or Target | Source Company |
|---|---|---|---|
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharmiceuticals Inc., Bethesda, MD/SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/Valentis |
| Wellferon | Interferon | lymphoblastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/Ribavirin | Interferon | PEGylated IFN-α2b/ribavirin | Schering-Plough Corporation, Kenilworth, NJ |
| IP-501 | Liver protection | antifibrotic | Indevus Pharmaceuticals Inc., Lexington, MA |

TABLE 1-continued

| Brand Name | Physiological Class | Type of Inhibitor or Target | Source Company |
|---|---|---|---|
| IDN-6556 | Liver protection | caspase inhibitor | Idun Pharmaceuticals Inc., San Diego, CA |
| ITMN-191 (R-7227) | Antiviral | serine protease inhibitor | InterMune Pharmaceuticals Inc., Brisbane, CA |
| GL-59728 | Antiviral | NS5B Replicase Inhibitor | Genelabs |
| ANA-971 | Antiviral | TLR-7 agonist | Anadys |

The compounds of the present disclosure may also be used as laboratory reagents. Compounds may be instrumental in providing research tools for designing of viral replication assays, validation of animal assay systems and structural biology studies to further enhance knowledge of the HCV disease mechanisms. Further, the compounds of the present disclosure are useful in establishing or determining the binding site of other antiviral compounds, for example, by competitive inhibition.

The compounds of this disclosure may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

This disclosure is intended to encompass compounds having Formula (I) when prepared by synthetic processes or by metabolic processes including those occurring in the human or animal body (in vivo) or processes occurring in vitro.

The abbreviations used in the present application, including particularly in the illustrative examples which follow, are well-known to those skilled in the art. Some of the abbreviations used are as follows: ca. for about; ACN or MECN for acetonitrile; TFA for trifluoroacetic acid; min or mins for minutes EtOAc or EtOAc or EA for ethyl acetate; DCM for dichloromethane; Hex for hexanes; THF for tetrahydrofuran; DMSO for dimethylsulfoxide; $Et_3N$ or TEA for triethylamine; TBS-Cl for tert-butyldimethylsilyl chloride; $Et_2O$ for diethyl ether; MeOH for methanol; EtOH for ethanol; rt or RT for room temperature or retention time (context will dictate); $R_t$ for retention time; Ts for para-tolylsulfonyl; Ph for phenyl; LiHMDS for lithium hexamethyldisilazide; Me for methyl; $iPr_2EtN$, DIEA, or DiPEA for diisopropylethylamine; h or hr or hrs for hours; ON for overnight; TBS for tert-butyldimethylsilyl; DMF for N,N-dimethylformamide; pTsOH for para-tolylsulfonic acid; AcOH for acetic acid; HATU for O-(7-azabenzotriazol-1-yl)-N,N,N',N'-tetramethyluronium hexafluorophosphate; BOC for tert-butoxycarbonyl; DME for 1,2-dimethoxyethane; DMAP for N,N-dimethylaminopyridine; HOBT for 1-hydroxybenzotriazole; and EDC for 1-ethyl-3-(3-dimethylaminopropyl)carbodiimide.

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

Starting materials can be obtained from commercial sources or prepared by well-established literature methods known to those of ordinary skill in the art.

Condition 1
Start % B=0
Final % B=100
Gradient time=2 min
Stop time=3 min
Flow rate=1 mL/min
Wavelength=220 nm
Solvent A=10% ACN/90% $H_2O$/0.1% TFA
Solvent B=90% ACN/10% $H_2O$/0.1% TFA
Column=Phenomenex-Luna C18, 30×2, 3 u
Condition 2
Start % B=0
Final % B=100
Gradient time=2 min
Stop time=3 min
Flow Rate=4 mL/min
Wavelength=220 nm
Solvent A=0.1% TFA in 10% methanol/90% water
Solvent B=0.1% TFA in 90% methanol/10% water
Column=Phenomenex-Luna 3.0×50 mm S10
Condition 3
Start % B=0
Final % B=100
Gradient time=4 min
Stop time=5 min
Flow rate=0.8 mL/min
Wavelength=220 nm
Solvent A=10% ACN/90% $H_2O$/0.1% TFA
Solvent B=90% ACN/10% $H_2O$/0.1% TFA
Column=Phenomenex-Luna C18, 50×2, 3 u
Condition 4
Start % B=2
Final % B=98
Gradient time=1 min
Stop time=1.5 min
Flow rate=0.8 mL/min
Wavelength=220 nm
Solvent A=100% $H_2O$/0.05% TFA
Solvent B=100% ACN/0.05% TFA
Column=Waters Acquity SDS
Condition 5
Start % B=0
Final % B=100
Gradient time=2 min Stop time=3 min
Flow Rate=1 mL/min
Wavelength=220 nm
Solvent A=0.1% TFA in 10% methanol/90% water
Solvent B=0.1% TFA in 90% methanol/10% water
Column=Phenomenex-Luna 2.0×30 mm 3 um
Condition 6
Start % B=10
Final % B=100
Gradient time=30 min
Stop time=33 min
Flow Rate=1 mL/min
Wavelength=220 nm
Solvent A=10 mM amm. bicarb (pH=9.5)/95% water/5% methanol
Solvent B=10 mM amm. bicarb (pH=9.5)/5% water/95% methanol
Column=Xbridge Phenyl 3.5 um, 3.0×150 mm
Condition 7
Start % B=10
Final % B=100
Gradient time=15 min
Stop time=18 min
Flow Rate=1 mL/min
Wavelength=220 nm
Solvent A=0.1% TFA/95% water/5% acetonitrile
Solvent B=0.1% TFA/5% water/95% acetonitrile
Column=Xbridge C18 3.5 um, 3.0×150 mm
Condition 8
Start % B=0
Final % B=100
Gradient time=4 min
Stop time=5 min
Flow rate=0.8 mL/min
Wavelength=220 nm
Solvent A=10% MeOH/90% $H_2O$/0.1% TFA
Solvent B=90% MeOH/10% $H_2O$/0.1% TFA
Column=Phenomenex-Luna C18, 50×2, 3 u
Oven Temp.=40° C.
Condition 9
Start % B=10
Final % B=50
Gradient time=20 min
Stop time=25 min
Flow rate=1 mL/min
Wavelength1=220 nm
Wavelength2=254 nm
Solvent A=5% ACN/95% $H_2O$/0.1% TFA
Solvent B=95% ACN/5% $H_2O$/0.1% TFA
Column=Waters Sunfire C18, 150×4.6, 3.5 u (low pH)
Condition 10
UPLC
Start % B=2
Final % B=98
Gradient time=1.5 min
Stop time=2 min
Flow rate=0.8 mL/min
Wavelength=220 nm
Solvent A=100% $H_2O$/0.05% TFA
Solvent B=100% ACN/0.05% TFA
Column=Waters Acquity UPLC BEH C18 2.1×50 mm, 1.7 μm Cap-1

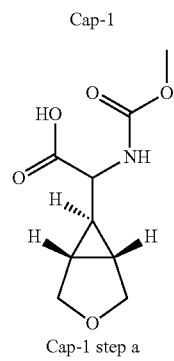

Cap-1 step a

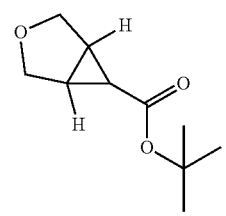

A solution of tert-butyl diazoacetate (1.832 mL, 13.22 mmol) in 50 mL of $CH_2Cl_2$ was added into a mixture of 2,5-dihydrofuran (9.76 mL, 132 mmol), Rhodium(II) acetate dimer (0.058 g, 0.132 mmol) in 40 mL of $CH_2Cl_2$ dropwise by a syringe pump over 5 h. The resulting mixture was then stirred at room temperature overnight. The solvent was removed under vacuum. The residue was purified by chromatography (silica gel, 0%-15% EtOAc/Hex) to afford Cap-1 step a (trans isomer) (720 mg) and Cap-1 step a (cis-isomer) (360 mg) as clear oil. Cap-1 step a (trans-isomer): $^1$H NMR (500 MHz, $CDCl_3$) δ ppm 3.88 (2H, d, J=8.55 Hz), 3.70 (2H, d, J=8.55 Hz), 2.03-2.07 (2H, m), 1.47 (1H, t, J=3.20 Hz), 1.41 (9H, s); Cap-1 step a (cis-isomer): $^1$H NMR (400 MHz, $CDCl_3$) δ ppm 4.06 (2H, d, J=8.53 Hz), 3.73 (2H, d, J=8.03 Hz), 1.81-1.86 (2H, m), 1.65-1.71 (1H, m), 1.43-1.47 (9H, m).

Cap-1 step b

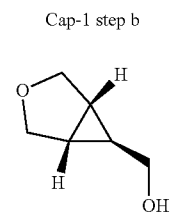

To a solution of (Cap-1 step a (trans isomer)) (700 mg, 3.80 mmol) in 15 mL of diethyl ether at −10° C. was added LiAlH4 (7.60 mL, 7.60 mmol) (1 M in THF) dropwise over 1 h. The resulting mixture was stirred at −10° C. for 1 h then at room temperature for 1 h. The mixture was then cooled to −5° C. 10 mL of Rochelle's salt (Potassium sodium tartrate) aqueous solution was added dropwise to quench the reaction. The mixture was stirred at room temperature for 30 min then extracted with EtOAc (3×). The combined organic layers were dried with $MgSO_4$ and concentrated to afford Cap-1 step b (380 mg) as light yellow oil. The product was used in the next step without purification. $^1$H NMR (400 MHz, $CDCl_3$) δ ppm 3.85 (2H, d, J=8.28 Hz), 3.68 (2H, d, J=8.53 Hz), 3.45-3.55 (2H, m), 1.50-1.56 (2H, m), 1.02-1.11 (1H, m).

Cap-1 step c

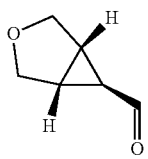

To a solution of DMSO (4.82 mL, 67.9 mmol) in CH$_2$Cl$_2$ (70 mL) was added oxalyl chloride (3.14 mL, 35.8 mmol) at −78° C. dropwise slowly. The resulting mixture was stirred at −78° C. for 15 min. A solution of Cap-1 step b (3.10 g, 27.2 mmol) in 35 mL of CH$_2$Cl$_2$ was added and the mixture was stirred at −78° C. for 1 h. Et$_3$N (18.93 mL, 136 mmol) was then added dropwise. After 30 min, the cooling bath was removed and the reaction was quenched with cold 20% K$_2$HPO$_4$ aq. solution (10 mL) and water. The mixture was stirred at room temperature for 15 min then diluted with Et$_2$O. The layers were separated. The aqueous layer was extracted with Et$_2$O (2×). The combined organic layers were washed with brine, dried with MgSO$_4$ and concentrated. The residue was purified by flash chromatography (silica gel, 100% CH$_2$Cl$_2$) to afford Cap-1 step c (2.71 g) as light yellow oil. $^1$H NMR (500 MHz, CDCl$_3$) δ ppm 9.41 (1H, d, J=4.27 Hz), 3.96 (2H, d, J=8.85 Hz), 3.80 (2H, d, J=8.55 Hz), 2.27-2.33 (2H, m), 1.93 (1H, m).

Cap-1 step d

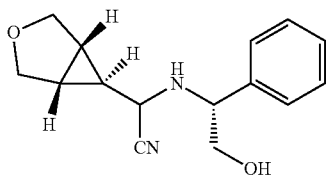

To a mixture of Cap-1 step c (2.7 g, 24.08 mmol) in 50 mL of water at 0° C. was added sodium bisulfite (2.506 g, 24.08 mmol) and KCN (1.631 g, 25.04 mmol), followed by a solution of (R)-2-amino-2-phenylethanol (3.30 g, 24.08 mmol) in 18 mL of MeOH. The resulting mixture was stirred at room temperature for 2 h and then heated to reflux overnight. The mixture was cooled to room temperature. 100 mL of EtOAc was added. After mixing for 15 min the layers were separated. The aqueous layer was extracted with EtOAc (2×). The combined organic layers were washed with brine, dried with MgSO$_4$ and concentrated. The crude diastereomeric mixture was purified by reverse phase HPLC (Column: Water Sunfire 30×150 mm, acetonitrile/water/NH$_4$OAc) to afford a two diastereomers of Cap-1 step d. The absolute stereochemistry of each isomer was not determined. Diastereomer 1 (later fraction) (570 mg): LC (Cond. 1): RT=0.97 min; LC/MS: Anal. Calcd. for [M+H]$^+$ C$_{15}$H$_{19}$N$_2$O$_2$ 259.14. found 259.2.

Cap-1 step e

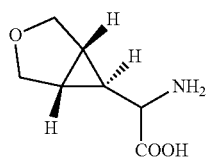

To a solution of Cap-1 step d (diastereomer 1) (570 mg, 2.207 mmol) in 20 mL of CH$_2$Cl$_2$ and 20 mL of MeOH at 0° C. was added lead tetraacetate (1174 mg, 2.65 mmol). The resulting orange mixture was stirred at 0° C. for 10 min. Water (20 mL) was then added into the mixture and the mixture was filtered through diatomaceous earth (Celite®). The filtrate was concentrated and diluted with 25 mL of 6 N HCl aq. solution. The resulting mixture was refluxed for 4 h. The mixture was filtered off and washed with CH$_2$Cl$_2$. The aqueous layer was concentrated to afford Cap-1 step e (HCl salt). The crude product was used in the next step without further purification. $^1$H NMR (500 MHz, MeOD) δ ppm 3.87-3.91 (2H, m), 3.73 (2H, dd, J=8.70, 2.90 Hz), 3.55 (1H, d, J=10.07 Hz), 2.02-2.07 (1H, m), 1.94-1.99 (1H, m), 1.03-1.10 (1H, m).

Cap-1

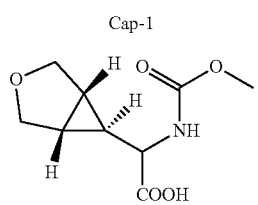

To a mixture of the above crude Cap-1 step e in 1 N NaOH aq. solution (10 mL) was added sodium bicarbonate (371 mg, 4.42 mmol). Methyl chloroformate (0.342 mL, 4.42 mmol) was then added dropwise. The resulting mixture was stirred at room temperature for 3 h. The mixture was neutralized with 1 N HCl aq. solution then extracted with EtOAc (3×). The combined organic layers were dried with MgSO$_4$ and concentrated to afford Cap-1 (100 mg, 21.1% over two steps) as light yellow oil. LC (Cond. 1): RT=0.54 min; LC/MS: Anal. Calcd. for [M+H]$^+$ C$_9$H$_{14}$NO$_5$ 216.09. found 216.1; 1H NMR (500 MHz, CDCl$_3$) δ ppm 5.29 (1H, br. s.), 3.53-4.02 (8H, m), 1.66-1.92 (2H, m), 1.08 (1H, br. s.).

Cap-2

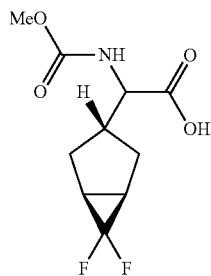

Racemic mixture

Racemic Mixture

Cap-2 step a

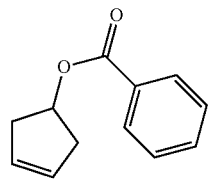

A solution of cyclopent-3-enol (5 g, 59.4 mmol) and Et₃N (9.94 mL, 71.3 mmol) in 50 mL of CH₂Cl₂ was stirred at room temperature for 15 min. Benzoyl chloride (8.28 mL, 71.3 mmol) was then added dropwise and the mixture was stirred at room temperature overnight. The mixture was then washed with water. The organic layer was dried with MgSO₄ and concentrated. The residue was purified by flash chromatography (silica gel, EtOAc/Hex 0-10%) to afford Cap-2 step a (9.25 g) as clear oil. LC (Cond. 1): RT=1.77 min; ¹H NMR (400 MHz, CDCl₃) δ ppm 8.01-8.07 (2H, m), 7.55 (1H, t, J=7.40 Hz), 7.43 (2H, t, J=7.65 Hz), 5.79 (2H, s), 5.64 (1H, tt, J=6.93, 2.60 Hz), 2.87 (2H, dd, J=16.56, 6.78 Hz), 2.52-2.63 (2H, m).

Cap-2 step a

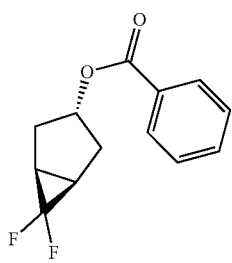

isomer 1

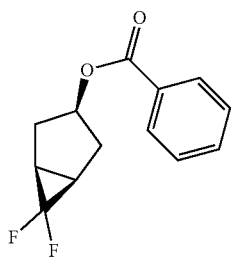

isomer 2

To a round bottom flask with a magnetic stirring bar was added neat sodium fluoride (5.02 mg, 0.120 mmol) and Cap-2 step a (2.25 g, 11.95 mmol). The flask was heated up to 100° C. and neat trimethylsilyl 2,2-difluoro-2-(fluorosulfonyl)acetate (5.89 mL, 29.9 mmol) was added slowly by syringe pump over 5 h. The mixture was stirred at 100° C. overnight. The mixture was then diluted with CH₂Cl₂, washed with water, sat. NaHCO₃ aq. solution and brine, dried with MgSO₄ and concentrated. The crude product was purified by flash chromatography (silica gel, 0-5% EtOAc/Hex) to afford Cap-2 step b (isomer 1) (750 mg) and Cap-2 step b (isomer 2) (480 mg) as clear oils. Relative stereochemical assignment was made by NOE study. Cap-2 step b (isomer 1): LC (Cond. 1): RT=1.83 min; LC/MS: Anal. Calcd. for [M+H]⁺ C₁₃H₁₃F₂O₂ 239.09. found 239.2; ¹H NMR (500 MHz, CDCl₃) δ ppm 7.99-8.04 (2H, m), 7.56 (1H, t, J=7.32 Hz), 7.43 (2H, t, J=7.63 Hz), 5.25-5.33 (1H, m), 2.50 (2H, dd, J=14.04, 6.71 Hz), 2.14-2.22 (2H, m), 2.08-2.14 (2H, m); Cap-2 step b (isomer 2): LC (Cond. 1): RT=1.79 min; LC/MS: Anal. Calcd. for [M+H]⁺ C₁₃H₁₃F₂O₂ 239.09. found 239.2; ¹H NMR (400 MHz, CDCl₃) δ ppm 7.98-8.08 (2H, m), 7.53-7.59 (1H, m), 7.41-7.48 (2H, m), 5.53-5.62 (1H, m), 2.59-2.70 (2H, m), 2.01-2.11 (4H, m).

Cap-2 step c

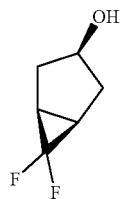

To a solution of Cap-2 step b (isomer 2) (480 mg, 2.015 mmol) in 4 mL of MeOH was added KOH (4 mL, 2.015 mmol) (10% aq.). The resulting mixture was stirred at room temperature overnight. The mixture was then extracted with CH₂Cl₂ (3×). The combined organic layers were dried with MgSO₄ and concentrated to afford Cap-2 step c (220 mg) as a light yellow solid. ¹H NMR (500 MHz, CDCl₃) δ ppm 4.41-4.54 (1H, m), 2.38-2.50 (2H, m), 1.89-1.99 (2H, m), 1.81 (2H, dd, J=14.50, 5.04 Hz).

Cap-2 step d

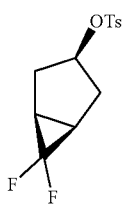

Tosyl-Cl (625 mg, 3.28 mmol) was added to a solution of Cap-2 step c (220 mg, 1.640 mmol) and pyridine (0.531 mL, 6.56 mmol) in 7 mL of CH₂Cl₂. The mixture was stirred at room temperature overnight and then diluted with CH₂Cl₂, washed with water and 1 N HCl aq. solution. The organic layer was dried (MgSO₄) and concentrated. The residue was purified by flash chromatography (silica gel, 0-15% EtOAc/Hexane) to afford Cap-2 step d (325 mg) as a clear oil. LC (Cond. 1): RT=1.72 min; LC/MS: Anal. Calcd. For [M+Na]⁺ C₁₃H₁₄F₂NaO₃S 311.05. found 311.2; ¹H NMR (500 MHz, CDCl₃) δ ppm 7.76 (2H, d, J=8.24 Hz), 7.34 (2H, d, J=8.24 Hz), 4.99-5.08 (1H, m), 2.45 (3H, s), 2.31-2.41 (2H, m), 1.84-1.94 (4H, m).

Cap-2 step e

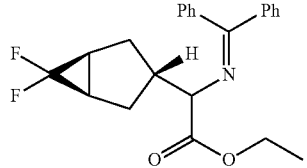

Racemic Mixture

To a microwave tube was added N-(diphenylmethylene) glycine ethyl ester (241 mg, 0.902 mmol) and Cap-2 step d (260 mg, 0.902 mmol) in 2 mL of toluene. The tube was sealed and LiHMDS (1.082 mL, 1.082 mmol) (1 N in THF) was added dropwise under $N_2$. The resulting dark brown solution was heated at 100° C. in microwave for 5 h. The mixture was then quenched with water, and extracted with EtOAc (3×). The combined organic layers were washed with water, dried with $MgSO_4$ and concentrated. The crude product was purified by flash chromatography (silica gel, 0-5% EtOAc/Hex) to afford a racemic mixture of Cap-2 step e (240 mg) as light yellow oil. The mixture was submitted to the next step without separation. LC (Cond. 2): RT=1.91 min; LC/MS: Anal. Calcd. for $[M+Na]^+$ $C_{23}H_{24}F_2NO_2$ 384.18. found 384.35. $^1$H NMR (500 MHz, $CDCl_3$) δ ppm 7.63-7.70 (2H, m), 7.43-7.51 (3H, m), 7.38-7.43 (1H, m), 7.31-7.38 (2H, m), 7.13-7.22 (2H, m), 4.13-4.22 (2H, m), 3.95 (1H, d, J=6.41 Hz), 2.67-2.79 (1H, m), 2.07-2.16 (1H, m), 1.97-2.07 (2H, m), 1.90 (2H, m), 1.65-1.76 (1H, m), 1.25 (3H, t, J=7.17 Hz).

Cap-2 step f

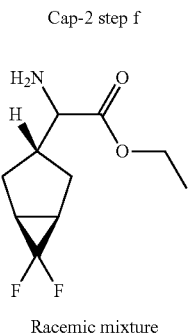

Racemic mixture

To a solution of Cap-2 step e (240 mg, 0.626 mmol) in 4 mL of THF was added HCl (1 mL, 2.0 mmol) (2 N aq.). The resulting mixture was stirred at room temperature for 2 h. The mixture was then washed with EtOAc, neutralized with sat. $NaHCO_3$ aq. solution then extracted with EtOAc (3×). The combined organic layers were dried with $MgSO_4$ and concentrated to afford Cap-2 step f (120 mg) as clear oil. LC (Cond. 2): RT=0.85 min; LC/MS: Anal. Calcd. for $[M+H]^+$ $C_{10}H_{16}F_2NO_2$ 220.11. found 220.26; $^1$H NMR (500 MHz, $CDCl_3$) δ ppm 4.14-4.25 (2H, m), 3.26 (1H, d, J=6.71 Hz), 2.22-2.35 (1H, m), 1.90-2.11 (5H, m), 1.79-1.90 (1H, m), 1.22-1.34 (3H, m).

Cap-2 step g

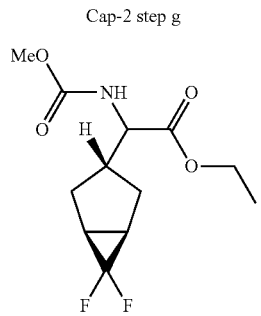

Racemic mixture

Racemic Mixture

To a solution of Cap-2 step f (120 mg, 0.547 mmol) in 2 mL of $CH_2Cl_2$ was added methyl chloroformate (0.085 mL, 1.095 mmol). The resulting mixture was stirred at room temperature for 1 h. The mixture was diluted with $CH_2Cl_2$ and washed with water. The organic layer was dried with $Na_2SO_4$ and concentrated to afford Cap-2 step g (150 mg) as a white solid. LC (Cond. 1): RT=1.45 min; LC/MS: Anal. Calcd. for $[M+H]^+$ $C_{12}H_{18}F_2NO_4$ 278.12. found 278.2; $^1$H NMR (500 MHz, $CDCl_3$) δ ppm 5.23 (1H, d, J=8.24 Hz), 4.29 (1H, t, J=7.48 Hz), 4.15-4.23 (2H, m), 3.68 (3H, s), 2.37 (1H, br. s.), 2.02-2.10 (1H, m), 1.85-2.00 (4H, m), 1.75-1.84 (1H, m), 1.27 (3H, t, J=7.02 Hz).

Cap-2

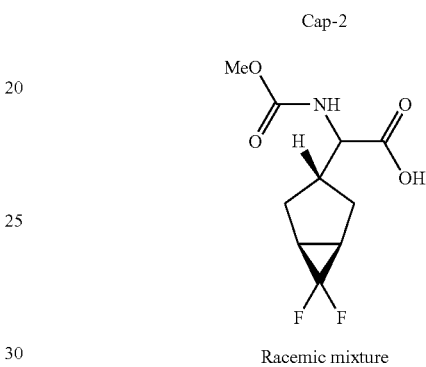

Racemic mixture

Racemic Mixture

To a mixture of Cap-2 step g (150 mg, 0.541 mmol) in 2 mL of THF and 1 mL of water was added LiOH (0.811 mL, 1.623 mmol) (2 N aq.). The resulting mixture was stirred at room temperature overnight. The mixture was neutralized with 1 N HCl aq. solution and extracted with EtOAc (3×). The combined organic layers were dried with $MgSO_4$ and concentrated to afford Cap-2 (133 mg) as a white solid. LC (Cond. 2): RT=1.07 min; LC/MS: Anal. Calcd. for $[M+H]^+$ $C_{10}H_{14}F_2NO_4$ 250.09. found 250.13; $^1$H NMR (500 MHz, $CDCl_3$) δ ppm 5.18-5.36 (1H, m), 4.28-4.44 (1H, m), 3.70 (3H, s), 2.37-2.56 (1H, m), 1.74-2.31 (6H, m).

Cap-3

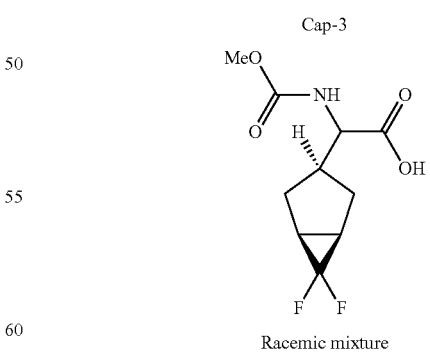

Racemic mixture

Cap-3 was synthesized from Cap-2 step b (isomer 1) according to the procedure described for Cap-2. LC (Cond.

2): RT=1.08 min; LC/MS: Anal. Calcd. for [M+H]$^+$ C$_{10}$H$_{14}$F$_2$NO$_4$ 250.09. found 249.86. $^1$H NMR (500 MHz, CDCl$_3$) δ ppm 5.15 (1H, d, J=8.24 Hz), 4.32 (1H, t, J=7.48 Hz), 3.69 (3H, s), 2.83-2.99 (1H, m), 1.96-2.26 (4H, m), 1.70 (1H, t, J=11.75 Hz), 1.59 (1H, t, J=12.05 Hz).

Cap-4

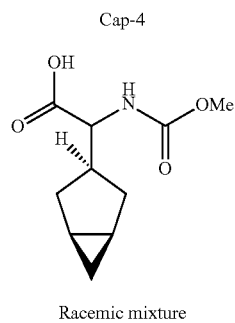 [SMILES: COC(=O)NC(C(=O)O)[C@@H]1C[C@@H]2C[C@@H]2C1]

Racemic Mixture

Cap-4 step a

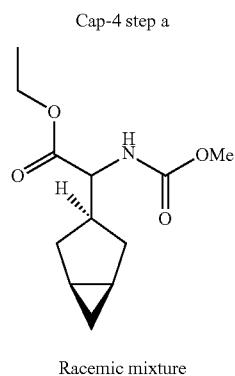 [SMILES: CCOC(=O)C(NC(=O)OC)[C@@H]1C[C@@H]2C[C@@H]2C1]

Racemic Mixture

A mixture of ethyl 2-amino-2-((1R,3r,5S)-bicyclo[3.1.0] hexan-3-yl)acetate (prepared from commercially available (1R,3r,5S)-bicyclo[3.1.0]hexan-3-ol by employing the same procedures described for the preparation of Cap-2; 350 mg, 1.910 mmol), DiPEA (0.667 mL, 3.82 mmol), methyl chloroformate (0.296 mL, 3.82 mmol) in 5 mL of CH$_2$Cl$_2$ was stirred at room temperature for 1 h. The mixture was then diluted with CH$_2$Cl$_2$ and washed with water. The organic layer was dried with MgSO$_4$ and concentrated to afford Cap-4 step a (461 mg) as yellow oil. LC (Cond. 1): RT=1.43 min; LC/MS: Anal. Calcd. for [M+H]$^+$ C$_{12}$H$_{20}$NO$_4$ 242.14. found 242.2; $^1$H NMR (500 MHz, CDCl$_3$) δ ppm 5.04 (1H, d, J=7.63 Hz), 4.09-4.20 (2H, m), 4.05 (1H, t, J=8.39 Hz), 3.63 (3H, s), 2.55-2.70 (1H, m), 1.96-2.09 (2H, m), 1.37-1.60 (4H, m), 1.24 (3H, t, J=7.17 Hz), 0.66-0.76 (1H, m), −0.03-0.06 (1H, m).

Cap-4

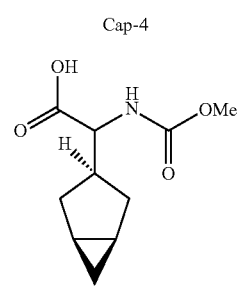

Racemic Mixture

To a mixture of ethyl ester Cap-4 step a (461 mg, 1.911 mmol) in 5 mL of THF and 2 mL of water was added LiOH (2.87 mL, 5.73 mmol) (2 N aq.). The resulting mixture was stirred at room temperature overnight. The mixture was then neutralized with 1 N HCl aqueous solution, and extracted with EtOAc (3×). The combined organic layers were dried with MgSO$_4$ and concentrated to afford Cap-4 (350 mg) as clear oil. LC (Cond. 1): RT=1.04 min; LC/MS: Anal. Calcd. for [2M+Na]$^+$ C$_{20}$H$_{30}$N$_2$NaO$_8$ 449.19. found 449.3; $^1$H NMR (500 MHz, CDCl$_3$) δ ppm 5.07 (1H, d, J=8.85 Hz), 4.13 (1H, t, J=8.24 Hz), 3.68 (3H, s), 2.64-2.79 (1H, m), 2.04-2.21 (2H, m), 1.23-1.49 (4H, m), 0.71-0.81 (1H, m), 0.03-0.12 (1H, m).

Cap 5.1 & Cap 5.2

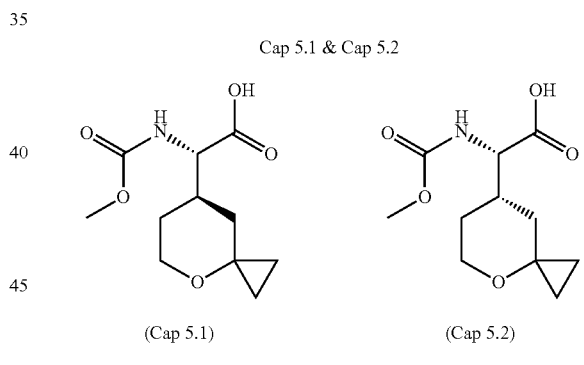

(Cap 5.1)    (Cap 5.2)

Cap 5, step a

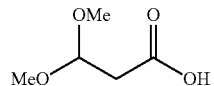

A mixture of methyl 3,3-dimethoxypropanoate (10 g, 68 mmol) and LiOH (8.08 g, 337 mmol) in MeOH (40 mL), THF (40 mL) and water (40 mL) was heated at 80° C. for 2 h. The mixture was then cooled down to room temperature and acidified with 1 N HCl aqueous solution (pH>3). The mixture was then extracted with CH$_2$Cl$_2$ (3×). The combined organic layers were dried with MgSO$_4$ and concentrated to give Cap 5, step a as a clear oil (6.3 g). The product was used in the next reaction without further purification. $^1$H NMR (500 MHz, CDCl$_3$) δ 4.82 (t, J=5.8 Hz, 1H), 3.36 (s, 6H), 2.69 (d, J=5.8 Hz, 2H); $^{13}$C NMR (125 MHz, CDCl$_3$) δ 175.22, 101.09, 53.68, 38.76.

Cap 5, step b

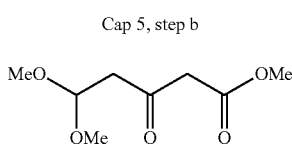 [SMILES: COC(=O)CC(=O)CC(OC)OC]

To a solution of Cap 5, step a (4.55 g, 33.9 mmol) in THF (40 mL) was added the suspension of N,N'-carbonyldiimidazole (6.60 g, 40.7 mmol) in THF (40 mL) dropwise. The solution turned yellow and gas evolution was observed. The mixture was stirred at room temperature for 2 h. At the same time, another flask with monomethyl monopotassium malonate (7.95 g, 50.9 mmol) and magnesium chloride (3.55 g, 37.3 mmol) in THF (80 mL) was stirred at room temperature for 2 h. The imidazolide solution was then transferred into the Mg(OOCCH$_2$COOMe)$_2$ solution by syringe and the resulting mixture was stirred at room temperature for 16 h. The mixture was then acidified with 2M NaHSO$_4$ (60 mL) and extracted with EtOAc (3×). The combined organic layers were washed with sat. NaHCO$_3$ aqueous solution, brine, dried with MgSO$_4$ and concentrated to give Cap 5, step b as a light purple colored oil (4.9 g). The oil was used in the next step without further purification. $^1$H NMR (500 MHz, CDCl$_3$) δ 4.75 (t, J=5.5 Hz, 1H), 3.72 (s, 3H), 3.50 (s, 2H), 3.35 (s, 6H), 2.84 (d, J=5.5 Hz, 2H).

Cap 5, step c

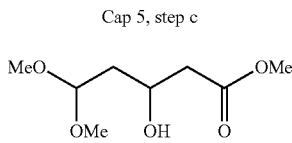 [SMILES: COC(=O)CC(O)CC(OC)OC]

To a solution of Cap 5, step b (4.9 g, 26 mmol) in MeOH (70 mL) was slowly added sodium borohydride (1.07 g, 28.3 mmol). The resulting mixture was stirred at room temperature for 3 h and then quenched with 1N HCl (15 mL). The mixture was extracted with EtOAc (3×). The combined organic layers were dried with MgSO$_4$ and concentrated to give Cap 5, step c as a light yellow oil (4.4 g). The product was used in the next step without further purification. $^1$H NMR (400 MHz, CDCl$_3$) δ 4.60 (t, J=5.5 Hz, 1H), 4.25-4.16 (m, 1H), 3.70 (s, 3H), 3.38 (s, 3H), 3.37 (s, 3H), 2.52-2.48 (m, 2H), 1.83-1.77 (m, 2H); $^{13}$C NMR (100 MHz, CDCl$_3$) δ 172.21, 102.73, 64.61, 53.22, 52.95, 51.30, 41.00, 38.65.

Cap 5, step d

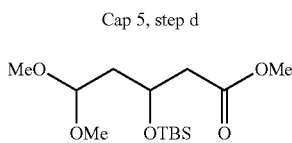

To a solution of Cap 5, step c (4.4 g, 22.89 mmol) in DMF (50 mL) was added imidazole (3.12 g, 45.8 mmol) and TBS-Cl (5.52 g, 36.6 mmol). The resulting mixture was stirred at room temperature for 3 days. The reaction was then diluted with CH$_2$Cl$_2$ and washed with water. The organic phase was washed with brine, dried with MgSO$_4$ and concentrated. The crude product was purified by flash chromatography (silica gel, 0-15% EtOAc/Hex) to give Cap 5, step d as a clear oil (5.0 g). $^1$H NMR (400 MHz, CDCl$_3$) δ 4.55-4.50 (m, 1H), 4.30-4.21 (m, 1H), 3.67 (s, 3H), 3.32 (s, 3H), 3.31 (s, 3H), 2.51 (d, J=6.3 Hz, 2H), 1.89-1.77 (m, 2H), 0.88 (s, 9H), 0.08 (s, 3H), 0.06 (s, 3H); $^{13}$C NMR (100 MHz, CDCl$_3$) δ 171.41, 101.24, 65.85, 52.35, 52.09, 51.04, 42.40, 39.92, 25.37, 25.27, 17.55, −3.95, −5.15.

Cap 5, step e

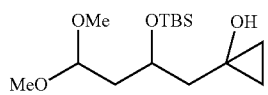

To a solution of Cap 5, step d (5.0 g, 16 mmol) in ether (50 mL) in a ice/water bath was added a solution of tetraisopropyl titanate (0.971 mL, 3.26 mmol) in ether (10 mL). Ethylmagnesium bromide (48.9 mL, 48.9 mmol) (1 M in THF) was then added dropwise by a syringe pump over 1 h. The mixture was then stirred in ice/water bath for 2 h. The mixture was diluted with ether and quenched with sat. NH$_4$Cl aqueous solution slowly. The resulting white precipitate was filtered off. The filtrate was extracted with Et$_2$O (3×). The combined organic layers were dried with MgSO$_4$ and concentrated. The crude product was then purified by flash chromatography (silica gel, 0-20% EtOAc/Hex) to give Cap 5, step e as a clear oil (4.02 g). $^1$H NMR (500 MHz, CDCl$_3$) δ 4.47 (t, J=5.6 Hz, 1H), 4.21-4.14 (m, 1H), 3.71 (s, 1H), 3.32 (s, 3H), 3.31 (s, 3H), 2.05-1.88 (m, 3H), 1.66-1.58 (m, 1H), 0.90 (s, 9H), 0.83-0.76 (m, 1H), 0.71-0.65 (m, 1H), 0.47 (m, 1H), 0.40-0.34 (m, 1H), 0.14 (s, 3H), 0.11 (s, 3H); $^{13}$C NMR (100 MHz, CDCl$_3$) δ 102.09, 69.97, 54.44, 52.97, 52.84, 43.27, 40.00, 25.92, 17.96, 14.04, 12.06, −4.32, −4.61.

Cap 5, step f

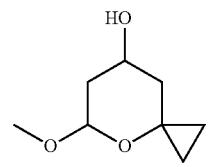

A solution of Cap 5, step e (4.02 g, 13.2 mmol) and p-toluenesulfonic acid monohydrate (3.01 g, 15.8 mmol) in MeOH (120 mL) was stirred at room temperature overnight. To the mixture was added aq. sat. NaHCO$_3$ (100 mL) and the mixture was extracted with CH$_2$Cl$_2$ (3×). The combined organic layers were dried with MgSO$_4$ and concentrated. The crude product was purified by passing it through a silica gel bed with 70% EtOAc/Hex to give Cap 5, step f as as a mixture of diastereomers (1.7 g; clear oil) and. $^1$H NMR (500 MHz, CDCl$_3$) δ 4.79 (t, J=3.7 Hz, 1H), 4.59 (dd, J=5.3, 2.9 Hz, 1H), 4.30-4.22 (m, 1H), 4.03 (br. s., 1H), 3.37 (s, 3H), 3.31 (s, 3H), 2.09-2.03 (m, 1H), 2.00 (dtd, J=13.1, 4.0, 1.5 Hz, 1H), 1.86 (dd, J=13.1, 3.7 Hz, 1H), 1.81-1.61 (m, 7H), 0.94-0.87 (m, 1H), 0.83-0.77 (m, 1H), 0.74-0.69 (m, 1H), 0.65-0.56 (m, 2H), 0.48-0.40 (m, 2H), 0.37-0.30 (m, 1H); $^{13}$C NMR (100 MHz, CDCl$_3$) δ 100.86, 100.27, 65.75, 64.35, 56.24, 55.92, 53.80, 52.35, 40.86, 39.92, 39.28, 38.05, 12.10, 12.06, 9.91, 9.37.

Cap 5, step g

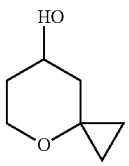

To a solution of Cap 5, step f (1.7 g, 11 mmol) in CH$_2$Cl$_2$ (20 mL) was added bis(trimethylsilyl)trifluoroacetamide (2.14 mL, 8.06 mmol). The mixture was stirred at room temperature for 2 h. The mixture was then cooled to −10° C. and triethylsilane (6.87 mL, 43.0 mmol) and then boron trifluoride ether complex (3.40 mL, 26.9 mmol) were added dropwise. The mixture was then allowed to warm to 0° C. slowly and stirred at 0° C. for 30 min. The reaction was then quenched with water and extracted with EtOAc (3×). The combined organic layers were dried with MgSO$_4$ and concentrated. The crude product was purified by passing it through a silica gel bed with 70% EtOAc/Hex give Cap 5, step g as a clear oil (1.5 g). $^1$H NMR (500 MHz, CDCl$_3$) δ 6.43 (br. s., 1H), 3.96 (tt, J=9.5, 4.7 Hz, 1H), 3.86 (dt, J=11.5, 4.0 Hz, 1H), 3.51 (td, J=11.1, 2.7 Hz, 1H), 1.98-1.84 (m, 2H), 1.66-1.50 (m, 2H), 0.86-0.79 (m, 1H), 0.66-0.59 (m, 1H), 0.53-0.46 (m, 1H), 0.34 (m, 1H); $^{13}$C NMR (100 MHz, CDCl$_3$) δ 67.41, 64.37, 57.99, 41.28, 35.22, 11.74, 11.32.

Cap 5, step h

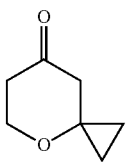

To a solution of oxalyl chloride (1.090 mL, 12.45 mmol) in CH$_2$Cl$_2$ (30 mL) at −78° C. was added dropwise a solution of DMSO (1.767 mL, 24.90 mmol) in CH$_2$Cl$_2$ (20 mL). The mixture was stirred for 20 min, and Cap 5, step g (1.33 g, 10.4 mmol) in CH$_2$Cl$_2$ (20 mL) was added dropwise. The mixture was stirred at −78° C. for 20 min. Et$_3$N (7.52 mL, 54.0 mmol) was then added and the mixture was warmed slowly to room temperature over 30 min. The mixture was then quenched with water and extracted with CH$_2$Cl$_2$ (3×). The organic layers were combined and dried with MgSO$_4$ and concentrated to give Cap 5, step h as a clear oil (1.3 g). The crude product was used in the next step without purification. $^1$H NMR (500 MHz, CDCl$_3$) δ 3.95 (t, J=6.0 Hz, 2H), 2.55-2.50 (m, 2H), 2.46 (s, 2H), 0.84 (m, 2H), 0.50 (m, 2H).

Cap 5, step i

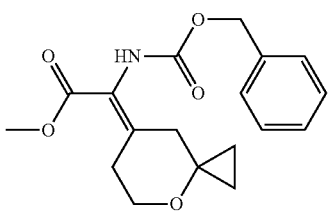

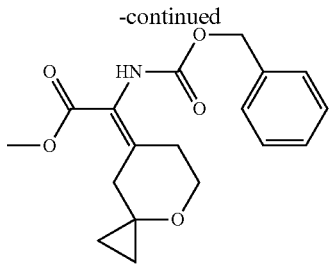

To a solution of methyl 2-(((benzyloxy)carbonyl)amino)-2-(dimethoxyphosphoryl)acetate (3.41 g, 10.3 mmol) in of THF (20 mL) at −20° C. was added 1,1,3,3-tetramethylguanidine (2.85 mL, 22.7 mmol). The resulting mixture was stirred at −20° C. for 1 h. Cap 5, step h (1.3 g, 10.30 mmol) in THF (10 mL) was then added. The resulting brown mixture was stirred at room temperature for 6 days. The reaction was then concentrated and the crude product was purified by flash chromatography (silica gel, 0-25% EtOAc/Hex) to give Cap 5, step i (mixture of isomers) as a white solid (850 mg. LC (Cond. 2): RT=1.88 min; LC/MS: Anal. Calcd. for [M+H]$^+$ C$_{18}$H$_{22}$NO$_5$ 332.15. found 332.14; $^1$H NMR (500 MHz, CDCl$_3$) δ 7.45-7.29 (m, 5H), 6.09-5.81 (m, 1H), 5.18-5.08 (m, 2H), 3.88-3.49 (m, 5H), 3.06-2.82 (m, 2H), 2.52-2.36 (m, 2H), 0.82-0.64 (m, 2H), 0.58-0.32 (m, 2H).

Cap 5.1 and Cap 5.2, step j

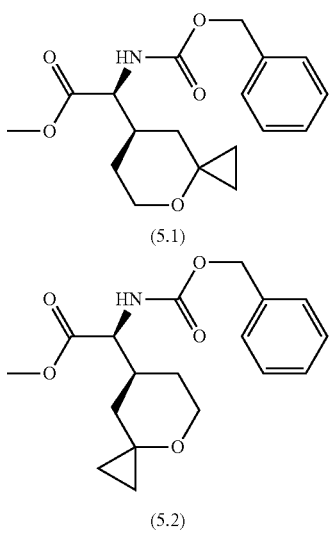

A solution of Cap 5, step i (mixture of isomers) (730 mg, 2.20 mmol) in MeOH (5 mL) in a 500 mL hydrogenation pressure bottle was bubbled with N$_2$ for 30 min. To the mixture was added (−)-1,2-bis((2S,5S)-2,5-dimethylphospholano)ethane(cyclooctadiene) rhodium (I) tetrafluoroborate (24.5 mg, 0.044 mmol) and the bottle was then put onto a Parr shaker and hydrogenated at 60 psi for 3 days. The mixture was concentrated and the crude product was separated by chiral HPLC (Chiralpak AD column, 21×250 mm, 10 um, eluting with 85% 0.1% diethylamine/Heptane-15% EtOH at 15 mL/min) to give Cap 5.1, step j (220 mg) (first eluting fraction) and Cap 5.2, step j (290 mg) (second eluting fraction) as clear oils. The absolute stereochemistry of the isomers was not determined.

Cap 5.1, step j: LC (Cond. 2): RT=1.89 min; LC/MS: Anal. Calcd. for [M+Na]⁺ C$_{18}$H$_{23}$NNaO$_5$ 356.15. found 356.16; ¹H NMR (500 MHz, CDCl$_3$) δ 7.41-7.28 (m, 5H), 5.34 (d, J=8.9 Hz, 1H), 5.10 (s, 2H), 4.37 (dd, J=9.0, 5.0 Hz, 1H), 3.89-3.82 (m, 1H), 3.75 (s, 3H), 3.48 (td, J=11.1, 3.1 Hz, 1H), 2.29-2.17 (m, 1H), 1.96 (t, J=12.7 Hz, 1H), 1.57-1.43 (m, 2H), 1.07-0.98 (m, 1H), 0.87-0.78 (m, 1H), 0.66-0.56 (m, 1H), 0.56-0.47 (m, 1H), 0.37-0.27 (m, 1H);

Cap 5.2, step j: LC (Cond. 2): RT=1.90 min; LC/MS: Anal. Calcd. for [M+Na]⁺ C$_{18}$H$_{23}$NNaO$_5$ 356.15. found 356.17; ¹H NMR (500 MHz, CDCl$_3$) δ 7.40-7.28 (m, 5H), 5.33 (d, J=8.5 Hz, 1H), 5.10 (s, 2H), 4.36 (dd, J=8.9, 5.8 Hz, 1H), 3.86 (dd, J=11.0, 3.1 Hz, 1H), 3.74 (s, 3H), 3.53-3.43 (m, 1H), 2.25-2.14 (m, 1H), 1.94 (t, J=12.5 Hz, 1H), 1.67-1.44 (m, 2H), 0.97-0.90 (m, 1H), 0.86-0.79 (m, 1H), 0.66-0.57 (m, 1H), 0.53-0.44 (m, 1H), 0.33-0.24 (m, 1H). [Note: see below for absolute stereochemical assignment]

Cap 5.1, step k

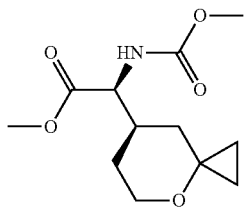

To a solution of Cap 5.1, step j (210 mg, 0.630 mmol) in MeOH (10 mL) in a hydrogenation flask was added dimethyl dicarbonate (0.135 mL, 1.26 mmol) and 10% Pd/C (33.5 mg, 0.031 mmol). The flask was put on a Parr shaker and the mixture was hydrogenated at 50 psi for 4 h. The mixture was then filtered through diatomaceous earth (Celite®) and the filtrate was concentrated to afford Cap 5.1, step k as a clear oil (165 mg). LC (Cond. 2): RT=1.56 min; LC/MS: Anal. Calcd. for [M+H]⁺ C$_{12}$H$_{20}$NO$_5$ 258.13. found 258.16; ¹H NMR (500 MHz, CDCl$_3$) δ 5.39 (d, J=8.5 Hz, 1H), 4.30 (dd, J=8.9, 5.2 Hz, 1H), 3.84-3.78 (m, 1H), 3.70 (s, 3H), 3.63 (s, 3H), 3.47-3.39 (m, 1H), 2.23-2.12 (m, 1H), 1.91 (t, J=12.5 Hz, 1H), 1.49-1.39 (m, 2H), 0.97 (dd, J=13.1, 2.4 Hz, 1H), 0.81-0.74 (m, 1H), 0.61-0.52 (m, 1H), 0.46 (dt, J=10.1, 6.0 Hz, 1H), 0.32-0.24 (m, 1H).

Cap 5.1

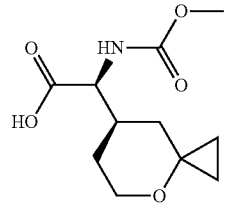

To a mixture of Cap 5.1, step k (165 mg, 0.641 mmol) in THF (2 mL) and water (1 mL) was added 2 M LiOH (1 mL, 2.0 mmol) (aqueous). The resulting mixture was stirred at room temperature overnight. The mixture was then washed with ether (1 mL). The aqueous phase was acidified with 1 N HCl aq. and extracted with ether (6×). The combined organic layers were dried with MgSO$_4$ and concentrated to give Cap 5.1 as a white solid (150 mg). LC (Cond. 2): RT=1.10 min; LC/MS: Anal. Calcd. for [M+H]⁺ C$_{11}$H$_{18}$NO$_5$ 244.12. found 244.09; ¹H NMR (500 MHz, CDCl$_3$-d) δ 5.27 (d, J=8.9 Hz, 1H), 4.39 (dd, J=8.5, 4.9 Hz, 1H), 3.94-3.86 (m, 1H), 3.70 (s, 3H), 3.56-3.46 (m, 1H), 2.36-2.24 (m, 1H), 2.01 (t, J=12.7 Hz, 1H), 1.63-1.48 (m, 2H), 1.14-1.05 (m, 1H), 0.92-0.80 (m, 1H), 0.69-0.60 (m, 1H), 0.58-0.49 (m, 1H), 0.40-0.31 (m, 1H).

Note: Cap 5.1 was coupled to (S)-1-(naphthalen-2-yl) ethanamine via a HATU coupling and the resulting amide was crystallized. X-ray crystal analysis of this analog established the relative and absolute stereochemistry of Cap 5.1 to be as shown.

Cap 5.2

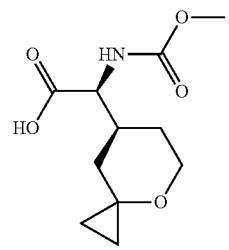

Cap 5.2 was prepared from Cap 5.2, step j according to the procedure described for Cap 5.1. LC (Cond. 2): RT=1.12 min; LC/MS: Anal. Calcd. for [M+H]⁺ C$_{11}$H$_{18}$NO$_5$ 244.12. found 244.09; ¹H NMR (500 MHz, CDCl$_3$) δ 5.27 (d, J=8.9 Hz, 1H), 4.38 (dd, J=8.2, 4.9 Hz, 1H), 3.91 (dd, J=11.1, 3.2 Hz, 1H), 3.69 (s, 3H), 3.52 (t, J=11.0 Hz, 1H), 2.34-2.23 (m, 1H), 2.07-1.97 (m, 1H), 1.72-1.61 (m, 1H), 1.54 (qd, J=12.6, 4.7 Hz, 1H), 1.04-0.96 (m, 1H), 0.90-0.82 (m, 1H), 0.68-0.61 (m, 1H), 0.56-0.49 (m, 1H), 0.39-0.30 (m, 1H).

Cap-6

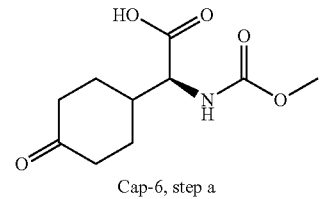

Cap-6, step a

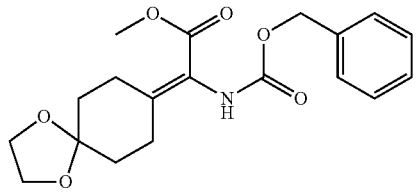

A solution of 1,4-dioxaspiro[4.5]decan-8-one (15 g, 96 mmol) in EtOAc (150 mL) was added to a solution of methyl 2-(benzyloxycarbonylamino)-2-(dimethoxyphosphoryl)acetate (21.21 g, 64.0 mmol) in 1,1,3,3-tetramethylguanidine (10.45 mL, 83 mmol) and EtOAc (150 mL). The resulting solution was the stirred at ambient temperature for 72 h and then it was diluted with EtOAc (25 mL). The organic layer was washed with 1N HCl (75 mL), H$_2$O (100 mL) and brine (100 mL), dried (MgSO$_4$), filtered and concentrated. The residue was purified via Biotage (5% to 25% EtOAc/Hexanes; 300 g column). The combined fractions containing the product were then concentrated under vacuum and the residue was re-crystallized from hexanes/EtOAc to give white crystals that corresponded to methyl 2-(benzyloxycarbonylamino)-2-(1,4-dioxaspiro[4.5]decan-8-ylidene)acetate (6.2 g) $^1$H NMR (400 MHz, CDCl$_3$-d) δ ppm 7.30-7.44 (5H, m), 6.02 (1H, br. s.), 5.15 (2H, s), 3.97 (4H, s), 3.76 (3H, br. s.), 2.84-2.92 (2H, m), 2.47 (2H, t, J=6.40 Hz), 1.74-1.83 (4H, m). LC (Cond. OL1): R$_f$=2.89 min. LC/MS: Anal. Calcd. For [M+Na]$^+$ C$_{19}$H$_{23}$NNaO$_6$: 745.21. found: 745.47.

Cap-6, step b

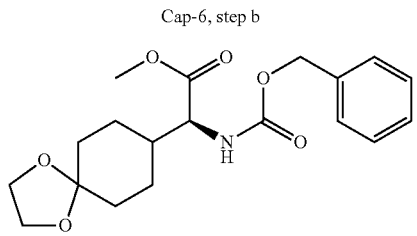 [SMILES: COC(=O)[C@@H](NC(=O)OCc1ccccc1)C1CCC2(CC1)OCCO2]

Ester Cap-176, step b was prepared from alkene Cap-176, step a according to the method of Burk, M. J.; Gross, M. F. and Martinez J. P. (*J. Am. Chem. Soc.,* 1995, 117, 9375-9376 and references therein): A 500 mL high-pressure bottle was charged with alkene Cap-176, step a (3.5 g, 9.68 mmol) in degassed MeOH (200 mL) under a blanket of N$_2$. The solution was then charged with (−)-1,2-Bis((2S,5S)-2,5-dimethylphospholano)ethane(cyclooctadiene)rhodium (I) tetrafluoroborate (0.108 g, 0.194 mmol) and the resulting mixture was flushed with N$_2$ (3×) and charged with H$_2$ (3×). The solution was shaken vigorously under 70 psi of H$_2$ at ambient temperature for 72 h. The solvent was removed under reduced pressure and the remaining residue was taken up in EtOAc. The brownish solution was then filtered through a plug of Silica Gel and eluted with EtOAc. The solvent was concentrated under vacuum to afford a clear oil corresponding to ester Cap-176, step b (3.4 g). $^1$H NMR (500 MHz, CDCl$_3$-d) δ ppm 7.28-7.43 (5H, m), 5.32 (1H, d, J=9.16 Hz), 5.06-5.16 (2H, m), 4.37 (1H, dd, J=9.00, 5.04 Hz), 3.92 (4H, t, J=3.05 Hz), 3.75 (3H, s), 1.64-1.92 (4H, m), 1.37-1.60 (5H, m). LC (Cond. OL1): R$_f$=1.95 min. LC/MS: Anal. Calcd. For [M+H]$^+$ C$_{19}$H$_{26}$NO$_6$: 364.18. found: 364.27.

Cap-6, step c

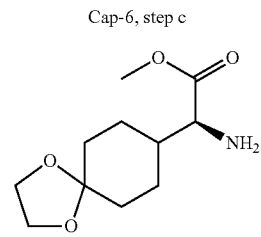 [SMILES: COC(=O)[C@@H](N)C1CCC2(CC1)OCCO2]

Cap-6, step b (6.68 g, 18.38 mmol) was dissolved in MeOH (150 mL) and charged with Pd/C (0.039 g, 0.368 mmol) and the suspension was placed under 1 atm of H$_2$. The reaction mixture was stirred at rt for 6 h and filtered though a plug of diatomaceous earth (Celite®) and volatiles were removed under reduced pressure. An amber oil corresponding to Cap-6, step c (3.8 g, 16.57 mmol, 90% yield) was recovered and used without further purification. $^1$H NMR (400 MHz, CDCl$_3$-d) δ 3.92 (br. s., 4H), 3.71 (s, 3H), 3.31 (d, J=4.0 Hz, 1H), 1.87-1.44 (m, 9H). $^{13}$C NMR (101 MHz, CDCl$_3$-d) δ 176.1, 108.7, 64.5 (2C), 59.1, 52.0, 41.1, 34.7, 34.6, 27.2, 25.4.

Cap-6, step d

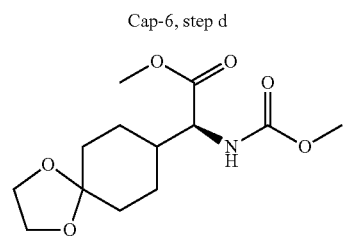 [SMILES: COC(=O)N[C@H](C(=O)OC)C1CCC2(CC1)OCCO2]

Methyl chloroformate (2.57 mL, 33.1 mmol) was added to a solution of Cap 6, step c (3.8 g, 16.57 mmol) and DIEA (23.16 mL, 133 mmol) in CH$_2$Cl$_2$ (200 mL). The resulting solution was stirred at rt for 3 h and volatiles were removed under reduced pressure. The residue was purified via Biotage (30% EtOAc/Hex; 160 g column). An amber oil corresponding to Cap-6, step d (3 g, 10.44 mmol, 63.0% yield) was recovered. $^1$H NMR (500 MHz, CDCl$_3$-d) δ 5.24 (d, J=8.5 Hz, 1H), 4.34 (dd, J=8.9, 4.9 Hz, 1H), 3.92 (s, 4H), 3.74 (s, 3H), 3.67 (s, 3H), 1.89-1.73 (m, 3H), 1.67 (d, J=12.5 Hz, 1H), 1.62-1.33 (m, 5H). $^{13}$C NMR (126 MHz, CDCl$_3$-d) 172.4, 156.7, 108.1, 64.2, 64.2, 57.7, 52.3, 52.2, 39.6, 34.2 (2C), 26.5, 25.0.

Cap-6, step e

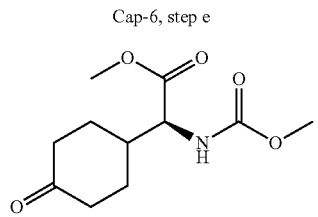 [SMILES: COC(=O)N[C@H](C(=O)OC)C1CCC(=O)CC1]

Cap-6, step d (1.15 g, 4.00 mmol) was dissolved in THF (50 mL) followed by sequential addition of water (30 mL), glacial AcOH (8.02 mL, 140 mmol) and dichloroacetic acid (1.985 mL, 24.02 mmol). The mixture was stirred overnight at room temperature and the reaction was quenched by slow addition of solid sodium carbonate with vigorous stirring until the release of gas was no longer visible. Crude product was extracted into 10% ethyl acetate-dichloromethane and the organic layers were combined, dried (MgSO$_4$), filtered and concentrated. The residue was purified via Biotage (0 to 30% EtOAc/Hex; 40 g column) and a clear oil corresponding to Cap-6, step e (0.72 g, 2.96 mmol, 73.9% yield) was recovered. $^1$H NMR (500 MHz, CDCl$_3$-d) δ 5.36 (d, J=8.2 Hz, 1H), 4.46 (dd, J=8.4, 5.0 Hz, 1H), 3.77 (s, 3H), 3.68 (s, 3H), 2.46-2.39 (m, 2H), 2.38-2.29 (m, 2H), 2.09-2.03 (m, 1H), 1.96-1.88 (m, 1H), 1.64-1.51 (m, 2H). $^{13}$C NMR (126 MHz, CDCl$_3$-d) δ 210.1, 171.9, 156.7, 57.2, 52.5 (2C), 40.2, 40.2, 39.4, 28.7, 27.6.

Cap-6

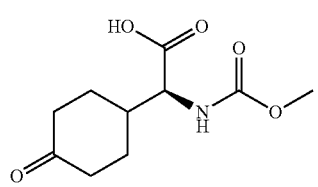

A solution of Cap-6, step e (0.68 g, 2.80 mmol) in THF (7.5 mL) and MeOH (7.50 mL) was cooled to 0° C. 2N aq. NaOH (1.9 mL, 3.80 mmol) was added dropwise and the resulting solution was stirred at room temperature for 2 h. A 1:1 mixture of hexanes:Et$_2$O (20 mL) was added and the organic layer was discarded. The aqueous layer was then acidified to pH~1 with 10% aq. KHSO$_4$ and the mixture was extracted with EtOAc (2×). The combined organic layers were dried (MgSO$_4$), filtered and concentrated. A white foam corresponding to Cap-6 (0.55 g)) was recovered and used without further purification. $^1$H NMR (500 MHz, DMSO-d$_6$) δ 12.70 (br. s., 1H), 7.49 (d, J=8.5 Hz, 1H), 4.01 (dd, J=8.2, 6.7 Hz, 1H), 3.54 (s, 3H), 2.45-2.30 (m, 2H), 2.23-2.13 (m, 3H), 1.94-1.79 (m, 3H), 1.57 (qd, J=12.7, 4.1 Hz, 1H), 1.47 (qd, J=12.7, 4.4 Hz, 1H). $^{13}$C NMR (126 MHz, DMSO-d$_6$) δ 210.2, 173.0, 156.8, 57.6, 51.5, 39.7 (2C), 36.9, 28.6, 27.5.

Cap-7

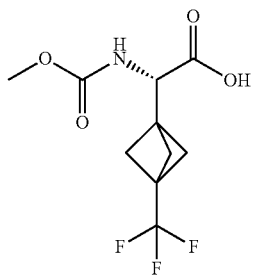

To a mixture of (S)-2-amino-2-(3-(trifluoromethyl)bicyclo[1.1.1]pentan-1-yl)acetic acid (obtained from a commercial source; 0.5151 g, 2.463 mmol) and sodium carbonate (0.131 g, 1.231 mmol) in sodium hydroxide, 1M aq (2.4 ml, 2.400 to mmol) at 0° C. was added methyl carbonochloridate (0.2 ml, 2.59 mmol) dropwise. The reaction was then stirred at room temperature for 4 hr. It was then cooled in an ice/water bath, and diethyl ether (25 mL) was added and stirred and the layers were separated. The aqueous layer was washed with diethyl ether (2×25 mL). The aqueous layer was cooled with an ice-water bath and acidified with 12N HCl to a pH region of 1-2. It was extracted with CH$_2$Cl$_2$ (3×50 mL), dried over MgSO$_4$, and concentrated in vacuo to afford Cap-7 as an off-white solid (480.7 mg) and was used without further purification. $^1$H NMR (400 MHz, DMSO-d$_6$) δ12.86 (br s, 1H), 7.61 (br d, J=8.0 Hz, 1H), 4.16 (d, J=8.0 Hz, 1H), 3.57 (s, 3H), 2.00 (d, J=8.3 Hz, 3H), 1.93 (d, J=9.3, 3H).

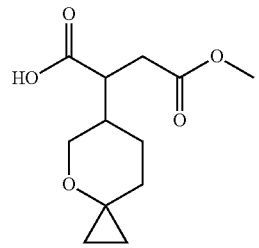

Cap 8.1 & Cap 8.2 (two stereoisomers)

Cap 8, step a

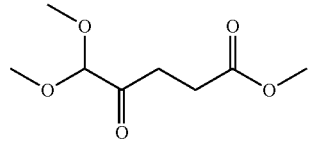

A mixture of 4-oxovaleric acid methyl ester (6 g, 46.1 mmol), diphenyl diselenide (14.39 g, 46.1 mmol) and ammonium persulfate (15.92 mL, 138 mmol) in MeOH (200 mL) was stirred at reflux temperature for 3 h. The mixture was then poured into water and extracted with CH$_2$Cl$_2$ (3×75 mL). The combined organic layers were washed with brine, dried with MgSO$_4$ and concentrated. The crude product was purified by flash chromatography (silica gel, 0-15% EtOAc/Hex) to give Cap 8, step a (7.1 g) as a yellow oil. $^1$H NMR (500 MHz, CDCl$_3$) δ 4.53 (s, 1H), 3.67 (s, 3H), 3.42 (s, 6H), 2.89 (t, J=6.6 Hz, 2H), 2.60 (t, J=6.6 Hz, 2H).

Cap-8, step b

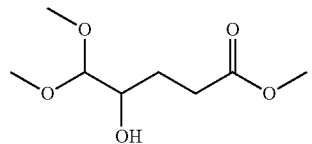

To a solution of Cap 8, step a (7.1 g, 37.3 mmol) in MeOH (100 mL) was slowly added sodium borohydride (1.554 g, 41.1 mmol). The resulting mixture was stirred at room temperature for 2 h. To the mixture was added a 1 N HCl aqueous solution until acidic and then extracted with CH$_2$Cl$_2$ (3×50 mL). The combined organic layers were washed with brine, dried with MgSO$_4$ and concentrated to give Cap 8, step b as an orange oil (7.1 g) which was contaminated in a 1:1.7 ratio with the corresponding cyclized byproduct, 5-(dimethoxymethyl)dihydrofuran-2(3H)-one. The mixture was used without further purification.

Cap-8, step c

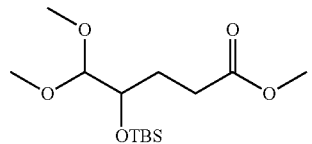

To a solution of Cap 8, step b (7.1 g, 36.9 mmol) in DMF (50 mL) was added imidazole (5.03 g, 73.9 mmol) and TBS-Cl (8.91 g, 59.1 mmol). The resulting mixture was stirred at room temperature for 16 h. The reaction was then diluted with CH$_2$Cl$_2$, washed with water and brine, dried with MgSO$_4$ and concentrated. The crude product was purified by flash chromatography (silica gel, 0-5% then 10% EtOAc/Hex) to give Cap 8, step c as a clear oil. $^1$H NMR (500 MHz, CDCl$_3$) δ 4.07 (d, J=5.5 Hz, 1H), 3.72-3.67 (m, 1H), 3.66 (s, 3H), 3.40 (s, 3H), 3.39 (s, 3H), 2.48-2.35 (m, 2H), 1.92 (dddd, J=13.8, 9.3, 6.9, 4.1 Hz, 1H), 1.82-1.71 (m, 1H), 0.88 (s, 9H), 0.07 (s, 3H), 0.05 (s, 3H).

Cap-8, step d

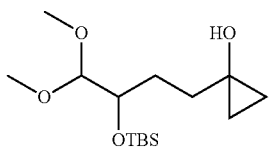

To a solution of Cap 8, step c (4.4 g, 14.36 mmol) in Et$_2$O (50 mL) in a water bath was added tetraisopropyl titanate (0.855 mL, 2.87 mmol) in ether (10 mL) and the solution turned yellow. Ethylmagnesium bromide (14.36 mL, 43.1 mmol, 1 M in THF) was then added dropwise by syringe pump over 1 h. The solution turned dark brown with some precipitate. The mixture was then stirred in a water bath for 2 h. The mixture was diluted with ether and quenched by slow addition of a saturated NH$_4$Cl aqueous solution. The mixture was filtered to remove the formed white precipitate. The two layers were separated and the aqueous layer was extracted with Et$_2$O (3×50 mL). The combined organic layers were dried with MgSO$_4$ and concentrated. The crude product was then purified by flash chromatography (silica gel, 0-20% EtOAc/Hex) to give Cap 8, step d as a clear oil (2.9 g). $^1$H NMR (500 MHz, CDCl$_3$) δ 4.26 (d, J=6.1 Hz, 1H), 3.81-3.72 (m, 1H), 3.46 (s, 3H), 3.43 (s, 3H), 1.90-1.75 (m, 3H), 1.52-1.43 (m, 1H), 0.90 (s, 9H), 0.82-0.74 (m, 1H), 0.73-0.67 (m, 1H), 0.47-0.40 (m, 2H), 0.11-0.10 (m, 6H).

Cap-8, step e

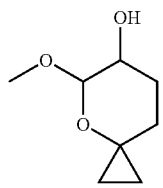

A solution of Cap 8, step d (2.9 g, 9.52 mmol) and p-TsOH.H$_2$O (2.174 g, 11.43 mmol) in MeOH (40 mL) was stirred at room temperature for 16 h. To the mixture was added 200 mL of a sat. NaHCO$_3$ solution and the mixture was extracted with CH$_2$Cl$_2$ (3×50 mL). The combined organic layers were dried with MgSO$_4$ and concentrated. The crude product was filtered through a plug of silica gel (eluted with 70% EtOAc/Hex) to give Cap 8, step e (1 g) as a clear oil which consisted of a mixture of diastereomers and were not separated. $^1$H NMR (500 MHz, CDCl$_3$) δ 4.16 (d, J=7.3 Hz, 1H), 3.55-3.46 (m, 1H), 3.44-3.38 (m, 2H), 2.50-2.22 (m, 1H), 2.13-2.00 (m, 1H), 1.71-1.59 (m, 1H), 1.22-1.14 (m, 1H), 0.99-0.77 (m, 1H), 0.70-0.59 (m, 1H), 0.57-0.46 (m, 1H), 0.45-0.30 (m, 1H).

Cap 8, step f

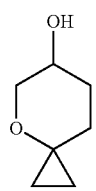

To a solution of Cap 8, step e (1 g, 6.32 mmol) in CH$_2$Cl$_2$ (15 mL) was added bis(trimethylsilyl)trifluoroacetamide (1.26 mL, 4.74 mmol). The mixture was stirred at room temperature for 2 h during which time it turned orange. The mixture was then cooled down to −10° C. and triethylsilane (4.04 mL, 25.3 mmol) was added dropwise, followed by boron trifluoride ether complex (2.00 mL, 15.80 mmol). The mixture turned light purple immediately upon adding the boron trifluoride ether complex. The mixture was then allowed to slowly warm to 0° C. and stirred at 0° C. for 30 mins. The reaction was then quenched with water and extracted with EtOAc (3×20 mL). The combined organic layers were dried with MgSO$_4$ and concentrated. The crude product was filtered through a plug of silica gel (eluted with 70% EtOAc/Hex) and the filtrate was concentrated to give Cap 8, step f (0.8 g) as a clear oil. $^1$H NMR (400 MHz, CDCl$_3$) δ 4.19 (d, J=6.8 Hz, 1H), 3.77 (dd, J=11.3, 2.5 Hz, 1H), 3.55 (d, J=6.0 Hz, 1H), 2.14-2.06 (m, 2H), 1.75-1.62 (m, 1H), 1.44 (dd, J=12.4, 7.2 Hz, 1H), 0.97-0.88 (m, 2H), 0.65 (dddd, J=10.8, 6.2, 4.8, 1.5 Hz, 1H), 0.59-0.51 (m, 1H), 0.48-0.40 (m, 2H).

Cap 8, step g

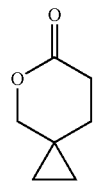

To a solution of oxalyl chloride (0.664 mL, 7.58 mmol) in CH$_2$Cl$_2$ (10 mL) at −78° C. was added dropwise DMSO (1.076 mL, 15.17 mmol) in CH$_2$Cl$_2$ (7 mL). The mixture was stirred for 20 min, and Cap 8, step f (810 mg, 6.32 mmol) in CH$_2$Cl$_2$ (7 mL) was added dropwise. The mixture was stirred at −78° C. for 20 min. Et$_3$N (4.58 mL, 32.9 mmol) was then added and the mixture was slowly warmed to room temperature over 30 min. The mixture was then quenched with water and extracted with CH$_2$Cl$_2$ (3×10 mL). The organic layers were combined and dried with MgSO$_4$ and concentrated to give Cap 8, step g (0.8 g) as a clear oil. The product was used without further purification. $^1$H NMR (500 MHz, CDCl$_3$) δ 4.56 (s, 1H), 4.00 (s, 1H), 2.53-2.46 (m, 1H), 2.40-2.32 (m, 1H), 2.08 (t, J=6.9 Hz, 1H), 1.82 (dt, J=13.5, 5.8 Hz, 1H), 1.09-0.99 (m, 1H), 0.89-0.82 (m, 1H), 0.70 (ddd, J=10.2, 6.9, 5.8 Hz, 1H), 0.54 (ddd, J=10.2, 6.7, 5.6 Hz, 1H).

Cap 8, step h

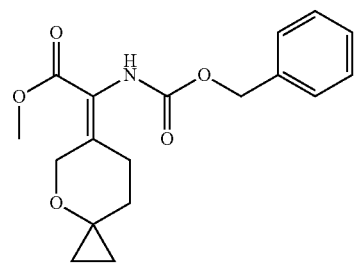

To a solution of methyl 2-(((benzyloxy)carbonyl)amino)-2-(dimethoxyphosphoryl)acetate (3.19 g, 9.63 mmol) in THF (10 mL) at −20° C. was added 1,1,3,3-tetramethylguanidine (2.42 mL, 19.26 mmol). The resulting mixture was stirred at −20° C. for 1 h and the mixture turned milky white. A solution of Cap 8, step g (810 mg, 6.42 mmol) in THF (5 mL) was added and the resulting brown mixture was then stirred at room temperature for two days. The reaction was then concentrated and the crude product was purified by flash chromatography (silica gel, 0-5% EtOAc/CH$_2$Cl$_2$) to give Cap 8, step h (mixture of cis-trans isomers) as a clear oil (400 mg). LC (Cond. 3): RT=1.74 min; LC/MS: Anal. Calcd. for [M+Na]$^+$ C$_{18}$H$_{21}$NNaO$_5$ 354.13. found 354.04. $^1$H NMR (500 MHz, CDCl$_3$) δ 7.42-7.31 (m, 10H), 5.19-5.10 (m, 4H), 4.66 (br. s., 1H), 4.23 (s, 1H), 3.84-3.70 (m, 5H), 3.39 (s, 3H), 2.68-2.53 (m, 2H), 1.81-1.74 (m, 2H), 1.30-1.21 (m, 2H), 0.96-0.80 (m, 4H), 0.76 (dt, J=11.1, 5.7 Hz, 1H), 0.56-0.39 (m, 4H).

Cap 8, step i

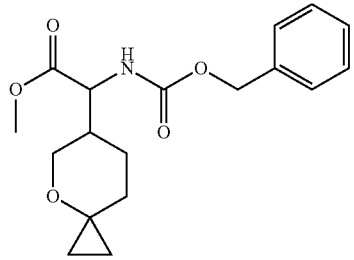

A solution of Cap 8, step h (mixture of isomers) (400 mg, 1.207 mmol) in MeOH (10 mL) in a 500 mL hydrogenation pressure tube was bubbled with N$_2$ for 30 mins. To the mixture was added (−)-1,2-bis((2S,5S)-2,5-dimethylphospholano)ethane(cyclooctadiene)rhodium (I) tetrafluoroborate (13.43 mg, 0.024 mmol) and the mixture was then put on Parr shaker and hydrogenated at 60 psi for 3 days. The mixture was then concentrated. The crude product was then separated by chiral HPLC (Chiralpak OJ column, 21×250 mm, 10 um) eluting with 90% 0.1% diethylamine/Heptane-10% EtOH at 15 mL/min to give Cap 8, step i.1 (55 mg; first eluting fraction) and Cap 8, step i.2 (65 mg; second eluting fraction) as clear oils. The absolute stereochemistry of the isomers was not determined.

Cap 8, step i.1: LC (Cond. 3): RT=1.93 min; LC/MS: Anal. Calcd. for [M+Na]$^+$ C$_{18}$H$_{23}$NNaO$_5$ 356.15. found 356.04; $^1$H NMR (500 MHz, CDCl$_3$) δ 7.45-7.30 (m, 5H), 5.38-5.30 (m, 1H), 5.18-5.06 (m, 2H), 4.41 (dd, J=8.9, 5.8 Hz, 1H), 3.83 (d, J=11.0 Hz, 1H), 3.77 (s, 3H), 3.35 (t, J=10.8 Hz, 1H), 2.21-2.09 (m, 1H), 2.07-1.98 (m, 1H), 1.70 (d, J=11.0 Hz, 2H), 1.54 (qd, J=12.1, 4.1 Hz, 1H), 1.19 (dt, J=13.6, 3.4 Hz, 1H), 0.83 (dt, J=11.1, 5.7 Hz, 1H), 0.63 (dt, J=10.5, 5.1 Hz, 1H), 0.49 (dt, J=10.1, 6.0 Hz, 1H), 0.36-0.29 (m, 1H).

Cap 8, step i.2: LC (Cond. 5): RT=1.55 min; LC/MS: Anal. Calcd. for [M+Na]$^+$ C$_{18}$H$_{23}$NNaO$_5$ 356.15. found 356.06; $^1$H NMR (500 MHz, CDCl$_3$) δ 7.40-7.32 (m, 5H), 5.31 (d, J=8.5 Hz, 1H), 5.12 (s, 2H), 4.39-4.33 (m, 1H), 3.77 (s, 3H), 3.74 (d, J=2.1 Hz, 1H), 3.39 (t, J=10.5 Hz, 1H), 2.07 (d, J=4.0 Hz, 1H), 2.04-1.95 (m, 1H), 1.82 (d, J=10.7 Hz, 1H), 1.34-1.21 (m, 2H), 0.82 (dt, J=11.0, 5.8 Hz, 1H), 0.68-0.61 (m, 1H), 0.49 (dt, J=9.9, 5.9 Hz, 1H), 0.34 (ddd, J=10.1, 6.4, 4.9 Hz, 1H).

Cap 8, step j.1

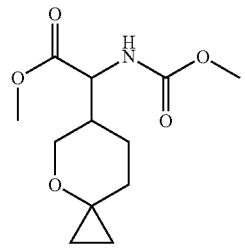

To a solution of Cap 8, step i.1 (55 mg, 0.165 mmol) in 10 mL of MeOH in a hydrogenation flask was added dimethyl dicarbonate (0.035 mL, 0.33 mmol) and Pd/C (8.78 mg, 08.25 μmol). The flask was put on a Parr shaker and the mixture was hydrogenated at 50 psi for 4 h. The mixture was then filtered through diatomaceous earth (Celite®) and the filtrate was concentrated to afford Cap 8, step j.1 as a clear oil (50 mg). LC (Cond. 1): RT=1.09 min; LC/MS: Anal. Calcd. for [M+H]$^+$ C$_{12}$H$_{20}$NO$_5$ 258.13. found 258.05; $^1$H NMR (500 MHz, CDCl$_3$) δ 4.39 (dd, J=8.7, 6.0 Hz, 1H), 3.85-3.80 (m, 1H), 3.79-3.76 (m, 3H), 3.71 (s, 3H), 3.36 (t, J=10.8 Hz, 1H), 2.14 (d, J=4.9 Hz, 1H), 2.03 (t, J=13.0 Hz, 1H), 1.71 (ddd, J=12.7, 3.7, 2.0 Hz, 1H), 1.55 (td, J=12.1, 4.1 Hz, 1H), 1.20 (d, J=13.4 Hz, 1H), 0.83 (dt, J=11.0, 5.8 Hz, 1H), 0.67-0.60 (m, 1H), 0.49 (dt, J=9.9, 6.0 Hz, 1H), 0.37-0.29 (m, 1H). Benzyl carbamate Cap 8, step i.2 was elaborated similarly to its methyl carbamate, Cap 8, step j.2.

Cap 8.1 & Cap 8.2

To a mixture of Cap 8, step j.1 (50 mg, 0.194 mmol) in THF (1 mL) and water (0.5 mL) was added LiOH (0.292 mL, 0.583 mmol) (2 M aqueous). The resulting mixture was stirred at room temperature overnight. The mixture was extracted with Et$_2$O (5 mL). The aqueous phase was acidified with 1 N HCl aq. solution and extracted with Et$_2$O (6×). The combined organic layers were dried with MgSO$_4$ and concentrated to give Cap 8.1 as a white solid (35 mg). LC (Cond. 1): RT=0.95 min; LC/MS: Anal. Calcd. for [M+H]$^+$ C$_{11}$H$_{18}$NO$_5$ 244.12. found 244.02; $^1$H NMR (400 MHz, CDCl$_3$) δ 5.24 (d, J=7.5 Hz, 1H), 4.43 (br. s., 1H), 3.89 (d, J=12.0 Hz, 1H), 3.73 (s, 3H), 3.41 (t, J=10.8 Hz, 1H), 2.22 (d, J=4.3 Hz, 1H), 2.11-2.00 (m, 1H), 1.78 (dt, J=12.6, 1.9 Hz, 1H), 1.65-1.54 (m, 1H), 1.30-1.18 (m, 2H), 0.85 (dt, J=11.1, 5.9 Hz, 1H), 0.70-0.61 (m, 1H), 0.50 (dt, J=10.0, 5.9 Hz, 1H), 0.40-0.31 (m, 1H).

Cap 8.2 was synthesized from Cap 8, step j.2 according to the procedure described for Cap-8.1. LC (Cond. 1): RT=0.96 min; LC/MS: Anal. Calcd. for [M+H]$^+$ C$_{11}$H$_{18}$NO$_5$ 244.12. found 244.02; $^1$H NMR (500 MHz, CDCl$_3$) δ 5.44 (d, J=8.5 Hz, 1H), 4.35 (t, J=7.6 Hz, 1H), 3.81 (d, J=8.9 Hz, 1H), 3.71 (s, 3H), 3.49-3.41 (m, 1H), 2.14 (br. s., 1H), 2.04-1.86 (m, 2H), 1.69-1.55 (m, 1H), 1.34-1.25 (m, 2H), 0.83 (dt, J=11.0, 5.8 Hz, 1H), 0.67 (dt, J=10.5, 5.1 Hz, 1H), 0.54-0.45 (m, 1H), 0.40-0.34 (m, 1H).

Cap 9.1 to Cap 9.4 (four stereoisomers)

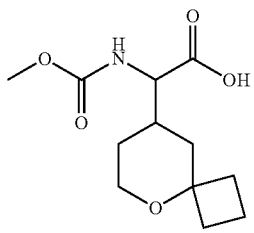

Cap 9, step a

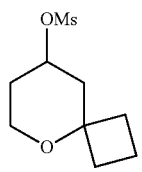

Methanesulfonic acid (3.89 mL, 59.9 mmol) was added to a stirred solution of but-3-en-1-ol (2.06 g, 28.5 mmol) and cyclobutanone (2.00 g, 28.5 mmol) in DCM (20 mL) and the reaction mixture was stirred overnight. The reaction was quenched slowly with sat. NaHCO$_3$ (aq) (until basic), the layers were separated and the aqueous layer extracted with DCM (20 mL). The combined organics were dried (MgSO$_4$) filtered and concentrated to a crude yellow oil. The crude oil was purified with a Biotage Horizon (90 g SiO$_2$, 0-40% EtOAc/hexanes) to yield Cap 9, step a (5.3 g) as an orange oil. $^1$H NMR (400 MHz, CDCl$_3$) δ 4.93-4.81 (m, 1H), 3.84 (dt, J=12.1, 4.1 Hz, 1H), 3.50 (ddd, J=12.1, 10.9, 2.6 Hz, 1H), 3.05 (s, 3H), 2.28 (ddd, J=12.7, 4.4, 1.8 Hz, 1H), 2.22-2.12 (m, 1H), 2.09-1.96 (m, 4H), 1.90-1.64 (m, 4H).

Cap 9, Step b

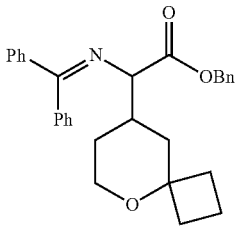

In a 35 mL pressure vessel, benzyl 2-((diphenylmethylene)amino)acetate (972 mg, 2.95 mmol) and Cap 9, step a (500 mg, 2.270 mmol) were dissolved into toluene (10 mL) and THF (2 mL) and the clear colorless solution was stirred under nitrogen for 5 min. Then, 1M LiHMDS/THF (2.95 mL, 2.95 mmol) was added and the vessel was sealed and then heated at 100° C. for 9 h. The reaction was allowed to cool and was poured into ½ sat NH$_4$Cl (aq) (~40 mL) and then extracted with EtOAc (~40 mL). The organic phase was washed with brine (~40 mL), dried (MgSO$_4$), filtered and concentrated. The crude orange oil was purified with a Biotage Horizon (0-30% EtOAc/hex, 40 g SiO$_2$) to yield Cap 9, step b (a mixture of four stereoisomers) (350 mg) as an orange-yellow oil. LC-MS retention time 1.920 min; m/z 454.32 (MH+). LC data was recorded on a Shimadzu LC-10AS liquid chromatograph equipped with a Phenomenex-Luna 3 u C18 2.0×50 mm column using a SPD-10AV UV-Vis detector at a detector wave length of 220 nM. The elution conditions employed a flow rate of 0.8 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% H$_2$O/0.1% trifluoroacetic acid and solvent B was 10% H$_2$O/90% acetonitrile/0.1% trifluoroacetic acid. MS data was determined using a Micromass Platform for LC in electrospray mode.

Cap 9, Step c

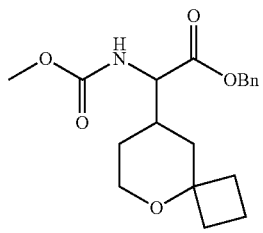

Cap 9, step b (345 mg, 0.761 mmol) in THF (8 mL) was treated with 1.5M HCl (3.04 mL, 4.56 mmol) (aq) and stirred for 1.5 h. The reaction mixture was then concentrated under high vacuum. The residue was dissolved into DCM (4 mL), treated with DIPEA (0.531 mL, 3.04 mmol) and methyl chloroformate (0.088 mL, 1.14 mmol) and stirred at rt over night. The reaction was diluted with water (~10 mL) and DCM (10 mL), separated and the aqueous layer extracted with DCM (10 mL). The combined organic layer was dried (MgSO$_4$), filtered and concentrated. The residue was purified by prep HPLC (water/ACN with TFA buffer) to yield Cap 9, step c (a mixture of four stereoisomers; 108 mg) as an orange glass. LC-MS retention time 2.833 min; m/z 348.3 (MH+). LC data was recorded on a Shimadzu LC-10AS liquid chromatograph equipped with a Phenomenex-Luna 3 u C18 2.0×50 mm column using a SPD-10AV UV-Vis detector at a detector wave length of to 220 nM. The elution conditions employed a flow rate of 0.8 mL/min, a gradient of 100% solvent A/0% solvent B to 0% solvent A/100% solvent B, a gradient time of 4 min, a hold time of 1 min, and an analysis time of 5 min where solvent A was 10% acetonitrile/90% H$_2$O/0.1% trifluoroacetic acid and solvent B was 10% H$_2$O/90% acetonitrile/0.1% trifluoroacetic acid. MS data was determined using a Micromass Platform for LC in electrospray mode.

The mixture of stereoisomers was separated by chiral preparative SFC purification:
Chiralpak AD-H preparative column, 30×250 mm, 5 μm
Mobile Phase: 15% 2:1 heptane:EtOH in CO$_2$ @ 150 bar
Temp: 35° C.
Flow rate: 70.0 mL/min. for 14 min.
UV monitored @ 220 nm
Injection: 0.35 mL of ~27 mg/mL in EtOH (~108 mg total via stacked injection) to yield:

Cap 9, step c.1: First eluting peak: 22.3 mg; $^1$H NMR (400 MHz, CDCl$_3$) δ 7.47-7.32 (m, 5H), 5.37-5.21 (m, 2H), 5.10 (d, J=12.0 Hz, 1H), 4.42 (dd, J=9.0, 4.8 Hz, 1H), 3.79-3.65 (m, 4H), 3.38 (td, J=11.5, 3.3 Hz, 1H), 2.15-2.01 (m, 2H), 1.98-1.65 (m, 4H), 1.56-1.14 (m, 5H).

Cap 9, step c.2: Second eluting peak: 20.6 mg; $^1$H NMR (400 MHz, CDCl$_3$) δ 7.45-7.32 (m, 5H), 5.26 (d, J=9.0 Hz, 1H), 5.20 (s, 2H), 4.37 (dd, J=9.0, 5.0 Hz, 1H), 3.77-3.67 (m, 4H), 3.41-3.29 (m, 1H), 2.16-1.99 (m, 2H), 1.96-1.68 (m, 4H), 1.58-1.19 (m, 5H).

Cap 9, step c.3: Third eluting peak: 25.0 mg; $^1$H NMR (400 MHz, CDCl$_3$) δ 7.44-7.31 (m, 5H), 5.27 (d, J=8.8 Hz, 1H), 5.20 (s, 2H), 4.37 (dd, J=9.0, 5.0 Hz, 1H), 3.77-3.66 (m, 4H), 3.40-3.28 (m, 1H), 2.14-2.00 (m, 2H), 1.97-1.69 (m, 4H), 1.62-1.23 (m, 5H).

Cap 9, step c.4: Fourth eluting peak: 22.4 mg; $^1$H NMR (400 MHz, CDCl$_3$) δ 7.45-7.32 (m, 5H), 5.37-5.21 (m, 2H), 5.10 (d, J=12.0 Hz, 1H), 4.42 (dd, J=9.0, 4.8 Hz, 1H), 3.78-3.66 (m, 4H), 3.38 (td, J=11.5, 3.3 Hz, 1H), 2.06 (q, J=10.1 Hz, 2H), 1.96-1.67 (m, 4H), 1.56-1.14 (m, 5H).

Based on $^1$H NMR analyses, Cap 9, step c.1 and Cap 9, step c.4 are enantiomers as are Cap 9, step c.2 and Cap 9, step c.3. Each single stereoisomer was elaborated independently.

Cap 9.1 to Cap 9.4

Cap 9, step c.1 (22.3 mg, 0.064 mmol) was dissolved in MeOH (3 mL) and added to 10% Pd/C (5.46 mg, 5.14 μmol). The reaction was vacuum flushed with nitrogen (4×) and then with hydrogen (4×) and allowed to stir under a balloon of hydrogen over night. The reaction was treated with diatomaceous earth (Celite®) and then filtered through diatomaceous earth (Celite®) and concentrated to yield Cap 9.1 (16.8 mg) as a colorless glass. LC-MS retention time 1.008 min; m/z 258.2 (MH+). LC data was recorded on a Shimadzu LC-10AS liquid chromatograph equipped with a Phenomenex-Luna 3 u C18 2.0×50 mm column using a SPD-10AV UV-Vis detector at a detector wave length of 220 nM. The elution conditions employed a flow rate of 0.8 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% H$_2$O/0.1% trifluoroacetic acid and solvent B was 10% H$_2$O/90% acetonitrile/0.1% trifluoroacetic acid. MS data was determined using a Micromass Platform for LC in electrospray mode. The other related stereoisomers Cap 9, step c.2 to c.4 were all independently debenylated using the procedure described above.

Cap 9.2: LC-MS retention time 1.011 min; m/z 258.15 (MH$^+$).

Cap 9.3: LC-MS retention time 1.054 min; m/z 258.2 (MH$^+$).

Cap 9.4: LC-MS retention time 1.045 min; m/z 258.2 (MH$^+$).

Cap 10.1 to 10.4 (four stereoisomers)

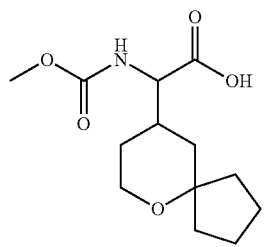

Cap 10, step a

Methanesulfonic acid (3.89 mL, 59.9 mmol) was added to a stirred solution of but-3-en-1-ol (2.058 g, 28.5 mmol) and cyclopentanone (2.40 g, 28.5 mmol) in DCM (20 mL) and the reaction mixture was stirred ON. The reaction was quenched slowly with sat NaHCO$_3$ (aq) (until basic), the layers were separated and the aqueous layer extracted with DCM (20 mL). The combined organics were dried (MgSO$_4$) filtered and concententrated to a crude orange oil. The crude oil was purified with a Biotage Horizon (90 g SiO$_2$, 0-40% EtOAc/hexanes) to yield Cap 10, step a (4.68 g) as an orange oil. $^1$H NMR (400 MHz, CDCl$_3$) δ 5.02-4.82 (m, 1H), 3.85 (dt, J=12.4, 4.2 Hz, 1H), 3.60 (ddd, J=12.4, 10.7, 3.0 Hz, 1H), 3.04 (s, 3H), 2.11-1.97 (m, 2H), 1.95-1.54 (m, 9H), 1.52-1.40 (m, 1H).

Cap 10, step b

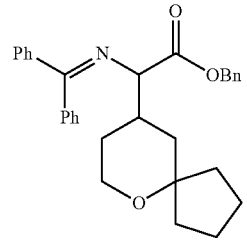

In a 48 mL pressure vessel, benzyl 2-((diphenylmethylene)amino)acetate (1.46 g, 4.44 mmol) and Cap 10, step a (800 mg, 3.41 mmol) were dissolved into toluene (15 mL) and THF (3 mL) and the clear colorless solution was stirred under nitrogen for 5 min. Then 1M LiHMDS (4.44 mL, 4.44 mmol) in THF was added and the vessel was sealed and then heated at 100° C. for 9 h. The reaction was allowed to cool and was then poured into ½ sat NH$_4$Cl (aq) (~60 mL) and extracted with EtOAc (~60 mL). The organic phase was washed with brine (~40 mL), dried (MgSO$_4$), filtered and concentrated. The crude orange oil was purified with a Biotage Horizon (0-40% EtOAc/hex, 90 g SiO$_2$) to yield Cap 10, step b (mixture of four stereoisomers) (480 mg) as a viscous orange oil. LC-MS retention time 1.991 min; m/z 468.4 (MH+). LC data was recorded on a Shimadzu LC-10AS liquid chromatograph equipped with a Phenomenex-Luna 3 u C18 2.0×50 mm column using a SPD-10AV UV-Vis detector at a detector wave length of 220 nM. The elution conditions employed a flow rate of 0.8 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% H$_2$O/0.1% trifluoroacetic acid and solvent B was 10% H$_2$O/90% acetonitrile/0.1% trifluoroacetic acid. MS data was determined using a Micromass Platform for LC in electrospray mode.

Cap 10, step c

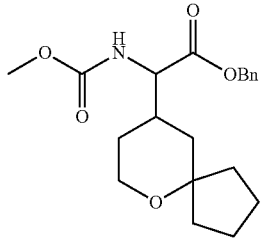

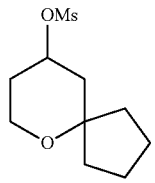

Cap 10, step b (475 mg, 1.02 mmol) was dissolved into THF (12 mL) and then treated with 1.5M HCl (4.06 mL, 6.09 mmol) (aq) and stirred 1.5 h. The reaction was concentrated under high vacuum. The residue was then dissolved in DCM (6 mL) and treated with DIPEA (0.710 mL, 4.06 mmol) and methyl chloroformate (0.118 mL, 1.52 mmol) and stirred at rt 1.5 d. The reaction was diluted with water (~10 mL) and DCM (10 mL) separated and the aqueous layer was further extracted with DCM (10 mL). The combined organics were dried (MgSO$_4$), filtered and concentrated. The residue was purified with a Biotage Horizon (12 g SiO$_2$, 0-25% EtOAc/hex) to yield 284 mg of an orange oil. This material was further purified by prep HPLC (water/ACN with a TFA buffer) to yield Cap 10, step c (mixture of four stereoisomers) (200 mg) as a clear nearly colorless glass. LC-MS retention time 3.025 min; m/z 362.3 (MH+). LC data was recorded on a Shimadzu LC-10AS liquid chromatograph equipped with a Phenomenex-Luna 3 u C18 2.0×50 mm column using a SPD-10AV UV-Vis detector at a detector wave length of 220 nM. The elution conditions employed a flow rate of 0.8 mL/min, a gradient of 100% solvent A/0% solvent B to 0% solvent A/100% solvent B, a gradient time of 4 min, a hold time of 1 min, and an analysis time of 5 min where solvent A was 10% acetonitrile/90% H$_2$O/0.1% trifluoroacetic acid and solvent B was 10% H$_2$O/90% acetonitrile/0.1% trifluoroacetic acid. MS data was determined using a Micromass Platform for LC in electrospray mode.

The mixture of stereoisomers was separated by chiral semi-preparative purification:
Chiralpak AD-H preparative column, 30×250 mm, 5 μm
Mobile Phase: 8% EtOH/heptane with 0.1% Et$_2$NH
UV monitored @ 220 nm
Injection: 0.5 mL of ~30 mg/mL in EtOH (~200 mg total) to yield:

Cap 10, step c. 1: First eluting peak: 30.5 mg; $^1$H NMR (400 MHz, CDCl$_3$) 7.45-7.31 (m, 5H), 5.34-5.19 (m, 2H), 5.10 (d, J=12.0 Hz, 1H), 4.39 (dd, J=9.0, 4.8 Hz, 1H), 3.78-3.66 (m, 4H), 3.51 (td, J=12.0, 2.6 Hz, 1H), 2.20-2.06 (m, 1H), 1.92-1.79 (m, 1H), 1.76-1.11 (m, 11H).

Cap 10, step c.2: Second eluting peak: 29.6 mg; $^1$H NMR (400 MHz, CDCl$_3$) δ 7.43-7.31 (m, 5H), 5.28-5.15 (m, 3H), 4.34 (dd, J=9.0, 5.3 Hz, 1H), 3.78-3.66 (m, 4H), 3.53-3.40 (m, 1H), 2.10 (td, J=10.6, 5.4 Hz, 1H), 1.94-1.82 (m, 1H), 1.76-1.62 (m, 3H), 1.59-1.24 (m, 8H).

Cap 10, step c.3: Third eluting peak: 27.8 mg; $^1$H NMR (400 MHz, CDCl$_3$) 7.46-7.31 (m, 5H), 5.30-5.14 (m, 3H), 4.34 (dd, J=8.9, 5.1 Hz, 1H), 3.79-3.63 (m, 4H), 3.53-3.40 (m, 1H), 2.10 (td, J=10.4, 5.5 Hz, 1H), 1.95-1.82 (m, 1H), 1.76-1.63 (m, 3H), 1.60-1.22 (m, 8H).

Cap 10, step c. 4: Fourth eluting peak: 21.7 mg; $^1$H NMR (400 MHz, CDCl$_3$) δ 7.45-7.32 (m, 5H), 5.36-5.18 (m, 2H), 5.10 (d, J=12.0 Hz, 1H), 4.39 (dd, J=9.0, 4.8 Hz, 1H), 3.79-3.67 (m, 4H), 3.51 (td, J=12.0, 2.6 Hz, 1H), 2.19-2.06 (m, 1H), 1.92-1.79 (m, 1H), 1.77-1.10 (m, 11H).

By $^1$H NMR Cap 10, step c.1 and Cap 10, step c.4 are an enantiomeric pair as are Cap 10, step c.2 and Cap 10, step c.3. Each single stereoisomer was carried forward independently.

Cap 10.1-10.4

Cap 10, step c. 1 (24.4 mg, 0.068 mmol) was dissolved in MeOH (3 mL) and added to 10% Pd/C (5.8 mg, 5.40 μmol). The reaction was vacuum flushed with nitrogen (4×) and then with hydrogen (4×) and allowed to stir under a balloon of hydrogen ON. The reaction was treated with diatomaceous earth (Celite®) and then filtered through diatomaceous earth (Celite®) and concentrated to yield Cap 10.1 (16.3 mg) as a colorless glass. LC-MS retention time 1.139 min; m/z 272.2 (MH+). LC data was recorded on a Shimadzu LC-10AS liquid chromatograph equipped with a Phenomenex-Luna 3 u C18 2.0×50 mm column using a SPD-10AV UV-Vis detector at a detector wave length of 220 nM. The elution conditions employed a flow rate of 0.8 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% H$_2$O/0.1% trifluoroacetic acid and solvent B was 10% H$_2$O/90% acetonitrile/0.1% trifluoroacetic acid. MS data was determined using a Micromass Platform for LC in electrospray mode. $^1$H NMR (400 MHz, MeOH-d$_4$) δ 4.11-4.03 (m, 1H), 3.77-3.70 (m, 1H), 3.66 (s, 3H), 3.65-3.56 (m, 1H), 3.37-3.34 (m, 1H), 2.22-2.08 (m, 1H), 2.02-1.93 (m, 1H), 1.77-1.28 (m, 11H).

The other three stereoisomers Cap 10, step c.2 to c. 4 were all independently debenylated using the procedure described above:

Cap 10.2 (colorless glass): LC-MS retention time 1.018 min; m/z 272.2 (MH+). $^1$H NMR (400 MHz, MeOH-d$_4$) δ 4.10-4.03 (m, 1H), 3.78-3.71 (m, 1H), 3.66 (s, 3H), 3.59 (td, J=12.1, 2.4 Hz, 1H), 3.38-3.34 (m, 1H), 2.22-2.09 (m, 1H), 2.06-1.96 (m, 1H), 1.79-1.27 (m, 11H).

Cap 10.3 (colorless glass): $^1$H NMR (400 MHz, MeOH-d$_4$) δ 4.10-4.03 (m, 1H), 3.78-3.70 (m, 1H), 3.66 (s, 3H), 3.59 (td, J=12.1, 2.4 Hz, 1H), 3.38-3.35 (m, 1H), 2.23-2.09 (m, 1H), 2.05-1.94 (m, 1H), 1.79-1.26 (m, 11H).

Cap 10.4 (colorless glass): $^1$H NMR (400 MHz, MeOH-d$_4$) δ 4.06 (d, J=6.0 Hz, 1H), 3.77-3.70 (m, 1H), 3.69-3.57 (m, 4H), 3.36 (s, 1H), 2.22-2.06 (m, 1H), 2.02-1.92 (m, 1H), 1.79-1.26 (m, 11H).

Cap-11 (racemix mixture)

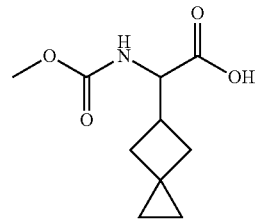

Cap-11, step a

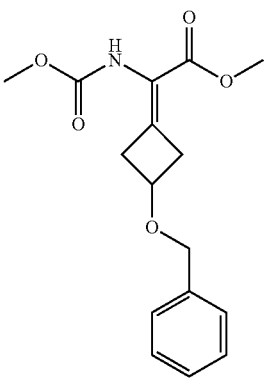

To a solution of 3-(benzyloxy)cyclobutanone (5 g, 28.4 mmol) in CH$_2$Cl$_2$ (200 ml) at 0° C. under nitrogen was added methyl 2-(dimethoxyphosphoryl)-2-(methoxycarbonylamino)acetate (14.48 g, 56.7 mmol) followed by the addition of 1,1,3,3-tetramethylguanidine (7.33 ml, 62.4 mmol). The reaction was removed from the cold bath and allowed to stir at ~25° C. under nitrogen for 24.5 h. The reaction was treated with saturated NH$_4$Cl (aq, 100 mL). The layers were separated and the aqueous layer was extracted with CH$_2$Cl$_2$ (2×100 mL). The combined organic layers were washed with brine (50 mL), dried over MgSO$_4$, filtered, and concentrated in vacuo. The viscous oil was diluted with chloroform (5 mL) and loaded on a Thomson's silica gel cartridge eluting with 25% ethyl acetate/hexanes to afford Cap-11, step a (6.84 g) as a light yellow viscous oil. LC/MS: Anal. Calcd. for [M+Na]$^+$ C$_{16}$H$_{19}$NNaO$_5$ 328.12. found 328.00. $^1$H NMR (400 MHz, DMSO-d$_6$) δ8.49 (br. s., 1H), 7.41-7.26 (m, 5H), 4.43 (s, 2H), 4.20-4.10 (m, 1H), 3.65 (s, 3H), 3.56 (s, 3H), 3.35-3.24 (m, 1H), 3.01 (ddt, J=17.4, 6.8, 3.5 Hz, 1H), 2.96-2.84 (m, 1H), 2.72-2.62 (m, 1H).

Cap-11, step b

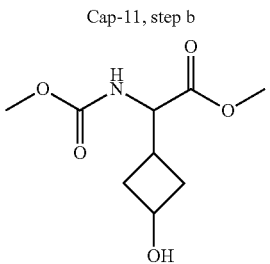

To a solution of Cap-11, step a (6.84 g, 22.40 mmol) in MeOH (100 mL) under nitrogen was added a suspension of palladium on carbon, 10% (2.384 g, 2.240 mmol) in MeOH (20 mL) under nitrogen. The mixture was then exposed to hydrogen under a balloon for 26 h. The reaction was filtered over diatomaceous earth (Celite®) and concentrated in vacuo to afford Cap-11, step b (4.84 g) as a light yellow viscous oil. LC/MS: Anal. Calcd. for [M+Na]$^+$ C$_9$H$_{15}$NNaO$_5$ 240.08. found 240.01. $^1$H NMR (400 MHz, MeOH-d$_4$) δ 7.40-7.25 (m, 1H), 4.91 (s, 2H), 4.19-3.99 (m, 2H), 3.72 (s, 3H), 3.67 (s, 3H), 2.42-2.25 (m, 2H), 2.24-2.02 (m, 1H), 1.91-1.61 (m, 1H).

Cap-11, step c

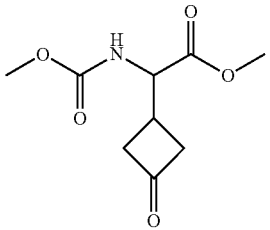

To a solution of DMSO (4.0 ml, 56.4 mmol) in CH$_2$Cl$_2$ (70 ml) at −78° C. under nitrogen was added oxalyl chloride, 2M solution in CH$_2$Cl$_2$ (15.3 ml, 30.6 mmol) dropwise. The reaction was stirred for 1 h. A solution of Cap-11, step b (4.814 g, 22.16 mmol) in CH$_2$Cl$_2$ (35.0 ml) was added to the reaction maintaining to stir at −78° C. under nitrogen. The reaction mixture was stirred for 1.5 h. Triethylamine (15.5 ml, 111 mmol) was added to the reaction dropwise with the reaction maintaining to stir at −78° C. under nitrogen. The reaction was stirred for 16 h. The reaction was quenched with cold 20% K$_2$HPO$_4$ (aq) (50 mL) and water (50 mL). The mixture was stirred at ~25° C. for 15 min. The reaction was diluted with ethyl acetate (50 mL) and the layers were separated. The aqueous layer was extracted with ethyl acetate (2×50 mL). The combined organic layers were washed with brine, dried over MgSO$_4$, filtered, and concentrated in vacuo. The residue was loaded on a Thomson's silica gel cartridge eluting with 40% ethyl acetate/hexanes to afford Cap-11, step c (3.71 g) as a light yellow viscous oil. $^1$H NMR (400 MHz, DMSO-d$_6$) δ7.86 (d, J=8.0 Hz, 1H), 4.27 (t, J=8.4 Hz, 1H), 3.65 (s, 3H), 3.57 (s, 3H), 3.16, 2.86 (m, 4H), 2.82-2.61 (m, 1H).

Cap-11, step d

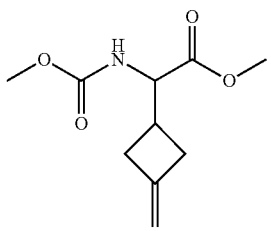

A mixture of methyltriphenylphosphonium bromide (3 g, 8.40 mmol) and potassium tert-butoxide (1 g, 8.91 mmol) in 1,4-dioxane (35 mL) was heated at 40° C. under nitrogen for 3 h. The reaction was removed from the heat and cooled in a cold bath to 10° C. A solution of Cap-11, step c (1.48 g, 6.88 mmol) in 1,4-dioxane (7 mL) was added dropwise and the reaction continued to stir at 10° C. under nitrogen for 45 h. All solvents were removed in vacuo. The residue was taken up in ethyl acetate (50 mL) and saturated NH$_4$Cl (aq, 50 mL). The layers were separated and the aqueous layer was extracted further with ethyl acetate (2×50 mL). The combined organic layers were washed with saturated NaCl (aq, 50 mL), dried over MgSO$_4$, filtered, and concentrated in vacuo. The residue was taken up in CHCl$_3$ (1 mL) and loaded on a Thomson's silica gel cartridge eluting with 5% to 15% ethyl acetate/hexanes over ~4 L to afford Cap-11, step d (533 mg) as a colorless viscous oil which solidified into a white solid upon standing. $^1$H NMR (400 MHz, CDCl$_3$) δ 5.21 (d, J=7.8 Hz, 1H), 4.83-4.74 (m, 2H), 4.41 (t, J=7.7 Hz, 1H), 3.74 (s, 3H), 3.70 (s, 3H), 2.82-2.52 (m, 5H).

Cap-11, step e

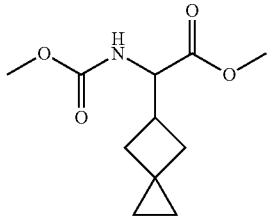

To CH$_2$Cl$_2$ (2.5 ml) at 0° C. under nitrogen was added diethylzinc, 1M in hexanes (6.69 ml, 6.69 mmol) followed by the addition of triflouroacetic acid (in 1 mL CH$_2$Cl$_2$) (0.516 ml, 6.69 mmol) dropwise over 10 min. After 1 h, diiodomethane (in 1 mL CH$_2$Cl$_2$) (0.540 ml, 6.69 mmol) was added dropwise over 10 min. followed by the addition of Cap-11, step d (in 1 mL CH$_2$Cl$_2$) (0.2378 g, 1.115 mmol) dropwise. After the addition, the reaction was removed from the cold bath and allowed to stir at ~25° C.

under nitrogen 12.5 h. The reaction was quenched with 0.1N HCl (aq, 50 mL). The product was extracted with ethyl acetate (3×50 mL). The combined organic layers were dried over MgSO₄, filtered, and concentrated in vacuo. The residue was loaded on a Thomson's silica gel cartridge eluting with 15% ethyl acetate/hexanes to afford Cap-11, step e (206.1 mg, 81% yield) as a white solid. $^1$H NMR (400 MHz, DMSO-d$_6$) δ7.65 (d, J=7.8 Hz, 1H), 4.08 (dd, J=9.5, 8.0 Hz, 1H), 3.62 (s, 3H), 3.56 (s, 3H), 2.76-2.57 (m, 1H), 2.11-2.00 (m, 3H), 2.00-1.90 (m, 1H), 0.48-0.28 (m, 4H).

Cap-11 (Racemic Mixture)

To a solution of Cap-11, step e (0.2804 g, 1.234 mmol) in MeOH (4 mL) at ~25° C. was added a solution of lithium hydroxide (0.035 g, 1.481 mmol) in water (2 mL). The reaction was stirred for 4 h, all volatile components were removed in vacuo. The residue was diluted with water (25 mL) and acidified with 6N HCl to pH~1-2. The product was extracted with ethyl acetate (3×25 mL), dried over MgSO₄, filtered, and concentrated in vacuo to afford Cap-11 (258.1 mg) as a white solid. $^1$H NMR (400 MHz, DMSO-d$_6$) δ12.52 (s, 1H), 7.48 (d, J=8.3 Hz, 1H), 3.99 (dd, 8.3 Hz, 1H), 3.55 (s, 3H), 2.74-2.57 (m, 1H), 2.17-1.89 (m, 4H), 0.49-0.25 (m, 4H).

Cap-12 (racemic mixture)

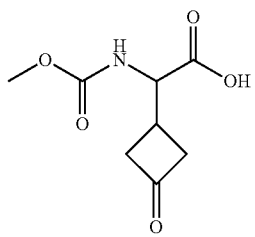

To a solution of Cap-11, step d (0.200 g, 0.938 mmol) in MeOH (3 mL) was added a solution of lithium hydroxide (0.027 g, 1.126 mmol) in water (1.5 mL) dropwise. The reaction was stirred at ~25° C. for 6 h. All volatile components were removed in vacuo. The residue was diluted with water (10 mL) and acidified with 6N HCl to pH~1-2. The product was extracted with ethyl acetate (3×25 mL). The combined organic layers were dried over MgSO₄, filtered, and concentrated in vacuo to afford Cap-12 (178 mg) as a white solid. $^1$H NMR (400 MHz, DMSO-d$_6$) δ12.59 (s, 1H), 7.54 (d, J=8.0 Hz, 1H), 4.75 (br. s., 2H), 3.95 (t, J=8.2 Hz, 1H), 3.55 (s, 3H), 2.76-2.51 (m, 4H), 2.51-2.42 (m, 1H).

Cap-13.1 and 13.2

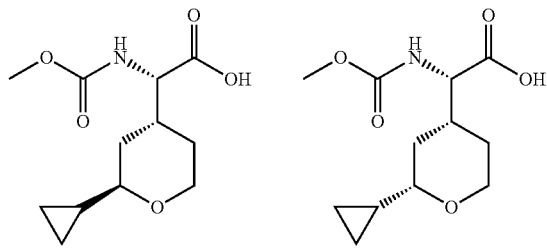

Cap 13, step a

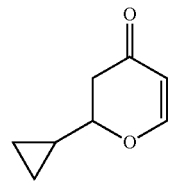

(Diethyloxonio)trifluoroborate (3.64 mL, 29.0 mmol) was added dropwise (over 10 min.) to a solution of cyclopropanecarbaldehyde (4.25 mL, 56.9 mmol) and (E)-((4-methoxybuta-1,3-dien-2-yl)oxy)trimethylsilane (4.90 g, 28.4 mmol) in Et₂O (100 mL) which had been cooled to −78° C. under nitrogen. The reaction was stirred at −78° C. for 2.5 h and then sat NaHCO₃ (aq) (50 mL) was added and the reaction was allowed to come to rt slowly and stirred ON. The layers were separated, the aqueous layer was extracted with Et₂O (100 mL) and the combined organic layers were washed with brine (~50 mL), dried (MgSO₄), filtered and concentrated to a crude orange oil. The crude oil was purified with a Biotage Horizon (80 g SiO₂, 0-30% EtOAC/hexanes) to yield Cap13, step a (2.826 g) as a yellow oil. The material was used without further purification. $^1$H NMR (400 MHz, CDCl₃) δ 7.37 (d, J=6.0 Hz, 1H), 5.40 (dd, J=6.0, 1.0 Hz, 1H), 3.70 (ddd, J=13.1, 8.8, 3.8 Hz, 1H), 2.74-2.63 (m, 1H), 2.60-2.52 (m, 1H), 1.24-1.14 (m, 1H), 0.75-0.61 (m, 2H), 0.54-0.46 (m, 1H), 0.35-0.28 (m, 1H).

Cap 13, step b

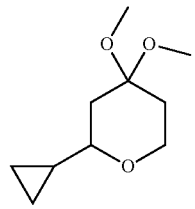

Cap 13, step a (800 mg, 5.79 mmol) was dissolved into methanol (50 mL) and then treated with 10% Pd/C (185 mg, 0.174 mmol). The reaction mixture was stirred and vacuum flushed with nitrogen (4×) and then with hydrogen (4×). The reaction was then allowed to stir under a balloon of hydrogen for 2 h. Diatomaceous earth (Celite®) was added to the reaction mixture and stirred, and then the reaction was filtered through diatomaceous earth (Celite®) and concentrated to a crude oil. The crude oil was purified with a Biotage Horizon (25 g SiO₂, 0-50% EtOAc/hexanes) to yield Cap 13, step b (650 mg contaminated with 25% w/w EtOAc) as a colorless nonviscous oil. $^1$H NMR (400 MHz, CDCl₃) δ 3.92 (ddd, J=11.5, 5.1, 1.8 Hz, 1H), 3.56-3.45 (m, 1H), 3.23 (s, 3H), 3.16 (s, 3H), 2.70 (ddd, J=11.2, 8.7, 2.1 Hz, 1H), 2.10 (dt, J=13.4, 2.6 Hz, 1H), 1.93-1.84 (m, 1H), 1.68-1.57 (m, 1H), 1.46 (dd, J=13.3, 11.5 Hz, 1H), 0.96-0.85 (m, 1H), 0.63-0.45 (m, 2H), 0.37 (dq, J=9.4, 4.8 Hz, 1H), 0.19 (dq, J=9.5, 4.8 Hz, 1H).

Cap 13, step c

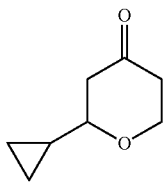

Cap 13, step b (650 mg, 2.65 mmol, contaminated with 25% w/w EtOAc) was dissolved into THF (7 mL) and then treated with 1.5M HCl (aq) (7.07 mL, 10.61 mmol) and stirred for 30 min. The reaction was diluted with brine (~30 mL), extracted with DCM (3×25 mL) and the combined organics were dried (MgSO$_4$), filtered and concentrated to yield Cap 13, step c (543 mg, contaminated with 12% w/w THF and other minor impurities) as a clear colorless oil. The material was used without further purification. $^1$H NMR (400 MHz, CDCl$_3$) δ 4.31 (ddd, J=11.5, 7.4, 1.6 Hz, 1H), 3.67-3.57 (m, 1H), 2.98-2.88 (m, 1H), 2.68-2.42 (m, 3H), 2.37-2.28 (m, 1H), 1.03 (qt, J=8.1, 4.8 Hz, 1H), 0.69-0.52 (m, 2H), 0.49-0.40 (m, 1H), 0.30-0.21 (m, 1H).

Cap 13, step d.1 and d.2

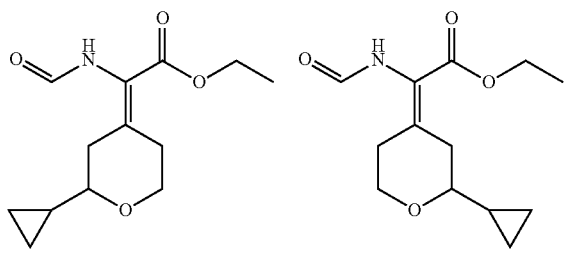

Ethyl 2-isocyanoacetate (390 mg, 3.45 mmol) was diluted with Et$_2$O (15 mL) and then treated with cuprous oxide (76 mg, 0.530 mmol). The slurry was stirred 10 min and then Cap 13, step c (371 mg, 2.65 mmol) in Et$_2$O (10 mL) was added and the reaction was stirred at room temperature for 3 h. The reaction was then cooled to 0° C., treated dropwise with 1M potassium tert-butoxide (3.45 mL, 3.45 mmol) in THF and stirred for 1 h at 0° C. Acetic acid (0.197 mL, 3.45 mmol) in DCM (2 mL) was added and the reaction was allowed to warm to room temperature and stirred ON. The crude reaction mixture was diluted with water (~20 mL) and extracted with EtOAc (3×25 mL). The combined organics were dried (MgSO$_4$), filtered and concentrated to a dark red oil. The oil was purified with a Biotage Horizon (25 g SiO$_2$, 50-75% EtOAc, hexanes) to yield racemic Cap 13, step d.1 ((Z)-isomer; 250 mg) and Cap 13, step d.2 ((E)-isomer; 243 mg), each as an off-white solid. The E/Z assignment was based on nOe studies. Cap 13, step d 1: LC-MS retention time 1.007 min; m/z 254.2 (MH+). $^1$H NMR (400 MHz, MeOH-d$_4$) δ 8.10 (s, 1H), 4.20 (q, J=7.0 Hz, 2H), 4.08 (ddd, J=11.2, 5.6, 1.8 Hz, 1H), 3.45-3.36 (m, 1H), 3.35-3.29 (m, 1H), 2.75-2.67 (m, 2H), 2.30 (ddd, J=13.9, 12.4, 5.5 Hz, 1H), 2.07 (dd, J=14.1, 11.0 Hz, 1H), 1.34-1.22 (m, 3H), 0.95 (qt, J=8.1, 4.8 Hz, 1H), 0.57-0.47 (m, 2H), 0.40-0.23 (m, 2H). Cap 13, step d.2: LC-MS retention time 1.067 min; m/z 254.2 (MH+). LC data was recorded on a Shimadzu LC-10AS liquid chromatograph equipped with a Phenomenex-Luna 3 u C18 2.0×30 mm column using a SPD-10AV UV-Vis detector at a detector wave length of 220 nM. The elution conditions employed a flow rate of 0.8 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% H$_2$O/0.1% trifluoroacetic acid and solvent B was 10% H$_2$O/90% acetonitrile/0.1% trifluoroacetic acid. MS data was to determined using a Micromass Platform for LC in electrospray mode. $^1$H NMR (400 MHz, METHANOL-d$_4$) δ 8.08 (s, 1H), 4.21 (q, J=7.0 Hz, 2H), 4.08 (ddd, J=11.1, 5.6, 1.9 Hz, 1H), 3.51 (dt, J=14.0, 2.0 Hz, 1H), 3.42 (td, J=11.5, 2.5 Hz, 1H), 2.70 (ddd, J=10.6, 8.2, 2.3 Hz, 1H), 2.49 (dq, J=14.1, 2.2 Hz, 1H), 2.26-2.12 (m, 2H), 1.34-1.24 (m, 3H), 0.96 (qt, J=8.1, 4.9 Hz, 1H), 0.58-0.49 (m, 2H), 0.37 (dddd, J=7.8, 6.3, 3.0, 1.3 Hz, 1H), 0.26 (dddd, J=5.2, 4.0, 2.9, 1.4 Hz, 1H).

Cap 13, step e.1 and e.2

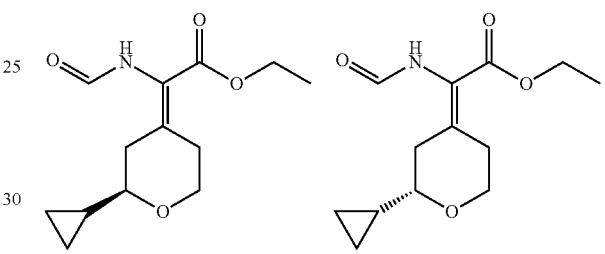

Racemic Cap 13, step d.1 (625 mg) was dissolved into 16 mL of EtOH and separated in multiple injections by prep chiral HPLC (ChiralPak AS column, 10% EtOH/Heptane 0.1% diethyl amine) to yield Cap 13, step e.1 (450 mg, first eluting peak) and Cap 13, step e.2 (360 mg, second eluting peak), each as an off-white solid. The enantiomers separated cleanly, and although each sample was clean by LC/MS and chiral analytical HPLC, an unidentified contaminate was present according to $^1$H NMR. Each material was used without further purification. $^1$H NMR (400 MHz, MeOH-d$_4$) δ 8.08 (s, 1H), 4.21 (q, J=7.0 Hz, 2H), 4.08 (ddd, J=11.1, 5.6, 1.9 Hz, 1H), 3.51 (dt, J=13.9, 2.1 Hz, 1H), 3.46-3.38 (m, 1H), 2.70 (ddd, J=10.7, 8.2, 2.3 Hz, 1H), 2.49 (dq, J=14.1, 2.2 Hz, 1H), 2.26-2.12 (m, 2H), 1.34-1.22 (m, 3H), 0.96 (qt, J=8.2, 5.0 Hz, 1H), 0.58-0.48 (m, 2H), 0.37 (dddd, J=7.7, 6.3, 2.9, 1.4 Hz, 1H), 0.28-0.22 (m, 1H).

Cap-13, step f.1 and f.2

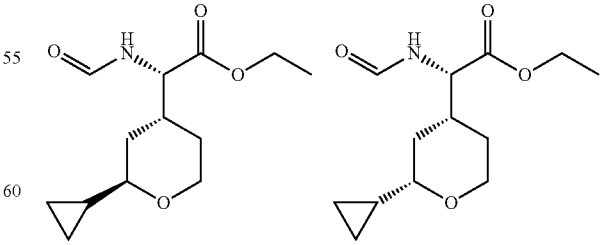

In a Parr Shaker 500 mL reaction vessel, Cap 13, step e.1 (310 mg, contaminated with an unknown impurity) was dissolved into MeOH (20 mL) and then (−)-1,2-bis((2S,5S)-2,5-dimethylphospholano)ethane(cyclooctadiene)rhodium (I) tetrafluoroborate (17.0 mg, 0.031 mmol) was added. Nitrogen was bubbled through the reaction mixture for 10 min, and then the reaction was vacuum flushed with nitrogen (4×) and then with hydrogen (4×). The reaction was then shaken under 60 psi of hydrogen for 2.5 days. The reaction was concentrated to a brown-yellow oil and then purified with a Biotage Horizon (12 g $SiO_2$, 60-80% EtOAc/hex) to yield Cap 13, step f.1 (201 mg) as a clear colorless oil. LC-MS retention time 1.681 min; m/z 256.25 (MH+). LC data was recorded on a Shimadzu LC-10AS liquid chromatograph equipped with a Phenomenex-Luna 3 u C18 2.0×50 mm column using a SPD-10AV UV-Vis detector at a detector wave length of 220 nM. The elution conditions employed a flow rate of 0.8 mL/min, a gradient of 100% solvent A/0% solvent B to 0% solvent A/100% solvent B, a gradient time of 4 min, a hold time of 1 min, and an analysis time of 5 min where solvent A was 10% acetonitrile/90% $H_2O$/0.1% trifluoroacetic acid and solvent B was 10% $H_2O$/90% acetonitrile/0.1% trifluoroacetic acid. MS data was determined using a Micromass Platform for LC in electrospray mode. By $^1$H NMR the material presents as a 12:1 mixture of amide rotamers. For the major rotamer: $^1$H NMR (400 MHz, $CDCl_3$) δ 8.26 (s, 1H), 6.09 (d, J=7.8 Hz, 1H), 4.88 (t, J=8.7 Hz, 1H), 4.25 (q, J=7.0 Hz, 2H), 3.89-3.72 (m, 2H), 2.89 (ddd, J=9.5, 6.2, 3.9 Hz, 1H), 2.32-2.20 (m, 1H), 1.80-1.70 (m, 1H), 1.69-1.58 (m, 2H), 1.50 (dt, J=6.8, 3.4 Hz, 1H), 1.33 (t, J=7.2 Hz, 3H), 1.13-1.03 (m, 1H), 0.63-0.49 (m, 2H), 0.44-0.35 (m, 1H), 0.18-0.10 (m, 1H).

Cap 13, step f.2 (a colorless oil) was prepared from Cap 13, step e.2 according to the procedure described above. LC-MS retention time 1.753 min; m/z 256.25 (MH+). $^1$H NMR (400 MHz, $CDCl_3$) δ 8.28 (s, 1H), 6.16 (d, J=8.8 Hz, 1H), 4.72 (dd, J=8.9, 4.6 Hz, 1H), 4.25 (q, J=7.1 Hz, 2H), 4.09-4.02 (m, 1H), 3.41-3.29 (m, 1H), 2.54 (ddd, J=10.9, 8.5, 2.0 Hz, 1H), 2.15-2.04 (m, 1H), 1.80 (dd, J=13.2, 1.9 Hz, 1H), 1.49-1.42 (m, 2H), 1.32 (t, J=7.2 Hz, 3H), 0.94-0.82 (m, 1H), 0.60-0.45 (m, 2H), 0.39-0.31 (m, 1H), 0.21-0.13 (m, 1H). The tentative assignment of the trans (Cap 13, step f.1) and cis (Cap 13, step f.2) stereoisomers were made based on the magnitude of the $^1$H NMR couplings on select THP protons.

Cap-13, step g

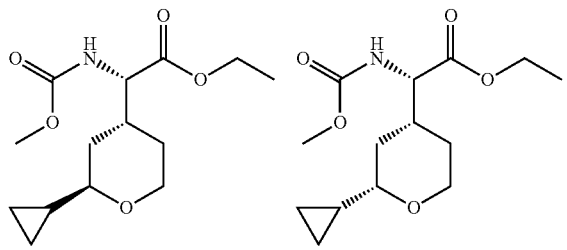

Cap 13, step f.1 (213 mg, 0.834 mmol) was dissolved in MeOH (5 mL) and then 1.5M HCl (1.11 mL, 1.67 mmol) was added and the reaction was sealed with a septum which was then pierced with a needle and left open to air. The reaction was then heated at 50° C. ON. The reaction was concentrated, dissolved in DCM (5 mL) and then treated with DIPEA (0.583 mL, 3.34 mmol) and methyl chloroformate (0.13 mL, 1.7 mmol) and stirred at room temperature for 3 h. The reaction was quenched with water (~5 mL), stirred, separated and the water layer was further extracted with DCM (3×5 mL). The combined organics were dried ($MgSO_4$) filtered and concentrated. The crude light brown oil was purified with a Biotage Horizon (12 g Sift, 25-25% EtOAc/hexanes) to yield Cap 13, step g.1 (131 mg). LC-MS retention time 2.020 min; m/z 286.2 (MH+). LC data was recorded on a Shimadzu LC-10AS liquid chromatograph equipped with a Phenomenex-Luna 3 u C18 2.0×50 mm column using a SPD-10AV UV-Vis detector at a detector wave length of 220 nM. The elution conditions employed a flow rate of 0.8 mL/min, a gradient of 100% solvent A/0% solvent B to 0% solvent A/100% solvent B, a gradient time of 4 min, a hold time of 1 min, and an analysis time of 5 min where solvent A was 10% acetonitrile/90% $H_2O$/0.1% trifluoroacetic acid and solvent B was 10% $H_2O$/90% acetonitrile/0.1% trifluoroacetic acid. MS data was determined using a Micromass Platform for LC in electrospray mode. $^1$H NMR (400 MHz, $CDCl_3$) δ 5.17 (d, J=9.3 Hz, 1H), 4.49 (t, J=8.7 Hz, 1H), 4.30-4.18 (m, 2H), 3.89-3.80 (m, 1H), 3.79-3.67 (m, 1H), 3.69 (s, 3H), 2.94-2.83 (m, 1H), 2.26-2.16 (m, 1H), 1.78-1.47 (m, 4H), 1.33 (t, J=7.2 Hz, 3H), 1.08 (dt, J=8.6, 4.4 Hz, 1H), 0.63-0.47 (m, 2H), 0.44-0.36 (m, 1H), 0.18-0.09 (m, 1H).

Cap 13, step g.2 was prepared from Cap 13, step f.2 according to the above procedure. LC-MS retention time 2.053 min; m/z 286.25 (MH+). $^1$H NMR (400 MHz, $CDCl_3$) δ 5.27 (d, J=8.8 Hz, 1H), 4.34 (dd, J=9.0, 4.8 Hz, 1H), 4.23 (q, J=7.3 Hz, 2H), 4.05 (dt, J=11.2, 3.2 Hz, 1H), 3.71 (s, 3H), 3.41-3.30 (m, 1H), 2.55 (ddd, J=10.7, 8.5, 1.9 Hz, 1H), 2.09-1.96 (m, 1H), 1.77 (d, J=12.8 Hz, 1H), 1.48-1.38 (m, 2H), 1.35-1.22 (m, 1H), 1.31 (t, J=7.3 Hz, 3H), 0.89 (qt, J=8.2, 4.9 Hz, 1H), 0.61-0.44 (m, 2H), 0.39-0.30 (m, 1H), 0.17 (dq, J=9.4, 4.7 Hz, 1H).

Cap 13.1 and 13.2

Cap 13, step g.1 (131 mg, 0.459 mmol) was dissolved in THF (5.5 mL) and then treated with 0.5 M aq LiOH (3.67 mL, 1.836 mmol) and stirred for 5 h. The reaction was quenched with 1N HCl (1.9 mL) and then concentrated under a stream of nitrogen. The material was diluted with water (~4 mL) and then extracted with DCM:MeOH (~5:1, 3×3 mL). The combined organics were concentrated to yield Cap 13.1 (117 mg) as a colorless glass. The material was used without further purification. LC-MS retention time 2.441 min; m/z 258.2 (MH+). LC data was recorded on a Shimadzu LC-10AS liquid chromatograph equipped with a Phenomenex-Luna 3 u C18 2.0×50 mm column using a SPD-10AV UV-Vis detector at a detector wave length of 220 nM. The elution conditions employed a flow rate of 0.8 mL/min, a gradient of 100% solvent A/0% solvent B to 0% solvent A/100% solvent B, a gradient time of 4 min, a hold time of 1 min, and an analysis time of 5 min where solvent A was 10% acetonitrile/90% $H_2O$/0.1% trifluoroacetic acid and solvent B was 10% $H_2O$/90% acetonitrile/0.1% trifluoroacetic acid. MS data was determined using a Micromass Platform for LC in electrospray mode.

Cap 13.2 was prepared from Cap 13, step g.2 using the above procedure. LC-MS retention time 2.553 min; m/z 258.2 (MH+).

Cap 14

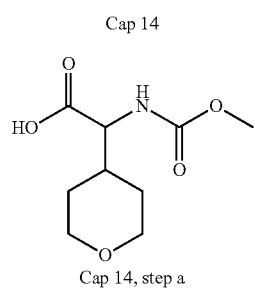

Cap 14, step a

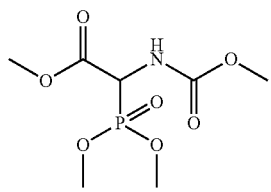

A solution of methyl 2-(benzyloxycarbonylamino)-2-(dimethoxyphosphoryl)acetate (300 mg, 0.906 mmol) in MeOH (10 mL) in a 500 mL hydrogenation pressure tube was bubbled with N₂ for 30 mins. To the mixture was added dimethyl dicarbonate (0.146 mL, 1.358 mmol) and Pd/C (48.2 mg, 0.045 mmol) (10%) and then put on Parr shaker and hydrogenated at 60 psi for 5 h. The mixture was filtered through a pad of diatomaceous earth (Celite®) and the filtrate was concentrated to give Cap 14, step a (230 mg) as a light yellow oil which was used without further purification. LC (Cond. 1): RT=1.60 min; LC/MS: Anal. Calcd. for [M+H]⁺ $C_7H_{15}NO_7P$, 256.06. found 256.20. ¹H NMR (400 MHz, CDCl₃) 5.54 (d, J=8.0 Hz, 1H), 5.00-4.86 (m, 1H), 3.87-3.82 (m, 9H), 3.73 (s, 3H).

Cap 14, step b

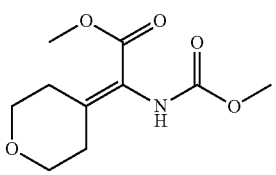

To a solution of Cap 14, step a (230 mg, 0.901 mmol) in THF (1 mL) at −20° C. was added 1,1,3,3-tetramethylguanidine (0.125 mL, 0.992 mmol). The resulting light yellow mixture was stirred at −20° C. for 1 h. Dihydro-2H-pyran-4(3H)-one (99 mg, 0.992 mmol) in THF (0.5 mL) was then added and the resulting mixture was stirred at room temperature for 16 h. The reaction mixture was diluted with EtOAc (5 mL) and washed with 0.1 N HCl solution. The aqueous layer was extracted with EtOAc (2×10 mL) and the combined organic layers were dried with MgSO₄ and concentrated. The crude product was purified by flash chromatography (silica gel, 50% EtOAc/Hex) to give Cap 14, step b as a white solid. ¹H NMR (500 MHz, CDCl₃) δ 5.93 (br. s., 1H), 3.81-3.75 (m, 7H), 3.73 (s, 3H), 2.95 (t, J=5.5 Hz, 2H), 2.44 (t, J=5.2 Hz, 2H).

Cap 14

To a mixture of Cap 14, step b (150 mg, 0.654 mmol) in THF (2 mL) and water (1 mL) was added LiOH (0.982 mL, 1.963 mmol) (2 M aqueous). The resulting mixture was stirred at room temperature overnight. The mixture was extracted with Et₂O (5 mL). The aqueous phase was acidified with 1 N HCl aq. solution and extracted with EtOAc (6×). The combined organic layers were dried with MgSO₄ and concentrated to give Cap 14 as a white solid (100 mg). ¹H NMR (400 MHz, CD₃OD) δ 8.34 (br. s., 1H), 3.73-3.67 (m, 4H), 3.65 (s, 3H), 3.29 (dt, J=3.3, 1.7 Hz, 2H), 2.38 (t, J=5.3 Hz, 2H).

Cap 15.1, 15.2, 15.3 and 15.4

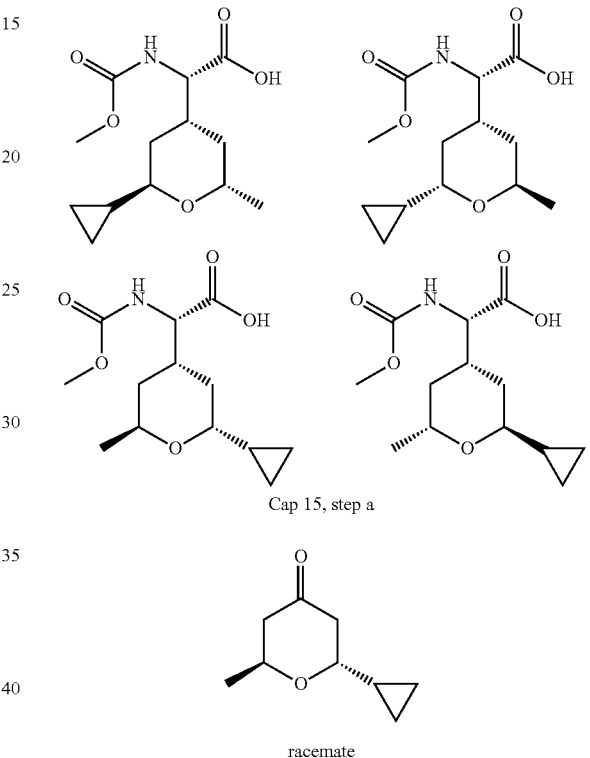

Cap 15, step a racemate

A 1.6 M solution of methyllithium (27.1 mL, 43.4 mmol) in diethyl ether was added to a stirred slurry of copper(I) iodide (5.51 g, 29.0 mmol) in diethyl ether (30 mL) which had been cooled to 0° C. under nitrogen and the reaction was stirred at 0° C. for 30 min. Then a solution of Cap 13, step a (2.00 g, 14.5 mmol) in diethyl ether (10 mL) was added over 20 min. The reaction mixture was allowed to warm to room temperature and stirred 2 h. Then the reaction mixture was cooled to 0° C., slowly quenched with cold aq. NH₄Cl (>10 g) and stirred over night. The reaction mixture was diluted with brine, the layers separated and the aqueous layer further extracted with diethyl ether (2×100 mL). The combined organics were dried (Na₂SO₄), filtered and concentrated. The residue was purified by flash silica chromatography (160 g silica, loading solvent: DCM, 0-20% Et₂O/hexanes) to yield racemic Cap 15, step a (1.24 g) as clear yellow oil. ¹H NMR (400 MHz, CDCl₃) δ 4.45-4.36 (m, 1H), 3.36 (dt, J=8.8, 5.5 Hz, 1H), 2.63 (ddd, J=14.1, 5.3, 1.5 Hz, 1H), 2.56 (ddd, J=14.1, 4.5, 1.5 Hz, 1H), 2.45 (ddd, J=14.1, 5.8, 1.5 Hz, 1H), 2.25 (ddd, J=14.1, 7.3, 1.4 Hz, 1H), 1.28 (d, J=6.5 Hz, 3H), 1.05-0.95 (m, 1H), 0.65-0.55 (m, 2H), 0.46-0.36 (m, 1H), 0.27-0.17 (m, 1H).

Cap 15Z and Cap15E, step b

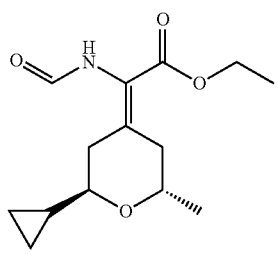

racemate
Z-isomer and

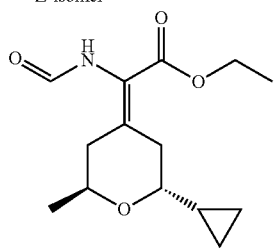

racemate
E-isomer

Ethyl 2-isocyanoacetate (0.868 mL, 7.78 mmol) was added to a stirred suspension of cuprous oxide (0.056 g, 0.389 mmol) in Et$_2$O (30 mL) and the reaction mixture was stirred at room temperature for 10 min. Then Cap15, step a (1.2 g, 7.8 mmol) in Et$_2$O (10 mL) was added and the reaction mixture was stirred at room temperature for 2.5 h. The reaction was cooled to 0° C., treated with 1M KOtBu (7.78 mL, 7.78 mmol) in THF and stirred 1 h. Then a solution of acetic acid (0.535 mL, 9.34 mmol) in 20 mL DCM was added and the reaction was allowed to warm to room temperature and stirred over night. The crude reaction mixture was diluted with EtOAc (60 mL) and DCM (40 mL), partitioned with saturated brine (100 mL), the aqueous layer was further extracted with EtOAc (50 mL). The combined organics were dried (Na$_2$SO$_4$), filtered and concentrated. The residue was purified by flash silica chromatography (80 g silica, loading solvent: DCM, 0-50% EtOAc/hexanes) to yield racemic Cap 15Z, step b (710 mg, first eluting product) and racemic racemic Cap 15E, step b (970 mg, second eluting product) each as a white solid. The double bond geometry was determined by NOE analysis of each olefin isomer.

Cap 15Z, step b the Z-isomer: The $^1$H NMR presents as a 7:3 mixture of amide rotamers. $^1$H NMR (400 MHz, CDCl$_3$) δ 8.25 (d, J=1.3 Hz, 0.7H), 7.99 (d, J=11.5 Hz, 0.3H), 6.84 (br. s., 0.7H), 6.73 (d, J=11.0 Hz, 0.3H), 4.29-4.15 (m, 3H), 3.20 (dd, J=14.3, 3.8 Hz, 0.3H), 3.11-3.02 (m, 1H), 2.99 (dd, J=14.2, 4.1 Hz, 0.7H), 2.82 (dd, J=14.1, 6.3 Hz, 0.7H), 2.70-2.61 (m, 0.6H), 2.57-2.48 (m, 1H), 2.32 (dd, J=13.9, 7.4 Hz, 0.7H), 1.35-1.28 (m, 3H), 1.26-1.20 (m, 3H), 1.04-0.94 (m, 1H), 0.61-0.46 (m, 2H), 0.37 (tt, J=9.3, 4.5 Hz, 1H), 0.20-0.12 (m, 1H). LC-MS retention time 1.90 min; m/z=290 [M+Na]$^+$. Column: Phenomenex LUNA C18, 50×2, 3 u. Solvent A=90% Water/10% Acetonitrile/0.1% TFA; Solvent B=10% Water/90% Acetonitrile/0.1% TFA. Start % B=10, Final % B=40. Gradient Time=4 min. Flow Rate=0.8 ml/min. Wavelength=220.

Cap 15E, step b the E-isomer: The $^1$H NMR presents as a 7:3 mixture of amide rotamers. $^1$H NMR (400 MHz, CDCl$_3$) δ 8.24 (d, J=1.3 Hz, 0.7H), 7.97 (d, J=11.3 Hz, 0.3H), 6.85 (br. s., 0.7H), 6.75 (d, J=11.3 Hz, 0.3H), 4.31-4.22 (m, 2H), 4.21-4.08 (m, 1H), 3.24-3.15 (m, 1H), 3.14-3.03 (m, 1.6H), 2.91 (ddd, J=13.8, 4.5, 0.8 Hz, 0.7H), 2.66 (dd, J=14.1, 3.8 Hz, 0.3H), 2.47 (dd, J=14.1, 3.3 Hz, 0.7H), 2.21 (dd, J=14.1, 7.5 Hz, 0.3H), 2.07 (dd, J=14.1, 8.3 Hz, 0.7H), 1.35-1.29 (m, 3H), 1.23-1.19 (m, 3H), 1.17-1.08 (m, 0.7H), 1.06-0.96 (m, 0.3H), 0.61-0.51 (m, 2H), 0.43-0.34 (m, 1H), 0.26-0.15 (m, 1H). LC-MS retention time 1.98 min; m/z=290 [M+Na]$^+$. Column: Phenomenex LUNA C18, 50×2, 3μ. Solvent A=90% Water/10% Acetonitrile/0.1% TFA; Solvent B=10% Water/90% Acetonitrile/0.1% TFA. Start % B=10, Final % B=40. Gradient Time=4 min. Flow Rate=0.8 ml/min. Wavelength=220.

Cap 15.1 and Cap15.2, step c

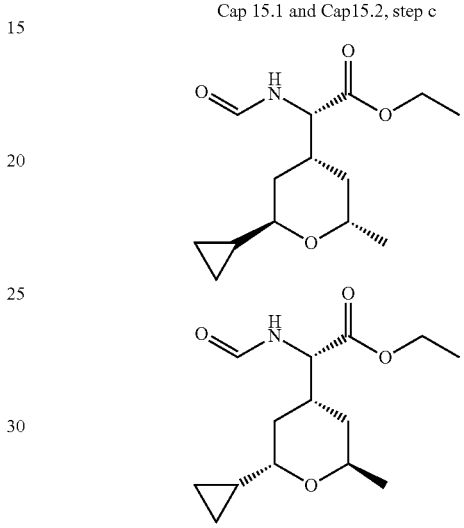

In a Parr shaker vessel, (−)-1,2-bis((2S,5S)-2,5-dimethylphospholano)-ethane(cyclooctadiene)rhodium (I) tetrafluoroborate (120 mg, 0.216 mmol) was added to a solution of Cap 15Z, step b (0.68 g, 2.5 mmol) in MeOH (20 mL). The reaction vessel was sealed, vacuum flushed with nitrogen (4×) and then with hydrogen (4×) and the reaction was shaken under 55 psi of hydrogen at room temperature for 2 d. The crude reaction mixture was concentrated to dryness and the residue was purified by flash silica chromatography (25 g silica, loading solvent: DCM, 0-50% EtOAc/hexanes) to yield a diastereomeric mixture of Cap 15.1 and Cap15.2, step c (607 mg) as clear colorless gel. The material was used in the next step without separating the diastereomers. LC-MS retention time 2.11 min; m/z=270 [M+H]$^+$. Column: Phenomenex LUNA C18, 50×2, 3μ. Solvent A=90% Water/10% Acetonitrile/0.1% TFA; Solvent B=10% Water/90% Acetonitrile/0.1% TFA. Start % B=10, Final % B=50. Gradient Time=4 min. Flow Rate=0.8 ml/min. Wavelength=220 nm.

Cap 15.3 and Cap 15.4, step c

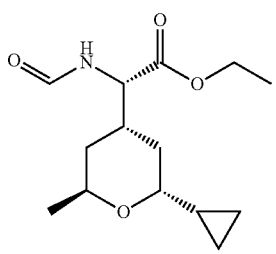

and

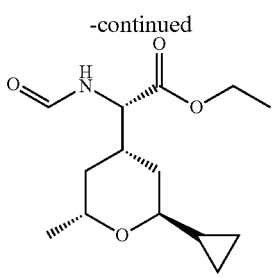

In a Parr shaker vessel, (−)-1,2-bis((2S,5S)-2,5-dimethylphospholano)-ethane(cyclooctadiene)rhodium (I) tetrafluoroborate (120 mg, 0.216 mmol) was added to a solution of Cap 15E, step b (0.94 g, 3.5 mmol) in MeOH (20 mL). The reaction vessel was sealed, vacuum flushed with nitrogen (4×) and then with hydrogen (4×) and shaken under 55 psi of hydrogen at room temperature for 2 d. The crude reaction mixture was concentrated to dryness and the residue was purified by flash silica chromatography (25 g silica, loading solvent: DCM, 0-50% EtOAc/hexanes) to yield a diastereomeric mixture of Cap 15.3 and Cap15.4, step c (889 mg) as a colorless gel. A portion (390 mg) of this mixture was purified by prep HPLC (H₂O-MeCN with 0.1% TFA buffer) to Cap 15.3, step c (0.19 g, as the first eluting product) and Cap15.4, step c (0.19 g as the second eluting product). The relative stereochemistries for each product were established using NOE and 2D NMR analysis of products resulting from subsequent steps.

Cap 15.3, step c: LC-MS retention time 1.14 min; m/z=270 [M+H]⁺. Column: Phenomenex LUNA C18, 50×2, 3 u. Solvent A=90% Water/10% Acetonitrile/0.1% TFA; Solvent B=10% Water/90% Acetonitrile/0.1% TFA. Start % B=20, Final % B=40. Gradient Time=4 min. Flow Rate=0.8 ml/min. Wavelength=220. Cap15.4, step c: LC-MS retention time 1.61 min; m/z=270 [M+H]⁺. Column: Phenomenex LUNA C18, 50×2, 3 u. Solvent A=90% Water/10% Acetonitrile/0.1% TFA; Solvent B=10% Water/90% Acetonitrile/0.1% TFA. Start % B=20, Final % B=40. Gradient Time=4 min. Flow Rate=0.8 ml/min. Wavelength=220.

Cap 15.1 and Cap 15.2, step d

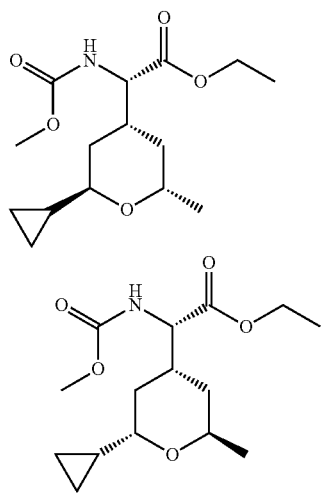

An aqueous solution of 1.5 N HCl (5.5 mL, 8.25 mmol) was added to a solution of a diastereomeric mixture of Cap 15.1 and Cap15.2, step c (590 mg, 2.19 mmol) in EtOH (6 mL) and the reaction was stirred at 52° C. for 16 h. The reaction was then concentrated to dryness to yield a crude white solid which was dissolved into DCM (10 mL), cooled to 0° C. and treated with methyl chloroformate (0.26 mL, 3.3 mmol) followed by DIPEA (1.15 mL, 6.57 mmol). The reaction mixture was stirred at room temperature for 16 h, concentrated and the residue was purified and partially separated by flash silica chromatography (25 g silica, loading solvent: DCM, 0-25% EtOAc/hexanes). Fractions containing diastereomeric mixtures of the desired products were further separated by flash silica chromatography (25 g silica, loading solvent: DCM, 0-40% EtOAc/hexanes). The corresponding single stereoisomer fractions from each chromatography were combined and concentrated to yield Cap 15.1, step d (230 mg, first eluting stereoisomer) and Cap15.2, step d (240 mg, second eluting stereoisomer), each as a clear colorless gel. The relative stereochemistries for each product were established using NOE analysis and 2D NMR.

Cap 15.1, step d: ¹H NMR (400 MHz, CDCl₃) δ 5.26 (d, J=9.0 Hz, 1H), 4.33 (dd, J=9.0, 4.8 Hz, 1H), 4.29-4.18 (m, 2H), 3.92-3.81 (m, 1H), 3.69 (s, 3H), 3.00 (dd, J=9.8, 5.5 Hz, 1H), 2.38 (ddt, J=12.4, 8.4, 4.0 Hz, 1H), 1.74-1.64 (m, 1H), 1.63-1.52 (m, 1H), 1.47 (d, J=12.3 Hz, 1H), 1.35-1.24 (m, 4H), 1.16 (d, J=6.0 Hz, 3H), 1.11-0.99 (m, 1H), 0.60-0.50 (m, 2H), 0.44-0.37 (m, 1H), 0.15-0.07 (m, 1H). LC-MS retention time 3.58 min; m/z=322 [M+Na]⁺. Column: Phenomenex LUNA C18, 50×2, 3 u. Solvent A=90% Water/10% Methanol/0.1% TFA; Solvent B=10% Water/90% Methanol/0.1% TFA. Start % B=0, Final % B=100. Gradient Time=4 min. Flow Rate=0.8 ml/min. Wavelength=220.

Cap15.2, step d: ¹H NMR (400 MHz, CDCl₃) δ 5.25 (d, J=8.8 Hz, 1H), 4.37-4.15 (m, 4H), 3.70 (s, 3H), 2.78 (ddd, J=11.1, 8.7, 2.0 Hz, 1H), 2.24 (td, J=12.4, 3.8 Hz, 1H), 1.74 (d, J=12.8 Hz, 1H), 1.67-1.65 (m, 1H), 1.59 (td, J=12.9, 5.8 Hz, 1H), 1.30 (t, J=7.2 Hz, 3H), 1.28-1.21 (m, 1H), 1.19 (d, J=7.0 Hz, 3H), 0.90-0.79 (m, 1H), 0.58-0.43 (m, 2H), 0.27 (dq, J=9.3, 4.8 Hz, 1H), 0.14 (dq, J=9.4, 4.8 Hz, 1H). LC-MS retention time 3.56 min; m/z=322 [M+Na]⁺. Column: Phenomenex LUNA C18, 50×2, 3μ. Solvent A=90% Water/10% Methanol/0.1% TFA; Solvent B=10% Water/90% Methanol/0.1% TFA. Start % B=0, Final % B=100. Gradient Time=4 min. Flow Rate=0.8 ml/min. Wavelength=220.

Cap 15.3, step d

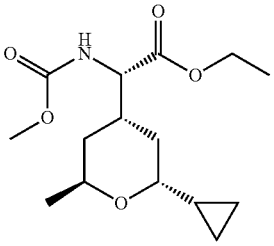

An aqueous solution of 1.5 N HCl (0.99 mL, 1.5 mmol) was added o a solution of Cap15.3, step c (160 mg, 0.594 mmol) in EtOH (2 mL) and the reaction mixture was stirred at 52° C. for 16 h. The reaction was concentrated and then azetroped with ethanol to afford crude as white solid. This crude material was dissolved in DCM (3 mL), cooled with an ice/H₂O bath and then treated with methyl chloroformate (0.069 mL, 0.89 mmol) and DIPEA (0.31 mL, 1.8 mmol).

The reaction mixture was stirred at room temperature for 16 h, diluted with EtOAc (20 mL), brine (10 mL) was added and the aqueous layer was further extracted with EtOAc (10 mL). The combined organic layers were concentrated to dryness and purified by flash silica chromatography (12 g silica, loading solvent: DCM, 0-40% Et$_2$O/hexanes) to yield Cap15.3, step d (129 mg) as clear colorless viscous oil. $^1$H NMR (400 MHz, CDCl$_3$) δ 5.25 (d, J=9.0 Hz, 1H), 4.35-4.17 (m, 4H), 3.70 (s, 3H), 2.77 (ddd, J=11.0, 8.5, 2.1 Hz, 1H), 2.28-2.16 (m, 1H), 1.69-1.56 (m, 3H), 1.42 (d, J=13.1 Hz, 1H), 1.31 (t, J=7.2 Hz, 3H), 1.21 (d, J=6.8 Hz, 3H), 0.89-0.79 (m, 1H), 0.58-0.43 (m, 2H), 0.31-0.24 (m, 1H), 0.14 (dq, J=9.5, 4.7 Hz, 1H). LC-MS retention time 3.60 min; m/z=322 [M+Na]$^+$. Column: Phenomenex LUNA C18, 50×2, 3 u. Solvent A=90% Water/10% Methanol/0.1% TFA; Solvent B=10% Water/90% Methanol/0.1% TFA. Start % B=0, Final % B=100. Gradient Time=4 min. Flow Rate=0.8 ml/min. Wavelength=220.

Cap 15.4, step d

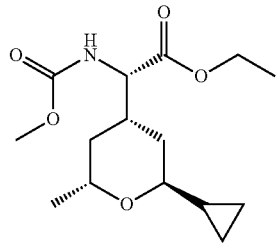

The reaction was performed as described above utilizing Cap15.4, step c as the starting material to yield Cap15.4, step d (141 mg) as clear colorless viscous oil. $^1$H NMR (400 MHz, CDCl$_3$) δ 5.25 (d, J=8.8 Hz, 1H), 4.39-4.14 (m, 3H), 3.95-3.83 (m, 1H), 3.70 (s, 3H), 3.06-2.98 (m, 1H), 2.46-2.34 (m, 1H), 1.67-1.48 (m, 3H), 1.33-1.23 (m, 1H), 1.30 (t, J=7.2 Hz, 3H), 1.17 (d, J=6.0 Hz, 3H), 1.14-1.02 (m, 1H), 0.62-0.48 (m, 2H), 0.46-0.37 (m, 1H), 0.10 (td, J=8.5, 4.4 Hz, 1H). LC-MS retention time 3.58 min; m/z=322 [M+Na]$^+$. Column: Phenomenex LUNA C18, 50×2, 3 u. Solvent A=90% Water/10% Methanol/0.1% TFA; Solvent B=10% Water/90% Methanol/0.1% TFA. Start % B=0, Final % B=100. Gradient Time=4 min. Flow Rate=0.8 ml/min. Wavelength=220.

Cap 15.1

Aqueous 1M LiOH (1.27 mL, 1.27 mmol) was added to a solution of Cap 15.1, step d (0.19 g, 0.64 mmol) in THF (3 mL) and the reaction mixture was stirred at room temperature for 16 h. The reaction was neutralized with aqueous 1M HCl (1.3 mL) and extracted with EtOAc (2×10 mL). The combined organic layers were dried (Na$_2$SO$_4$), filtered and concentrated to yield Cap 15.1 (0.19 g) as white solid, which was used without further purification. LC-MS retention time 3.38 min; m/z=294 [M+Na]$^+$. Column: Phenomenex LUNA C18, 50×2, 3μ. Solvent A=90% Water/10% Methanol/0.1% TFA; Solvent B=10% Water/90% Methanol/0.1% TFA. Start % B=0, Final % B=100. Gradient Time=4 min. Flow Rate=0.8 ml/min. Wavelength=220 nm.

| Cap 15.2, 15.3 and 15.4 The reactions and product analyses were performed as described for Cap 15.1. | | | |
|---|---|---|---|
| Starting Material (quant.) | Product (quant.) | Ret.time | m/z (M + Na)$^+$ |
| Cap 15.2, step d (210 mg) | Cap 15.2 (210 mg) | 3.20 min | 294 |
| Cap 15.3, step d (115 mg) | Cap 15.3 (116 mg) | 3.32 min | 294 |
| Cap 15.4, step d (120 mg) | Cap 15.4 (122 mg) | 3.34 min | 294 |

Cap 16

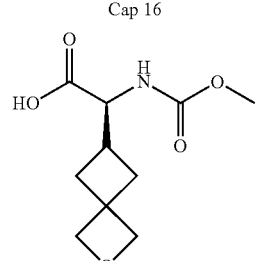

Cap 16, step a

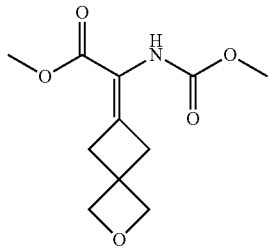

To a solution of 2-oxaspiro[3.3]heptan-6-one (0.54 g, 4.82 mmol), (for preparation, see WO 2011 130146) in CH$_2$Cl$_2$ (30 mL) under nitrogen at 0° C. was added methyl 2-(dimethoxyphosphoryl)-2-((methoxycarbonyl)amino)acetate (2.458 g, 9.63 mmol) followed by the addition of 1,1,3,3-tetramethylguanidine (1.244 mL, 10.60 mmol). The reaction was removed from the cold bath and allowed to stir at ~25° C. for 16 h. All solvents were removed in vacuo. The residue was loaded on a Thomson's silica gel cartridge (90 g) eluting with 45% ethyl acetate/hexanes to afford two fractions, 384 mg (viscous colorless oil which solidfied into an off-white solid upon standing) and 627 mg (viscous light yellow oil which solidified into an off-white solid upon standing). The $^1$H NMR of the two fractions were consistent with the product and thus they were combined to afford one batch of Cap 16, step a as a light yellow solid (1.014 g). $^1$H NMR (400 MHz, DMSO-d$_6$) δ8.40 (br. s., 1H), 4.62 (d, J=6.5 Hz, 2H), 4.58 (d, J=6.3 Hz, 2H), 3.65 (s, 3H), 3.56 (s, 3H), 3.24 (s, 2H), 2.97 (s, 2H).

Cap 16, step c

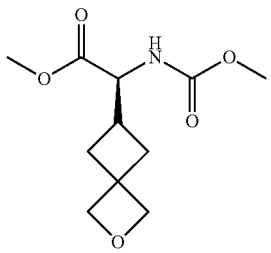

A solution of Cap 16, step a (1 g, 4.15 mmol) and (+1,2-Bis((2S,5S)-2,5-dimethylphospholano)ethane(cyclooctadiene)rhodium (I) tetrafluoroborate (0.100 g, 0.180 mmol) in MeOH (50 mL) in a 500 mL Parr reaction vessel was thoroughly flushed with nitrogen, exposed to vacuum and flushed with nitrogen again several times before being filled with hydrogen to 60 psi. The reaction was shaken vigorously at ~25° C. for 72 h. The reaction was removed from the Parr hydrogenation apparatus. All solvents were removed in vacuo. The residue was loaded on to a Thomson's silica gel cartridge (90 g) eluting with 50% ethyl acetate/hexanes to afford Cap 16, step b as a light yellow viscous oil (846 mg). $^1$H NMR (400 MHz, DMSO-$d_6$). $^1$H NMR (400 MHz, DMSO-$d_6$) δ7.58 (d, J=7.8 Hz, 1H), 4.57 (d, J=1.0 Hz, 1H), 4.55 (d, J=1.0 Hz, 1H), 4.44 (d, J=1.0 Hz, 1H), 4.42 (d, J=1.0 Hz, 1H), 3.93 (t, J=8.4 Hz, 1H), 3.62 (s, 3H), 3.56 (s, 3H), 2.43-2.29 (m, 1H), 2.29-2.16 (m, 2H), 2.08-1.94 (m, 2H).

Cap 16

To a solution of Cap 16, step b (0.300 g, 1.233 mmol) in MeOH (4 mL) was added a solution of lithium hydroxide (0.032 g, 1.36 mmol) in water (2 mL). The reaction was stirred at ~25° C. for 17.5 h. All volatile components were removed in vacuo. The residue was diluted with water (4 mL) and acidified to pH~2 with 6N HCl. The product was extracted with ethyl acetate (3×20 mL). The combined organic layers was washed with brine (20 mL), dried over MgSO$_4$, filtered, and concentrated in vacuo to afford Cap 16 as a clear colorless viscous oil which solidified into a white solid upon standing (215.8 mg). $^1$H NMR (400 MHz, DMSO-$d_6$) δ 12.49 (br. s., 1H), 7.40 (d, J=8.3 Hz, 1H), 4.62-4.49 (m, 2H), 4.49-4.37 (m, 2H), 3.84 (t, J=8.3 Hz, 1H), 3.55 (s, 3H), 2.46-2.29 (m, 1H), 2.29-2.14 (m, 2H), 2.11-1.94 (m, 2H).

Cap 17.1 & Cap 17.2

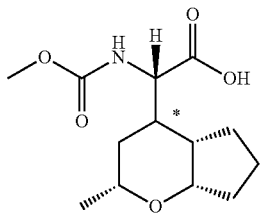

Cap 17:1 Diastereomer-1

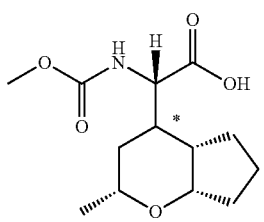

Cap 17:1 Diastereomer-2

Cap 17, step a

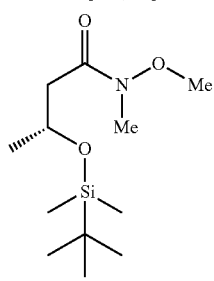

A solution of 2M isopropylmagnesium chloride (97 mL, 195 mmol) in THF was added dropwise over the course of 20 min to a cold, nitrogen purged, solution of Cap 16, step a (16.0 g, 64.9 mmol) and N,O-dimethylhydroxylamine, HCl (9.82 g, 101 mmol) in dry THF (150 mL) while maintaining a reaction temperature below −20° C. (cryocool bath). The reaction mixture was stirred for 2 h at the same temperature before it was quenched with saturated NH$_4$Cl solution (100 mL), and diluted with ether (100 mL). The aqueous layer was washed with ether (100 mL) and the combined ether extracts were washed with brine and dried (MgSO$_4$). Concentration of the organic material gave a colorless oil (21.43 g) which was charged (hexanes) to a Thomson 300 g silica gel cartridge and gradient eluted with 5-100% EtOAc/hexanes over 3 L. Cap 17, step a was isolated as a colorless oil (17.65 g). $^1$H NMR (500 MHz, CDCl$_3$) δ 4.41-4.35 (m, 1H), 3.71 (s, 3H), 3.19 (s, 3H), 2.80-2.76 (m, 1H), 2.37 (dd, J=14.7, 5.7 Hz, 1H), 1.24 (d, J=6.1 Hz, 3H), 0.89 (s, 9H), 0.09 (s, 3H), 0.06 (s, 3H).

Cap 17, step b

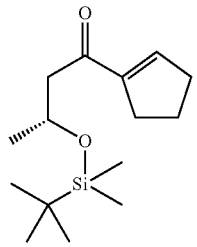

tert-Butyllithium (32.4 mL, 55.1 mmol) was added dropwise to a solution of 1-bromocyclopent-1-ene (4.05 g, 27.5 mmol) in THF (200 mL) under nitrogen at −78° C. After being stirred for 30 min, the resultant vinyllithium was transferred via cannula into a solution of Cap 17, step a (6.0 g, 23 mmol) in THF (50 mL) at −78° C. The reaction was stirred for 2 h, warmed to 0° C. for 1 h, and quenched with saturated NH$_4$Cl solution (40 mL). Brine (40 mL) was added, and the aqueous phase was extrated with Et$_2$O (2×). The combined organic layers were dried (MgSO$_4$), and evaporated in vacuo and the resultant crude product (8 g; contains residual solvent) was carried forward. For characterization purpose, a small portion (~500 mg) was was charged (DCM) to a 40 g Thomson silica gel cartridge and gradient elution was performed from 5-35% EtOAc/hexanes over 1 L. $^1$H NMR (500 MHz, CDCl$_3$) δ 6.79-6.78 (m, 1H), 4.36-4.32 (m, 1H), 2.97 (dd, J=14.5, 7.3 Hz, 1H), 2.60-2.53 (m, 5H), 1.94 (m, 2H), 1.2 (d, J=6.1 Hz, 3H), 0.86 (s, 9H), 0.06 (s, 3H), 0.001 (s, 3H).

Cap 17, step c

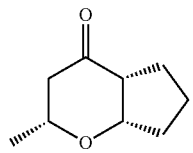

Amberlyst 15 (2.4 g dry form, Fluka 06423) was added to a nitrogen purged solution of Cap 17, step b (3 g, 11.17 mmol) in acetonitrile (60 mL) and the reaction mixture was heated at 50° C. for 1 h. The resin was removed by filtration and the solvent was removed by rotory evaporation. The crude product was charged (DCM) to a 240 g Thomson silica gel cartridge, and gradient elution was performed 5-50% EtOAc/hexanes over 2 L to provide Cap 17, step c (1.9 g). $^1$H NMR (500 MHz, CDCl$_3$) δ 4.24 (t, J=4.3 Hz, 1H), 3.82-3.76 (m, 1H), 2.46 (dt, J=9.5, 4.1 Hz, 1H), 2.37 (dd, J=15.6, 4.6 Hz, 1H), 2.30 (ddd, J=13.7, 2.9, 1.0 Hz, 1H), 2.00-1.86 (m, 5H), 1.72-1.67 (m, 1H), 1.31 (d, (dd, J=6.1 Hz, 3H).

Cap 17, step d

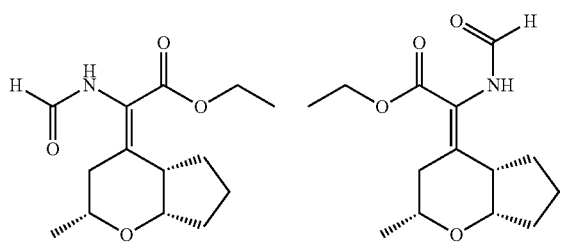

Ethyl 2-isocyanoacetate (1.51 g, 13.20 mmol) was diluted under nitrogen with ether (30 mL) and treated with copper (I)oxide (257 mg, 1.80 mmol). The slurry was stirred 5 min and the product of Cap 17, step c (1.85 g, 12.0 mmol) in ether (15 mL) was added, and the reaction mixture was stirred at room temperature for 2 h. The reaction was cooled to 0° C. and 12 mL of 1M tert-butoxide in THF was added (Note: reaction solidfied after addition of 10 mL), and the reaction mixture was allowed to stand for 18 h. Acetic acid (0.76 mL, 13.20 mmol) in 20 mL DCM was added (a spatula was used to break up the solid mass) and the solution was stirred for 30 min before being filtered. The filtrate was diluted with DCM and washed with water. The aqueous layer was extracted with DCM and the combined organic layers were washed with brine, and dried (MgSO$_4$). The crude product was charged (DCM) to a 110 g Thomson silica gel cartridge and gradient elution was performed from 15-100% EtOAc/DCM over 1.5 L to give Cap 17, step d (3.0 g; note: $^1$H NMR shows 20% residual EtOAc) as a mixture of cis-trans isomers, which was carried forward as such. Note: A sample (~40 mg) was subjected to chiral prep HPLC [chiralpak AS 21×250 mm 10 μm; (12% isocratic w/0.5 mL injection dissolved in total of 3 mL EtOH) run over 20 min. A=0.1% diethylamine/heptane B=EtOH]. Peak eluting at 8 min and 13 min were collected. Peak eluting at 8 min: UPLC (Conditions 10): 0.946 min; Anal. Calcd. for [M+H]$^+$ C$_{14}$H$_{22}$NO$_4$ 268.15. found 268.10. $^1$H NMR (500 MHz, CDCl$_3$) δ 8.23 (s, 0.7H)/7.95 (d, J=11.4 Hz, 0.3H), 6.67-6.61 (m, 1H), 4.28-4.23 (m, 2H), 3.98-3.94 (m, 1H), 3.60-3.43 (m, 2H), 2.63/2.32 (d, J=15.1 Hz, 1H), 2.10-2.04 (m, 1H), 2.01-1.93 (m, 2H), 1.91-1.78 (m, 2H), 1.82-1.69 (m, 2H), 1.35-1.24 (m, 6H). Peak eluting at 13 min: UPLC (Conditions 10): 0.966 min; Anal. Calcd. for [M+H]$^+$ C$_{14}$H$_{22}$NO$_4$ 268.15. found 268.10. $^1$H NMR (400 MHz, CDCl$_3$) δ 8.26 (s, 0.55H)/7.99 (d, J=11.3 Hz, 0.45H), 6.67-6.62 (m, 1H), 4.28-4.22 (m, 2H), 4.00-3.93 (m, 1H), 3.57-3.40 (m, 2H), 2.79-2.58 (m, 1H), 2.16-1.91 (m, 2H), 1.90-1.67 (m, 5H), 1.35-1.26 (m, 6H).

Cap 17, step e

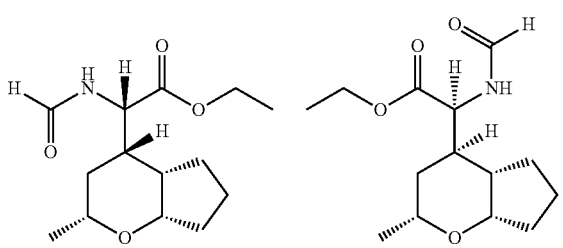

The (−)-1,2-Bis((2,S,5S)-2,5-dimethylphospholano)ethane(cyclooctadiene) rhodium (I) tetrafluorborate (0.312 g, 0.561 mmol) was added to a nitrogen purged solution of the isomeric mixture Cap 17, step e (3.0 g with ~20% residual EtOAc) in MeOH (37 mL) and the solution was flushed 3× with hydrogen and shaken at 60 PSI for 3 days. The solvent was removed by rotory evaporation, and the crude product was charged (DCM) to a 110 g Thomson silica gel cartridge and gradient elution was performed from 5-100% EtOAc/DCM over 2 L to provide the reduced product (2.4 g).

Cap 17, step f

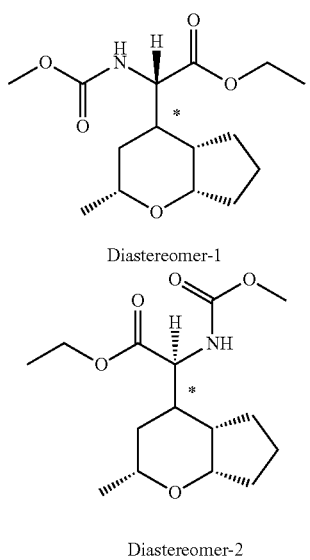

Diastereomer-1

Diastereomer-2

A 2.5 mL HCl (1.5N) as added to the mixture of stereoisomers obtained in Cap 17, step e (1.75 g, 6.50 mmol) in ethanol (20 mL) and the reaction was heated at 50° C. for 6 h (capped with septum fitted with needle to oil bubbler). The volatile component was removed on a rotory evaporator and the residue was exposed to house vacuum for 18 h to give the amine intermediate (~1.6 g). The product was taken up in DCM (30 mL), Hunig's Base (3.46 mL, 19.89 mmol) was added under nitrogen at −25° C. followed by dropwise addition of methyl chloroformate (0.820 mL, 10.61 mmol). The reaction was stirred for 3 h at the same temperature before it was quenched with water (10 mL) and diluted with DCM (50 mL). The organic layer was separated, dried (MgSO$_4$) and evaporated in vacuo. The resultant crude product was charged (DCM) to a 110 g Thomson silica gel cartridge, and gradient elution was performed with 15-100% EtOAc/DCM over 2 L to give the methyl carbamate (1.56 g). The product was repurified with a reverse phase HPLC (Axia-Luna column, 30×100 mm C18; MeOH/water/TFA) followed by preparative SFC (Chiralpak AD-H column, 30×250 mm, 5 μm; Mobile Phase: 10% EtOH in CO$_2$; Flow rate: 50.0 mL/min. for 15 min; UV monitored @ 220 nm) to afford two primary products. Diastereomer-1 (359 mg): LCMS: Condition 10, R$_t$=1.02 min Anal. Calcd. For [M+H]$^+$ C$_{15}$H$_{26}$NO$_5$ 300.37. found 300.1. $^1$H NMR (500 MHz, CDCl$_3$) δ 5.16 (d, J=8.9 Hz, 1H), 4.57 (t, J=8.2 Hz, 1H), 4.26-4.19 (m, 2H), 3.96-3.94 (m, 1H), 3.75-3.71 (m, 1H), 3.70 (s, 3H), 2.04 (br s, 1H), 1.85-1.62 (series m, 6H), 1.52-1.44 (m, 2H), 1.41-1.35 (m, 1H), 1.29 (t, J=7.2 Hz, 3H), 1.15 (d, J=6.3 Hz, 3H). Diastereomer-2 (89 mg): LC/MS: Condition 10, R$_t$=1.04 min; Anal. Calcd. For [M+H]$^+$ C$_{15}$H$_{26}$NO$_5$ 300.37. found 30.15. $^1$H NMR (500 MHz, CDCl$_3$) δ 5.08 (d, J=8.7 Hz, 1H), 4.26-4.19 (m, 3H), 3.84 (s, 1H), 3.76-3.75 (m, 1H), 3.70 (s, 3H), 3.41-3.47 (m, 1H), 2.27 (br s, 1H), 1.90-1.85 (m, 2H), 1.76-1.72 (m, 3H), 1.66-1.55 (m, 3H), 1.31 (t, J=7.2 Hz, 3H), 1.19 (d, J=6.3 Hz, 3H).

Cap 17.1

To a solution of Cap 18, step f (diastereomer-1; 56 mg, 0.187 mmol) in THF (5.6 mL)/Water (1.5 mL) was added lithium hydroxide monohydrate (24 mg, 0.561 mmol). The reaction mixture was stirred for 18 h before being concentrated, diluted with water (10 mL), and washed with Et$_2$O. The aqueous layer was acidified with 1 mL of 1N HCl, extracted with EtOAc, and the organic layer was washed with brine and dried (MgSO$_4$) to obtain Cap 17.1 (49 mg) which was used in the next step without further purification.

Cap 17.2

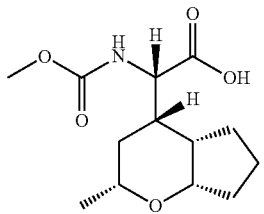

To a solution of Example Cap 17, step f (diastereomer-2; 75 mg, 0.25 mmol) in THF (7 mL)/Water (3 mL) was added lithium hydroxide monohydrate (31 mg, 0.75 mmol). The reaction mixture was stirred for 18 h before being concentrated, diluted with water (10 mL), and washed with Et$_2$O. The aqueous layer was acidified with 1 mL of 1N HCl, extracted with EtOAc, and the organic layer was washed with brine and dried (MgSO$_4$) and evaporated in vacuo to afford Cap 17.2 (55 mg) which was used in the next step without purification.

Cap 18

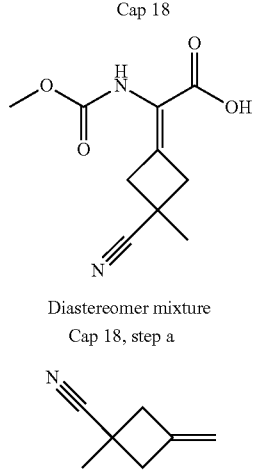

Diastereomer mixture
Cap 18, step a

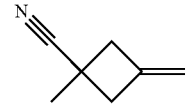

To a solution of diisopropylamine (18.36 ml, 129 mmol) in THF (20 ml) under nitrogen at −78° C. was added n-butyllithium, 2.5M in hexanes (51.5 ml, 129 mmol) dropwise. The reaction was stirred at −78° C. for 15 min then brought up to 0° C. for 30 min.

To a solution of 3-methylenecyclobutanecarbonitrile (10 g, 107 mmol) in THF (300 ml) at −78° C. under nitrogen was added the above LDA solution dropwise. The reaction was stirred for 45 min before iodomethane (8.02 ml, 129 mmol) was added dropwise. The reaction was maintained at −78° C. for 30 min. then removed from the cold bath and allowed to stir at ~25° C. for 19 h. The reaction was quenched with a solution of saturated NH$_4$Cl (aq, 100 mL), then extracted with ether (3×100 mL). The combined organic layer was washed with water, brine, dried over MgSO$_4$, filtered, and concentrated in vacuo to afford a dark oil. The product was used in the next step without further purification. $^1$H NMR (400 MHz, CDCl$_3$) δ 4.97-4.90 (m, 2H), 3.32-3.27 (m, 1H), 3.27-3.22 (m, 1H), 2.75-2.69 (m, 1H), 2.67 (dt, J=4.1, 2.2 Hz, 1H), 1.55 (s, 3H).

Cap 18, step b

A mixture of water (108 ml, 5992 mmol) and 1,4-dioxane (339 ml, 3959 mmol), Cap 18, step a (11.47 g, 107 mmol), and osmium tetraoxide, 4 wt. % in water (2.72 g, 0.428 mmol) was stirred for 5 min at ~25° C. Sodium periodate (48.1 g, 225 mmol) was added in portions over a period of 30 min. The reaction was stirred for 19.5 h at ~25° C. The reaction was diluted with CH$_2$Cl$_2$ (150 mL) and water (150 mL). The mixture was filtered and the solid was washed with CH$_2$Cl$_2$ (100 mL). The filtrate was separated and the aqueous layer was extracted with CH$_2$Cl$_2$ (2×100 mL). The combined organic layers was washed with water (50 mL), brine (50 mL), dried over MgSO$_4$, filtered, and concentrated in vacuo. The residue was loaded on a Thomson's silica gel cartridge eluting with 25% ethyl acetate/hexanes to afford Cap 18, step b as a light yellow oil (9.13 g). $^1$H NMR (400 MHz, CDCl$_3$) δ 3.79-3.74 (m, 1H), 3.74-3.67 (m, 1H), 3.21-3.16 (m, 1H), 3.16-3.10 (m, 1H), 1.74 (s, 3H).

Cap 18, step c

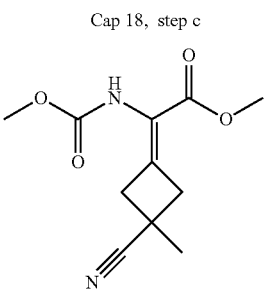

To a solution of Cap 18, step b (2 g, 18.33 mmol) in CH$_2$Cl$_2$ (100 mL) in a cold bath at 0° C. under nitrogen was added methyl 2-(dimethoxyphosphoryl)-2-((methoxycarbonyl)amino)acetate (7.01 g, 27.5 mmol) followed by the addition of 1,1,3,3-tetramethylguanidine (3.23 mL, 27.5 mmol). The reaction was removed from the cold bath and allowed to stir at ~25° C. under nitrogen for 23 h. The reaction was treated with saturated NH$_4$Cl (aq, 25 mL). The layers were separated and the aqueous layer was extracted with CH$_2$Cl$_2$ (2×50 mL). The combined organic layers were washed with brine (25 mL), dried over MgSO$_4$, filtered, and concentrated in vacuo. The residue was loaded on a Thomson's silica gel cartridge eluting with 25% ethyl acetate/hexanes to afford Cap 18, step c as a colorless viscous oil (2.77 g). $^1$H NMR (400 MHz, DMSO-d$_6$) δ8.61 (br. s., 1H), 3.67 (s, 3H), 3.58 (s, 3H), 3.50 (dt, J=17.8, 1.6 Hz, 1H), 3.27 (dd, J=17.7, 3.4 Hz, 1H), 3.15 (dt, J=17.9, 1.7 Hz, 1H), 2.88 (dt, to J=17.8, 1.7 Hz, 1H), 1.52 (s, 3H).

Cap 18

To a solution of Cap 18, step c (0.4083 g, 1.714 mmol) in MeOH (6 ml) was added a solution of lithium hydroxide (0.049 g, 2.057 mmol) in water (3.00 ml). The reaction was stirred at ~25° C. for 6.5 h. All volatile components were removed in vacuo. The residue was diluted with water (15 mL) and washed with ethyl acetate (25 mL). The layers were separated and the aqueous phase was acidifed with 6N HCl to pH~1-2. The product was extracted with ethyl acetate (3×25 mL). The combined organic layers wash washed with brine (25 mL), dried over MgSO$_4$, filtered, and concentrated in vacuo to afford Cap 18 as a white foam (345 mg). The product was used without further purification. $^1$H NMR (400 MHz, DMSO-d$_6$) 12.66 (br. s., 1H), 8.43 (br. s., 1H), 3.57 (s, 3H), 3.49 (dd, J=17.8, 3.0 Hz, 1H), 3.24 (dd, J=17.6, 3.3 Hz, 1H), 3.19-3.07 (m, 1H), 2.92-2.78 (m, 1H), 1.51 (s, 3H).

Examples QC-1.1, QC-1.2 & QC-1.3

To a solution of 4,4'-bis(2-((1R,3S,5R)-2-azabicyclo[3.1.0]hexan-3-yl)-1H-imidazol-4-yl)biphenyl, 4 HCl (50 mg, 0.084 mmol), and Cap-2 (racemic mixture) (41.9 mg, 0.168 mmol) in 2 mL of DMF was added DIEA (0.088 ml, 0.505 mmol). To the resulting mixture was added HATU (64.0 mg, 0.168 mmol) and the mixture was stirred at ~25° C. for 2 h. The solvent was then removed to afford a crude mixture of 3 diastereomers with a ratio of ~1:2:1 when analyzed under LC (Cond. 3). The mixture was then purified by reverse phase HPLC (Column: Water Sunfire 30×150 mm; acetonitrile/water/NH$_4$OAc) to afford the free bases of three diastereomers (Example QC-1.1, QC-1.2 & QC-1.3) as white solids. Example QC-1.1 (9.1 mg): LC (Cond. 1): R$_t$=1.15 min; >95%; LC/MS: Anal. Calcd. for [M+H]$^+$ C$_{48}$H$_{51}$F$_4$N$_8$O$_6$ 911.39. found 456.5 (M/2+1); HRMS: Anal. Calcd. for [M+H]$^+$ C$_{48}$H$_{51}$F$_4$N$_8$O$_6$ 911.3862. found 911.3869; $^1$H NMR (500 MHz, CD$_3$OD) δ ppm 7.61-7.88 (8H, m), 7.36 (2H, br. s.), 5.09-5.21 (2H, m), 4.66-4.77 (2H, m), 3.69 (6H, s), 2.36-2.62 (6H, m), 1.86-2.14 (16H, m), 1.03-1.17 (2H, m), 0.70-0.84 (2H, m). Example QC-1.2 (24.5 mg,): LC (Cond. 1): R$_t$=1.19 min; >97% pure. LC/MS: Anal. Calcd. for [M+H]$^+$ C$_{48}$H$_{51}$F$_4$N$_8$O$_6$ 911.39. found 456.5 (M/2+1); HRMS: Anal. Calcd. for [M+H]$^+$ C$_{48}$H$_{51}$F$_4$N$_8$O$_6$ 911.3862. found 911.3865; $^1$H NMR (500 MHz, CD$_3$OD) δ ppm 7.59-7.89 (8H, m), 7.36 (2H, d, J=4.88 Hz), 5.08-5.24 (2H, m), 4.60-4.76 (2H, m), 3.69 (6H, s), 2.36-2.71 (6H, m), 1.82-2.20 (16H, m), 1.16-1.25 (1H, m), 1.03-1.14 (1H, m), 0.66-0.83 (2H, m). Example QC-1.3 (14.7 mg): LC (Cond. 1): R$_t$=1.22 min; >99% pure. LC/MS: Anal. Calcd. for [M+H]$^+$ C$_{48}$H$_{51}$F$_4$N$_8$O$_6$ 911.39. found 456.5 (M/2+1); HRMS: Anal. Calcd. for [M+H]$^+$ C$_{48}$H$_{51}$F$_4$N$_8$O$_6$ 911.3862. found 911.3864. $^1$H NMR (500 MHz, CD$_3$OD) δ ppm 7.61-7.88 (8H, m), 7.36 (2H, br. s.), 5.09-5.21 (2H, m), 4.66-4.77 (2H, m), 3.69 (6H, s), 2.36-2.62 (6H, m), 1.86-2.14 (16H, m), 1.03-1.17 (2H, m), 0.70-0.84 (2H, m).

Examples QC-2.1 t0 QC-4.3

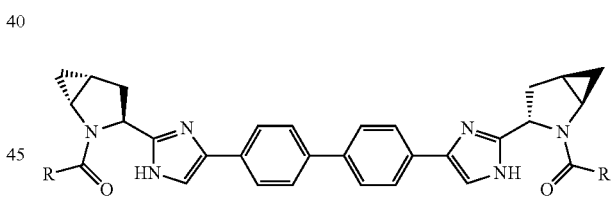

Examples QC-2.1 to QC-3.3 were prepared according to the procedure described for Example QC-1 by using appropriate caps. Example QC-4.1 to QC-4.3 were also prepared similarly with the exception that a MeOH/water/TFA solvent

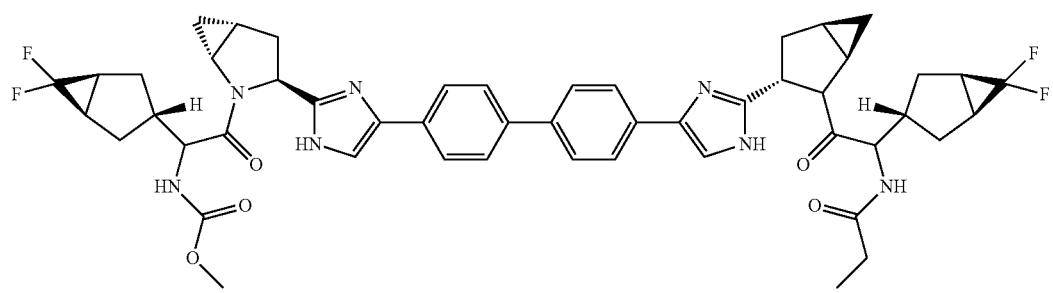 [SMILES: CCC(=O)NC(C(=O)C1[C@H](c2nc(-c3ccc(-c4ccc(-c5c[nH]c([C@@H]6C[C@H]7C[C@H]7N6C(=O)C(NC(=O)OC)[C@@H]6C[C@@H]7[C@H](C6)C7(F)F)n5)cc4)cc3)c[nH]2)C[C@H]2C[C@@H]12)[C@@H]1C[C@@H]2[C@H](C1)C2(F)F]

system (Column: WATERS Atlantis OBD 30×100 mm 5 u) was employed for the reverse phase HPLC purification. Even though only one compound was expected when using Cap-1, 3 different diastereomers were obtained, indicating that racemization might have occurred during the synthesis of Cap-1.

| Example | | Isomer | RT (LC-Cond); % homogeneity index; MS data |
|---|---|---|---|
| QC-2.1 to QC-2.3 | [structure with MeO-carbamate, difluorocyclopropane-fused bicyclic] | 1 | $R_t$ = 1.99 min (Cond. 3); 100%; LC/MS: Anal. Calcd. for [M + H]$^+$ C$_{48}$H$_{51}$F$_4$N$_8$O$_6$ 911.39; found 456.2 (M/2 + 1); HRMS: Anal. Calcd. for [M + H]$^+$ C$_{48}$H$_{51}$F$_4$N$_8$O$_6$ 911.3862; found 911.3873 |
| | | 2 | $R_t$ = 2.06 min (Cond. 3); >97%; LC/MS: Anal. Calcd. for [M + H]$^+$ C$_{48}$H$_{51}$F$_4$N$_8$O$_6$ 911.39; found 456.2 (M/2 + 1); HRMS: Anal. Calcd. for [M + H]$^+$ C$_{48}$H$_{51}$F$_4$N$_8$O$_6$ 911.3862; found 911.3868 |
| | | 3 | $R_t$ = 2.14 min (Cond. 3); >99%; LC/MS: Anal. Calcd. for [M + H]$^+$ C$_{48}$H$_{51}$F$_4$N$_8$O$_6$ 911.39; found 456.2 (M/2 + 1); HRMS: Anal. Calcd. for [M + H]$^+$ C$_{48}$H$_{51}$F$_4$N$_8$O$_6$ 911.3862; found 911.3866 |
| QC-3.1 to QC3.3 | [structure with MeO-carbamate, bicyclic cyclopropane-fused cyclopentane] | 1 | $R_t$ = 1.17 min (Cond. 1); >98%; LC/MS: Anal. Calcd. for [M + H]$^+$ C$_{48}$H$_{55}$N$_8$O$_6$ 839.42; found 839.8; HRMS: Anal. Calcd. for [M + H]$^+$ C$_{48}$H$_{55}$N$_8$O$_6$ 839.4239; found 839.4243 |
| | | 2 | $R_t$ = 1.21 min (Cond. 1); 100%; LC/MS: Anal. Calcd. for [M + H]$^+$ C$_{48}$H$_{55}$N$_8$O$_6$ 839.42; found 839.8 |
| | | 3 | $R_t$ = 1.25 min (Cond. 1); >97%; LC/MS: Anal. Calcd. for [M + H]$^+$ C$_{48}$H$_{55}$N$_8$O$_6$ 839.42; found 839.8; HRMS: Anal. Calcd. for [M + H]$^+$ C$_{48}$H$_{55}$N$_8$O$_6$ 839.4239; found 839.4242 |
| QC-4.1 to QC4.3 | [structure with MeO-carbamate, oxabicyclic cyclopropane-fused tetrahydrofuran] | 1 | $R_t$ = 0.93 min (Cond. 1); >96%; LC/MS: Anal. Calcd. for [M + H]$^+$ C$_{46}$H$_{51}$N$_8$O$_8$ 843.38; found 843.7; HRMS: Anal. Calcd. for [M + H]$^+$ C$_{46}$H$_{51}$N$_8$O$_8$ 843.3824; found 843.3834 |
| | | 2 | $R_t$ = 1.18 min (Cond. 2); >93%; LC/MS: Anal. Calcd. for [M + H]$^+$ C$_{46}$H$_{51}$N$_8$O$_8$ 843.38; found 843.53; HRMS: Anal. Calcd. for [M + H]$^+$ C$_{46}$H$_{51}$N$_8$O$_8$ 843.3824; found 843.3823 |
| | | 3 | $R_t$ = 0.99 min (Cond. 1); LC/MS: Anal. Calcd. for [M + H]$^+$ C$_{46}$H$_{51}$N$_8$O$_8$ 843.38; found 843.6. |

Example QC-5.1, QC-5.2 & QC-5.3

Three Diastereomers Regarding the Non-Specified Stereogenic Center

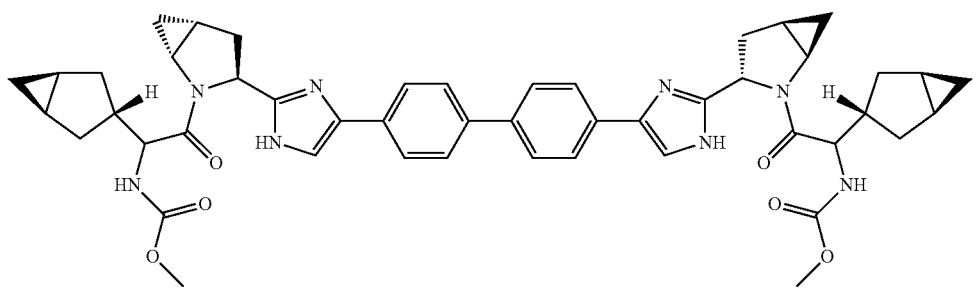 [SMILES: COC(=O)NC(C(=O)N1[C@@H]2C[C@@H]2C[C@H]1c1nc(-c2ccc(-c3ccc(-c4c[nH]c([C@@H]5C[C@H]6C[C@H]6N5C(=O)C(NC(=O)OC)[C@H]5C[C@@H]6C[C@@H]6C5)n4)cc3)cc2)c[nH]1)[C@H]1C[C@@H]2C[C@@H]2C1]

Example QC-5 step a

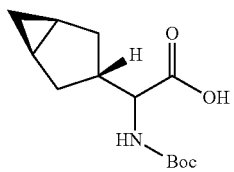

Racemic mixture 2-((1R,3s,5S)-bicyclo[3.1.0]hexan-3-yl)-2-(tert-butoxycarbonylamino) acetic acid (Example QC-5 step a) was prepared from commercially available (cis)-bicyclo[3.1.0]hexan-3-ol, which was first converted to its (trans)-bicyclo[3.1.0]hexan-3-ol isomer using standard Mitsubobu's protocol and then elaborated to ethyl 2-amino-2-((1R,3s,5S)-bicyclo[3.1.0]hexan-3-yl)acetate following the reaction sequence described from Cap-2 step d through Cap-2 step f. The amine was then protected as it's BOC derivative followed by the hydrolysis of the ethyl ester under standard protocols to afford acid Example QC-5 step a.

Example QC-5 step b

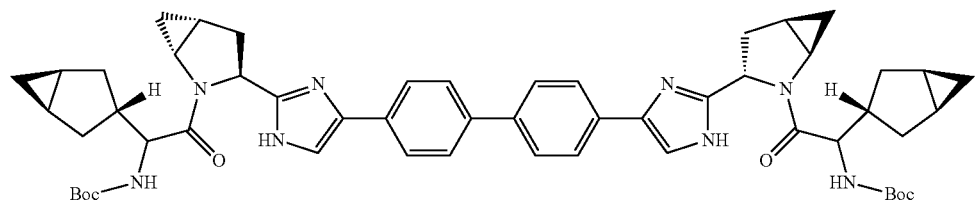 [SMILES: CC(C)(C)OC(=O)NC(C(=O)N1[C@@H]2C[C@@H]2C[C@H]1c1nc(-c2ccc(-c3ccc(-c4c[nH]c([C@@H]5C[C@H]6C[C@H]6N5C(=O)C(NC(=O)OC(C)(C)C)[C@H]5C[C@@H]6C[C@@H]6C5)n4)cc3)cc2)c[nH]1)[C@H]1C[C@@H]2C[C@@H]2C1]

To a solution of 4,4'-bis(2-((1R,3S,5R)-2-azabicyclo[3.1.0]hexan-3-yl)-1H-imidazol-4-yl)biphenyl, 4 HCl (50 mg, 0.084 mmol), and acid Example QC-5 step a (43.0 mg, 0.168 mmol) in 2 mL of DMF was added DIEA (0.088 ml, 0.505 mmol) and HATU (64.0 mg, 0.168 mmol). The mixture was stirred at ~25° C. for 2 h. The solvent was then removed in vacuo and the crude product was purified by reverse phase HPLC (Column: WATERS Atlantis OBD 30×100 mm 5 u, MeOH/water/THF) to afford the TFA salt of Example QC-5 step b as a white solid (97 mg). LC (Cond. 1): $R_f$=1.47 min; LC/MS: Anal. Calcd. for $[M+H]^+$ $C_{54}H_{67}N_8O_6$ 923.52. found 462.8 (M/2+1); $^1$H NMR (500 MHz, CD$_3$OD) δ ppm 7.82-7.91 (10H, m), 5.08-5.18 (2H, m), 4.57 (1H, d, J=7.63 Hz), 4.48 (1H, d, J=8.24 Hz), 4.06-4.12 (1H, m), 3.79-3.86 (1H, m), 3.02 (3H, s), 2.88 (3H, s), 2.66-2.75 (2H, m), 2.43-2.54 (2H, m), 2.01-2.16 (4H, m), 1.88-1.97 (2H, m), 1.68-1.82 (4H, m), 1.57-1.68 (2H, m), 1.47 (9H, s), 1.41 (9H, s), 1.25-1.36 (6H, m), 1.16-1.24 (1H, m), 1.04-1.11 (1H, m), 0.81-0.93 (2H, m), 0.29-0.39 (2H, m), 0.19-0.27 (2H, m).

Example QC-5 step c

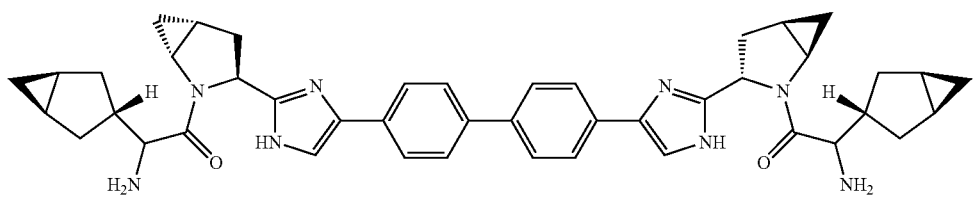 [SMILES: NC(C(=O)N1[C@@H]2C[C@@H]2C[C@H]1c1nc(-c2ccc(-c3ccc(-c4c[nH]c([C@@H]5C[C@H]6C[C@H]6N5C(=O)C(N)[C@H]5C[C@@H]6C[C@@H]6C5)n4)cc3)cc2)c[nH]1)[C@H]1C[C@@H]2C[C@@H]2C1]

To a mixture of Example QC-5 step b (97 mg, 0.084 mmol) in 1 mL of CH$_2$Cl$_2$ was added HCl (2 mL, 4.00 mmol) (2 N in diethyl ether). The resulting mixture was stirred at room temperature for 2 h. The solvent was then removed to afford the HCl salt of Example QC-5 step c as a yellow solid (73 mg). LC (Cond. 1): $R_f$=0.84 min; LC/MS: Anal. Calcd. for $[M+H]^+$ $C_{44}H_{51}N_8O_2$ 723.41. found 723.6.

Example QC-5.1, QC-5.2 & QC-5.3

To a mixture of the HCl salt of Example QC-5 step b (73 mg, 0.084 mmol) in 2 mL of CH$_2$Cl$_2$ was added DIEA (0.117 mL, 0.672 mmol) and methyl chloroformate (0.026 mL, 0.336 mmol). The resulting mixture was stirred at room temperature for 1 h. Ammonia (2 mL, 4.00 mmol) (2 N in Methanol) was added and the resulting mixture was stirred for 2 h. The solvent was then removed in vacuo and the crude material was purified by a reverse phase HPLC (Column: Water Sunfire 30×150 mm, acetonitrile/water/NH$_4$OAc) to afford the free bases of three diastereomers (Example QC-5.1, QC-5.2 & QC-5.3) as white to light yellow solids. Example QC-5.1 (8.5 mg): LC (Cond. 3): $R_f$=2.05 min, >95% pure; LC/MS: Anal. Calcd. for $[M+H]^+$ $C_{48}H_{55}N_8O_6$ 839.42. found 839.7. HRMS: Anal. Calcd. for $[M+H]^+$ $C_{48}H_{55}N_8O_6$ 839.4239. found 839.4243. $^1$H NMR (500 MHz, CD$_3$OD) δ ppm 7.64-7.87 (8H, m), 7.37 (2H, br. s.), 5.10-5.22 (2H, m), 4.57-4.72 (2H, m), 3.68 (6H, s), 2.38-2.58 (4H, m), 1.90-2.31 (6H, m), 1.55-1.87 (6H, m), 1.20-1.38 (6H, m), 1.04-1.19 (2H, m), 0.72-0.85 (2H, m), 0.28-0.37 (2H, m), 0.22-0.28 (2H, m). Example QC-5.2 (18 mg): LC (Cond. 3): $R_t$=2.14 min; >99% pure; LC/MS: Anal. Calcd. for [M+H]$^+$ $C_{48}H_{55}N_8O_6$ 839.42. found 839.7; HRMS: Anal. Calcd. for [M+H]$^+$ $C_{48}H_{55}N_8O_6$ 839.4239. found 839.4243; $^1$H NMR (500 MHz, CD$_3$OD) δ ppm 7.63-7.86 (8H, m), 7.37 (2H, d), 5.11-5.22 (2H, m), 4.51-4.70 (2H, m), 3.68 (6H, d), 2.38-2.59 (4H, m), 1.90-2.15 (6H, m), 1.57-1.84 (6H, m), 1.18-1.38 (6H, m), 1.03-1.16 (2H, m), 0.72-0.83 (2H, m), 0.28-0.39 (2H, m), 0.22-0.28 (2H, m). Example QC-5.3 (9.1 mg): LC (Cond. 3): $R_t$=2.23 min; >95% pure. LC/MS: Anal. Calcd. for [M+H]$^+$ $C_{48}H_{55}N_8O_6$ 839.42. found 839.7; HRMS: Anal. Calcd. for [M+H]$^+$ $C_{48}H_{55}N_8O_6$ 839.4239. found 839.4242. $^1$H NMR (500 MHz, CD$_3$OD) δ ppm 7.63-7.93 (8H, m), 7.36 (2H, s), 5.17-5.29 (2H, m), 4.55 (2H, d, J=8.5 Hz), 3.69 (6H, s), 2.39-2.64 (4H, m), 1.92-2.20 (6H, m), 1.58-1.86 (6H, m), 1.27-1.45 (6H, m), 1.17-1.27 (2H, m), 0.70-0.84 (2H, m), 0.31-0.45 (2H, m), 0.20-0.30 (2H, m).

Example QC-6 to QC-7

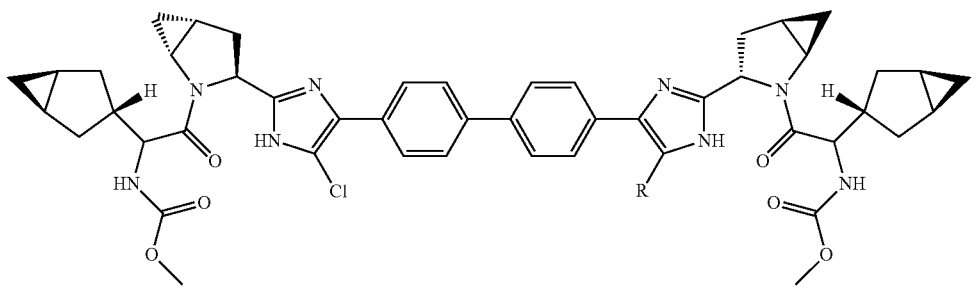

To a mixture of Example QC-2.1 (50 mg, 0.044 mmol) in 1 mL of DMF was added NCS (7.03 mg, 0.053 mmol). The resulting mixture was stirred at 50° C. overnight. The solvent was then removed and the crude product was purified by reverse phase HPLC (Column: WATERS Sunfire C18 OBD 30×100 mm 5 u, MeOH/water/TFA) to afford the TFA salts of Example QC-6 and Example CQ-7 as white and light yellow solids, respectively. Example QC-6 (20 mg): LC (Cond. 2): $R_t$=1.72 min, >99% pure; LC/MS: Anal. Calcd. for [M+H]$^+$ $C_{48}H_{50}ClF_4N_8O_6$ 945.35. found 473.16 (M/2+1); HRMS: Anal. Calcd. for [M+H]$^+$ $C_{48}H_{50}ClF_4N_8O_6$ 945.3472. found 945.3440; $^1$H NMR (500 MHz, CD$_4$OD) δ ppm 7.77-7.92 (9H, m), 5.06-5.13 (1H, m), 4.97-5.04 (1H, m), 4.61-4.70 (2H, m), 3.78-3.85 (1H, m), 3.71-3.75 (1H, m), 3.69 (6H, d), 2.63-2.74 (1H, m), 2.39-2.55 (5H, m), 1.83-2.14 (14H, m), 1.00-1.12 (2H, m), 0.81-0.89 (1H, m), 0.72-0.79 (1H, m). Example QC-7 (19 mg): LC (Cond. 2): $R_t$=2.03 min, >96% pure; LC/MS: Anal. Calcd. for [M+H]$^+$ $C_{48}H_{49}Cl_2F_4N_8O_6$ 979.31. found 490.17 (M/2+1); HRMS: Anal. Calcd. for [M+H]$^+$ $C_{48}F_{49}Cl_2F_4N_8O_6$ 979.3083. found 979.3043; $^1$H NMR (500 MHz, CD$_3$OD) δ ppm 7.74-7.88 (8H, m), 4.97-5.05 (2H, m), 4.63-4.71 (2H, m), 3.71-3.78 (2H, m), 3.69 (6H, s), 2.39-2.55 (6H, m), 1.87-2.11 (14H, m), 1.01-1.11 (2H, m), 0.73-0.81 (2H, m).

Example QC-8.1

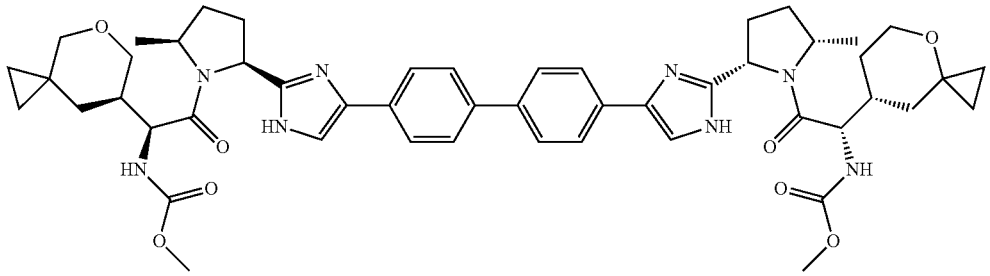 [SMILES: COC(=O)N[C@H](C(=O)N1[C@@H](C)CC[C@H]1c1nc(-c2ccc(-c3ccc(-c4c[nH]c([C@@H]5CC[C@H](C)N5C(=O)[C@@H](NC(=O)OC)[C@@H]5CCOC6(CC6)C5)n4)cc3)cc2)c[nH]1)[C@@H]1COCC2(CC2)C1]

To a solution of 4,4'-bis(2-((2S,5S)-5-methylpyrrolidin-2-yl)-1H-imidazol-4-yl)-1,1'-biphenyl, 4 HCl (25 mg, 0.042 mmol), and Cap 5.1 (20.32 mg, 0.084 mmol) in 2 mL of DMF was added DIEA (0.044 mL, 0.251 mmol). To the resulting mixture was added HATU (31.8 mg, 0.084 mmol) and the mixture was stirred at room temperature for 2 h. The solvent was removed under vacuum. The crude product was purified by a reverse phase HPLC (Column: WATERS Sunfire C18 OBD 30×100 mm 5 u, methanol/water/TFA) to give the TFA salt of Example QC-8.1 as a white solid (32 mg, 64.3%). LC (Cond. 1): $R_t$=1.04 min; LC/MS: Anal. Calcd. for [M+H]$^+$ $C_{50}H_{63}N_8O_8$ 903.48. found: 903.7; HRMS: Anal. Calcd. for [M+H]$^+$ $C_{50}H_{63}N_8O_8$ 903.4763. found: 903.4753; $^1$H NMR (500 MHz, CD$_3$OD) δ 8.03-7.78 (m, 10H), 5.16 (dd, J=10.5, 7.2 Hz, 2H), 4.84-4.73 (m, 2H), 4.33-4.18 (m, 2H), 3.92-3.78 (m, 2H), 3.74-3.63 (m, 6H), 3.61-3.43 (m, 2H), 2.69-2.47 (m, 2H), 2.43-2.07 (m, 6H), 2.06-1.95 (m, 2H), 1.95-1.74 (m, 4H), 1.56 (d, J=6.4 Hz, 6H), 1.42 (m, 2H), 0.83-0.70 (m, 2H), 0.67-0.49 (m, 4H), 0.45-0.33 (m, 2H), 0.21-0.10 (m, 2H).

Example QC-8.2

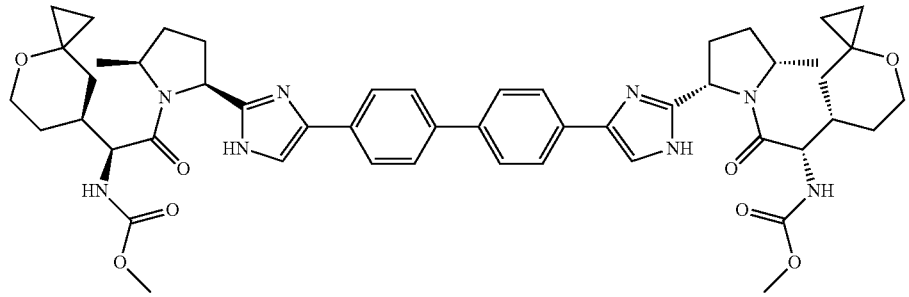 [SMILES: COC(=O)N[C@H](C(=O)N1[C@@H](C)CC[C@H]1c1nc(-c2ccc(-c3ccc(-c4c[nH]c([C@@H]5CC[C@H](C)N5C(=O)[C@@H](NC(=O)OC)[C@H]5CCOC6(CC6)C5)n4)cc3)cc2)c[nH]1)[C@H]1CCOC2(CC2)C1]

The TFA salt of Example QC-8.2 was prepared by substituting Cap 5.2 for Cap 5.1 using the same procedure described for Example QC-8.1. LC (Cond. 1): $R_t$=1.01 min; LC/MS: Anal. Calcd. for [M+H]$^+$ $C_{50}H_{63}N_8O_8$ 903.48. found: 903.7; HRMS: Anal. Calcd. for [M+H]$^+$ $C_{50}H_{63}N_8O_8$ 903.4763. found: 903.4761; $^1$H NMR (500 MHz, CD$_3$OD) δ 8.05-7.78 (m, 10H), 5.16 (dd, J=10.4, 7.0 Hz, 2H), 4.83-4.75 (m, 2H), 4.36-4.18 (m, 2H), 3.92-3.75 (m, 2H), 3.74-3.61 (m, 6H), 3.57-3.37 (m, 2H), 2.72-2.47 (m, 2H), 2.44-2.24 (m, 4H), 2.24-2.07 (m, 2H), 1.99 (m, 2H), 1.95-1.77 (m, 2H), 1.58 (d, J=6.4 Hz, 6H), 1.52-1.40 (m, 2H), 1.39-1.19 (m, 4H), 0.76 (m, 2H), 0.67-0.44 (m, 4H), 0.38 (m, 2H).

Example QC-9 to QC16 and Example OL1 to OL10 were prepared using the same procedure described for Example QC-1.1, combining the corresponding core (see references within the table) with either Cap 5.1 or Cap 5.2 and the products were purified with a reverse phase HPLC condition and obtained as TFA salts Example OL10 was prepared from appropriate core and Cap 6 by using standard EDC/CH$_2$Cl$_2$ coupling condition, and the product was purified with a reverse phase HPLC condition and obtained as free base. Example OL11 to OL12 were prepared from appropriate core and Cap 7 by using standard HATU/DIEA/DMF coupling condition, and the products were purified with a reverse phase HPLC condition and obtained as TFA salts.

| Example | Structure | Ref. for penultimate precursor | R—OH | LCMS analysis |
|---|---|---|---|---|
| QC9 | 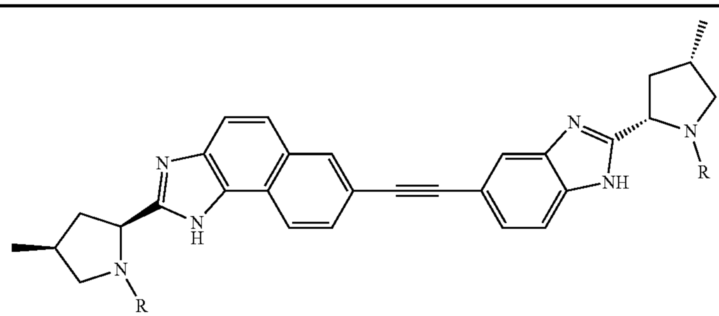 | WO2010/096302 | Cap 5.2 | LC (Cond. 4): $R_t$ = 0.81 min; LC/MS: Anal. Calcd. for [M + H]$^+$ $C_{52}H_{61}N_8O_8$ 925.46; found 926.12; HPLC (Cond. 6): $R_t$ = 27.33; 100% |

-continued

| Example | Structure | Ref. for penultimate precursor | R—OH | LCMS analysis |
|---|---|---|---|---|
| QC10 | 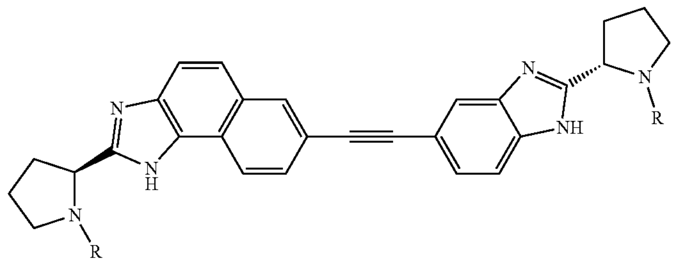 | WO2010/096302 | Cap 5.2 | LC (Cond. 5): $R_t$ = 1.66 min; LC/MS: Anal. Calcd. for [M + H]$^+$ $C_{48}H_{57}N_8O_8$ 873.43; found 873.51; HPLC (Cond. 6): $R_t$ = 24.01; 99% |
| QC11 | 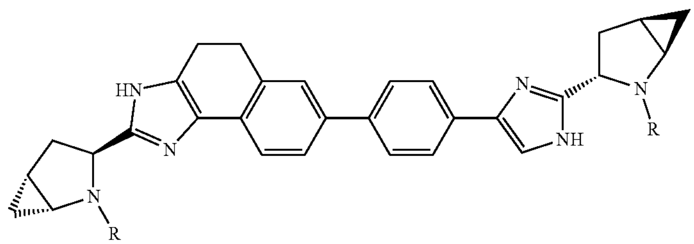 | WO2009/102633 | Cap 5.2 | LC (Cond. 4): $R_t$ = 0.75 min; LC/MS: Anal. Calcd. for [M + H]$^+$ $C_{52}H_{61}N_8O_8$ 925.46; found 925.87; HPLC (Cond. 6): $R_t$ = 25.22; 97% |
| QC12 | 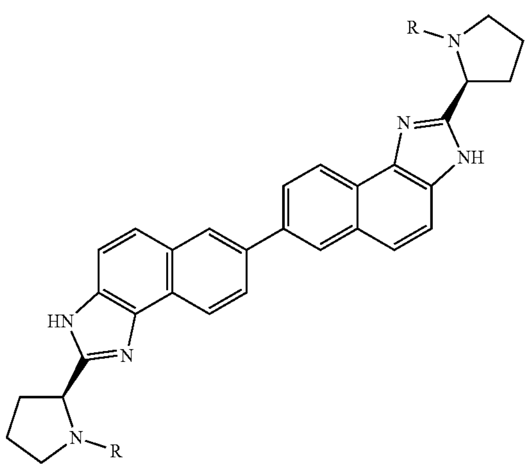 | WO2009/102633 | Cap 5.2 | LC (Cond. 4): $R_t$ = 0.76 min; LC/MS: Anal. Calcd. for [M + H]$^+$ $C_{52}H_{59}N_8O_8$ 923.45; found 923.82; HPLC (Cond. 6): $R_t$ = 26.01; 100% |
| QC13 | 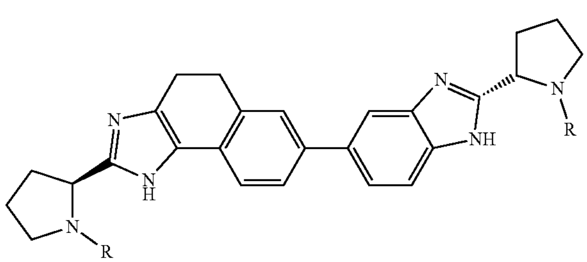 | WO2010/096302 | Cap 5.2 | LC (Cond. 5): $R_t$ = 1.52 min; LC/MS: Anal. Calcd. for [M + H]$^+$ $C_{48}H_{59}N_8O_8$ 875.45; found 875.47 HPLC (Cond. 6): $R_t$ = 23.98; 99% |

| Example | Structure | Ref. for penultimate precursor | R—OH | LCMS analysis |
|---|---|---|---|---|
| OL1 | 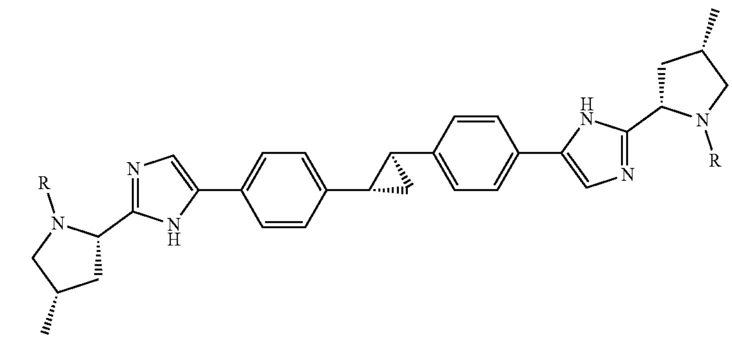 | WO2010/117635 | Cap 5.1 | LC (Cond. 4): $R_t$ = 0.8 min; LC/MS: Anal. Calcd. for [M + H]$^+$ $C_{53}H_{66}N_8O_8$ 943.51; found 943.88; HPLC (Cond. 7): $R_t$ = 11.32; 94% |
| OL2 | 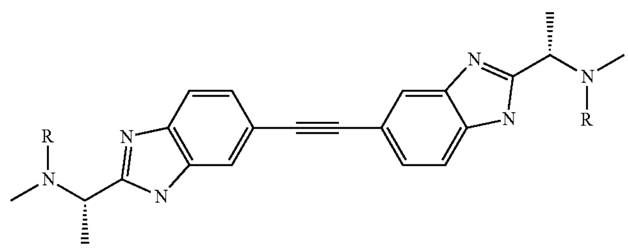 | WO2010/017401 | Cap 5.2 | LC (Cond. 5): $R_t$ = 1.77 min; LC/MS: Anal. Calcd. for [M + H]$^+$ $C_{44}H_{55}N_8O_8$ 823.41; found 823.40; HPLC (Cond. 7): $R_t$ = 11.34; 95% |
| OL3 | 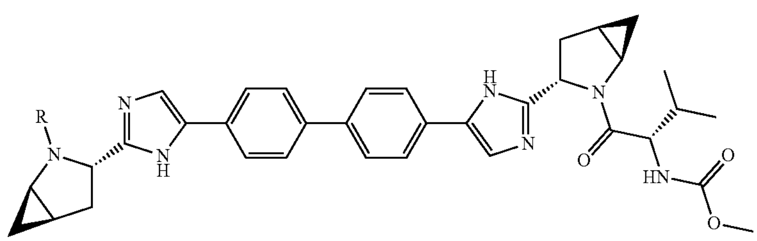 | WO2008/021927 | Cap 5.2 | LC (Cond. 5): $R_t$ = 1.62 min; LC/MS: Anal. Calcd. for [M + H]$^+$ $C_{48}H_{55}N_8O_7$ 831.43; found 831.40; HPLC (Cond. 7): $R_t$ = 10.76; 93% |
| OL4 | 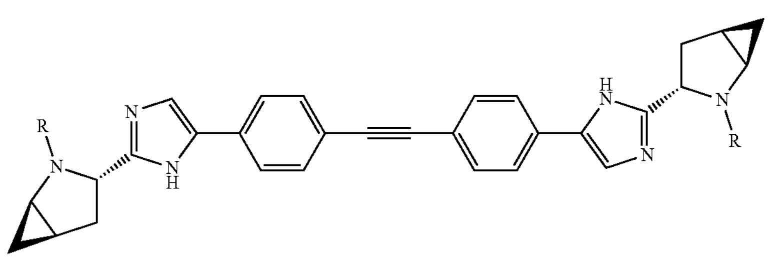 | WO2010/117635 | Cap 5.2 | LC (Cond. 4): $R_t$ = 0.78 min; LC/MS: Anal. Calcd. for [M + H]$^+$ $C_{52}H_{59}N_8O_8$ 923.45; found 923.77; HPLC (Cond. 7): $R_t$ = 11.65; 93% |

-continued

| Example | Structure | Ref. for penultimate precursor | R—OH | LCMS analysis |
|---|---|---|---|---|
| OL5 | 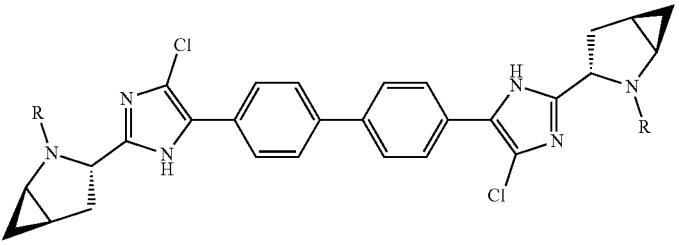 | | Cap 5.2 | LC (Cond. 4): $R_t$ = 0.98 min; LC/MS: Anal. Calcd. for [M + H]$^+$ $C_{50}H_{57}Cl_2N_8O_8$ 967.37; found 967.32; HPLC (Cond. 7): $R_t$ = 13.44; 95% |
| OL6 | 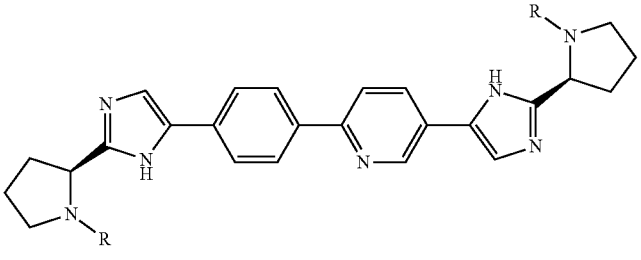 | WO2008/021928 | Cap 5.2 | LC (Cond. 5): $R_t$ = 1.55 min; LC/MS: Anal. Calcd. for [M + H]$^+$ $C_{47}H_{58}N_9O_8$ 876.44; found 876.39; HPLC (Cond. 7): $R_t$ = 4.93; 93% |
| OL7 | 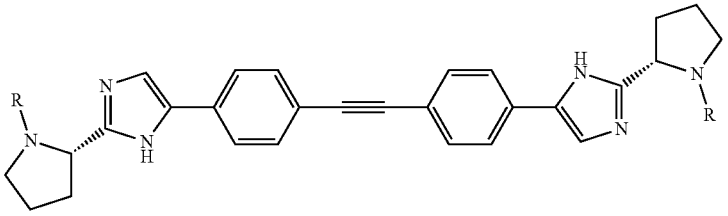 | WO2010/117635 | Cap 5.2 | LC (Cond. 5): $R_t$ = 1.65 min; LC/MS: Anal. Calcd. for [M + H]$^+$ $C_{50}H_{59}N_8O_8$ 899.45; found 899.51; HPLC (Cond. 7): $R_t$ = 5.79; 95% |
| QC14 | 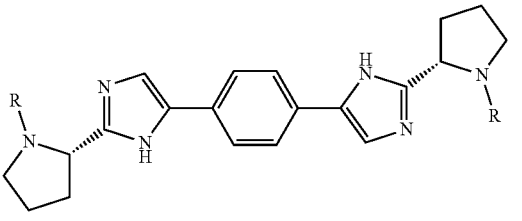 | See the note below the Table | Cap 5.2 | LC (Cond. 4): $R_t$ = 0.65 min; LC/MS: Anal. Calcd. for [M + H]$^+$ $C_{42}H_{55}N_8O_8$ 799.41; found 799.50; HPLC (Cond. 6): $R_t$ = 20.85; 97% |

-continued

| Example | Structure | Ref. for penultimate precursor | R—OH | LCMS analysis |
|---|---|---|---|---|
| OL8 | 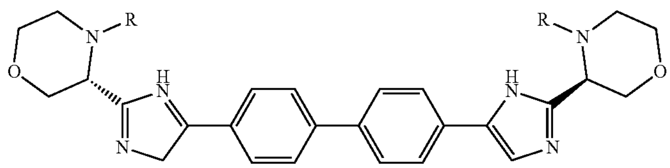 | See WO2008/021927 for a relevant procedure | Cap 5.2 | LC (Cond. 5): $R_t$ = 1.61 min; LC/MS: Anal. Calcd. for [M + H]$^+$ $C_{48}H_{59}N_8O_{10}$ 907.44; found 907.26; HPLC (Cond. 7): $R_t$ = 5.49; 93% |
| QC15 | 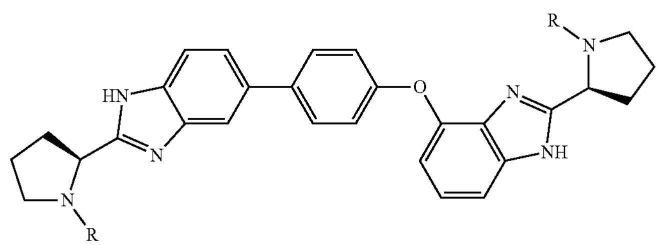 | WO2010/017401 | Cap 5.2 | LC (Cond. 4): $R_t$ = 0.76 min; LC/MS: Anal. Calcd. for [M + H]$^+$ $C_{50}H_{59}N_8O_9$ 915.44; found 915.68; HPLC (Cond. 6): $R_t$ = 25.90; 99% |
| QC16 | 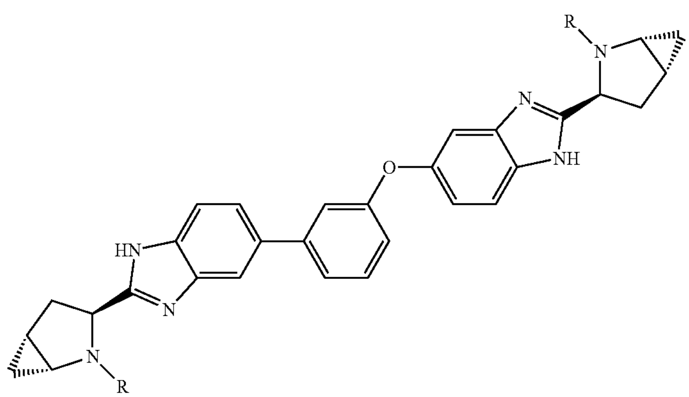 | WO2010/017401 | Cap 5.2 | LC (Cond. 4): $R_t$ = 0.78 min; LC/MS: Anal. Calcd. for [M + H]$^+$ $C_{52}H_{59}N_8O_9$ 939.44; found 939.73; HPLC (Cond. 6): $R_t$ = 26.17 93% |
| OL9 | 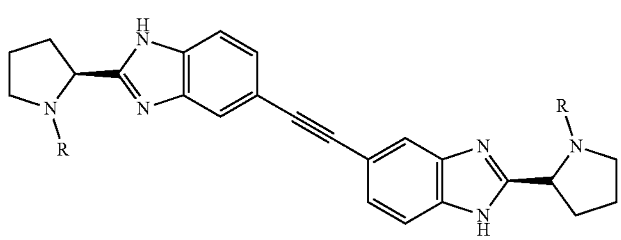 | WO2010/017401 | Cap 5.2 | LC (Cond. 5): $R_t$ = 1.67 min; LC/MS: Anal. Calcd. for [M + H]$^+$ $C_{46}H_{55}N_8O_8$ 847.41; found 847.6; HPLC (Cond. 7): $R_t$ = 5.38; 95% |

-continued

| Example | Structure | Ref. for penultimate precursor | R—OH | LCMS analysis |
|---|---|---|---|---|
| OL10 | 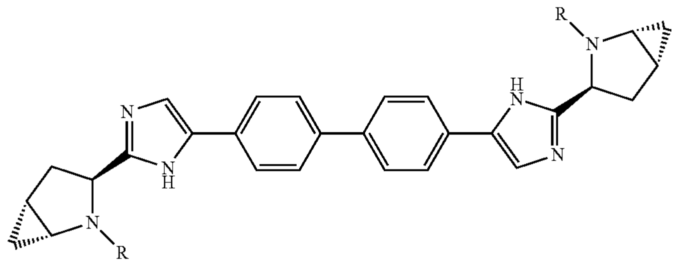 | WO2008/021927 | Cap 6 | LC (Cond. 3): $R_t$ = 2.37 min; LC/MS: Anal. Calcd. for [M + H]$^+$ $C_{48}H_{55}N_8O_8$ 871.41; found 871.6; HPLC (Cond. 7): $R_t$ = 7.29; 95% |
| OL11 | 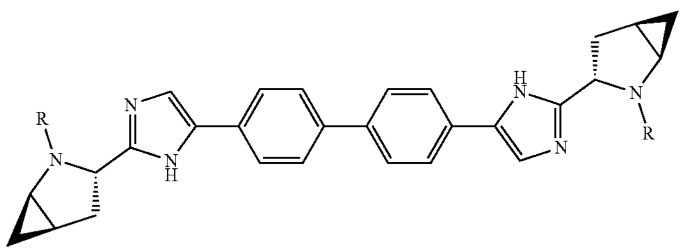 | WO2008/021927 | Cap 7 | LC/MS (Cond. 8): $R_t$ = 3.36 min; LC/MS: Anal. Calcd. for [M + H]$^+$ $C_{48}H_{49}F_6N_8O_6$ 947.37; found 947.39; HPLC (Cond. 9): $R_t$ = 16.28; 100% |
| OL12 | 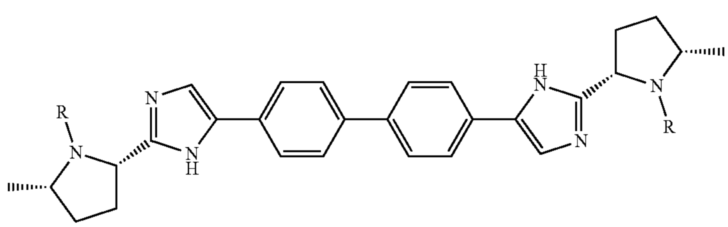 | WO2009/102325 | Cap 7 | LC/MS (Cond. 8): $R_t$ = 3.446 min; LC/MS: Anal. Calcd. for [M + H]$^+$ $C_{48}H_{53}F_6N_8O_6$ 951.40; found 951.41; HPLC (Cond. 9): $R_t$ = 17.44; 100% |

*The penultimate precursor of Example QC14 was prepared starting from 1,1'-(1,4-phenylene)bis(2-aminoethanone) dihydrochloride (see TL, 1986, p. 5759 for a preparative procedure) and Boc-L-proline according to a three-step protocol (amide coupling, cyclization of ketoamide to imidazole, and Boc-deprotection) described in WO2008/021927.

Example QC-17.1

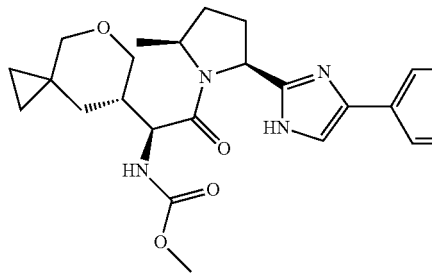

Example QC-17.1, step a

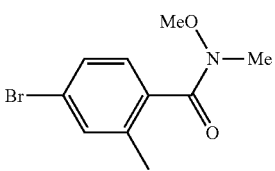

To a solution of 4-bromo-2-methylbenzoic acid (10 g, 46.5 mmol) in DMF (150 mL) was added N, O-dimethylhydroxylamine hydrochloride (5.44 g, 55.8 mmol) at room temperature followed by HOBT (8.55 g, 55.8 mmol). Then EDC (10.7 g, 55.8 mmol) was added followed by DIEA (24.4 mL, 140 mmol) and the reaction mixture was stirred at room temperature for 12 h. The reaction mixture was then diluted with EtOAc (150 mL), washed with water (3×250 mL) and brine (150 mL), dried over $Na_2SO_4$, filtered and concentrated in vacuo to afford crude QC-17.1, step a (9.5 g), which was submitted to the next step as such. $^1$H NMR ($CDCl_3$, δ=7.26 ppm, 400 MHz): δ 7.37 (d, J=1.6 Hz, 1H), 7.34 (dd, J=8.0, 1.6 Hz, 1H), 7.14 (d, J=8.0 Hz, 1H), 3.47 (s, 3H), 3.30 (s, 3H), 2.31 (s, 3H). LC/MS: Anal. Calcd. For $[M+H]^+$ $C_{10}H_{13}{}^{81}BrNO_2$: 260.01. found 260.0.

Example QC-17.1, step b

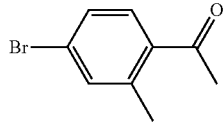

QC-17.1, step a (9.5 g, 36.8 mmol) was dissolved in diethyl ether (150 mL) and cooled to 0° C. Then methylmagnesium iodide (3.0 M in diethyl ether, 24.54 mL, 73.6 mmol) was added drop wise over 10 min. The reaction was stirred for 6 h at 40° C. and then brought to room temperature and stirred for 12 h. The reaction mixture was cooled to 0° C., quenched with ice and then with 1.5N HCl (50 mL). The organic layer was separated and the aqueous layer was extracted with methyl tert-butyl ether (2×100 mL), dried over $Na_2SO_4$ and concentrated under reduced pressure. The crude was purified by flash chromatography (Silica gel, 60-120, EtOAc: petroleum ether, 2:98) to afford QC-17.1, step b (6.25 g) as pale yellow liquid. $^1$H NMR ($CDCl_3$, δ=7.26 ppm, 400 MHz): δ 7.55 (d, J=8.0 Hz, 1H), 7.41 (s, 1H), 7.40 (d, J=8.0 Hz, 1H), 2.55 (s, 3H), 2.50 (s, 3H).

Example QC-17.1, step c

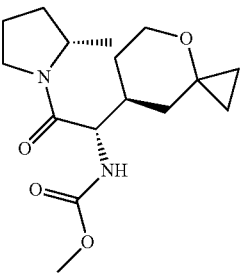

4-Acetylphenylboronic acid (5.39 g, 32.9 mmol) was added to a sealed tube containing QC-17.1, step b (7.0 g, 32.9 mmol) in MeOH (75.0 mL) and the reaction mixture was purged with nitrogen for 10 min. Then $K_2CO_3$ (9.08 g, 65.7 mmol) was added followed by $Pd(Ph_3P)_4$ (1.139 g, 0.986 mmol) and the reaction mixture was purged with nitrogen for further 10 min. The reaction mixture was heated to 75° C. for 12 h. Then the reaction mixture was concentrated under reduced pressure and the residue was diluted with EtOAc (100 mL) and washed with water (2×100 mL), brine (50 mL), dried over $Na_2SO_4$, filtered and concentrated under reduced pressure. The residue was purified by combiflash (Silicycle, $SiO_2$, 10-15% EtOAc/petroleum ether) to afford QC-17.1, step c (6.5 g) as a white solid. $^1$H NMR ($CDCl_3$, δ=7.26 ppm, 400 MHz): δ 8.06-8.04 (m, 2H), 7.81 (d, J=8.0 Hz, 1H), 7.72-7.70 (m, 2H), 7.54-7.49 (m, 2H), 2.65 (s, 3H), 2.63 (s, 6H).

Example QC-17.1, step d

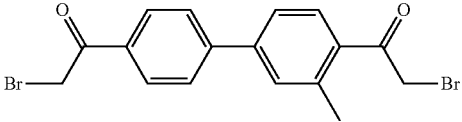

Bromine (1.12 mL, 21.8 mmol) (diluted in 10 mL of dioxane) was added slowly (over 10 min) to a solution of QC-17.1, step c (2.75 g, 10.90 mmol) in dioxane (50 mL) at 10° C., and the mixture was stirred at room temperature for 2 h. The reaction was quenched with 10% $NaHCO_3$ (25 mL) and extracted with DCM (50 mL). The organic phase was dried over $Na_2SO_4$ and concentrated under reduced pressure to afford crude QC-17.1, step d (5.0 g) which was used as such in the next step without purification. LC/MS: Anal. Calcd. For $[M+H]^+$ $C_{17}H_{15}{}^{79/81}Br_2O_2$: 410.94. found 411.0.

Example QC-17.1, step e

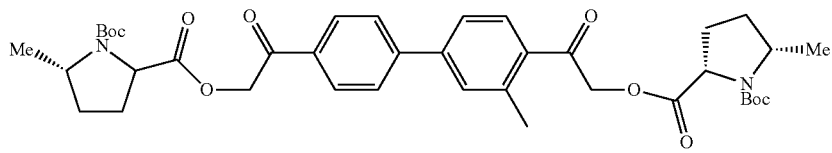

To a solution of crude QC-17.1, step d (5.1 g, 12 mmol) in acetonitrile (75 mL) was added QC-17.1, step a (5.70 g, 24.9 mmol) followed by DIEA (8.69 mL, 49.7 mmol) at 0° C. After 10 min, the temperature was raised to room temperature and stirred for 2 h. Then the reaction mixture was diluted with EtOAc (100 mL) and washed with 10% NaHCO$_3$ (50 mL), brine (50 mL), dried over Na$_2$SO$_4$, filtered and concentrated under reduced pressure. The residue was purified by combiflash (Silicycle, SiO$_2$, 25-30% EtOAc/petroleum ether) to afford QC-17.1, step e (5.8 g) as a pale yellow oil. $^1$H NMR (CDCl$_3$, δ=7.26 ppm, 400 MHz): δ 8.00 (app bd, 2H), 7.71 (app d, 3H), 7.53-7.51 (m, 2H), 5.61-5.34 (m, 2H), 5.29-5.04 (m, 2H), 4.51-4.36 (m, 2H), 4.09-3.91 (m, 2H), 2.59 (s, 3H), 2.35-2.21 (m, 4H), 2.15-2.04 (m, 2H), 1.80-1.63 (m, 2H), 1.47/1.44 (s, 18H), 1.35-1.27 (m, 6H). LC/MS: Anal. Calcd. for [M–H]$^-$ C$_{39}$H$_{49}$N$_2$O$_{10}$: 705.35. found 705.30.

Example QC-17.1, step f

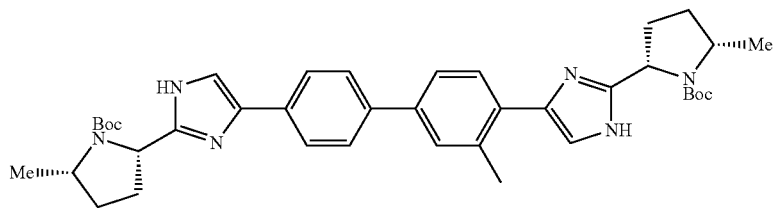

To a solution of QC-17.1, step e (5.6 g, 7.92 mmol) in xylenes (75 mL) was added NH$_4$OAc (12.21 g, 158 mmol), and the reaction mixture was purged with nitrogen for 10 min. After heating for 18 h at 130° C., the reaction mixture was cooled to room temperature and the volatile components were removed under reduced pressure. Then the reaction mixture was diluted with EtOAc (100 mL) and washed with 10% NaHCO$_3$ (50 mL), brine (50 mL), dried over Na$_2$SO$_4$, filtered and concentrated under reduced pressure. The residue was purified by combiflash (Redi Sep, C-18 column, 30-40% acetonitrile:10 mM ammonium bicarbonate) to afford QC-17.1, step f (2.3 g) as pale yellow solid. $^1$H NMR (DMSO-d$_6$, δ=2.50 ppm, 400 MHz): δ 12.27/12.0/11.77/11.71 (s, 2H), 7.92-7.63 (m, 5H), 7.58-7.47 (m, 3H), 7.24 (br s, 1H), 4.90-4.75 (m, 2H), 3.92-3.84 (m, 2H), 2.54 (s, 3H), 2.20-2.01 (m, 6H), 1.73-1.65 (m, 2H), 1.48-1.12 (m, 24H). LC/MS: Anal. Calcd. For [M–H]$^-$ C$_{39}$H$_{49}$N$_6$O$_4$: 665.39. found 665.4.

Example QC-17.1, step g

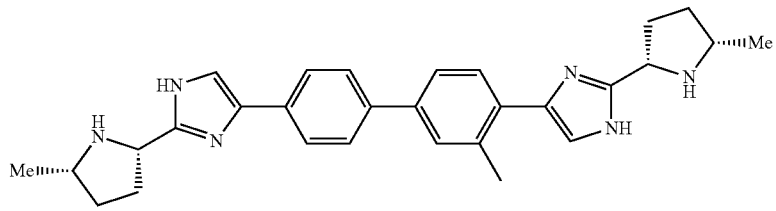 [SMILES: Cc1cc(-c2ccc(-c3c[nH]c([C@@H]4CC[C@H](C)N4)n3)cc2)ccc1-c1c[nH]c([C@@H]2CC[C@H](C)N2)n1]

To a solution of QC-17.1, step f (1.55 g, 2.32 mmol) in MeOH (10 mL) was added in HCl/MeOH (4N, 58.1 mL) and stirred at room temperature for 2 h. The volatile components were removed in vacuo, and the residue was co-evaporated with dry DCM (3×25 mL). The resulting solid was exposed to high vacuum to afford the HCl salt of QC-17.1, step e (1.3 g) as a pale yellow solid. $^1$H NMR (MeOD, δ=3.34 ppm, 400 MHz): δ 8.06 (br s, 1H), 7.98 (d, J=8.4 Hz, 2H), 7.90 (d, J=8.4 Hz, 2H), 7.86 (br s, 1H), 7.78 (br s, 1H), 7.74 (d, J=8.4 Hz, 1H), 7.71 (d, J=8.4 Hz, 1H), 5.27-5.20 (m, 2H), 4.04-4.00 (m, 2H), 2.80-2.67 (m, 4H), 2.59 (s, 3H), 2.55-2.46 (m, 2H), 2.15-2.06 (m, 2H), 1.60 (d, J=6.4, 6H). LC/MS: Anal. Calcd. For [[M+H]$^+$ C$_{29}$H$_{35}$N$_6$: 467.28. found 467.2.

Example QC-17.1

HATU (37.2 mg, 0.098 mmol) was added to a stirred solution of Cap 5.2 (26.2 mg, 0.108 mmol) and Example QC-17.1, step g (30 mg, 0.049 mmol) in DMF (2 mL) and DIEA (0.051 ml, 0.294 mmol). The reaction mixture was stirred at room temperature for 2 h and concentrated under vacuum. The residue was diluted with MeOH, filtered and purified by prep HPLC (Waters Sunfire C18 OBD 30×100 mm 5 u; MeOH/water w/TFA buffer) to afford the TFA salt of Example QC-17.1 (34 mg) as an off-white solid. LC/MS (Cond. 1): R$_t$=1.743 min; LC/MS: Anal. Calcd. for [M+H]$^+$ C$_{51}$H$_{65}$N$_8$O$_8$: 917.12. found 917.9; HPLC (Cond. 6): R$_t$=26.27; 97% homogeneity. $^1$H NMR (500 MHz, CD$_3$OD) δ 8.05-7.92 (m, 1H), 7.90-7.83 (m, 4H), 7.75 (s, 1H), 7.72-7.65 (m, 1H), 7.63 (s, 1H), 7.56 (d, J=8.2 Hz, 1H), 5.25-5.10 (m, 2H), 4.84-4.78 (m, 2H), 4.27-4.15 (m, 2H), 3.79 (d, J=7.9 Hz, 2H), 3.65 (s, 4H), 3.49-3.38 (m, 2H), 2.59-2.51 (m, 2H), 2.47 (s, 3H), 2.42-2.33 (m, 2H), 2.33-2.23 (m, 2H), 2.16 (d, J=17.7 Hz, 2H), 2.04-1.95 (m, 2H), 1.82 (t, J=12.2 Hz, 1H), 1.67-1.52 (m, 6H), 1.51-1.38 (m, 2H), 1.36-1.21 (m, 5H), 0.83-0.72 (m, 2H), 0.63-0.45 (m, 4H), 0.43-0.30 (m, 2H).

Example QC-17.2

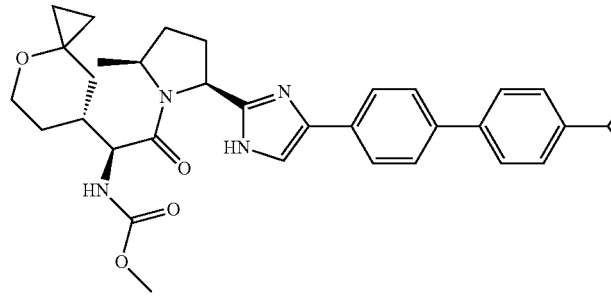

The TFA salt of Example QC-17.2 was prepared by substituting Cap 5.1 for Cap 5.2 and using the same procedure described for Example QC-17.1. LC/MS (Cond. 1): R$_t$=1.710 min; LC/MS: Anal. Calcd. for [M+H]$^+$ C$_{51}$H$_{65}$N$_8$O$_8$ 917.12. found 917.6; HPLC (Cond. 6): R$_t$=26.05; 98% homogeneity. $^1$H NMR (500 MHz, CD$_3$OD) δ 8.01-7.95 (m, 1H), 7.90 (s, 1H), 7.88-7.80 (m, 5H), 7.75 (s, 1H), 7.72-7.66 (m, 2H), 7.63 (s, 1H), 7.54 (d, J=7.9 Hz, 1H), 5.16 (dd, J=10.1, 7.3 Hz, 2H), 4.82-4.74 (m, 2H), 4.22 (d, J=8.9 Hz, 2H), 3.89-3.81 (m, 2H), 3.67 (s, 6H), 3.53-3.45 (m, 2H), 2.58-2.50 (m, 3H), 2.47 (s, 3H), 2.42-2.33 (m, 3H), 2.27 (br. s., 2H), 2.15 (dd, J=19.5, 10.1 Hz, 2H), 1.98 (dd, J=11.7, 5.3 Hz, 2H), 1.89 (t, J=12.4 Hz, 2H), 1.79 (d, J=12.2 Hz, 2H), 1.55 (t, J=6.7 Hz, 6H), 1.46-1.38 (m, 2H), 1.35-1.27 (m, 3H), 0.76 (dt, J=11.1, 5.3 Hz, 2H), 0.69-0.50 (m, 5H), 0.38 (d, J=5.5 Hz, 2H), 0.25-0.12 (m, 2H).

Example QC-18.1

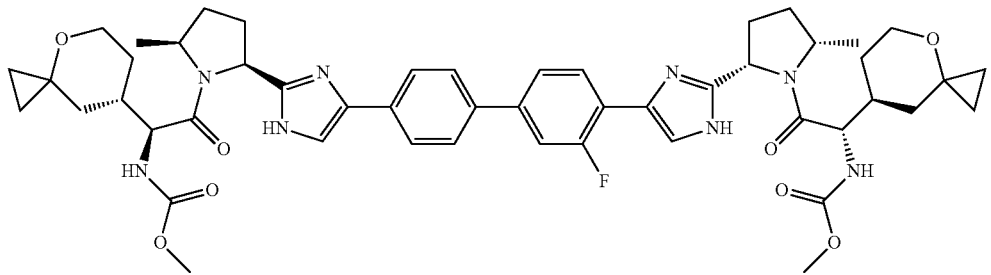 [SMILES: COC(=O)N[C@H](C(=O)N1[C@@H](C)CC[C@H]1c1nc(-c2ccc(-c3ccc(-c4c[nH]c([C@@H]5CC[C@H](C)N5C(=O)[C@@H](NC(=O)OC)[C@H]5CCOC6(CC6)C5)n4)c(F)c3)cc2)c[nH]1)[C@H]1CCOC2(CC2)C1]

Example QC-18.1, step a

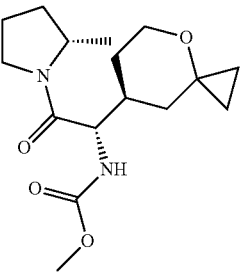

To a solution of 1-(4-bromo-2-fluorophenyl)ethanone (5.0 g, 23 mmol) in dioxane (150 mL) and ether (150 mL) in a ice-water bath at 0° C. was added bromine (1.18 mL, 23.0 mmol) dropwise. The reaction was stirred for 1 h, allowed to warm to room temperature and stirred for 16 h. The mixture was partitioned between EtOAc (50 mL) and sat. NaHCO$_3$ (50 mL), and the organic layer was washed with water and dried over Na$_2$SO$_4$. The volatile component was evaporated in vacuo and the solid was dried under vacuum overnight to afford Example 18.1, step a (6.94 g) as white solid. $^1$H NMR (DMSO-d$_6$, δ=2.5 ppm, 400 MHz): 7.87-7.79 (m, 2H), 7.62-7.60 (m, 1H), 4.84 (s, 2H).

Example QC-18.1, step b

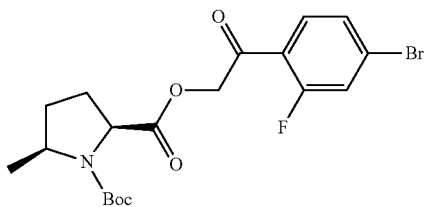 [SMILES: C[C@H]1CC[C@@H](C(=O)OCC(=O)c2ccc(Br)cc2F)N1C(=O)OC(C)(C)C]

To a solution of Example 18.1, step a (2.58 g, 8.72 mmol) and (2S,5S)-1-(tert-butoxycarbonyl)-5-methylpyrrolidine-2-carboxylic acid (2.00 g, 8.72 mmol) in acetonitrile (50 mL) was added DIEA (2.285 mL, 13.08 mmol), and the mixture was stirred at room temperature for 64 h. Solvent was removed in vacuo and the residue was partitioned between EtOAc (40 mL) and water (30 mL). The organic layer was washed with sat. NaHCO$_3$ and brine, dried with Na$_2$SO$_4$ and evaporated in vacuo to afford Example 18.1, step b (3.8 g) as yellow solid. $^1$H NMR (CDCl$_3$, 400 MHz): 7.87 (m, 1H), 7.44 (m, 2H), 5.42-5.09 (m, 2H), 4.53-4.40 (m, 1H), 4.10-3.95 (m, 1H), 2.31 (m, 2H), 2.09 (m, 1H), 1.75 (m, 1H), 1.49-1.46 (two singlet, 9H), 1.33 (m, 3H). LC/MS: Anal. Calcd. for [M+Na]$^+$ C$_{19}$H$_{24}$BrNNaO$_5$: 466.06. found: 466.03.

Example QC-18.1, step c

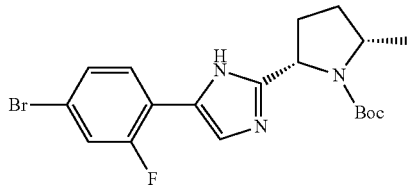 [SMILES: C[C@H]1CC[C@@H](c2ncc(-c3ccc(Br)cc3F)[nH]2)N1C(=O)OC(C)(C)C]

To a pressure tube containing a solution of Example 18.1, step b (3.8 g, 8.6 mmol) in xylenes (40 mL) was added ammonium acetate (6.59 g, 86 mmol), and the reaction vessel was capped and heated at 140° C. for 6 h. The volatile component was evaporated in vacuo and the residue was partitioned between DCM (80 mL) and water (50 mL). The organic layer was separated and washed with sat. NaHCO$_3$, and dried with Na$_2$SO$_4$. Removal of the solvent in vacuo resulted in a red oil which was purified by flash chromatograph (0-40% EtOAc/Hexane) to afford Example 18.1, step c (2.3 g) as brown solid. $^1$H NMR (DMSO-d$_6$, δ=2.5 ppm, 400 MHz): 7.98 (app. t, J=8.4 Hz, 1H), 7.65 (dd, J=11, 1.9 Hz, 1H), 7.45 (dd, J=8.3, 2, 1H), 7.36 (m, 1H), 4.85 (m, 1H), 3.90 (m, 1H), 2.15-2.07 (m, 3H), 1.73 (m, 1H), 1.40-1.17 (m, 12H). LC/MS: Anal. Calcd. for [M+Na]$^+$ C$_{19}$H$_{23}$$^{79}$BrFN$_3$NaO$_2$: 446.09. found: 446.00.

Example QC-18.1, step d

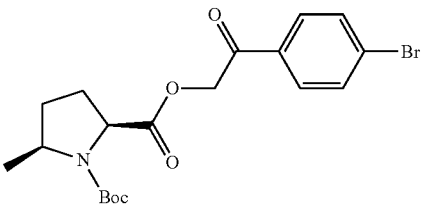 [SMILES: C[C@H]1CC[C@@H](C(=O)OCC(=O)c2ccc(Br)cc2)N1C(=O)OC(C)(C)C]

To a solution of 2-bromo-1-(4-bromophenyl)ethanone (2.425 g, 8.72 mmol) and (2S,5S)-1-(tert-butoxycarbonyl)-5-methylpyrrolidine-2-carboxylic acid (2 g, 8.72 mmol) in acetonitrile (50 mL) was added DIEA (1.524 mL, 8.72 mmol), and the mixture was stirred at room temperature for 16 h. Solvent was removed in vacuo and the residue was partitioned between EtOAc (40 mL) and water (30 mL). The organic phase was washed with sat. NaHCO$_3$ and brine, and dried with Na$_2$SO$_4$. Removal of the volatile component in vacuo afforded Example 18.1, step d (1.74 g) as light yellow solid, which was used without further purification. $^1$H NMR (DMSO-d$_6$, δ=2.5 ppm, 400 MHz): 7.95-7.90 (m, 2H), 7.81 (m, 1H), 7.79 (m, 1H), 5.63-5.44 (m, 2H), 4.36 (m, 1H), 3.99 (m, 1H), 2.27 (m, 1H), 2.09 (m, 2H), 1.63 (m, 1H), 1.41-1.37 (two singlet, 9H), 1.19 (m, 3H). LC/MS: Anal. Calcd. for [M+Na]$^+$ C$_{19}$H$_{24}$BrNNaO$_5$: 448.07. found: 448.06.

Example QC-18.1, step e

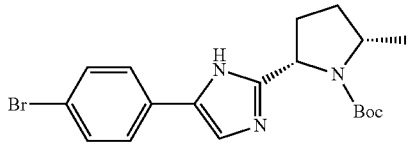 [SMILES: C[C@H]1CC[C@@H](c2ncc(-c3ccc(Br)cc3)[nH]2)N1C(=O)OC(C)(C)C]

To a pressure tube containing a solution of Example 18.1, step d (3.4 g, 8.0 mmol) in xylenes (40 mL) was added ammonium acetate (6.15 g, 80 mmol), and the mixture was heated at 140° C. for 6 h. The volatile component was removed in vacuo, the residue was partitioned carefully between DCM (60 mL) and sat. NaHCO$_3$ (30 mL), and the organic layer was separated and dried with Na$_2$SO$_4$. The solvent was removed in vacuo to give red solid, which was purified by flash chromatograph (5-50% EtOAc/Hexane) to afford Example 18.1, step e (2.65 g) as light brown solid. $^1$H NMR (DMSO-d$_6$, δ=2.5 ppm, 400 MHz): 7.73-7.71 (m, 2H), 7.59-7.50 (m, 3H), 4.80 (m, 1H), 3.89 (m, 1H), 2.10 (m, 3H), 1.71 (m, 1H), 1.40-1.17 (m, 12H). LC/MS: Anal. Calcd. for [M+Na]$^+$ C$_{19}$H$_{24}$BrN$_3$NaO$_2$: 428.09. found: 428.07.

Example QC-18.1, step f

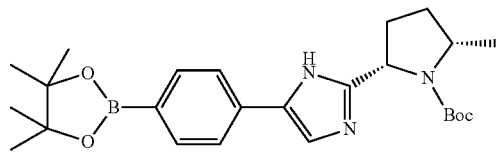

To a solution of Example 18.1, step e (2.64 g, 6.50 mmol) and 4,4,4',4',5,5,5',5'-octamethyl-2,2'-bi(1,3,2-dioxaborolane) (3.30 g, 13.0 mmol) in dioxane (40 mL) was added potassium acetate (1.594 g, 16.24 mmol). The mixture was degassed by bubbling nitrogen for 10 min, Pd(Ph$_3$P)$_4$ (0.375 g, 0.325 mmol) was added and degassing was continued for an additional 15 min. The reaction vessel was then sealed and heated at 80° C. for 16 h. The volatile component was evaporated in vacuo and the residue was partitioned between DCM (100 mL) and half sat. NaHCO$_3$ (50 mL). The organic layer was separated, dried with Na$_2$SO$_4$, and evaporated in vacuo to afford a crude red oil which was purified by flash chromatograph (10-90% EtOAc/hexanes). Example 18.1, step f (2.7 g) was obtained as yellow foam. $^1$H NMR (DMSO-d$_6$, δ=2.5 ppm, 400 MHz): 7.77 (d, J=8.3 Hz, 2H), 7.64-7.53 (m, 3H), 4.80 (m, 1H), 3.88 (m, 1H), 2.09 (m, 3H), 1.73 (m, 1H), 1.43-1.08 (m, 24H). LC/MS: Anal. Calcd. for [M+H]$^+$ C$_{25}$H$_{37}$BrBN$_3$O$_4$: 454.29. found: 454.23.

Example QC-18.1, step g

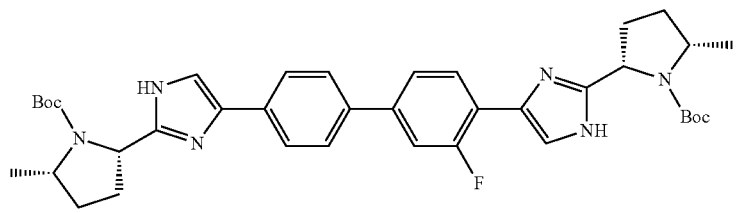

To a pressure tube containing a solution of Example 18.1, step f (2.70 g, 5.96 mmol) and Example 4, step c (2.30 g, 5.42 mmol) in DME (70 mL) were added water (17.50 mL) and sodium bicarbonate (2.27 g, 27.1 mmol). The mixture was degassed by bubbling nitrogen for 15 min and Pd(Ph$_3$P)$_4$ (0.313 g, 0.271 mmol) was added and degassing was continued for an additional 15 min. The reaction vessel was sealed and heated at 80° C. for 15 h. The solvent was evaporated in vacuo and the residue was partitioned between DCM (100 mL) and water (50 mL). The organic layer was separated, dried with Na$_2$SO$_4$ and the volatile component was removed in vacuo and the resultant red crude solid was purified by flash chromatograph (30-100% EtOAc/Hexane). Example 18.1, step g (1.95 g) was obtained as yellow solid. $^1$H NMR (DMSO-d$_6$, δ=2.5 ppm, 400 MHz): 8.10 (m, 1H), 7.87-7.71 (m, 4H), 7.61-7.55 (m, 3H), 7.37 (m, 1H), 4.85 (m, 2H), 3.91 (m, 2H), 2.11 (m, 6H), 1.76 (m, 2H), 1.42-1.08 (m, 24H). LC/MS: Anal. Calcd. for [M+H]$^+$ C$_{35}$H$_{48}$FN$_6$O$_4$: 671.37. found: 671.35.

Example QC-18.1, step h

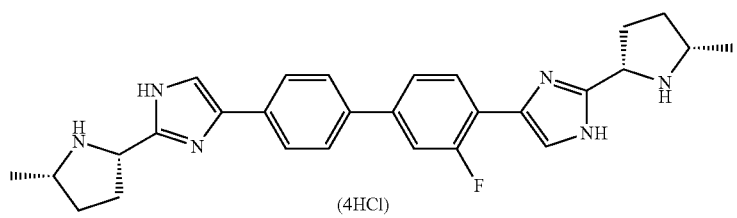

To a suspension of Example 18.1, step g (1.95 g, 2.91 mmol) in dioxane (10 mL) was added 4N HCl in dioxane (9.72 mL, 320 mmol), and the mixture was stirred at room temperature for 6 h. Methanol (1 mL) was added and stirring was continued for 1 h. The volatile component was removed in vacuo and the residue was dried under vacuum overnight. The HCl salt of Example 18.1, step h (1.7 g) was retrieved as yellow solid. $^1$H NMR (DMSO-d$_6$), δ=2.5 ppm, 400 MHz): 10.34/10.29/9.43/9.08 (four broad S, ~4H), 8.16 (t, J=8.3 Hz, 1H), 8.10 (br s, 1H), 8.00 (d, J=8.3 Hz, 2H), 7.92 (d, J=8.3 Hz, 2H), 7.78-7.72 (m, 3H), 4.99-4.89 (m, 2H), 3.80 (m, 2H), 2.53-2.42 (m, 4H), 2.25 (m, 2H), 1.87 (m, 2H), 1.44 (d, J=6.5, 3H), 1.43 (d, J=6.5, 3H). LC/MS: Anal. Calcd. for [M+H]$^+$ C$_{28}$H$_{32}$FN$_6$: 471.27. found: 471.17.

Example QC-18.1

HATU (37.0 mg, 0.097 mmol) was added to a stirred solution of Cap 5.2 (26.0 mg, 0.107 mmol) and Example QC-18.1, step f (30 mg, 0.049 mmol) in DMF (2 mL) and DIEA (0.051 ml, 0.294 mmol). The reaction mixture was stirred at room temperature for 2 h and concentrated under vacuum. The residue was diluted with MeOH, filtered and purified by prep HPLC (Waters Sunfire C18 OBD 30×100 mm 5 u; MeOH/water w/TFA buffer) to afford the TFA salt of Example QC-17.1 (34 mg) as an off-white solid. LC/MS (Cond. 1): R$_f$=1.77 min; LC/MS: Anal. Calcd. for [M+H]$^+$ C$_{50}$H$_{62}$FN$_8$O$_8$ 921.47. found 921.11; HPLC (Cond. 6): R$_f$=26.39; 99% homogeneity. $^1$H NMR (500 MHz, CD$_3$OD) δ 8.13-7.98 (m, 1H), 7.95-7.84 (m, 5H), 7.82 (s, 1H), 7.75-7.67 (m, 2H), 5.24-5.12 (m, 2H), 4.82-4.76 (m, 2H), 4.28-4.17 (m, 2H), 3.87-3.75 (m, 2H), 3.72-3.61 (m, 6H), 3.42 (t, J=11.6 Hz, 2H), 2.52 (d, J=3.4 Hz, 2H), 2.44-2.23 (m, 4H), 2.18-2.08 (m, 2H), 2.03-1.94 (m, 2H), 1.82 (t, J=12.2 Hz, 2H), 1.58 (d, J=6.7 Hz, 6H), 1.47 (td, J=12.1, 8.2 Hz, 2H), 1.33-1.18 (m, 5H), 0.84-0.74 (m, 2H), 0.57 (br. s., 2H), 0.50 (br. s., 2H), 0.37 (d, J=4.0 Hz, 2H).

Example QC-18.2

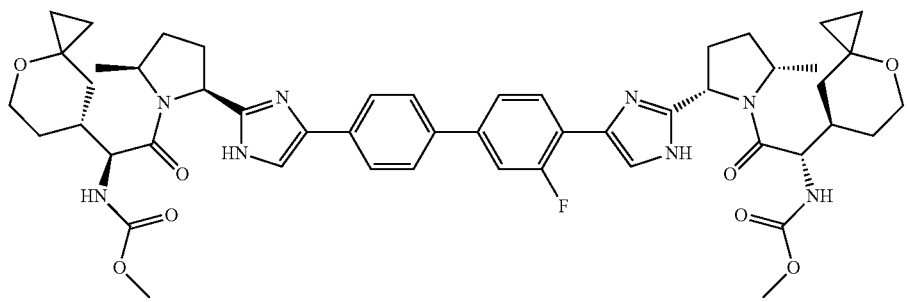 [SMILES: COC(=O)N[C@H](C(=O)N1[C@@H](C)CC[C@H]1c1nc(-c2ccc(-c3ccc(-c4c[nH]c([C@@H]5CC[C@H](C)N5C(=O)[C@@H](NC(=O)OC)[C@@H]5CCOC6(CC6)C5)n4)c(F)c3)cc2)c[nH]1)[C@@H]1CCOC2(CC2)C1]

The TFA salt of Example QC-18.2 was prepared by substituting Cap 5.1 for Cap 5.2 using the same procedure described for Example QC-18.1. LC/MS (Cond. 1): $R_t$=1.75 min; LC/MS: Anal. Calcd. for [M+H]$^+$ $C_{50}H_{62}FN_8O_8$ 921.47. found 921.25; HPLC (Cond. 6): $R_t$=26.02 min; 98% homogeneity. $^1$H NMR (400 MHz, CD$_3$OD) δ 7.96 (d, J=9.3 Hz, 1H), 7.92-7.80 (m, 6H), 7.79-7.64 (m, 4H), 5.26-5.12 (m, 2H), 4.22 (d, J=6.5 Hz, 3H), 3.84 (d, J=7.8 Hz, 3H), 3.73-3.64 (m, 7H), 3.48 (t, J=11.8 Hz, 3H), 2.56-2.48 (m, 2H), 2.45-2.23 (m, 5H), 2.18-2.09 (m, 2H), 2.04-1.94 (m, 3H), 1.94-1.74 (m, 5H), 1.55 (d, J=6.3 Hz, 6H), 1.47-1.35 (m, 3H), 1.29 (br. s., 4H), 1.03-0.84 (m, 3H), 0.81-0.70 (m, 3H), 0.63 (t, J=13.6 Hz, 3H), 0.54 (d, J=4.8 Hz, 2H), 0.38 (d, J=5.3 Hz, 2H), 0.24-0.08 (m, 2H).

Example QC-19

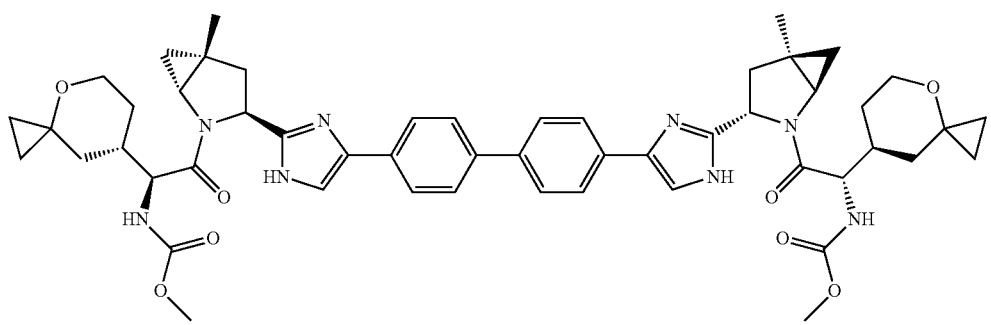 [SMILES: COC(=O)N[C@H](C(=O)N1[C@H](c2nc(-c3ccc(-c4ccc(-c5c[nH]c([C@@H]6C[C@@]7(C)C[C@H]7N6C(=O)[C@@H](NC(=O)OC)[C@H]6CCOC7(CC7)C6)n5)cc4)cc3)c[nH]2)C[C@@]2(C)C[C@@H]12)[C@H]1CCOC2(CC2)C1]

Example QC-19, step a

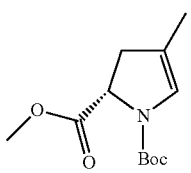

The above ester was prepared as a diastereomeric mixture from (S)-1-tert-butyl 2-methyl 5-oxopyrrolidine-1,2-dicarboxylate according to the procedure described in *Tetrahedon Letters*, 2003, 3203-3205.

Example QC-19, step b

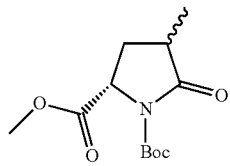 [SMILES: COC(=O)[C@@H]1CC(C)C(=O)N1C(=O)OC(C)(C)C]

To a cooled (-50° C.) toluene (45 mL) solution of Example QC-19, step a (4.75 g, 18.5 mmol) was added Superhydride (19.20 mL of 1M/THF, 19.20 mmol) dropwise over 10 min. Hunig's base (13.6 mL, 78 mmol) was added, and stirred for 10 min; DMAP (0.122 g, 0.997 mmol) was added as a solid, stirred for 15 min; and, trifluoroacetic anhydride (2.98 mL, 21.1 mmol) was added dropwise over 15 min, the cooling bath was removed, and stirring was continued for 4 hr while allowing it to warm to room temperature. The reaction mixture was washed with water (50 mL), sat. NaCl (30 mL), and the organic phase was concentrated in vacuo. The resulting crude material was purified with flash chromatography (8-60% EtOAc/Hexane) to afford Example QC-19, step b as yellow oil (2.85 g). $^1$H NMR (CDCl$_3$, 400 MHz): 6.36 (s, 0.5H), 6.25 (s, 0.5H), 4.70-4.57 (m, 1H), 3.78 (s, 3H), 2.96 (m, 1H), 2.54 (m, 1H), 1.70 (s, 3H), 1.50 (s, 4.5H), 1.44 (s, 4.5H).

Example QC-19, step c

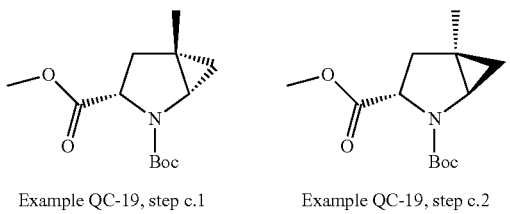 [SMILES: COC(=O)[C@@H]1C[C@]2(C)C[C@@H]2N1C(=O)OC(C)(C)C ; COC(=O)[C@@H]1C[C@@]2(C)C[C@H]2N1C(=O)OC(C)(C)C]

Example QC-19, step c.1    Example QC-19, step c.2

Diethylzinc (1.1 M in toluene, 59.1 mL, 65.0 mmol) was added dropwise over 20 min to a cooled (−23° C.) toluene (60 mL) solution of Example QC-19, step b (5.23 g, 21.7 mmol), and stirred for 10 min. Chloroiodomethane (9.44 mL, 130 mmol) was added dropwise over 10 min, and the reaction mixture was stirred at −21° C. for 16 h. Sat. NaHCO₃ (60 mL) was added to the reaction mixture, the cooling bath was removed, and the mixture was stirred for 10 min. It was then filtered, and the filter cake was washed with toluene (50 mL). The filtrate was partitioned, and the organic layer was dried with Na₂SO₄, and concentrated in vacuo. The resulting crude material was purified with flash chromatography (2-10% EtOAc/Hexane) to afford Example QC-19, step c.1 (first elute; colorless oil; 2.88 g) and Example QC-19, step c.2 (second elute; colorless oil; 1.01 g). Relative stereochemical assignment was made based on NOE studies. Example QC-19, step c.1: $^1$H NMR (CDCl$_3$, 400 MHz): 4.65-4.52 (m, 1H), 3.72 (s, 3H), 3.28-3.17 (m, 1H), 2.44-2.32 (m, 1H), 2.16-2.10 (m, 1H), 1.51-1.42 (two s, 9H), 1.24 (s, 3H), 1.07 (m, 1H), 0.69-0.60 (m, 1H). Example QC-19, step c.2: $^1$H NMR (CDCl$_3$, 400 MHz): 4.0 (m, 1H), 3.76 (s, 3H), 3.32-3.16 (m, 1H), 2.43 (m, 1H), 2.01 (m, 1H), 1.44 (s, 9H), 1.35 (s, 3H), 0.76-0.66 (m, 2H).

Example QC-19, step d

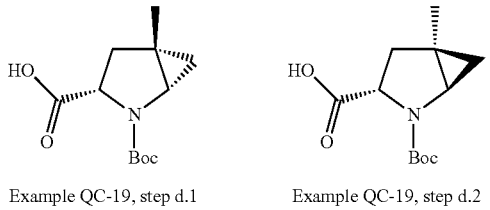 [SMILES: CC(C)(C)OC(=O)N1[C@H]2C[C@@]2(C)C[C@H]1C(=O)O ; CC(C)(C)OC(=O)N1[C@H](C(=O)O)C[C@@]2(C)C[C@@H]12]

Example QC-19, step d.1    Example QC-19, step d.2

To a solution of Example QC-19, step c.1 (2.88 g, 11.3 mmol) in ethanol (20 mL) was added a solution of LiOH (0.324 g, 13.5 mmol) in water (10.00 mL), and the reaction mixture was stirred at room temperature for 6 h. Most of the volatile component was removed in vacuo, and the residue was partitioned between water (20 mL) and ether (20 mL). The aqueous layer was chilled in an ice-water bath, acidified with a 1N HCl to a pH region of 2, and extracted with EtOAc (30 mL, 4×). The combined organic phase was dried with Na₂SO₄ and evaporated in vacuo to afford Example QC-19, step d.1 as a sticky solid (2.55 g). $^1$H NMR (CDCl$_3$, 400 MHz): 4.64 (m, 1H), 3.25 (appt s, 1H), 2.70-2.40 (m, 1H), 2.14 (m, 1H), 1.54-1.44 (m, 9H), 1.27 (s, 3H), 1.10-0.80 (m, 1H), 0.67 (m, 1H). Example QC-19, step d.2 was prepared similarly from Example QC-19, step c.2. $^1$H NMR (CDCl$_3$, 400 MHz): 4.13 (app br s, 1H), 3.06 (app br s, 1H), 2.55/2.41 (overlapping app br s, 2H), 1.51 (s, 9H), 1.27 (s, 3H), 0.76 (app t, J=5.6 Hz, 1H), 0.60 (app br s, 1H).

Example QC-19, step e

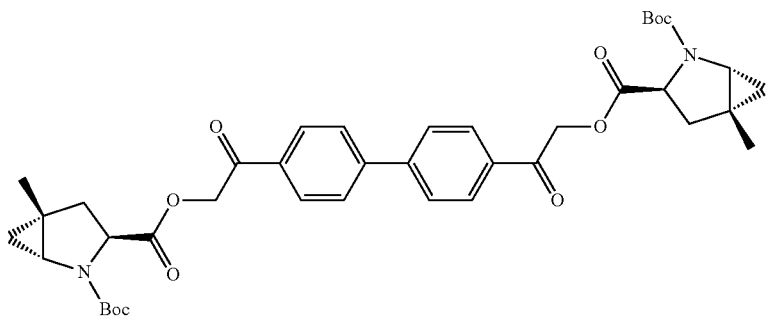 [SMILES: CC(C)(C)OC(=O)N1[C@H](C(=O)OCC(=O)c2ccc(-c3ccc(C(=O)COC(=O)[C@@H]4C[C@@]5(C)C[C@H]5N4C(=O)OC(C)(C)C)cc3)cc2)C[C@@]2(C)C[C@@H]12]

To a suspension of Example QC-19, step d.2 (1.09 g, 4.52 mmol) and 1,1'-(biphenyl-4,4'-diyl)bis(2-bromoethanone) (0.869 g, 2.19 mmol) in acetonitrile (40 mL) was added DIEA (0.789 mL, 4.52 mmol), and the mixture was stirred at room temperature for 4 h. The volatile component was removed in vacuo, and the residue was partitioned between EtOAc (70 mL) and water (50 mL). The organic layer was washed with sat. NaHCO₃ (50 mL), dried with Na₂SO₄, evaporated in vacuo and dried under vacuum to give Example QC-19, step e (1.54 g) as white foam. $^1$H NMR (DMSO-d$_6$, δ=2.5 ppm, 400 MHz): 8.13 (d, J=8.3 Hz, 4H), 7.99 (d, J=8.5 Hz, 4H), 5.70-5.54 (m, 4H), 4.17 (m, 2H), 3.13-3.11 (m, 2H), 2.58-2.46 (m, 2H), 2.19 (m, 2H), 1.42-1.37 (two s, 18H), 1.24 (s, 6H), 0.76-0.70 (m, 4H). LC/MS: Anal. Calcd. for [M+Na]$^+$ C$_{40}$H$_{48}$N$_2$NaO$_{10}$: 739.32. found: 739.52.

Example QC-19, step f

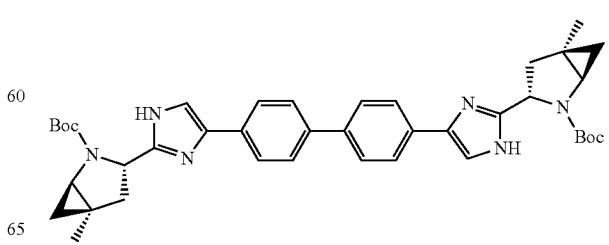

To a pressure tube containing a solution of Example QC-19, step e (1.54 g, 2.15 mmol) in xylenes (40 mL) was added ammonium acetate (1.656 g, 21.48 mmol), and the vessel was capped and heated at 140° C. for 5 h. The volatile component was removed in vacuo and the residue was carefully partitioned between DCM (50 mL) and water (50 mL) while adding sufficient saturated NaHCO$_3$ solution so that at the end of partitioning, the aqueous phase is neutral or basic. The organic layer was dried with Na$_2$SO$_4$, evaporated in vacuo, and the resulting crude material was purified by flash chromatograph (10-100% EtOAc/Hexane) to afford Example QC-19, step f (0.65 g) as brown solid. $^1$H NMR (DMSO-d$_6$, δ=2.5 ppm, 400 MHz): 7.84-7.65 (m, 8H), 7.55-7.54 (m, 1.7H), 7.32-7.30 (m, 0.3H), 4.60 (m, 2H), 3.20 (m, 2H), 2.48-2.43 (m, 2H), 2.12 (m, 2H), 1.45-1.07 (m, 24H), 0.77 (m, 2H), 0.69 (m, 2H). LC/MS: Anal. Calcd. for [M+H]$^+$ C$_{40}$H$_{49}$N$_6$O$_4$: 677.38. found: 677.45.

Example QC-19, step g

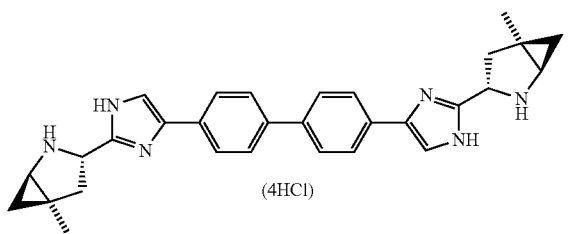 [SMILES: C[C@@]12C[C@@H](c3nc(-c4ccc(-c5ccc(-c6c[nH]c([C@@H]7C[C@@]8(C)C[C@H]8N7)n6)cc5)cc4)c[nH]3)N[C@@H]1C2]

(4HCl)

To a solution of Example QC-19, step f (0.65 g, 0.960 mmol) in dioxane (5 mL) was added 4N HCl in dioxane (5.84 mL, 192 mmol), and the mixture was stirred at room temperature for 6 h. The volatile component was removed in vacuo and dried under vacuum overnight to afford the HCl salt of Example QC-19, step g (0.6 g) as brown solid. $^1$H NMR (DMSO-d$_6$, =2.5 ppm, 400 MHz): 10.5-10 (br s, ~3.2H), 7.99 (br s, 2H), 7.95 (d, J=8.5, 4H), 7.85 (d, J=8.5 Hz, 4H), 4.76 (m, 2H), 3.18 (m, 2H), 2.61-2.46 (m, 4H; overlapped with solvent signal), 1.35 (s, 6H), 1.30 (m, 2H), 0.82 (app br t, J=7.1, 2H). LC/MS: Anal. Calcd. for [M+H]$^+$ C$_{30}$H$_{33}$N$_6$: 477.28. found: 477.22.

Example QC-19

HATU (37.0 mg, 0.097 mmol) was added to a stirred solution of Cap 5.2 (23.5 mg, 0.096 mmol) and Example QC-19, step g, (30 mg, 0.048 mmol) in DMF (2 mL) and IDEA (0.051 ml, 0.294 mmol). The reaction mixture was stirred at room temperature for 2 h and concentrated under vacuum. The residue was diluted with MeOH, filtered and purified by prep HPLC (Waters Sunfire C18 OBD 30×100 mm 5 u; MeOH/water w/TFA buffer) to afford the TFA salt of Example QC-191 (31 mg) as an off-white solid. LC/MS (Cond. 1): R$_t$=1.72 min; LC/MS: Anal. Calcd. for [M+H]$^+$ C$_{52}$H$_{63}$N$_8$O$_8$ 927.48. found 927.05; HPLC (Cond. 6): R$_t$=26.32; 100% homogeneity. $^1$H NMR (500 MHz, CD$_3$OD) δ 7.96-7.74 (m, 10H), 5.02 (t, J=8.5 Hz, 2H), 4.56 (d, J=7.9 Hz, 2H), 3.82 (d, J=10.7 Hz, 2H), 3.66 (s, 5H), 3.60 (d, J=3.4 Hz, 2H), 3.54-3.44 (m, 2H), 2.77 (dd, J=13.3, 9.3 Hz, 2H), 2.32-2.15 (m, 4H), 1.88 (t, J=12.5 Hz, 2H), 1.53 (br. s., 4H), 1.41 (s, 6H), 1.11 (d, J=11.9 Hz, 2H), 1.00 (d, J=5.5 Hz, 2H), 0.95 (d, J=5.5 Hz, 2H), 0.76 (dt, J=10.8, 5.5 Hz, 2H), 0.64-0.58 (m, 2H), 0.52-0.45 (m, 2H), 0.42-0.32 (m, 2H).

Example 1.1 and 1.2

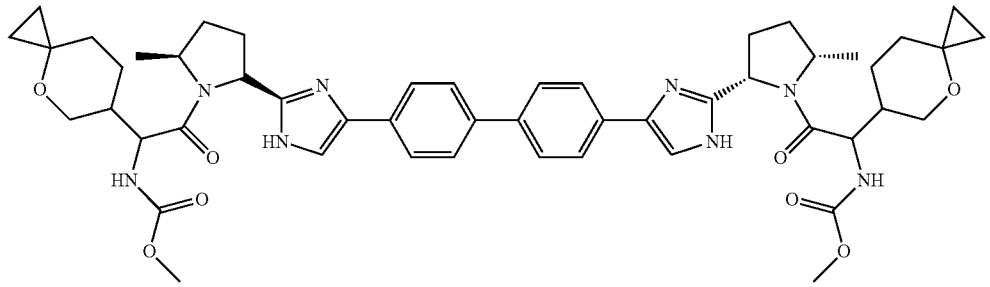

The TFA salt of Example 1.1 was prepared from Cap 8.2 according to the procedure described for Example QC-8.1. LC (Cond. 1): R$_t$=1.15 min; LC/MS: Anal. Calcd. for [M+H]$^+$ C$_{50}$H$_{63}$N$_8$O$_8$ 903.48. found: 903.50; HRMS: Anal. Calcd. for [M+H]$^+$ C$_{50}$H$_{63}$N$_8$O$_8$ 903.4763. found: 903.4755; $^1$H NMR (500 MHz, DMSO-d$_6$) δ 7.89 (br. s., 8H), 7.73 (d, J=7.9 Hz, 2H), 5.02 (t, J=8.5 Hz, 2H), 4.71-4.61 (m, 2H), 4.11 (t, J=8.7 Hz, 2H), 3.78-3.67 (m, 3H), 3.55 (s, 6H), 3.24 (t, J=10.5 Hz, 2H), 2.36 (br. s., 2H), 2.30-2.06 (m, 4H), 1.98 (d, J=9.8 Hz, 2H), 1.89-1.72 (m, 3H), 1.49 (d, J=6.4 Hz, 6H), 1.23 (d, J=5.8 Hz, 1H), 1.09 (d, J=13.4 Hz, 2H), 0.68 (dt, J=10.6, 5.2 Hz, 2H), 0.56-0.40 (m, 4H), 0.36-0.27 (m, 2H).

The TFA salt of Example 1.2 was prepared by using Cap 8.1 according to the procedure described for Example QC-8.1. LC (Cond. 1): R$_t$=1.19 min; LC/MS: Anal. Calcd. for [M+H]$^+$ C$_{50}$H$_{63}$N$_8$O$_8$ 903.48. found: 903.50; $^1$H NMR (500 MHz, DMSO-d$_6$) δ8.02-7.87 (m, 8H), 7.71 (d, J=8.5 Hz, 2H), 5.09-4.97 (m, 2H), 4.62 (t, J=6.7 Hz, 2H), 4.30 (t, J=9.0 Hz, 2H), 3.56 (s, 6H), 3.38 (d, J=8.9 Hz, 2H), 3.17 (dd, J=10.8, 8.1 Hz, 2H), 2.36 (br. s., 2H), 2.29-2.08 (m, 4H), 1.99 (d, J=3.4 Hz, 2H), 1.86-1.75 (m, 3H), 1.54 (d, J=9.2 Hz, 2H), 1.47 (d, J=6.7 Hz, 6H), 1.42 (br. s., 2H), 1.26 (d, J=6.1 Hz, 1H), 0.68-0.59 (m, 2H), 0.57-0.48 (m, 2H), 0.45-0.31 (m, 4H).

Example 2.1 to 2.4

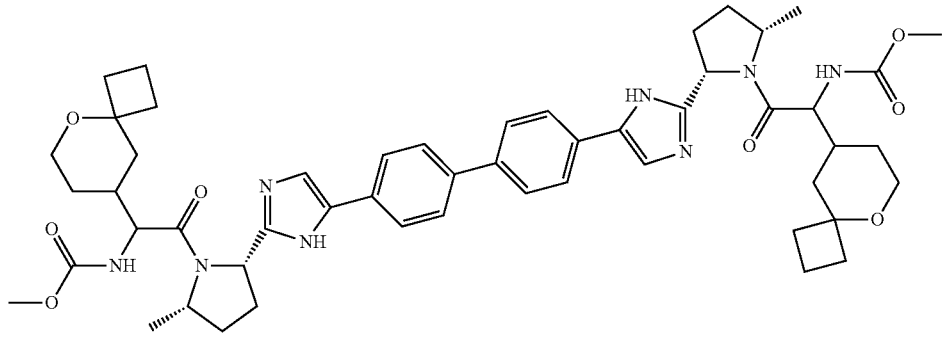

HATU (24.38 mg, 0.064 mmol) was added to a stirred solution of 4,4'-bis(2-((2S,5S)-5-methylpyrrolidin-2-yl)-1H-imidazol-5-yl)-1,1'-biphenyl, 4 HCl (18.3 mg, 0.031 mmol) and Cap 9.1 (16.5 mg, 0.064 mmol) in DMF (0.8 mL) and DIEA (0.037 mL, 0.21 mmol). The reaction was flushed with nitrogen, sealed and then stirred at room temperature for 2 h. The reaction was partially concentrated under a stream of nitrogen and then purified by prep HPLC (ACN/water with a TFA buffer) to yield the TFA salt of Example 2.1 as an off-white solid (23.1 mg). LC-MS retention time 2.205 min; ½ m/z 466.55 (MH+). LC data was recorded on a Shimadzu LC-10AS liquid chromatograph equipped with a Phenomenex-Luna 3 u C18 2.0×50 mm column using a SPD-10AV UV-Vis detector at a detector wave length of 220 nM. The elution conditions employed a flow rate of 0.8 mL/min, a gradient of 100% solvent A/0% solvent B to 0% solvent A/100% solvent B, a gradient time of 4 min, a hold time of 1 min, and an analysis time of 5 min where solvent A was 10% acetonitrile/90% H$_2$O/0.1% trifluoroacetic acid and solvent B was 10% H$_2$O/90% acetonitrile/0.1% trifluoroacetic acid. MS data was determined using a Micromass Platform for LC in electrospray mode.

The TFA salt of Example 2.2 to 2.4 were prepared and characterized in a similar manner to the procedure described for Example 2.1 unless noted otherwise.

| Example # | Starting acid | Ret.time | ½ m/z (MH+) |
|---|---|---|---|
| Example 2.2 | Cap 9.2 | 2.183 | 466.55 |
| Example 2.3 | Cap 9.3 | 1.145* | 466.55 |
| Example 2.4 | Cap 9.4 | 1.183* | 466.55 |

*A gradient time of 2 min, a hold time of 1 min, and an analysis time of 3 min

Example 3.1 to 3.4

HATU (22.8 mg, 0.060 mmol) was added to a stirred clear solution of 4,4'-bis(2-((2S,5S)-5-methylpyrrolidin-2-yl)-1H-imidazol-5-yl)-1,1'-biphenyl, 4 HCl (17.1 mg, 0.029 mmol) and Cap10.1 (16.3 mg, 0.060 mmol) in DMF (0.8 mL) and DIEA (0.035 mL, 0.200 mmol). The reaction was flushed with nitrogen, sealed and then stirred at room temperature for 2 h. The reaction was partially concentrated under a stream of nitrogen and then purified by prep HPLC (ACN/water with a TFA buffer) to yield the TFA salt of Example 3.1 (23.4 mg) as a a white solid. LC-MS retention time 2.425 min; ½ m/z 480.55 (MH+). LC data was recorded on a Shimadzu LC-10AS liquid chromatograph equipped with a Phenomenex-Luna 3 u C18 2.0×50 mm column using a SPD-10AV UV-Vis detector at a detector wave length of 220 nM. The elution conditions employed a flow rate of 0.8 mL/min, a gradient of 100% solvent A/0% solvent B to 0% solvent A/100% solvent B, a gradient time of 4 min, a hold time of 1 min, and an analysis time of 5 min where solvent A was 10% acetonitrile/90% H$_2$O/0.1% trifluoroacetic acid and solvent B was 10% H$_2$O/90% acetonitrile/0.1% trifluoroacetic acid. MS data was determined using a Micromass Platform for LC in electrospray mode. $^1$H NMR (400 MHz, MeOH-d$_4$) δ 7.96-7.83 (m, 10H), 5.32 (t, J=8.4 Hz, 2H), 4.56 (t, J=6.4 Hz, 2H), 4.34 (d, J=8.3 Hz, 2H), 3.81-3.53 (m, 10H), 2.70-2.59 (m, 2H), 2.42-2.21 (m, 4H), 2.12-1.91 (m, 6H), 1.81-1.42 (m, 28H).

The TFA salt of Example 3.2 to 3.4 were prepared and characterized in a similar manner to the procedure described for Example 10.1 unless noted otherwise.

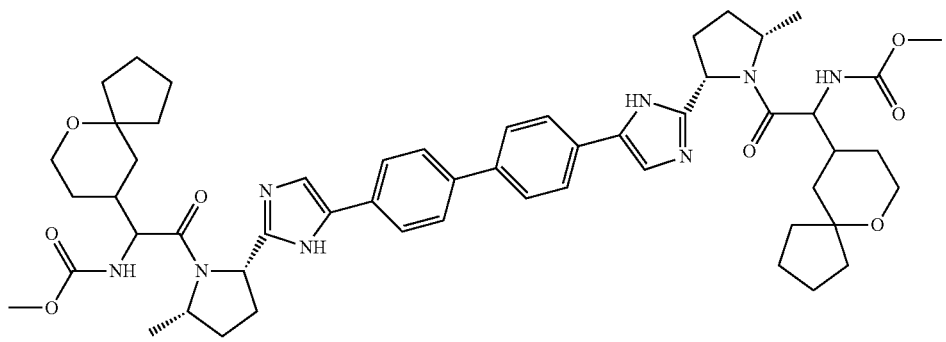

| Example # | Starting acid | Ret.time | ½ m/z (MH⁺) |
|---|---|---|---|
| Example 3.2 | Cap 10, step d.2 | 1.332* | 480.5 |
| Example 3.3 | Cap 10, step d.3 | 2.126 | 480.6 |
| Example 3.4 | Cap 10, step d.4 | 2.273 | 480.6 |

*A gradient time of 2 min, a hold time of 1 min, and an analysis time of 3 min

Example 4.1 and 4.2 (two symmetrical diastereomers)

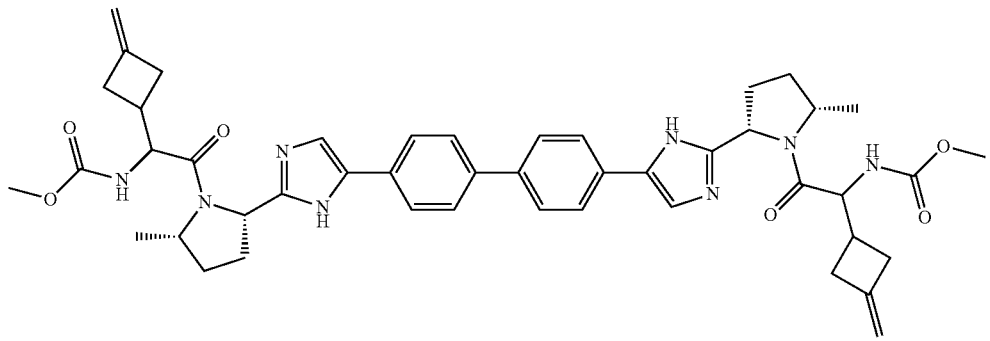

To a solution of 4,4'-bis(2-((2S,5S)-5-methylpyrrolidin-2-yl)-1H-imidazol-5-yl)-1,1'-biphenyl tetrahydrochloride (0.134 g, 0.224 mmol), Cap-12 (0.1034 g, 0.519 mmol), and N,N-diisopropylethylamine (0.313 mL, 1.791 mmol) in DMF (1.5 mL) was added HATU (0.179 g, 0.470 mmol). The reaction was stirred at ~25° C. for 3.5 h. The reaction was diluted with MeOH (3.5 mL) and the product was purified by prep-HPLC (injection volume: 2000 µL; gradient time: 15 min; start % B: 30, final % B: 100; flow rate: 30 mL/min; stop time: 15 min; Solvent A: 10% MeOH—90% H$_2$O—0.1% TFA, Solvent B: 90% MeOH—10% H$_2$O—0.1% TFA; Column: XTERRA 30×100 mm S5; Collect by UV: 220 nm) to afford a mixture of diastereomers. The mixture of diastereomers was further separated by prep-HPLC (injection volume: 2000 µL; gradient time: 30 min; start % B: 10, final % B: 50; flow rate: 30 mL/min; stop time: 30 min; Solvent A: 10% Acetonitrile—90% H$_2$O—0.1% TFA, Solvent B: 90% Acetonitrile—10% H$_2$O—0.1% TFA; Column: Waters-SunFire 30×100 mm S5; Collect by UV: 220 nm) to isolate the two symmetrical diastereomers: Example 4.1 (first elute) (35.5 mg) as an off-white foam. LC (Cond. 1): R$_t$=13.696 min. LC/MS: Anal. Calcd. for [M+H]⁺ C$_{46}$H$_{55}$N$_8$O$_6$ 815.42. found 815.49; Example 4.2 (last elute) (38.3 mg) as an off-white foam. LC (Cond. 1): R$_t$=14.492 min. LC/MS: Anal. Calcd. for [M+H]⁺ C$_{46}$H$_{55}$N$_8$O$_6$ 815.42. found 815.49.

Example 5.1 and 5.2 (two symmetrical diastereomers)

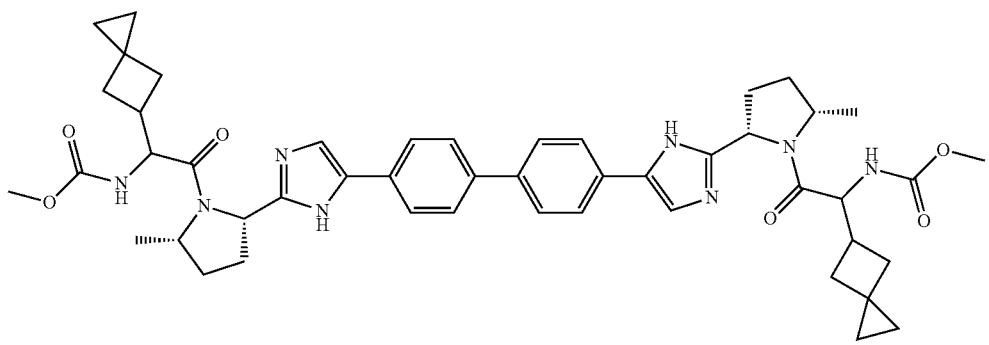

Example 5.1 and 5.2 were prepared from 4,4'-bis(2-((2S,5S)-5-methylpyrrolidin-2-yl)-1H-imidazol-5-yl)-1,1'-biphenyl tetrahydrochloride and Cap-11 according to the procedure described for Example 4.1 and 4.2. Example 5.1 (first elute) (56.4 mg) as a light yellow foam: LC (Cond. 1): $R_t$=15.124 min. LC/MS: Anal. Calcd. for $[M+H]^+$ $C_{48}H_{59}N_8O_6$ 843.46. found 843.40; and Example 5.2 (last elute) (50.7 mg) as a white foam. LC (Cond. 1): $R_t$=16.559 min. LC/MS: Anal. Calcd. for $[M+H]^+$ $C_{48}H_{59}N_8O_6$ 843.46. found 843.40.

Example 6

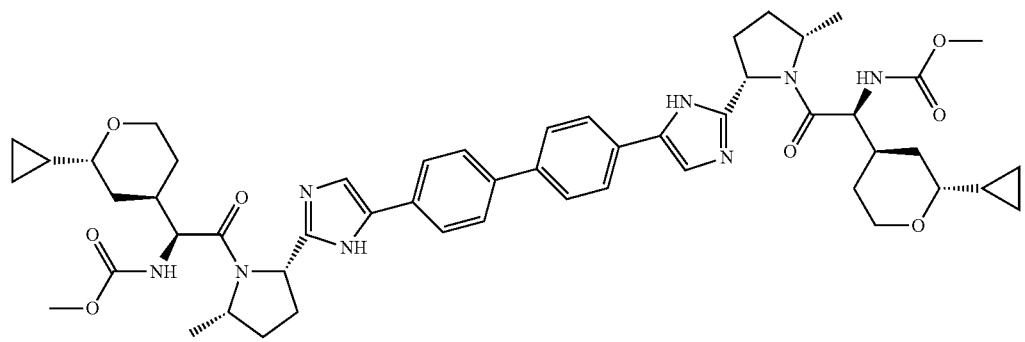 [SMILES: COC(=O)N[C@H](C(=O)N1[C@@H](C)CC[C@H]1c1ncc(-c2ccc(-c3ccc(-c4cnc([C@@H]5CC[C@H](C)N5C(=O)[C@@H](NC(=O)OC)[C@@H]5CCO[C@@H](C6CC6)C5)[nH]4)cc3)cc2)[nH]1)[C@@H]1CCO[C@@H](C2CC2)C1]

HATU (173 mg, 0.455 mmol) was added to a stirred clear solution of 4,4'-bis(2-((2S,5S)-5-methylpyrrolidin-2-yl)-1H-imidazol-5-yl)-1,1'-biphenyl, 4 HCl (109 mg, 0.182 mmol) and Cap 13.1 (117 mg, 0.455 mmol) in DMF (2.0 mL) and DIEA (0.222 mL, 1.27 mmol). The reaction was flushed with nitrogen, sealed and then stirred at room temperature overnight. The reaction was partially concentrated under a stream of nitrogen and then purified by prep HPLC (ACN/water with a TFA buffer) to yield the TFA salt of Example 6 (135 mg) as an off-white solid. LC-MS retention time 2.196 min; m/z 931.7 ($MH^+$). LC data was recorded on a Shimadzu LC-10AS liquid chromatograph equipped with a Phenomenex-Luna 3 u C18 2.0×50 mm column using a SPD-10AV UV-Vis detector at a detector wave length of 220 nM. The elution conditions employed a flow rate of 0.8 mL/min, a gradient of 100% solvent A/0% solvent B to 0% solvent A/100% solvent B, a gradient time of 4 min, a hold time of 1 min, and an analysis time of 5 min where solvent A was 10% acetonitrile/90% $H_2O$/0.1% trifluoroacetic acid and solvent B was 10% $H_2O$/90% acetonitrile/0.1% trifluoroacetic acid. MS data was determined using a Micromass Platform for LC in electrospray mode. $^1H$ NMR (400 MHz, MeOH-$d_4$) δ 7.96 (s, 2H), 7.88 (s, 8H), 5.20 (dd, J=10.7, 7.2 Hz, 2H), 4.79 (t, J=6.8 Hz, 2H), 4.31-4.24 (m, 2H), 3.85-3.76 (m, 2H), 3.74-3.69 (m, 2H), 3.67 (s, 6H), 2.91-2.83 (m, 2H), 2.55 (dt, J=12.8, 6.7 Hz, 2H), 2.47-2.23 (m, 6H), 2.00 (dd, J=12.3, 5.8 Hz, 2H), 1.79 (d, J=12.3 Hz, 2H), 1.69-1.27 (m, 12H), 1.15 (dd, J=8.3, 4.3 Hz, 2H), 0.47 (td, J=8.5, 3.9 Hz, 2H), 0.34-0.21 (m, 4H), −0.01--0.09 (m, 2H).

Example 7

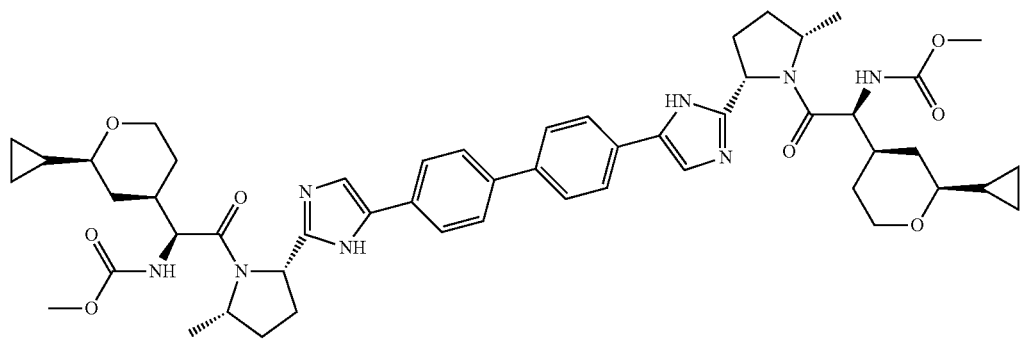 [SMILES: COC(=O)N[C@H](C(=O)N1[C@@H](C)CC[C@H]1c1ncc(-c2ccc(-c3ccc(-c4cnc([C@@H]5CC[C@H](C)N5C(=O)[C@@H](NC(=O)OC)[C@@H]5CCO[C@H](C6CC6)C5)[nH]4)cc3)cc2)[nH]1)[C@@H]1CCO[C@H](C2CC2)C1]

The TFA salt of Example 7 was prepared from Cap 13.2 and characterized in a similar manner to the procedure described for Example 6. LC-MS retention time 2.208 min; m/z 931.7 (MH⁺).

Example 8

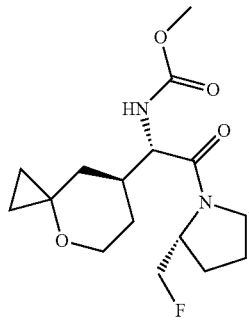

as colorless oil (1.96 g). LC (Cond. II): $R_t$=0.78 min; LC/MS: Anal. Calcd. for [M+H]⁺ $C_5H_9FNO$: 118.07. found: 118.0. ¹H NMR (CDCl₃, δ=7.26 ppm, 400 MHz) δ 6.07 (br. s., 1H), 4.51 (dd, 3.5 Hz, 0.5H), 4.43-4.31 (m, 1H), 4.23 (dd, J=9.5, 7.3 Hz, 0.5H), 4.06-3.91 (m, 1H), 2.48-2.34 (m, 2H), 2.32-2.18 (m, 1H), 1.84 (m, 1H).

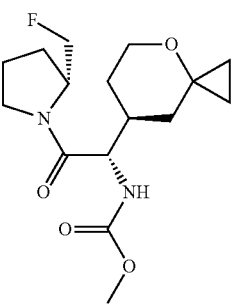

Example 8, Step a

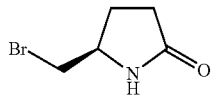

Example 8, Step c

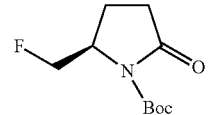

To a suspension of (R)-5-(hydroxymethyl)pyrrolidin-2-one (5 g, 43.4 mmol) and triphenylphosphine (17.09 g, 65.1 mmol) in acetonitrile (300 mL) at 0° C. in an ice-water bath was added dropwise a solution of carbontetrabromide (21.60 g, 65.1 mmol) in acetonitrile (80 mL). The suspension gradually changed to clear solution in 1 h and the bath was removed and stirred at room temperature for 23 h. The solvent was removed in vacuo and the resultant crude material was submitted to flash chromatography (30-100% EtOAc/Hexane, 10-20% MeOH/EtOAc) to afford Example 8, Step a as brown oil (6.3 g). LC (Cond. II): $R_t$=1.29 min; LC/MS: Anal. Calcd. for [M+H]⁺ $C_5H_9BrNO$: 179.99. found: 178.11. ¹H NMR (CDCl₃, δ=7.26 ppm, 400 MHz) δ 6.09 (br. s., 1H), 4.07-3.92 (m, 1H), 3.46 (dd, J=10.3, 4.8 Hz, 1H), 3.36 (dd, J=10.3, 7.5 Hz, 1H), 2.55-2.30 (m, 3H), 1.99-1.81 (m, 1H).

Example 8, Step b

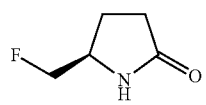

To a mixture solid of Example 8, Step a (6.33 g, 35.6 mmol) and Silver(I) fluoride (14.21 g, 112 mmol) was added acetonitrile (500 mL) slowly by syringe while the reaction flask was covered with aluminum foil. The reaction mixture was stirred at room temperature for 40 h. It was filtrated through diatomaceous earth (Celite®) and the solvent was removed in vacuo. The resultant crude material was submitted to flash chromatography (50-100% EtOAc/Hex, EtOAc, 10-20% MeOH/EtOAc) to afford Example 8, Step b To a solution of Example 8, Step b (2.61 g, 22.28 mmol) and DMAP (0.109 g, 0.891 mmol) in DCM (110 mL) was added di-tert-butyl dicarbonate (5.11 g, 23.40 mmol) in three portions in an ice-water bath at 0° C. in 10 mins. The bath was removed and it was stirred at room temperature for 20 h. 50% sat. NaHCO₃ (30 mL) was added and stirred for 10 min. Organic layer was separated and dried with Na₂SO₄. The solvent was evaporated in vacuo to afford crude product as yellow oil. The resultant crude material was submitted to flash chromatography (0-80% EtOAc/Hexane) to afford Example 8, Step c as colorless oil (3.87 g). LC (Cond. II): $R_t$=2.64 min; LC/MS: Anal. Calcd. for [M+Na]⁺ $C_{10}H_{16}FNNaO_3$: 240.10. found: 240.14. ¹H NMR (CDCl₃, δ=7.26 ppm, 500 MHz) δ 4.68 (ddd, J=48.2, 9.8, 3.5 Hz, 1H), 4.50 (ddd, J=45.7, 9.8, 2.5 Hz, 1H), 4.31 (ddm, J=27.7, 8.8 Hz, 1H), 2.69 (dtd, J=17.7, 9.8, 1.9 Hz, 1H), 2.44 (ddq, J=17.7, 9.8, 1.1 Hz, 1H), 2.20 (m, 1H), 2.06 (m, 1H), 1.51 (s, 9H).

Example 8, Step d

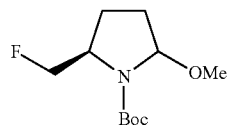 [SMILES: COC1CC[C@H](CF)N1C(=O)OC(C)(C)C]

To a solution of Example 8, Step c (2.67 g, 12.29 mmol) in THF (50 mL) in a dry ice-acetone bath at −78° C. was added dropwise Superhydride (14.75 mL, 14.75 mmol). The reaction mixture was stirred at −78° C. for 40 min. Sat. NaHCO₃ aq. solution (15 mL) was added and the dry ice-acetone bath was removed and temperature raised to room temperature. 20 drops of 50% H₂O₂ was added drop wise and it was stirred for 20 min. The organic layer was separated and aqueous layer was extracted with Ether (2×40 mL), the combined organic layer was dried with Na₂SO₄, evaporated the solvent in vacuo to afford a crude intermediate (2.34 g) as clear oil. This crude intermediate was dissolved in methanol (30 mL) and p-toluenesulfonic acid monohydrate (0.223 g, 1.174 mmol) was added, it was stirred at room temperature for 16 h. Aq. sat. NaHCO$_3$ (5 mL) was added, extracted with ether (3×35 mL), dried with Na$_2$SO$_4$, evaporated in vacuo to afford a clear oil as crude product. The resultant crude material was submitted to flash chromatography (0-40% EtOAc/Hexane) to afford Example 8, Step d as colorless oil (1.97 g). LC (Cond. II): R$_t$=3.43 min; LC/MS: Anal. Calcd. for [M+Na]$^+$ C$_{11}$H$_{20}$FNNaO$_3$: 256.13. found: 256.19. $^1$H NMR (CDCl$_3$, δ=7.26 ppm, 400 MHz) δ 5.27-5.16 (m, 1H), 4.59-4.26 (m, 2H), 4.03 (br. s., 1H), 3.29 (br. s., 3H), 2.17-1.96 (m, 2H), 1.96-1.85 (m, 1H), 1.85-1.70 (m, 1H), 1.55-1.39 (m, 9H).

Example 8, Step e

To a solution of 8e-cis (0.51 g, 2.234 mmol) in dioxane (3 mL) was added HCl (12M, 3 mL, 99 mmol). It was heated to 80° C. for 8 h. The solvent was evaporated in vacuo and dried under vacuum for 16 h to give crude intermediate (0.55 g) as yellow solid. This crude intermediate (0.55 g) was dissolved in THF (4 mL), NaOH (2M, 3.44 mL, 6.89 mmol) and di-tert-butyl dicarbonate (0.719 g, 3.30 mmol) were added and it was stirred at room temperature for 17 h. The solvent was evaporated in vacuo and water (5 mL) and ether (5 mL) were added. The aqueous layer was separated and acidified by 10% HCl to pH 3 in an ice-water bath, EtOAc (15 mL, 3×) extracted and dried with Na$_2$SO$_4$, evaporated the solvent in vacuo to afford Example 8, step f as yellow solid (0.50 g). $^1$H NMR (CDCl$_3$, δ=7.26 ppm, 400 MHz): δ 4.69-4.14 (m, 4H), 2.29-2.07 (m, 4H), 1.50-1.48 (two s, 9H).

Example 8

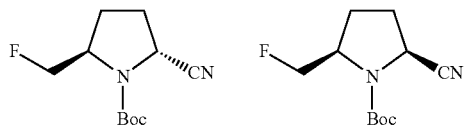 [SMILES: CC(C)(C)OC(=O)N1[C@@H](CF)CC[C@@H]1C#N ; CC(C)(C)OC(=O)N1[C@@H](CF)CC[C@H]1C#N]

To a solution of Example 8, Step d (1.97 g, 8.44 mmol) in DCM (50 mL) cooled with −78° C. dry ice-acetone bath was added trimethylsilyl cyanide (1.698 mL, 12.67 mmol), followed by boron trifluoride ether complex (1.605 mL, 12.67 mmol). It was stirred for 1 h. Sat. NaHCO$_3$ (20 mL) was added and the bath was removed, and it was stirred at room temperature for 2 h. The organic layer was separated and extracted with DCM (40 mL×2), dried with Na$_2$SO$_4$, evaporated in vacuo. The resultant crude material was submitted to flash chromatography (0-40%, 40-55% EtOAc/Hexane) to afford first elute Example 8, Step e.1 (trans; 1.12 g) and second elute Example 8, Step e.2 (cis; 0.63 g) as white solids. LC (Cond. II): R$_t$=3.04 min; LC/MS: Anal. Calcd. for [M+Na]$^+$ C$_{11}$H$_{17}$FN$_2$NaO$_2$: 251.12. found: 251.16. $^1$H NMR (CDCl$_3$, δ=7.26 ppm, 400 MHz): δ 4.67-4.44 (m, 3H), 4.12-4.06 (m, 1H), 2.32 (br s, 2H), 2.18 (br s, 2H), 1.52 (s, 9H).

Example 8, Step f

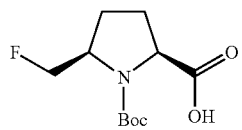 [SMILES: CC(C)(C)OC(=O)N1[C@@H](CF)CC[C@H]1C(=O)O]

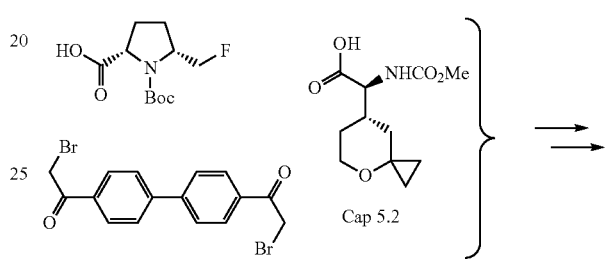

Example 8

Example 8, step f was elaborated to Example 8 according to the procedure described for the synthesis of Example QC17.1 by using indicated and other appropriate precursors. LC/MS: Anal. Calcd. for [M+H]$^+$ C$_{50}$H$_{61}$F$_2$N$_8$O$_8$: 939.46. found: 939.77. R$_t$=15.99 min under the following LC condition: Start % B=10; Final % B=98; Gradient time=35 min; Stop time=35 min; Flow Rate=0.35 mL/min; Wavelength=306 nm; Solvent A=Water with 0.05% TFA; Solvent B=Acetonitrile with 0.05% TFA; Column=Waters Acquity BEH C18; 1.7 um; 150×2.1 mm ID; (at 35° C.).

Example 9.1

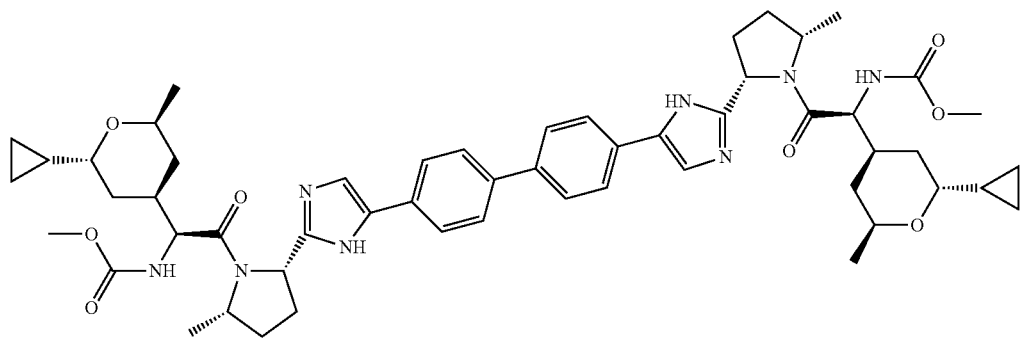 [SMILES: COC(=O)N[C@H](C(=O)N1[C@@H](C)CC[C@H]1c1ncc(-c2ccc(-c3ccc(-c4cnc([C@@H]5CC[C@H](C)N5C(=O)[C@@H](NC(=O)OC)[C@@H]5C[C@H](C)O[C@@H](C6CC6)C5)[nH]4)cc3)cc2)[nH]1)[C@@H]1C[C@H](C)O[C@@H](C2CC2)C1]

HATU (44.8 mg, 0.118 mmol) was added to a solution of an HCl salt of 4,4'-bis(2-((2S,5S)-5-methylpyrrolidin-2-yl)-1H-imidazol-5-yl)-1,1'-biphenyl (32 mg, 0.054 mmol) and Cap 15.1 (32 mg, 0.12 mmol) in DMF (0.5 mL) and DIEA (0.075 mL, 0.43 mmol) and the mixture was stirred at room temperature for 2 h. The crude reaction mixture was purified via preparative LC/MS with the following conditions to afford Example 9.1 (24.1 mg): Column: Waters XBridge C18, 19×200 mm, 5-µm particles; Guard Column: Waters XBridge C18, 19×10 mm, 5-µm particles; Mobile Phase A: water with 20-mM ammonium acetate; Mobile Phase B: 95:5 acetonitrile:water with 20-mM ammonium acetate; Gradient: 40-80% B over 20 min, then a 5-minute hold at 100% B; Flow: 20 mL/min. Fractions containing the desired product were combined and dried via centrifugal evaporation. LC/MS retention time 2.99 min; m/z=960 [M+H]$^+$. Column: Waters BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 min, then a 0.5-min hold at 100% B; Flow: 1 mL/min.

Example 9.2

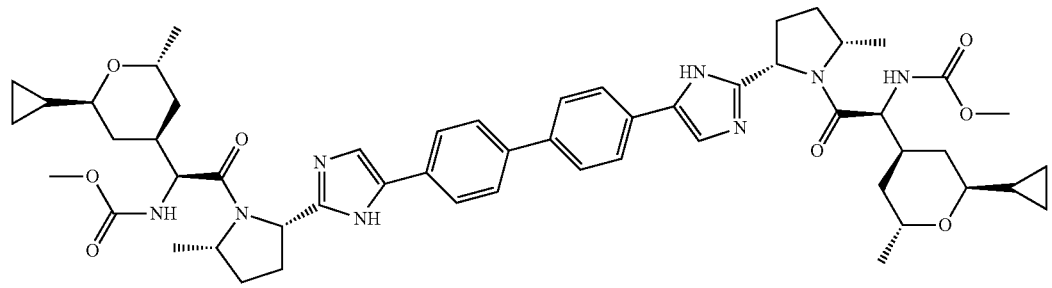 [SMILES: COC(=O)N[C@H](C(=O)N1[C@@H](C)CC[C@H]1c1ncc(-c2ccc(-c3ccc(-c4cnc([C@@H]5CC[C@H](C)N5C(=O)[C@@H](NC(=O)OC)[C@@H]5C[C@@H](C)O[C@H](C6CC6)C5)[nH]4)cc3)cc2)[nH]1)[C@@H]1C[C@@H](C)O[C@H](C2CC2)C1]

The reaction was performed as described above utilizing Cap 15.2 (38 mg, 0.14 mmol) as a starting material to yield Example 9.2 (20.8 mg). LC/MS retention time 2.99 min; m/z=960 [M+H]$^+$. Column: Waters BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 min, then a 0.5-min hold at 100% B; Flow: 1 mL/min.

Example 9.3

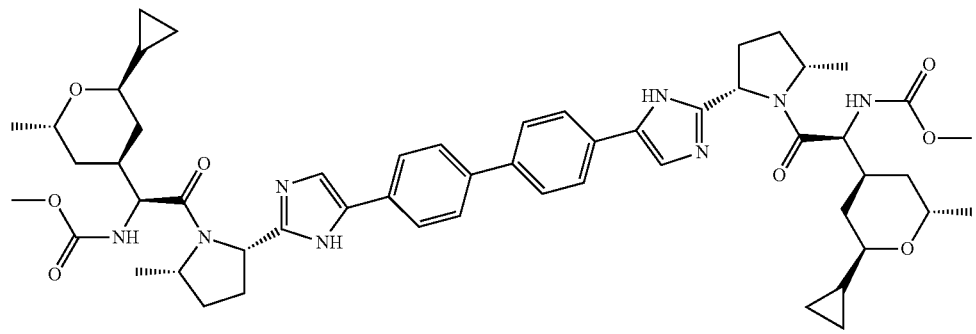

The reaction was performed as described above utilizing Cap 15.3 (34 mg, 0.13 mmol) as a starting material to yield Example 9.3 (39.7 mg). LC/MS retention time 3.01 min; m/z=960 [M+H]$^+$. Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 min, then a 0.5-min hold at 100% B; Flow: 1 mL/min. $^1$H NMR (500 MHz, DMSO-d$_6$) δ7.89-7.40 (m, 12H), 5.38-4.92 (m, 2H), 4.69-4.60 (m, 2H), 4.25-3.91 (m, 6H), 3.55 (s, 6H), 2.84-2.65 (m, 2H), 2.30-2.20 (m, 2H), 2.19-1.96 (m, 4H), 1.95-1.87 (m, 2H), 1.84-1.52 (m, 4H), 1.60-1.24 (m, 8H), 1.22-1.03 (m, 4H), 0.99-0.81 (m, 6H), 0.79-0.65 (m, 2H), 0.45-0.28 (m, 4H), 0.20--0.04 (m, 4H).

Example 9.4

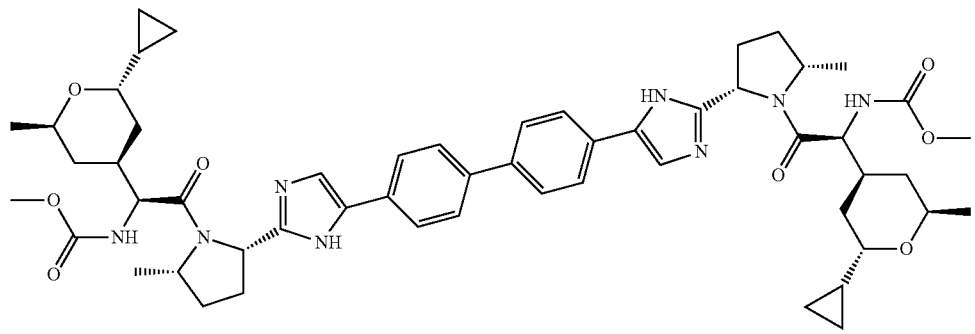

The reaction was performed as described above utilizing Cap 15.4 (34 mg, 0.13 mmol) as a starting material to yield Example 9.4 (25.5 mg). LC/MS retention time 3.03 min; m/z=960 [M+H]$^+$. Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 min, then a 0.5-min hold at 100% B; Flow: 1 mL/min. $^1$H NMR (500 MHz, DMSO-d$_6$) δ 8.10-7.64 (m, 12H), 5.10-4.98 (m, 2H), 4.69-4.54 (m, 2H), 4.08-3.95 (m, 2H), 3.79-3.69 (m, 2H), 3.56 (s, 6H), 2.97-2.72 (m, 4H), 2.43-2.05 (m, 8H), 1.90-1.79 (m, 2H), 1.75-1.64 (m, 2H), 1.49 (d, J=5.8 Hz, 6H), 1.33-1.14 (m, 6H), 1.09-0.81 (m, 8H), 0.54-0.36 (m, 4H), 0.24-0.66 (m, 2H), 0.66-0.02 (m, 2H).

Example 10

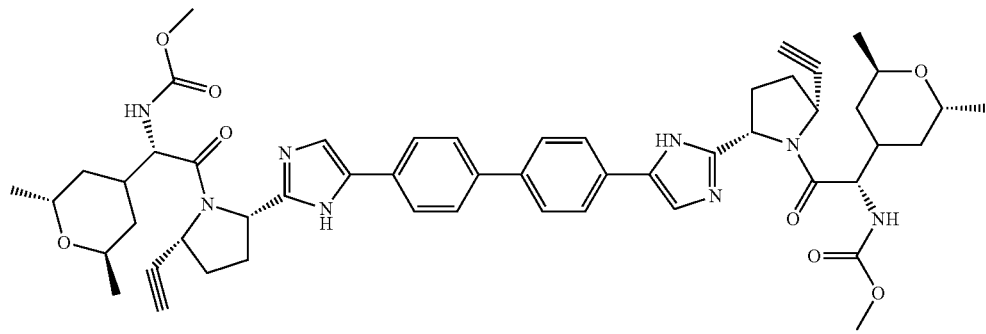

Example 10, Step a.1-a.2

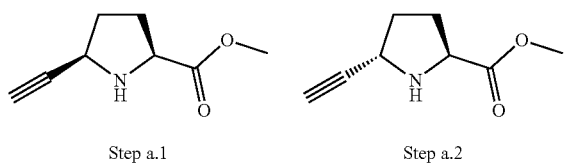

Step a.1      Step a.2

The two esters were prepared according to the procedure described in the following two references: Madar, D. J. et al. *J. Med. Chem.*, 2006, 49, 6416; Biellmann, J. et al., *J. Org. Chem.*, 1992, 57, 2060).

Example 10, Step b

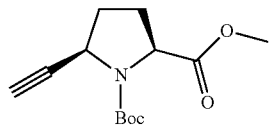 [SMILES: C#C[C@H]1CC[C@@H](C(=O)OC)N1C(=O)OC(C)(C)C]

To a suspension of Example 10, Step a.1 (3.05 g, 19.9 mmol) and DMAP (0.122 g, 0.996 mmol) in DCM (150 mL) was added di-tert-butyl dicarbonate (5.21 g, 23.89 mmol), and the reaction mixture was stirred at room temperature for 17 h. The solvent was evaporated in vacuo and the resultant crude material was submitted to flash chromatography (0-60% EtOAc/Hex) to afford Example 10, Step b as colorless oil (3.26 g). LC/MS: Anal. Calcd. for [M+Na]$^+$ $C_{13}H_{19}NNaO_4$: 276.12. found: 276.02. $^1$H NMR (CDCl$_3$, δ=7.26 ppm, 400 MHz) δ 4.66-4.53 (two br. s., 1H), 4.34-4.22 (m, 1H), 3.04 (s, 3H), 2.35-2.12 (m, 5H), 1.51-1.45 (two br. S., 9H)

Example 10, Step c

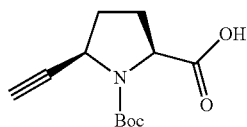 [SMILES: C#C[C@H]1CC[C@@H](C(=O)O)N1C(=O)OC(C)(C)C]

To a solution of Example 10, Step b (2.05 g, 8.09 mmol) in ethanol (20 mL) was added a solution of lithium hydroxide (0.233 g, 9.71 mmol) in water (10 mL), it was stirred at room temperature for 5 h. The solvent was evaporated and ether (10 mL) and water (10 mL) were added, and to the aqueous layer was added 1 N HCl to adjust its pH to 2. The aqueous phase was extracted with EtOAc (3×20 mL), dried with Na$_2$SO$_4$, evaporated in vacuo to afford Example 10, Step c (1.65 g) as light yellow oil. LC/MS: Anal. Calcd. for [M+Na]$^+$ $C_{12}H_{17}NNaO_4$: 262.11. found: 262.02. $^1$H NMR (CDCl$_3$, δ=7.26 ppm, 400 MHz) δ 4.67-4.36 (m, 2H), 2.54-2.13 (m, 5H), 1.53 (br. S, 9H).

Example 10

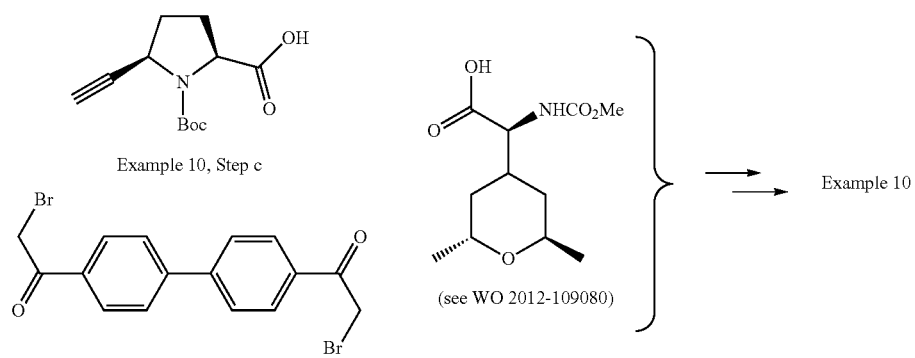

Example 10, step c was elaborated to Example 10 according to the procedure described for the synthesis of Example QC17.1 and by using the indicated and other appropriate precursors. LC (Cond. 8): R$_t$=2.98 min; LC/MS: Anal. Calcd. for [M+H]$^+$ $C_{52}H_{63}N_8O_8$: 927.48. found: 927.47.

Example 10.1

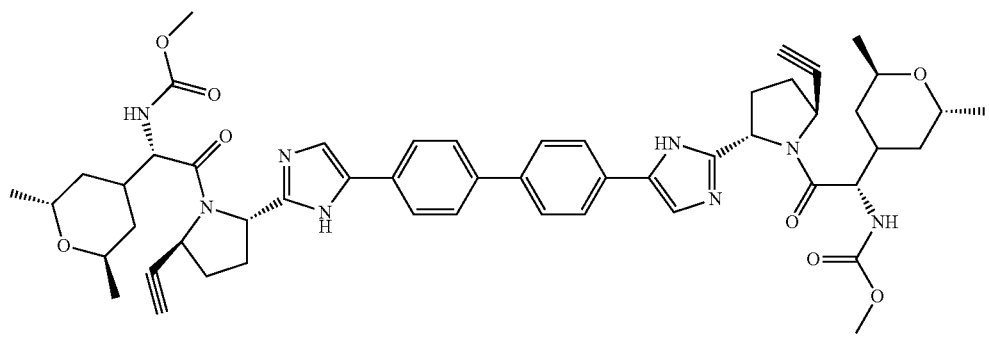

Example 10.1 was prepared from Example 10, Step a.2 according to the procedure described for Example 10. LC (Cond. 8): $R_t$=2.95 min; LC/MS: Anal. Calcd. for $[M+H]^+$ $C_{52}H_{63}N_8O_8$: 927.48. found: 927.47.

Example 11

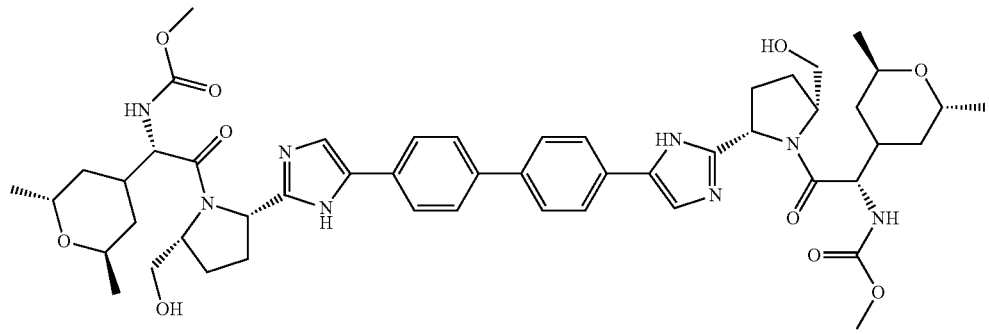

Example 11, Step a

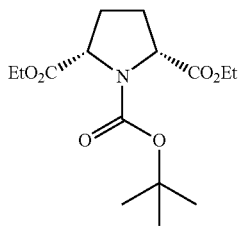 [SMILES: CCOC(=O)[C@H]1CC[C@@H](C(=O)OCC)N1C(=O)OC(C)(C)C]

To a solution of Cis-diethyl 1-benzylpyrrolidine-2,5-dicarboxylate hydrochloride (prepared according to procedures described in *J. Med. Chem.,* 2006, 49, 3068) (17.35 g, 50.8 mmol) in Ethanol (300 mL) was added potassium carbonate (14.03 g, 102 mmol) and palladium hydroxide on carbon (20%), it was flushed with niotrogen and then hydrogen ballon was put on and stirred at room temperature for 6 h. Di-tert-butyl dicarbonate (27.7 g, 127 mmol) was added and stirred at room temperature for 72 h under a balloon of hydrogen. The reaction mixture was filtered through Celite and washed by methanol. Solvent was evaporated and it was partitioned between EtOAc (80 mL) and water (50 mL), the aqueous layer was extracted with EtOAc (20 mL, 2×) and the combined organic layer was dried with $Na_2SO_4$. Solvent was evaporated in vacuo and the resultant crude material was submitted to flash chromatography (0-30% EtOAc/Hex) to afford Example 11, Step a as colorless oil (13.3 g). LC (Cond. 8): $R_t$=3.44 min; LC/MS: Anal. Calcd. for $[M+Na]^+$ $C_{15}H_{25}NNaO_6$: 338.16. found: 338.11. $^1$H NMR ($CDCl_3$, δ=7.26 ppm, 400 MHz) δ 4.41 (m, 1H), 4.30 (m, 1H), 4.23 (m, 4H), 2.24-2.12 (m, 4H), 1.45 (s, 9H), 1.30 (m, 6H).

Example 11, Step b

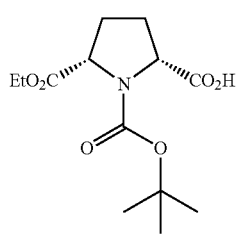 [SMILES: CCOC(=O)[C@@H]1CC[C@H](C(=O)O)N1C(=O)OC(C)(C)C]

To a solution of Example 11, step a (16.8 g, 53.3 mmol) in ethanol (150 mL) at 0° C. in a ice-water bath was added a solution of potassium hydroxide (2.99 g, 53.3 mmol) in ethanol (100 mL) dropwise over 20 min. The ice-water bath was removed and the mixture was stirred at room temperature for 23 h. The solvent was evaporated, water (40 mL) was added followed by 1N HCl to adjust the pH to 8-9. The aqueous layer was washed with hexanes (35 mL, 2×), its pH was adjusted to 4-5 range by the addition of 1 N HCl, and extracted with EtOAc (70 mL×3). The combined organic layer was dried with $Na_2SO_4$, and the volatile component was removed in vacuo to afford Example 11, Step b (8.45 g) as colorless oil. LC (Cond. 8): $R_t$=3.10 min; LC/MS: Anal. Calcd. for $[M+Na]^+$ $C_{13}H_{21}NNaO_6$: 310.13. found: 310.10. $^1$H NMR ($CDCl_3$, δ=7.26 ppm, 400 MHz) δ 4.63-4.50, 4.44-4.20 (a collection of m, 4H), 2.49-2.27 (m, 2H), 2.11-2.05 (m, 2H), 1.48 (two s, 9H), 1.38-1.30 (m, 3H).

Example 11, Step c

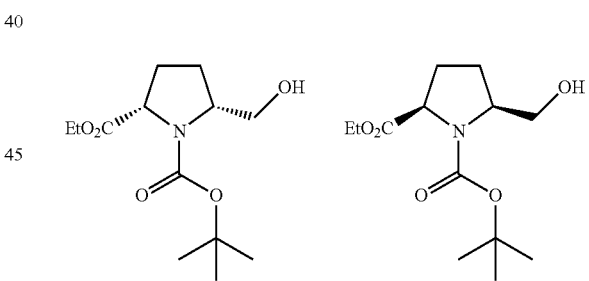

To a solution of Example 11, step b (1.6 g, 5.57 mmol) in THF (35 mL) at 0° C. in a ice-water bath was added Borane-methyl sulfide complex (2.78 mL, 5.57 mmol) dropwise over 15 min. After 10 min of stirring, the bath was removed and it was stirred at room temperature for 5 h. Methanol (10 mL) was added and it was stirred at room temperature for an additional 1 h. The solvent was evaporated and the residue was partitioned between EtOAc (80 mL) and water (50 mL). The organic layer was separated, dried with $Na_2SO_4$, the volatile component was evaporated in vacuo. The resultant crude material was submitted to flash chromatography (0-35% EtOAc/Hex) to afford Example 11, Step c as colorless oil (0.91 g). The two enantiomers were separated by chiral SFC (Column IC-2×15 cm; 15% i-PrOH/ 0.1% diethyl amine/$CO_2$): peak 1 (402 mg) and peak 2 (414 mg). LC (Cond. 8): $R_t$=3.01 min; LC/MS: Anal. Calcd. for $[M+Na]^+$ $C_{13}H_{23}NNaO_5$: 296.15. found: 296.10.

Example 11, Step d

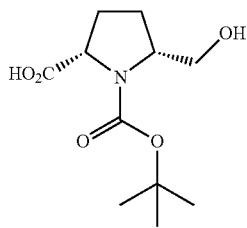 [SMILES: CC(C)(C)OC(=O)N1[C@@H](CO)CC[C@H]1C(=O)O]

To a solution of Example 11, step c (peak 1, 402 mg, 1.471 mmol) in ethanol (4 mL) was added a solution of lithium hydroxide (42.3 mg, 1.765 mmol) in water (2 mL), and the mixture was stirred at room temperature for 5 h. The mixture was concentrated, diluted with water (10 mL), and washed with EtOAc (10 mL). The aqueous layer was cooled with an ice-water bath, 1 N HCl was added to adjust it pH to ~2, and it was extracted with EtOAc (3×30 mL). The combined organic layer was dried with $Na_2SO_4$, and the volatile component was evaporated in vacuo to afford Example 11, step d (0.29 g) as yellow solid. LC/MS: Anal. Calcd. for $[M+Na]^+$ $C_{11}H_{19}NNaO_5$: 268.12. found: 268.126. $^1H$ NMR ($CDCl_3$, δ=7.26 ppm, 400 MHz) δ 4.45-4.40, 4.17-4.03, 3.68-3.58 (a collection of m, 4H), 2.27-1.95 (m, 4H), 1.47 (br. s, 9H).

Example 11

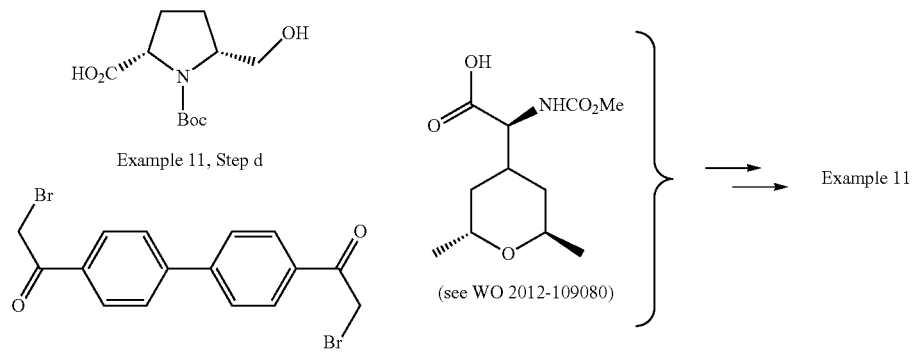

Example 11, step d was elaborated to Example 11 according to the procedure described for the synthesis of Example QC17.1 by using the indicated intermediates and other appropriate precursors. $R_t$=15.99 min under the following LC condition: Start % B=10; Final % B=98; Gradient time=35 min; Stop time=35 min; Flow Rate=0.35 mL/min; Wavelength=306 nm; Solvent A=Water with 0.05% TFA; Solvent B=Acetonitrile with 0.05% TFA; Column=Waters Acquity BEH C18; 1.7 um; 150×2.1 mm ID; (at 35° C.). LC/MS: Anal. Calcd. for $[M+H]^+$ $C_{50}H_{61}F_2N_8O_8$: 939.46. found: 939.77.

Example 11.1

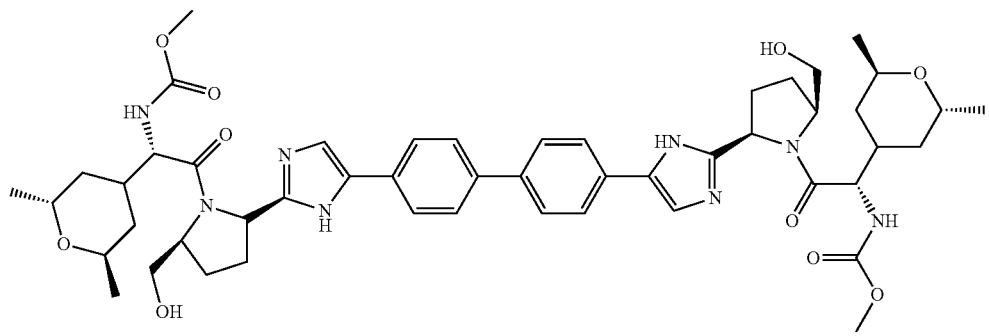

Example 11.1 was prepared from Example 11, step c (peak 2) according to the procedure described for Example 11. $R_t$=12.51 min under the following LC condition: Start % B=10; Final % B=98; Gradient time=35 min; Stop time=35 min; Flow Rate=0.35 mL/min; Wavelength=306 nm; Solvent A=Water with 0.05% TFA; Solvent B=Acetonitrile with 0.05% TFA; Column=Waters Acquity BEH C18; 1.7 um; 150×2.1 mm ID; (at 35° C.). LC/MS: Anal. Calcd. for $[M+H]^+$ $C_{50}H_{67}N_8O_{10}$: 940.11. found: 939.88.

Example 12.1 and 12.2

(Two symmetrical diastereomers regarding the non-specified stereogenic center)

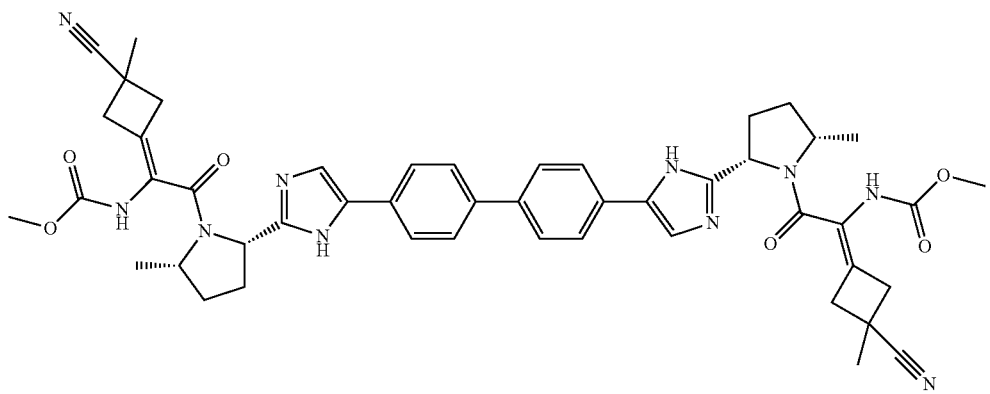

To a solution of 4,4'-bis(2-((2S,5S)-5-methylpyrrolidin-2-yl)-1H-imidazol-5-yl)-1,1'-biphenyl (4HCl; 0.100 g, 0.167 mmol), Cap 18 (0.094 g, 0.418 mmol), and N,N-diisopropylethylamine (0.233 mL, 1.337 mmol) in DMF (2 mL) was added HATU (0.140 g, 0.368 mmol). The reaction was stirred at room temperature for 4 h. The reaction was diluted with MeOH (6 mL) and the product was purified by a reverse phase prep-HPLC (XTERRA 30×100 mm S5; MeOH/water/TFA) to afford a light yellow solid as a mixture of three diastereomers (110 mg). The sample was further purified by prep-chiral SFC [Column: ChiralCel OJ-H, 30×250 mm, 5 μm; Mobile phase: 20% EtOH (w/0.2% DEA)/80% $CO_2$; Pressure: 120 bar; Temperature: 35° C.; Flow rate 70 mL/min; UV: 320 nm] to afford three diastereomers. In order to remove minor contaminants, the two symmetrical diastereomers were further purified individually by prep-HPLC (Waters-Sunfire 30×100 mm S5; acetonitrile/water/TFA). Example 12.1 (yellow solid; 11.0 mg): LC (Cond. 8): $R_t$=3.05 min; LC/MS: Anal. Calcd. for $[M+H]^+$ $C_{48}H_{53}N_{10}O_6$ 865.41. found 865.60. Example 12.2 (yellow solid; 7.6 mg): LC (Cond. 8): $R_t$=3.01 min; LC/MS: Anal. Calcd. for $[M+H]^+$ $C_{48}H_{53}N_{10}O_6$ 865.41. found 865.73.

Example 13

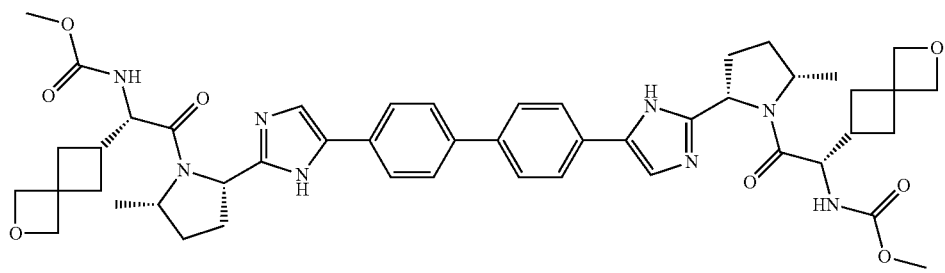 [SMILES: COC(=O)N[C@H](C(=O)N1[C@@H](C)CC[C@H]1c1ncc(-c2ccc(-c3ccc(-c4cnc([C@@H]5CC[C@H](C)N5C(=O)[C@@H](NC(=O)OC)C5CC6(COC6)C5)[nH]4)cc3)cc2)[nH]1)C1CC2(COC2)C1]

To a solution of 4,4'-bis(2-((2S,5S)-5-methylpyrrolidin-2-yl)-1H-imidazol-5-yl)-1,1'-biphenyl (4HCl; 0.05 g, 0.084 mmol), Cap 16 (0.042 g, 0.184 mmol), and N,N-diisopropylethylamine (0.117 mL, 0.668 mmol) in DMF (2 mL) was added HATU (0.067 g, 0.175 mmol). The reaction was stirred at ~25° C. for 4 h. The reaction was diluted with MeOH (6 mL) and the product was purified by prep-HPLC (Xbridge C18, 30×100 mm 5 µm; acetonitrile/water/ammonium acetate) followed by a second reverse phase HPLC (Waters XBridge C18, 19×200 mm, 5 µm; acetonitrile/water/ammonium acetate) to afford Example 13 as a white solid (11.4 mg): LC (Cond. 8): $R_f$=2.78 min; LC/MS: Anal. Calcd. for [M+H]$^+$ $C_{48}H_{59}N_8O_8$ 875.45. found 875.72.

Example JLR-1.0

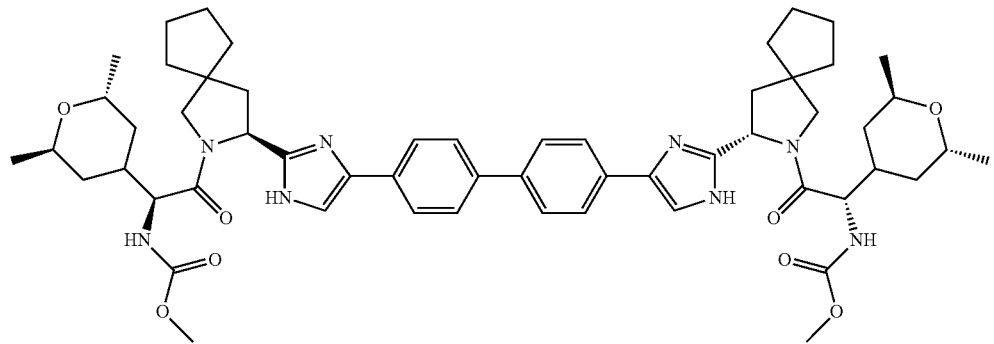

Example JLR-1.0, step a

A solution of 1M lithium bis(trimethylsilyl)amide (61.7 mL, 61.7 mmol) in THF was added over a 10 min period to a nitrogen purged solution of (S)-1-tert-butyl 2-methyl 5-oxopyrrolidine-1,2-dicarboxylate (15 g, 61.7 mmol) in THF (225 mL) at −78° C. The reaction was stirred 1 h before addition of 3-bromoprop-1-ene (5.22 mL, 61.7 mmol) at the same temperature, and the reaction was stirred 1.5 h before removing the cold bath and stirring at room temperature for 18 h. The reaction was quenched by diluted acetic acid (12 mL in 50 mL water) and concentrated to remove THF. The residue was taken up in EtOAc and washed with water, brine, and dried (Na$_2$SO$_4$).

The crude product was dissolved in a minimum volume of 10% EtOAc/Hex and charged to a 300 g Thomson silica gel cartridge. Gradient elution was performed from 10-80% EtOAc/hexanes over 3 L. Note: pure fractions were set aside and mixed fractions were combined and resubjected to chromatography a second time. The first band to elute was (S)-1-tert-butyl 2-methyl 4,4-diallyl-5-oxopyrrolidine-1,2-dicarboxylate (4.63 g), followed by mono alkylation trans product (3.56 g), and then mono alkylation cis product (2.0 g). Trans product: $^1$H NMR (500 MHz, MeOD) δ 5.79 (ddt, J=17.1, 10.0, 7.1 Hz, 1H), 5.20-5.05 (m, 2H), 4.66 (dd, J=9.8, 1.9 Hz, 1H), 3.81 (s, 3H), 2.76 (dtd, J=11.3, 8.8, 4.4 Hz, 1H), 2.57 (dddt, J=14.3, 6.7, 4.4, 1.3 Hz, 1H), 2.29-2.17 (m, 2H), 2.16-2.06 (m, 1H), 1.49 (s, 9H). Bis-alkylated product: $^1$H NMR (CDCl$_3$; 500 MHz): δ 5.81-5.70 (m, 2H), 5.19-5.07 (series of m, 4H), 4.56 (dd, J=9.9, 5.6 Hz, 1H), 3.79 (s, 3H), 2.40-2.34 (m, 3H), 2.30-2.25 (m, 2H), 1.94 (dd, J=13.7, 5.6 Hz, 1H), 1.49 (s, 9H).

Example JLR-1.0, step b

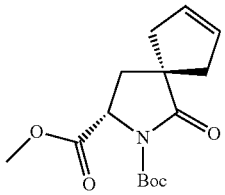

Grubbs I catalyst (0.117 g, 0.417 mmol) was added to a nitrogen purged solution of (S)-1-tert-butyl 2-methyl 4,4-diallyl-5-oxopyrrolidine-1,2-dicarboxylate (2.7 g, 8.35 mmol) in dichloromethane (130 mL) and stirred for 18 h at 24° C. The reaction mixture was partially concentrated (~1/5 vol) and charged to a 160 g Thomson silica gel cartridge. Gradient elution was performed from 5-75% EtOAc/Hexanes over 2 L to afford (S)-2-tert-butyl 3-methyl 1-oxo-2-azaspiro[4.4]non-7-ene-2,3-dicarboxylate (1.98 g). $^1$H NMR (CDCl$_3$, 500 MHz): δ 5.67-5.65 (m, 1H), 5.61-5.59 (m, 1H), 4.68 (dd, J=9.3, 4.0 Hz, 1H), 3.81 (s, 3H), 2.88 (dt, J=16.8, 2.3 Hz 1H), 2.77 (dt, J=16.6, 2.3 Hz 1H), 2.44-2.29 (series m, 3H), 2.12 (dd, J=13.2, 4.0 Hz 1H), 1.50 (s, 9H).

Example JLR-1.0, Step c

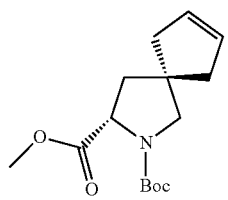

A 1M solution of superhydride (7.7 mL, 7.72 mmol) in THF was added dropwise to a nitrogen purged solution of (S)-2-tert-butyl 3-methyl 1-oxo-2-azaspiro[4.4]non-7-ene-2,3-dicarboxylate (1.9 g, 6.43 mmol) in THF (40 mL) at −78° C. and stirred 1 h.

The reaction mixture was warmed to 0° C. over 1 h, recooled to −78° C. and 6 mL more of superhydride was added with stirring at −78° C. for 1 hr before being placed in a freezer to stand for 18 h at −5° C. The reaction mixture was quenched while cold with saturated NaHCO₃ solution (16 mL) and kept at 0° C., and 30% hydrogen peroxide solution (1.8 mL) was added. The reaction was stirred for 20 min at the same temperature before removing the solvent by rotory evaporation. The residue was extracted with DCM (3×60 mL), and the combined organic layers were washed with water and dried (Na₂SO₄). The solvent was reduced to 35 mL volume, triethylsilane (1.1 mL, 6.76 mmol) was added, and the reaction was cooled to −78° C. Boron trifluoride etherate (0.98 mL, 7.72 mmol) was added under nitrogen, and after 30 min, additional triethylsilane (1.1 mL, 6.76 mmol) and additional boron trifluoride etherate (0.98 mL, 7.72 mmol) were added. The reaction mixture was stirred 2 h, quenched with saturated NaHCO₃ solution (10 mL), extracted with DCM (3×60 mL), and the organic layer was dried (Na₂SO₄). The crude product was charged (DCM) to a 160 g Thomson silica gel cartridge and gradient elution was performed from 5-50% EtOAc/Hexanes over 2 L to afford (S)-2-tert-butyl 3-methyl 2-azaspiro[4.4]non-7-ene-2,3-dicarboxylate (1.44 g). ¹H NMR (MeOD, 500 MHz): δ 5.70-5.67 (m, 2H), 4.30 (t, J=7.9 Hz, 1H), 3.76 (s, 3H), 3.47-3.44 (m, 1H), 3.38-3.31 (m, 1H), 2.48-2.29 (series m, 5H), 1.98-1.93 (m, 1H), 1.47/1.42 (s, 9H).

Example JLR-1.0, step d

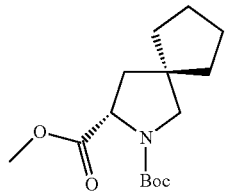

Palladium on carbon (10%; 182 mg) was added to a nitrogen purged solution of (S)-2-tert-butyl 3-methyl 2-azaspiro[4.4]non-7-ene-2,3-dicarboxylate (480 mg, 1.71 mmol) in EtOAc (50 mL) and the reaction mixture was flushed with hydrogen (ballon) and stirred for 18 h. The catalyst was removed by filtration over Celite, and the solvent removed upon concentration by rotory evaporation. The residue was taken up in benzene and concentrated by rotory evaporation (2×) to insure removal of EtOAc. There was obtained (S)-2-tert-butyl 3-methyl 2-azaspiro[4.4]nonane-2,3-dicarboxylate (472 mg) which was used without further purification. For purposes of characterizations, a sample (25 mg) was charged to a 12 g Thomson silica gel cartridge and gradient elution was performed from 15-100% EtAOc/hexanes over 1.5 L. ¹H NMR (MeOD, 500 MHz): δ 4.29-4.25 (m, 1H), 3.75 (s, 3H), 3.37-3.35 (m, 1H), 3.29-3.24 (m, 1H), 2.24-2.20 (m, 1H), 1.91-1.84 (m, 1H), 1.72-1.66 (m, 5H), 1.57-1.54 (m, 3H), 1.47/1.42 (s, 9H).

Example JLR-1.0, step e

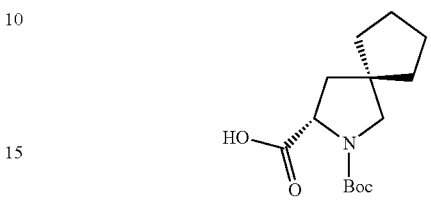

To a solution of (S)-2-tert-butyl 3-methyl 2-azaspiro[4.4]nonane-2,3-dicarboxylate (445 mg, 1.57 mmol) in MeOH (3.5 mL)/Water (1 mL) was added lithium hydroxide monohydrate (99 mg, 2.356 mmol). The reaction mixture was stirred for 18 h before being concentrated, diluted with water (20 mL), and washed with Et₂O. The aqueous layer was acidified with 2.5 mL of 1N HCl, extracted with EtOAc, and the organic layer was washed with brine and dried (MgSO₄) to obtain (338 mg) which was used without further purification. ¹H NMR (MeOD, 500 MHz): δ 4.26-4.19 (m, 1H), 3.37-3.35 (m, 1H), 3.29-3.25 (m, 1H), 2.25-2.21 (m, 1H), 1.93-1.89 (m, 1H), 1.72-1.67 (m, 5H), 1.59-1.55 (m, 3H), 1.48/1.44 (s, 9H). LC/MS: Anal. Calcd. for [M−H]⁻ C₃₉H₄₉N₂O₁₀: 705.35. found 705.30.

Example JLR-1.0, step f

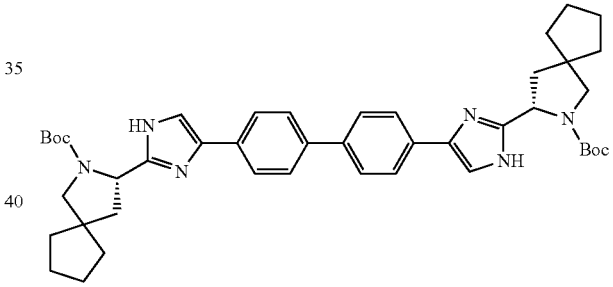

Hunig's base (0.21 mL, 1.23 mmol) was added to a solution of (S)-2-(tert-butoxycarbonyl)-2-azaspiro[4.4]nonane-3-carboxylic acid (330 mg, 1.23 mmol) and 1,1'-([1,1'-biphenyl]-4,4'-diyl)bis(2-bromoethanone) (243 mg, 0.613 mmol) in acetonitrile (6 mL) and stirred for 18 h at 24° C. The solvent was removed by rotory evaporation and the residue was taken up in EtOAc, washed with saturated NaHCO₃ solution, brine, and dried (Na₂SO₄). The crude product was charged (DCM) to a 25 g Thomson silica gel cartridge and gradient elution was performed from 15-100% EtOAc/hexanes over 1 L to give (387 mg) of a diester intermediate which was taken up in xylenes (7 mL) and placed in a glass, screw-top pressure vessel. NH₄OAc (579 mg, 0.5 mmol) was added, and the sealed vessel was heated at 140° C. for 3 h. The reaction mixture was cooled to room temperature, diluted with EtOAc (40 mL), washed with saturated NaHCO₃, brine, dried (Na₂SO₄). The crude product was charged (DCM) to a 25 g Thomson silica gel cartridge and gradient elution was performed from 15-100% EtOAc/DCM over 1 L to afford the bisimidazole product (170 mg). ¹H NMR (MeOD, 500 MHz): δ 7.78 (d, J=8.1 Hz, 4H), 7.69 (d, J=8.1 Hz, 4H), 7.39 (s, 2H), 4.12 (q, J=7.2 Hz, 2H), 3.51 (br s, 4H), 2.28-2.24 (m, 2H), 2.13-2.08 (m, 2H), 1.77-1.48 (series m, 16H), 1.24 (s, 18H). HPLC: Conditions 10, R$_f$=1.0 min; Anal. Calcd. For [M+H]⁺ C₄₄H₅₇N₆O₄: 733.47. found 733.40.

Example JLR-1.0, step g

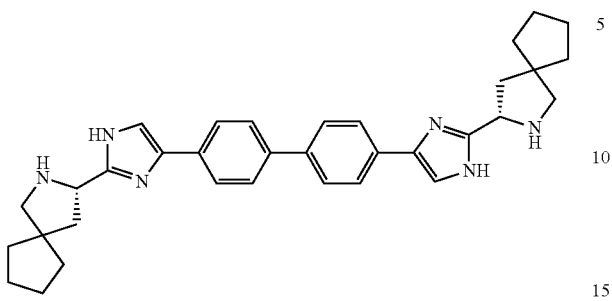

Example JLR-2.0, step a

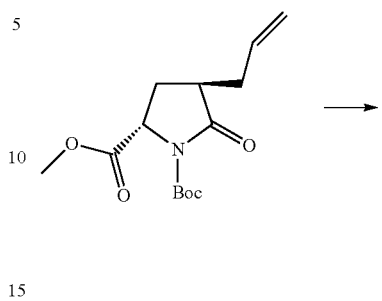

To a solution of AR-1.0, step f (150 mg, 0.20 mmol) in MeOH (5 mL) was added 4N HCl in dioxane (10 mL) and the reaction mixture was stirred at room temperature for 5 h. The volatile components were removed in vacuo, and the residue was exposed to house vacuum for 18 h. (LC/MS: Conditions 2, $R_f$=1.78 min; Anal. Calcd. For $[M+H]^+$ $C_{34}H_{41}N_6$: 533.34. found 533.36.

Example JLR-1.0

HATU (74.9 mg, 0.197 mmol) was added to a solution of AR-1.0, step g (tetra HCl salt; 50 mg, 0.094 mmol), (S)-2-((2R,6R)-2,6-dimethyltetrahydro-2H-pyran-4-yl)-2-((methoxycarbonyl)amino)acetic acid (48.3 mg, 0.197 mmol), and Hunig's base (0.154 mL, 0.939 mmol) in DMF (5 mL) and stirred for 5 h. The reaction mixture was subjected to prep HPLC on phenonmenex-Luna column (30×100 mm S10; MeOH/water/TFA) to afford the TFA salt of Example JLR-1.0 (46 mg) as a yellow solid. UPLC (Conditions 10): $R_f$=0.9 min; Anal. Calcd. for $[M+H]^+$ $C_{56}H_{75}N_8O_8$ 987.57. found 987.65. $^1$H NMR (500 MHz, MeOD) δ 7.97 (s, 2H), 7.88 (s, 8H), 5.21 (dd, J=10.8, 7.3 Hz 2H), 4.22-4.18 (m, 4H), 4.13 (d, J=8.8 Hz, 2H), 3.67 (s, 6H), 3.37-3.29 (m, 4H), 2.46-2.42 (m, 2H), 2.29 (t, J=11.4 Hz, 2H), 2.20-2.16 (m, 2H), 1.85-1.72 (m, 14H), 1.61-1.41 (m, 6H), 1.22 (d, J=6.9 Hz, 6H), 1.22-1.9 (m, 2H), 1.02 (d, J=6.1 Hz, 6H), 0.96 (q, J=11.4 Hz, 2H).

1-Methyl-3-nitro-1-nitrosoguanidine (4.9 g, 33.5 mmol) was slowly added to a solution of 10 N sodium hydroxide (14 mL, 100 mmol) in ether (30 mL) and water (20 mL) in specially coated glassware and stirred for 15 min at 0° C. The resultant solution was decanted to a specially coated separatory funnel and ether layer was added dropwise to a solution of the mono alkylation, trans product of Example JLR-1.0, step a (790 mg, 2.79 mmol) and Pd(OAc)$_2$ (43.8 mg, 0.195 mmol) in THF (25 mL) at 0° C. The reaction was stirred 45 min before warming to room temperature with continued stirring for 2 h. The catalyst was removed by filtration through celite and the filtrate was concentrated. The crude product was charged (DCM) to a 110 g Thomson silica gel cartridge and gradient elution was performed from 5-60% EtOAc/hexanes over 2 L to obtain the cyclopropyl adduct (486 mg).

Example JLR-2.0

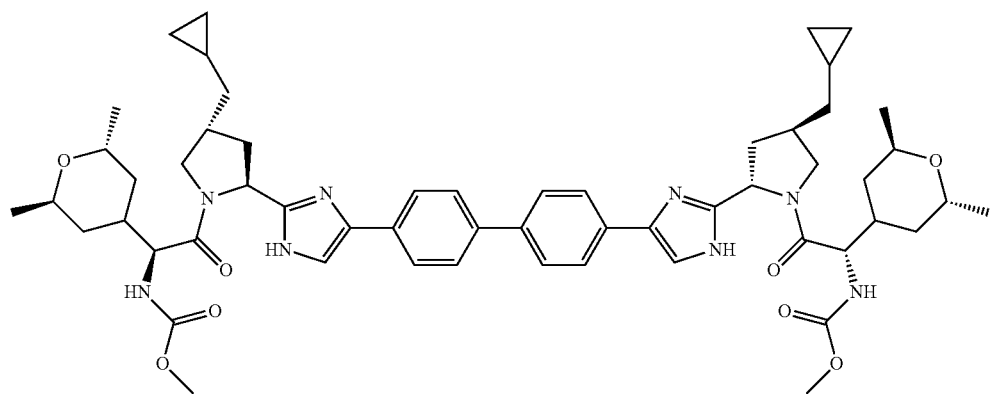

Example JLR-2.0, step b

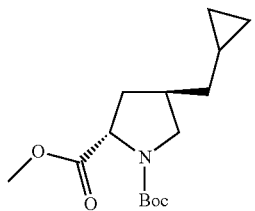 [SMILES: COC(=O)[C@@H]1C[C@@H](CC2CC2)CN1C(=O)OC(C)(C)C]

A 1M solution of superhydride (3 mL, 2.89 mmol) in THF was added dropwise to a nitrogen purged solution of (2S,4R)-1-tert-butyl 2-methyl 4-(cyclopropylmethyl)-5-oxopyrrolidine-1,2-dicarboxylate (383 mg, 1.3 mmol) in THF (15 mL) at −78° C. and stirred 45 min. The reaction mixture was quenched while cold with satuareted NaHCO$_3$ solution (18 mL), warmed to 0° C., and 30% hydrogen peroxide solution (0.8 mL) was added, and the reaction was stirred for 20 min at the to same temperature before removing the solvent by rotory evaporation. The residue was extracted with DCM (3×20 mL), and the combined organic layers were washed with water and dried (Na$_2$SO$_4$). The solvent was reduced to 15 mL volume, triethylsilane (315 mg, 2.71 mmol) was added, and the reaction was cooled to −78° C. Boron trifluoride etherate (402 mg, 2.83 mmol) was added under nitrogen, and after 30 min, additional triethylsilane and additional boron trifluoride etherate were added as above. The reaction mixture was stirred for 2 h, quenched with saturated NaHCO$_3$ solution (8 mL), extracted with DCM (3×20 mL), and the organic layer was dried (Na$_2$SO$_4$). The crude product was charged (DCM) to a 90 g Thomson silica gel cartridge and gradient elution was performed from 5-60% EtOAc/hexanes over 2 L to give (2S,4R)-1-tert-butyl 2-methyl 4-(cyclopropylmethyl)pyrrolidine-1,2-dicarboxylate (242 mg). $^1$H NMR (MeOD, 500 MHz): δ 4.33-4.29 (m, 1H), 3.75 (s, 3H), 3.72-3.68 (m, 1H), 3.07-3.02 (m, 1H), 2.42-2.38 (m, 1H), 2.16-2.11 (m, 1H), 2.01-1.92 (m, 3H), 1.48/1.42 (s, 9H), 1.32-1.28 (m, 2H), 0.71-0.67 (m, 1H), 0.48-0.45 (m, 2H).

Example JLR-2.0, step c

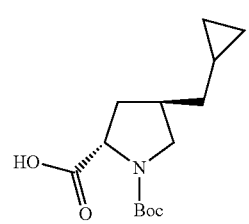 [SMILES: CC(C)(C)OC(=O)N1C[C@H](CC2CC2)C[C@H]1C(=O)O]

To a solution of (2S,4R)-1-tert-butyl 2-methyl 4-(cyclopropylmethyl) pyrrolidine-1,2-dicarboxylate (242 mg, 0.85 mmol) in MeOH (2 mL)/Water (0.5 mL) was added lithium hydroxide monohydrate (53 mg, 1.28 mmol). The reaction mixture was stirred for 18 h before being concentrated, diluted with water (10 mL), and washed with Et$_2$O. The aqueous layer was acidified with 2 mL of 1N HCl, extracted with EtOAc, and the organic layer was washed with brine and dried (MgSO$_4$) to obtain the acid (212 mg) which was used without further purification.

Example JLR-2.0, step d

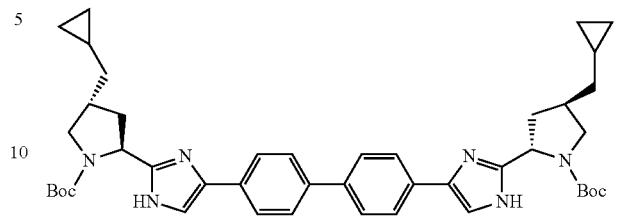

Hunig's base (0.14 mL, 0.79 mmol) was added to a solution of (2S,4R)-1-(tert-butoxycarbonyl)-4-(cyclopropylmethyl)pyrrolidine-2-carboxylic acid (212 mg, 0.79 mmol) and 1,1'-([1,1'-biphenyl]-4,4'-diyl)bis(2-bromoethanone) (156 mg, 0.395 mmol) in acetonitrile (4 mL) and stirred for 18 h at 24° C. The solvent was removed by rotory evaporation and the residue was taken up in EtOAc, washed with saturated NaHCO$_3$ solution, brine, and dried (Na$_2$SO$_4$). The crude product was charged (DCM) to a 25 g Thomson silica gel cartridge and gradient elution was performed from 15-100% EtOAc/hexanes over 1 L to give a bis-ketoester intermediate (225 mg), which was taken up in xylenes (7 mL) and placed in a glass, screw-top pressure vessel. NH$_4$OAc (224 mg, 2.91 mmol) was added, and vessel was sealed, and the reaction mixture was heated at 140° C. After being stirred for 3 h the reaction mixture was cooled to room temperature, diluted with EtOAc, washed with saturated NaHCO$_3$, brine, dried (Na$_2$SO$_4$). The crude product was charged (DCM) to a 25 g Thomson silica gel cartridge and gradient elution was performed from 5-100% EtOAc/hexanes over 1 L to give the bisimidazole product (144 mg). $^1$H NMR (MeOD, 500 MHz): δ 7.78 (br s, 4H), 7.69 (d, J=7.9 Hz, 4H), 7.35 (m, 2H), 7.39 (s, 2H), 5.07-5.01 (m, 2H), 3.94-3.87 (m, 2H), 3.17-3.13 (m, 2H), 2.54 (br s, 2H), 2.27-2.07 (m, 4H), 1.5/1.3 (s, 18H), 1.38-1.36 (m, 4H), 0.74-0.73 (m, 2H), 0.49-0.47 (m, 4H), 0.09 (br s, 4H). UPLC: Conditions 10, R$_t$=1.0 min; Anal. Calcd. For [M+H]$^+$ C$_{44}$H$_{57}$N$_6$O$_4$: 733.47. found 733.45.

Example JLR-2.0, step e

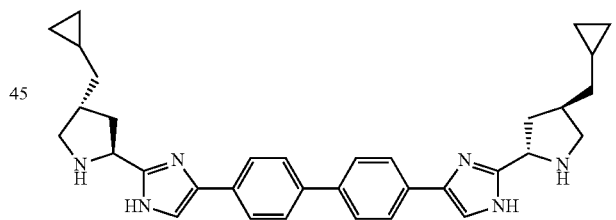

To a solution of AR-2.0, step d (138 mg, 0.188 mmol) in MeOH (3 mL) was added 4N HCl in dioxane (7 mL) and the reaction mixture was stirred at room temperature for 6 h. The volatile components were removed in vacuo, and the residue was exposed to house vacuum for 18 h. $^1$H LC/MS: Conditions 10, R$_t$=0.8 min; Anal. Calcd. For [M+H]$^+$ C$_{34}$H$_{41}$N$_6$: 533.34. found 533.30.

Example JLR-2.0

HATU (86 mg, 0.225 mmol) was added to a solution of AR-2.0, step e (tetra HCl salt; 60 mg, 0.113 mmol), (S)-2-((2R,6R)-2,6-dimethyltetrahydro-2H-pyran-4-yl)-2-((methoxycarbonyl)amino)acetic acid (55.2 mg, 0.225 mmol), and Hunig's base (0.2 mL, 1.1 mmol) in DMF (3 mL) and stirred for 3 h. The reaction mixture was subjected to a reverse phase prep HPLC on phenonmenex-Luna column (30×100 mm S10; MeOH/water/TFA) to afford the TFA salt of Example JLR-2.0 (52 mg) as a white solid. UPLC (Conditions 10): $R_t$=0.92 min; Anal. Calcd. for [M+H]$^+$ $C_{56}H_{75}N_8O_8$ 987.57. found 987.60. $^1$H NMR (500 MHz, MeOD) δ 7.94 (s, 2H), 7.91-7.88 (m, 8H), 5.37 (dd, J=8.6, 5.2 Hz 2H), 4.26-4.21 (m, 4H), 4.13-4.09 (m, 2H), 3.76-3.72 (m, 4H), 3.69 (s, 6H), 3.37-3.29 (m, 4H), 2.46-2.42 (m, 2H), 2.79-2.74 (m, 2H), 2.40-2.26 (m, 2H), 1.61-1.58 (m, 2H), 1.51-1.35 (series m, 4H), 1.24 (d, J=6.8 Hz, 6H), 1.08 (d, J=6.3 Hz, 6H), 1.04 (q, J=11.6 Hz, 2H), 0.83-0.78 (m, 2H), 0.55-0.50 (m, 4H), 0.16-0.13 (m, 4H).

Example JLR-3.0

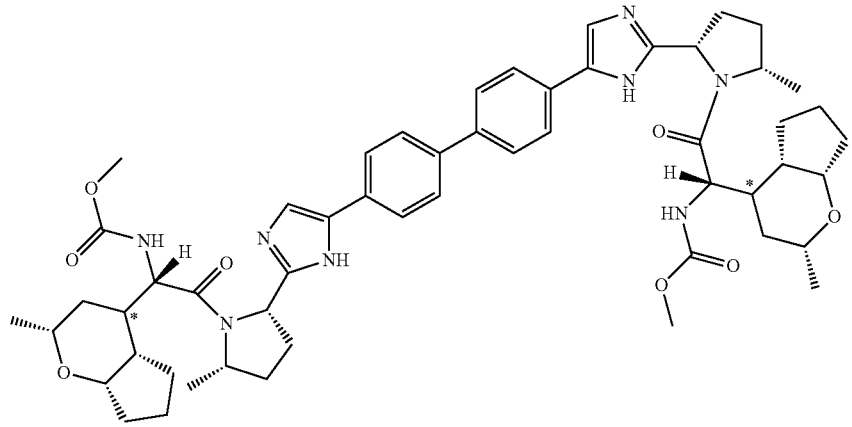

Diastereomer-1
Same but unknown stereochemistry at C*

HATU (72 mg, 0.188 mmol) was added to a solution of Cap 17.1 (49 mg, 0.184 mmol), 4,4'-bis(2-((2S,5S)-5-methylpyrrolidin-2-yl)-1H-imidazol-5-yl)-1,1'-biphenyl (tetra HCl salt; 55 mg, 0.092 mmol), and Hunig's base (0.16 mL, 0.92 mmol) in DMF (5.5 mL) and stirred for 4 h. The reaction mixture was subjected to a reverse phase prep HPLC on phenonmenex-Luna column (30×100 mm S10; MeOH/water/TFA) to afford the TFA salt of Example JLR-3.0 (36 mg) as a white solid. UPLC (Conditions 10): $R_t$=0.90 min; Anal. Calcd. for [M+H]$^+$ $C_{54}H_{71}N_8O_8$ 959.64. found 959.50. $^1$H NMR (500 MHz, MeOD) δ 7.90 (s, 2H), 7.89-7.78 (m, 8H), 5.20 (dd, J=10.7, 7.2 Hz, 2H), 4.73-4.67 (m, 4H), 4.04-4.00 (m, 2H), 3.70 (s, 6H), 3.64-3.60 (m, 4H), 2.58-2.52 (m, 2H), 2.46-2.23 (m, 6H), 2.02-1.99 (m, 2H), 1.81-1.67 (m, 6H), 1.57 (d, J=6.6 Hz, 6H), 1.53-1.38 (m, 8H), 1.25-1.21 (m, 2H), 1.09 (d, J=6.1 Hz, 6H).

Example JLR-3.1

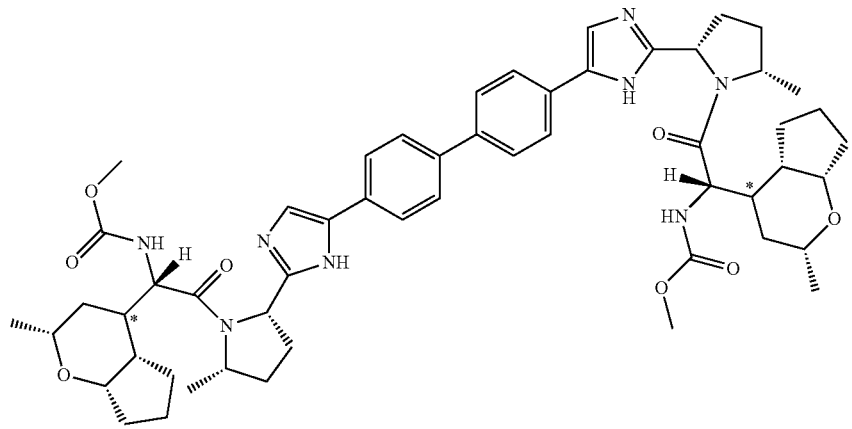

Diastereomer-2
Same but unknown stereochemistry at C*

Example JLR-3.1

HATU (78 mg, 0.21 mmol) was added to a solution of Cap 17.2 (54 mg, 0.20 mmol), 4,4'-bis(2-((2S,5S)-5-methylpyrrolidin-2-yl)-1H-imidazol-5-yl)-1,1'-biphenyl (tetra HCl salt; 60 mg, 0.092 mmol), and Hunig's base (0.17 mL, 1.0 mmol) in DMF (6 mL) and stirred for 4 h. The reaction mixture was subjected to a reverse phase prep HPLC (phenonmenex-Luna column (30×100 mm S10), MeOH/water/TFA) to afford the TFA salt of Example JLR-3.1 (48 mg) as a white solid. UPLC (Conditions 10): $R_f$=0.88 min; Anal. Calcd. for $[M+H]^+$ $C_{54}H_{71}N_8O_8$ 959.64. found 959.50. $^1H$ NMR (500 MHz, MeOD) δ 7.94 (s, 2H), 7.88 (s, 8H), 5.18 (dd, J=10.9, 7.2 Hz, 2H), 4.98-4.92 (m, 2H), 4.28-4.21 (m, 2H), 3.83-3.82 (m, 2H), 3.68 (s, 6H), 3.27-3.23 (m, 2H), 2.58-2.52 (m, 2H), 2.46-2.37 (m, 2H), 2.23-2.27 (m, 4H), 2.03-1.97 (m, 4H), 1.87-1.76 (m, 6H), 1.72-1.61 (m, 8H), 1.58 (d, J=6.7 Hz, 6H), 1.30-1.11 (m, 4H), 1.09 (d, J=6.1 Hz, 6H).

BIOLOGICAL ACTIVITY

An HCV Replicon assay was utilized in the present disclosure, and was prepared, conducted and validated as described in commonly owned PCT/US2006/022197 and in O'Boyle et. al. *Antimicrob Agents Chemother.* 2005 April; 49(4):1346-53. Assay methods incorporating luciferase reporters have also been used as described (Apath.com).

HCV-neo replicon cells and replicon cells containing resistance substitutions in the NS5A region were used to test the currently described family of compounds. The compounds were determined to have differing degrees of reduced inhibitory activity on cells containing mutations vs. the corresponding inhibitory potency against wild-type cells. Thus, the compounds of the present disclosure can be effective in inhibiting the function of the HCV NS5A protein and are understood to be as effective in combinations as previously described in application PCT/US2006/022197 and commonly owned WO/04014852. It should be understood that the compounds of the present disclosure can inhibit multiple genotypes of HCV. Table 2 shows the $EC_{50}$ (Effective 50% inhibitory concentration) values of representative compounds of the present disclosure against the HCV 1b genotype.

The compounds of the present disclosure may inhibit HCV by mechanisms in addition to or other than NS5A inhibition. In one embodiment the compounds of the present disclosure inhibit HCV replicon and in another embodiment the compounds of the present disclosure inhibit NS5A. Compounds of the present disclosure may inhibit multiple genotypes of HCV. $EC_{50}$ ranges against HCV 1b are as follows: A (900.01 pM-0.7 μM); B (100.01 pM-900 pM); C (5.01 pM-100 pM); D (0.5 pM-5 pM).

TABLE 2

| Example | 1b (μM) | Range | Name |
|---|---|---|---|
| QC1.1 | | D | dimethyl (4,4'-biphenyldiylbis(1H-imidazole-4,2-diyl(1R,3S,5R)-2-azabicyclo[3.1.0]hexane-3,2-diyl(1-((1R,3s,5S)-6,6-difluorobicyclo[3.1.0]hex-3-yl)-2-oxo-2,1-ethanediyl)))biscarbamate (diastereomer 1) |
| QC1.2 | 4.90E−06 | D | dimethyl (4,4'-biphenyldiylbis(1H-imidazole-4,2-diyl(1R,3S,5R)-2-azabicyclo[3.1.0]hexane-3,2-diyl(1-((1R,3s,5S)-6,6-difluorobicyclo[3.1.0]hex-3-yl)-2-oxo-2,1-ethanediyl)))biscarbamate (diastereomer 2) |
| QC1.3 | | B | dimethyl (4,4'-biphenyldiylbis(1H-imidazole-4,2-diyl(1R,3S,5R)-2-azabicyclo[3.1.0]hexane-3,2-diyl(1-((1R,3s,5S)-6,6-difluorobicyclo[3.1.0]hex-3-yl)-2-oxo-2,1-ethanediyl)))biscarbamate (diastereomer 3) |
| QC2.1 | | D | dimethyl (4,4'-biphenyldiylbis(1H-imidazole-4,2-diyl(1R,3S,5R)-2-azabicyclo[3.1.0]hexane-3,2-diyl(1-((1R,3r,5S)-6,6-difluorobicyclo[3.1.0]hex-3-yl)-2-oxo-2,1-ethanediyl)))biscarbamate (diastereomer 1) |
| QC2.2 | | C | dimethyl (4,4'-biphenyldiylbis(1H-imidazole-4,2-diyl(1R,3S,5R)-2-azabicyclo[3.1.0]hexane-3,2-diyl(1-((1R,3r,5S)-6,6-difluorobicyclo[3.1.0]hex-3-yl)-2-oxo-2,1-ethanediyl)))biscarbamate (diastereomer 2) |
| QC2.3 | 1.08E−03 | A | dimethyl (4,4'-biphenyldiylbis(1H-imidazole-4,2-diyl(1R,3S,5R)-2-azabicyclo[3.1.0]hexane-3,2-diyl(1-((1R,3r,5S)-6,6-difluorobicyclo[3.1.0]hex-3-yl)-2-oxo-2,1-ethanediyl)))biscarbamate (diastereomer 3) |
| QC3.1 | | D | dimethyl (4,4'-biphenyldiylbis(1H-imidazole-4,2-diyl(1R,3S,5R)-2-azabicyclo[3.1.0]hexane-3,2-diyl(1-((1R,3r,5S)-bicyclo[3.1.0]hex-3-yl)-2-oxo-2,1-ethanediyl)))biscarbamate (diastereomer 1) |
| QC3.2 | | C | dimethyl (4,4'-biphenyldiylbis(1H-imidazole-4,2-diyl(1R,3S,5R)-2-azabicyclo[3.1.0]hexane-3,2-diyl(1-((1R,3r,5S)-bicyclo[3.1.0]hex-3-yl)-2-oxo-2,1-ethanediyl)))biscarbamate (diastereomer 2) |
| QC3.3 | | B | dimethyl (4,4'-biphenyldiylbis(1H-imidazole-4,2-diyl(1R,3S,5R)-2-azabicyclo[3.1.0]hexane-3,2-diyl(1-((1R,3r,5S)-bicyclo[3.1.0]hex-3-yl)-2-oxo-2,1-ethanediyl)))biscarbamate (diastereomer 3) |
| QC4.1 | | C | dimethyl (4,4'-biphenyldiylbis(1H-imidazole-4,2-diyl(1R,3S,5R)-2-azabicyclo[3.1.0]hexane-3,2-diyl(1-((1R,5S,6s)-3-oxabicyclo[3.1.0]hex-6-yl)-2-oxo-2,1-ethanediyl))biscarbamate (diastereomer 1) |
| QC4.2 | | B | dimethyl (4,4'-biphenyldiylbis(1H-imidazole-4,2-diyl(1R,3S,5R)-2-azabicyclo[3.1.0]hexane-3,2-diyl(1-((1R,5S,6s)-3-oxabicyclo[3.1.0]hex-6-yl)-2-oxo-2,1-ethanediyl)))biscarbamate (diastereomer 2) |
| QC4.3 | | | dimethyl (4,4'-biphenyldiylbis(1H-imidazole-4,2-diyl(1R,3S,5R)-2-azabicyclo[3.1.0]hexane-3,2-diyl(1-((1R,5S,6s)-3-oxabicyclo[3.1.0]hex-6-yl)-2-oxo-2,1-ethanediyl)))biscarbamate (diastereomer 3) |
| QC5.1 | 5.93E−07 | D | dimethyl (4,4'-biphenyldiylbis(1H-imidazole-4,2-diyl(1R,3S,5R)-2-azabicyclo[3.1.0]hexane-3,2-diyl(1-((1R,3s,5S)-bicyclo[3.1.0]hex-3-yl)-2-oxo-2,1-ethanediyl)))biscarbamate (diastereomer 1) |

TABLE 2-continued

| Example | 1b (μM) | Range | Name |
|---|---|---|---|
| QC5.2 | | D | dimethyl (4,4'-biphenyldiylbis(1H-imidazole-4,2-diyl(1R,3S,5R)-2-azabicyclo[3.1.0]hexane-3,2-diyl(1-((1R,3s,5S)-bicyclo[3.1.0]hex-3-yl)-2-oxo-2,1-ethanediyl)))biscarbamate (diastereomer 2) |
| QC5.3 | 5.55E−06 | C | dimethyl (4,4'-biphenyldiylbis(1H-imidazole-4,2-diyl(1R,3S,5R)-2-azabicyclo[3.1.0]hexane-3,2-diyl(1-((1R,3s,5S)-bicyclo[3.1.0]hex-3-yl)-2-oxo-2,1-ethanediyl)))biscarbamate (diastereomer 3) |
| QC6 | | D | methyl (2-((1R,3S,5R)-3-(4-(4'-(4-chloro-2-((1R,3S,5R)-2-(((1R,3s,5S)-6,6-difluorobicyclo[3.1.0]hex-3-yl)((methoxycarbonyl)amino)acetyl)-2-azabicyclo[3.1.0]hex-3-yl)-1H-imidazol-5-yl)-4-biphenylyl)-1H-imidazol-2-yl)-2-azabicyclo[3.1.0]hex-2-yl)-1-((1R,3s,5S)-6,6-difluorobicyclo[3.1.0]hex-3-yl)-2-oxoethyl)carbamate |
| QC7 | | D | dimethyl (4,4'-biphenyldiylbis((4-chloro-1H-imidazole-5,2-diyl)(1R,3S,5R)-2-azabicyclo[3.1.0]hexane-3,2-diyl(1-((1R,3s,5S)-6,6-difluorobicyclo[3.1.0]hex-3-yl)-2-oxo-2,1-ethanediyl)))biscarbamate |
| QC8.1 | | D | dimethyl (4,4'-biphenyldiylbis(1H-imidazole-4,2-diyl((2S,5S)-5-methyl-2,1-pyrrolidinediyl)(1-(4-oxaspiro[2.5]oct-7-yl)-2-oxo-2,1-ethanediyl)))biscarbamate (diastereomer 1) |
| QC8.2 | | D | dimethyl (4,4'-biphenyldiylbis(1H-imidazole-4,2-diyl((2S,5S)-5-methyl-2,1-pyrrolidinediyl)(1-(4-oxaspiro[2.5]oct-7-yl)-2-oxo-2,1-ethanediyl)))biscarbamate (diastereomer 2) |
| QC9 | | C | methyl (2-((2S,4S)-2-(7-((2-((2S,4S)-1-(((methoxycarbonyl)amino)(4-oxaspiro[2.5]oct-7-yl)acetyl)-4-methyl-2-pyrrolidinyl)-1H-benzimidazol-5-ypethynyl)-1H-naphtho[1,2-d]imidazol-2-yl)-4-methyl-1-pyrrolidinyl)-1-(4-oxaspiro[2.5]oct-7-yl)-2-oxoethyl)carbamate |
| QC10 | 2.59E−04 | B | methyl (2-((2S)-2-(7-(2-((2S)-1-(((methoxycarbonyl)amino)(4-oxaspiro[2.5]oct-7-yl)acetyl)-2-pyrrolidinyl)-1H-benzimidazol-5-yl)-1H-naphtho[1,2-d]imidazol-2-yl)-1-pyrrolidinyl)-1-(4-oxaspiro[2.5]oct-7-yl)-2-oxoethyl)carbamate |
| QC11 | | C | methyl (2-((1R,3S,5R)-3-(4-(4-(2-((1R,3S,5R)-2-(((methoxycarbonyl)amino)(4-oxaspiro[2.5]oct-7-yl)acetyl)-2-azabicyclo[3.1.0]hex-3-yl)-4,5-dihydro-3H-naphtho[1,2-d]imidazol-7-yl)phenyl)-1H-imidazol-2-yl)-2-azabicyclo[3.1.0]hex-2-yl)-1-(4-oxaspiro[2.5]oct-7-yl)-2-oxoethyl)carbamate |
| QC12 | | B | methyl (2-((2S)-2-(7-(2-((2S)-1-(((methoxycarbonyl)amino)(4-oxaspiro[2.5]oct-7-yl)acetyl)-2-pyrrolidinyl)-1H-benzimidazol-5-yl)-4,5-dihydro-1H-naphtho[1,2-d]imidazol-2-yl)-1-pyrrolidinyl)-1-(4-oxaspiro[2.5]oct-7-yl)-2-oxoethyl)carbamate |
| QC13 | | C | dimethyl (1H,1'H-7,7'-binaphtho[1,2-d]imidazole-2,2'-diylbis((2S)-2,1-pyrrolidinediyl(1-(4-oxaspiro[2.5]oct-7-yl)-2-oxo-2,1-ethanediyl)))biscarbamate |
| OL1 | | C | dimethyl (((3S,3'S,5S,5'S)-5,5'-(5,5'-((1S,2S)-cyclopropane-1,2-diylbis(4,1-phenylene))bis(1H-imidazole-5,2-diyl))bis(3-methylpyrrolidine-5,1-diyl))bis(2-oxo-1-(4-oxaspiro[2.5]octan-7-yl)ethane-2,1-diyl))dicarbamate |
| OL2 | | C | methyl (2-(((1S)-1-(5-((2-((1S)-1-((((methoxycarbonyl)amino)(4-oxaspiro[2.5]oct-7-yl)acetyl)(methyl)amino)ethyl)-1H-benzimidazol-6-yl)ethynyl)-1H-benzimidazol-2-yl)ethyl)(methyl)amino)-1-(4-oxaspiro[2.5]oct-7-yl)-2-oxoethyl)carbamate |
| OL3 | | C | methyl ((2S)-1-((1R,3S,5R)-3-(5-(4'-(2-((1R,3S,5R)-2-(((methoxycarbonyl)amino)(4-oxaspiro[2.5]oct-7-yl)acetyl)-2-azabicyclo[3.1.0]hex-3-yl)-1H-imidazol-5-yl)biphenyl-4-yl)-1H-imidazol-2-yl)-2-azabicyclo[3.1.0]hex-2-yl)-3-methyl-1-oxobutan-2-yl)carbamate |
| OL4 | | C | dimethyl (((1R,1'R,3S,3'S,5R,5'R)-3,3'-(5,5'-(ethyne-1,2-diylbis(4,1-phenylene))bis(1H-imidazole-5,2-diyl))bis(2-azabicyclo[3.1.0]hexane-3,2-diyl))bis(2-oxo-1-(4-oxaspiro[2.5]octan-7-yl)ethane-2,1-diyl))dicarbamate |
| OL5 | | C | dimethyl (((1R,1'R,3S,3'S,5R,5'R)-3,3'-([1,1'-biphenyl]-4,4'-diyl)bis(4-chloro-1H-imidazole-5,2-diyl))bis(2-azabicyclo[3.1.0]hexane-3,2-diyl))bis(2-oxo-1-(4-oxaspiro[2.5]octan-7-yl)ethane-2,1-diyl))dicarbamate |
| OL6 | | B | methyl (2-((2S)-2-(5-(6-(4-(2-((2S)-1-(((methoxycarbonyl)amino)(4-oxaspiro[2.5]oct-7-yl)acetyl)pyrrolidin-2-yl)-1H-imidazol-5-yl)phenyl)pyridin-3-yl)-1H-imidazol-2-yl)pyrrolidin-1-yl)-1-(4-oxaspiro[2.5]oct-7-yl)-2-oxoethyl)carbamate |
| OL7 | | C | dimethyl (((2S,2'S)-2,2'-(5,5'-(ethyne-1,2-diylbis(4,1-phenylene))bis(1H-imidazole-5,2-diyl))bis(pyrrolidine-2,1-diyl))bis(2-oxo-1-(4-oxaspiro[2.5]octan-7-yl)ethane-2,1-diyl))dicarbamate |
| QC14 | 1.45E−02 | A | dimethyl (benzene-1,4-diylbis(1H-imidazole-4,2-diyl(2S)pyrrolidine-2,1-diyl(1-(4-oxaspiro[2.5]oct-7-yl)-1-oxoethane-2,1-diyl)))biscarbamate |
| OL8 | | B | dimethyl (((3R,3'R)-3,3'-(5,5'-([1,1'-biphenyl]-4,4'-diyl)bis(1H-imidazole-5,2-diyl))bis(morpholine-4,3-diyl))bis(2-oxo-1-(4-oxaspiro[2.5]octan-7-yl)ethane-2,1-diyl))dicarbamate |
| QC15 | | C | methyl (2-((2S)-2-(5-(4-(2-((2S)-1-(((methoxycarbonyl)amino)(4-oxaspiro[2.5]oct-7-yl)acetyl)pyrrolidin-2-yl)-1H-benzimidazol-4-yl)oxy)phenyl)-1H-benzimidazol-2-yl)pyrrolidin-1-yl)-1-(4-oxaspiro[2.5]oct-7-yl)-2-oxoethyl)carbamate |
| QC16 | | B | methyl (2-((2S)-2-(7-(2-((2S)-1-(((methoxycarbonyl)amino)(4-oxaspiro[2.5]oct-7-yl)acetyl)-2-pyrrolidinyl)-1H-benzimidazol-5-yl)-4,5-dihydro-1H-naphtho[1,2-d]imidazol-2-yl)-1-pyrrolidinyl)-1-(4-oxaspiro[2.5]oct-7-yl)-2-oxoethyl)carbamate |
| OL9 | | B | dimethyl (((2S,2'S)-2,2'-(5,5'-(ethyne-1,2-diyl)bis(1H-benzo[d]imidazole-5,2-diyl))bis(pyrrolidine-2,1-diyl))bis(2-oxo-1-(4-oxaspiro[2.5]octan-7-ypethane-2,1-diyl))dicarbamate |

TABLE 2-continued

| Example | 1b (μM) | Range | Name |
|---|---|---|---|
| OL10 | | B | dimethyl (4,4'-biphenyldiylbis(1H-imidazole-4,2-diyl(1R,3S,5R)-2-azabicyclo[3.1.0]hexane-3,2-diyl((1S)-2-oxo-1-(4-oxocyclohexyl)-2,1-ethanediyl)))biscarbamate |
| OL11 | | C | dimethyl (4,4'-biphenyldiylbis(1H-imidazole-4,2-diyl(1R,3S,5R)-2-azabicyclo[3.1.0]hexane-3,2-diyl((1S)-2-oxo-1-(3-(trifluoromethyl)bicyclo[1.1.1]pent-1-yl)-2,1-ethanediyl)))biscarbamate |
| OL12 | | B | dimethyl (4,4'-biphenyldiylbis(1H-imidazole-4,2-diyl((2S,5S)-5-methyl-2,1-pyrrolidinediyl)((1S)-2-oxo-1-(3-(trifluoromethyl)bicyclo[1.1.1]pent-1-yl)-2,1-ethanediyl)))biscarbamate |
| QC17.1 | | D | dimethyl ((3-methyl-4,4'-biphenyldiyl)bis(1H-imidazole-4,2-diyl((2S,5S)-5-methyl-2,1-pyrrolidinediyl)(1-(4-oxaspiro[2.5]oct-7-yl)-2-oxo-2,1-ethanediyl)))biscarbamate (diastereomer 1) |
| QC17.2 | | D | dimethyl ((3-methyl-4,4'-biphenyldiyl)bis(1H-imidazole-4,2-diyl((2S,5S)-5-methyl-2,1-pyrrolidinediyl)(1-(4-oxaspiro[2.5]oct-7-yl)-2-oxo-2,1-ethanediyl)))biscarbamate (diastereomer 2) |
| QC18.1 | | D | dimethyl ((3-fluoro-4,4'-biphenyldiyl)bis(1H-imidazole-4,2-diyl((2S,5S)-5-methyl-2,1-pyrrolidinediyl)(1-(4-oxaspiro[2.5]oct-7-yl)-2-oxo-2,1-ethanediyl)))biscarbamate (diastereomer 1) |
| QC18.2 | | D | dimethyl ((3-fluoro-4,4'-biphenyldiyl)bis(1H-imidazole-4,2-diyl((2S,5S)-5-methyl-2,1-pyrrolidinediyl)(1-(4-oxaspiro[2.5]oct-7-yl)-2-oxo-2,1-ethanediyl)))biscarbamate (diastereomer 2) |
| QC19 | | C | dimethyl (4,4'-biphenyldiylbis(1H-imidazole-4,2-diyl((1R,3S,5R)-5-methyl-2-azabicyclo[3.1.0]hexane-3,2-diyl)(1-(4-oxaspiro[2.5]oct-7-yl)-2-oxo-2,1-ethanediyl)))biscarbamate |
| 1.1 | | C | |
| 1.2 | | C | |
| 2.1 | | A | |
| 2.2 | | A | |
| 2.3 | 4.88E−06 | D | |
| 2.4 | | C | |
| 3.1 | | A | |
| 3.2 | | A | |
| 3.3 | 5.04E−06 | C | |
| 3.4 | | C | |
| 4.1 | | D | |
| 4.2 | 2.43E−04 | B | |
| 5.1 | | D | |
| 5.2 | 9.07E−03 | A | |
| 6 | | C | |
| 7 | | C | |
| 8 | | C | |
| 9.1 | | D | dimethyl ((R,S,R,1S,1'S)-((2S-2'S,5S,5'S)-5,5'-(5,5'-([1,1'-biphenyl]-4,4'-diyl)bis(1H-imidazole-5,2-diyl))bis(2-methylpyrrolidine-5,1-diyl))bis(1-((2R,4R,6S)-2-cyclopropyl-6-methyltetrahydro-2H-pyran-4-yl)-2-oxoethane-2,1-diyl))dicarbamate |
| 9.2 | | D | dimethyl ((S,R,S,R,1S,1'S)-((2S-2'S,5S,5'S)-5,5'-(5,5'-([1,1'-biphenyl]-4,4'-diyl)bis(1H-imidazole-5,2-diyl))bis(2-methylpyrrolidine-5,1-diyl))bis(1-((2S,4R,6R)-2-cyclopropyl-6-methyltetrahydro-2H-pyran-4-yl)-2-oxoethane-2,1-diyl))dicarbamate |
| 9.3 | | C | dimethyl ((S,R,S,1S,1'S)-((2S,2'S,5S,5'S)-5,5'-(5,5'-([1,1'-biphenyl]-4,4'-diyl)bis(1H-imidazole-5,2-diyl))bis(2-methylpyrrolidine-5,1-diyl))bis(1-((2R,4S,6S)-2-cyclopropyl-6-methyltetrahydro-2H-pyran-4-yl)-2-oxoethane-2,1-diyl))dicarbamate |
| 9.4 | 9.30E−06 | C | dimethyl ((R,S,S,1S,1'S)-((2S,2'S,5S,5'S)-5,5'-(5,5'-([1,1'-biphenyl]-4,4'-diyl)bis(1H-imidazole-5,2-diyl))bis(2-methylpyrrolidine-5,1-diyl))bis(1-((2S,4S,6R)-2-cyclopropyl-6-methyltetrahydro-2H-pyran-4-yl)-2-oxoethane-2,1-diyl))dicarbamate |
| 10 | | C | dimethyl (4,4'-biphenyldiylbis(1H-imidazole-5,2-diyl((2S,5R)-5-ethynyl-2,1-pyrrolidinediyl)((1S)-1-((2R,6R)-2,6-dimethyltetrahydro-2H-pyran-4-yl)-2-oxo-2,1-ethanediyl)))biscarbamate |
| 10.1 | 2.63E−04 | B | dimethyl (4,4'-biphenyldiylbis(1H-imidazole-4,2-diyl((2S,5S)-5-ethynyl-2,1-pyrrolidinediyl)((1S)-1-((2R,6R)-2,6-dimethyltetrahydro-2H-pyran-4-yl)-2-oxo-2,1-ethanediyl)))biscarbamate |
| 11 | | A | dimethyl (4,4'-biphenyldiylbis(1H-imidazole-4,2-diyl((2S,5R)-5-hydroxymethyl)-2,1-pyrrolidinediyl)((1S)-1-((2R,6R)-2,6-dimethyltetrahydro-2H-pyran-4-yl)-2-oxo-2,1-ethanediyl)))biscarbamate |
| 11.1 | | A | dimethyl (4,4'-biphenyldiylbis(1H-imidazole-4,2-diyl((2S,5R)-5-(hydroxymethyl)-2,1-pyrrolidinediyl)((1S)-1-((2R,6R)-2,6-dimethyltetrahydro-2H-pyran-4-yl)-2-oxo-2,1-ethanediyl)))biscarbamate |
| 12.1 | | A | dimethyl (4,4'-biphenyldiylbis(1H-imidazole-4,2-diyl((2S,5S)-5-methyl-2,1-pyrrolidinediyl)(1-(3-cyano-3-methylcyclobutylidene)-2-oxo-2,1-ethanediyl)))biscarbamate |
| 12.2 | | A | dimethyl (4,4'-biphenyldiylbis(1H-imidazole-4,2-diyl((2S,5S)-5-methyl-2,1-pyrrolidinediyl)(1-(3-cyano-3-methylcyclobutylidene)-2-oxo-2,1-ethanediyl)))biscarbamate |
| 13 | | C | dimethyl (4,4'-biphenyldiylbis(1H-imidazole-5,2-diyl((2S,5S)-5-methyl-2,1-pyrrolidinediyl)((1S)-1-(2-oxaspiro[3.3]hept-6-yl)-2-oxo-2,1-ethanediyl)))biscarbamate |
| JLR-1.0 | | C | dimethyl (4,4'-biphenyldiylbis(1H-imidazole-4,2-diyl(3S)-2-azaspiro[4.4]nonane-3,2-diyl((1S)-1-((2R,6R)-2,6-dimethyltetrahydro-2H-pyran-4-yl)-2-oxo-2,1-ethanediyl)))biscarbamate |
| JLR-2.0 | | C | dimethyl (4,4'-biphenyldiylbis(1H-imidazole-4,2-diyl((2S,4R)-4-(cyclopropylmethyl)-2,1-pyrrolidinediyl)((1S)-1-((2R,6R)-2,6-dimethyltetrahydro-2H-pyran-4-yl)-2-oxo-2,1-ethanediyl)))biscarbamate |
| JLR-3.0 | | D | dimethyl (4,4'-biphenyldiylbis(1H-imidazole-4,2-diyl((2S,5S)-5-methyl-2,1-pyrrolidinediyl)((1S)-1-((2R,4R,4aS,7aS)-2-methyloctahydrocyclopenta[b]pyran-4-yl)-2-oxo-2,1-ethanediyl)))biscarbamate |

TABLE 2-continued

| Example | 1b (μM) | Range | Name |
|---|---|---|---|
| JLR-3.1 | 6.72E−07 | D | dimethyl (4,4'-biphenyldiylbis(1H-imidazole-4,2-diyl((2S,5S)-5-methyl-2,1-pyrrolidinediyl)((1S)-1-((2R,4S,4aS,7aS)-2-methyloctahydrocyclopenta[b]pyran-4-yl)-2-oxo-2,1ethanediyl)))biscarbamate |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound selected from:
dimethyl ((R,S,R,1S,1'S)-((2S,2'S,5S,5'S)-5,5'-(5,5'-([1,1'-biphenyl]-4,4'-diyl)bis(1H-imidazole-5,2-diyl))bis(2-methylpyrrolidine-5,1-diyl))bis(1-((2R,4R,6S)-2-cyclopropyl-6-methyltetrahydro-2H-pyran-4-yl)-2-oxoethane-2,1-diyl))dicarbamate;
dimethyl ((S,R,R,1S,1'S)-((2S,2'S,5S,5'S)-5,5'-(5,5'-([1,1'-biphenyl]-4,4'-diyl)bis(1H-imidazole-5,2-diyl))bis(2-methylpyrrolidine-5,1-diyl))bis(1-((2S,4R,6R)-2-cyclopropyl-6-methyltetrahydro-2H-pyran-4-yl)-2-oxoethane-2,1-diyl))dicarbamate;
dimethyl ((S,R,S,1S,1'S)-((2S,2'S,5S,5'S)-5,5'-(5,5'-([1,1'-biphenyl]-4,4'-diyl)bis(1H-imidazole-5,2-diyl))bis(2-methylpyrrolidine-5,1-diyl))bis(1-((2R,4S,6S)-2-cyclopropyl-6-methyltetrahydro-2H-pyran-4-yl)-2-oxoethane-2,1-diyl))dicarbamate;
dimethyl (4,4'-biphenyldiylbis(1H-imidazole-4,2-diyl((2S,5S)-5-methyl-2,1-pyrrolidinediyl)(1-(3-cyano-3-methylcyclobutylidene)-2-oxo-2,1-ethanediyl)))biscarbamate; and
dimethyl (4,4'-biphenyldiylbis(1H-imidazole-4,2-diyl((2S,5S)-5-methyl-2,1-pyrrolidinediyl)(1-(3-cyano-3-methylcyclobutylidene)-2-oxo-2,1-ethanediyl)))biscarbamate;
or a pharmaceutically acceptable salt thereof.

2. A compound selected from:
dimethyl (4,4'-biphenyldiylbis(1H-imidazole-5,2-diyl((2S,5R)-5-ethynyl-2,1-pyrrolidinediyl)((1S)-1-((2R,6R)-2,6-dimethyltetrahydro-2H-pyran-4-yl)-2-oxo-2,1-ethanediyl)))biscarbamate;
dimethyl (4,4'-biphenyldiylbis(1H-imidazole-4,2-diyl((2S,5S)-5-ethynyl-2,1-pyrrolidinediyl)((1S)-1-((2R,6R)-2,6-dimethyltetrahydro-2H-pyran-4-yl)-2-oxo-2,1-ethanediyl)))biscarbamate;
dimethyl (4,4'-biphenyldiylbis(1H-imidazole-4,2-diyl((2S,5R)-5-(hydroxymethyl)-2,1-pyrrolidinediyl)((1S)-1-((2R,6R)-2,6-dimethyltetrahydro-2H-pyran-4-yl)-2-oxo-2,1-ethanediyl)))biscarbamate;
dimethyl (4,4'-biphenyldiylbis(1H-imidazole-4,2-diyl((2S,5R)-5-(hydroxymethyl)-2,1-pyrrolidinediyl)((1S)-1-((2R,6R)-2,6-dimethyltetrahydro-2H-pyran-4-yl)-2-oxo-2,1-ethanediyl)))biscarbamate;
dimethyl (4,4'-biphenyldiylbis(1H-imidazole-4,2-diyl(3S)-2-azaspiro[4.4]nonane-3,2-diyl((1S)-1-((2R,6R)-2,6-dimethyltetrahydro-2H-pyran-4-yl)-2-oxo-2,1-ethanediyl)))biscarbamate; and
dimethyl (4,4'-biphenyldiylbis(1H-imidazole-4,2-diyl((2S,4R)-4-(cyclopropylmethyl)-2,1-pyrrolidinediyl)((1S)-1-((2R,6R)-2,6-dimethyltetrahydro-2H-pyran-4-yl)-2-oxo-2,1-ethanediyl)))biscarbamate;
or a pharmaceutically acceptable salt thereof.

3. A compound selected from:
dimethyl (4,4'-biphenyldiylbis(1H-imidazole-5,2-diyl((2S,5S)-5-methyl-2,1-pyrrolidinediyl)((1S)-1-(2-oxaspiro[3.3]hept-6-yl)-2-oxo-2,1-ethanediyl)))biscarbamate;
dimethyl (4,4'-biphenyldiylbis(1H-imidazole-4,2-diyl((2S,5S)-5-methyl-2,1-pyrrolidinediyl)((1S)-1-((2R,4R,4aS,7aS)-2-methyloctahydrocyclopenta[b]pyran-4-yl)-2-oxo-2,1-ethanediyl)))biscarbamate; and
dimethyl (4,4'-biphenyldiylbis(1H-imidazole-4,2-diyl((2S,5S)-5-methyl-2,1-pyrrolidinediyl)((1S)-1-((2R,4S,4aS,7aS)-2-methyloctahydrocyclopenta[b]pyran-4-yl)-2-oxo-2,1-ethanediyl)))biscarbamate;
or a pharmaceutically acceptable salt thereof.

4. A compound which is
dimethyl ((R,S,S,1S,1'S)-((2S,2'S,5S,5'S)-5,5'-(5,5'-([1,1'-biphenyl]-4,4'-diyl)bis(1H-imidazole-5,2-diyl))bis(2-methylpyrrolidine-5,1-diyl))bis(1-((2S,4S,6R)-2-cyclopropyl-6-methyltetrahydro-2H-pyran-4-yl)-2-oxoethane-2,1-diyl))dicarbamate;
or a pharmaceutically acceptable salt thereof.

5. A composition comprising a compound of claim 1, or a pharmaceutically acceptable salt thereof, and a pharmaceutically acceptable carrier.

6. The composition of claim 5 further comprising at least one additional compound having anti-HCV activity.

7. A composition comprising a compound of claim 2, or a pharmaceutically acceptable salt thereof, and a pharmaceutically acceptable carrier.

8. The composition of claim 7 further comprising at least one additional compound having anti-HCV activity.

9. A composition comprising a compound of claim 3, or a pharmaceutically acceptable salt thereof, and a pharmaceutically acceptable carrier.

10. The composition of claim 9 further comprising at least one additional compound having anti-HCV activity.

11. A composition comprising a compound of claim 4, or a pharmaceutically acceptable salt thereof, and a pharmaceutically acceptable carrier.

12. The composition of claim 11 further comprising at least one additional compound having anti-HCV activity.

13. A method of inhibiting or relieving an HCV infection in a patient, comprising administering to the patient a therapeutically effective amount of a compound of claim 1, or a pharmaceutically acceptable salt thereof.

14. A method of inhibiting or relieving an HCV infection in a patient, comprising administering to the patient a therapeutically effective amount of a compound of claim 2, or a pharmaceutically acceptable salt thereof.

15. A method of inhibiting or relieving an HCV infection in a patient, comprising administering to the patient a therapeutically effective amount of a compound of claim 3, or a pharmaceutically acceptable salt thereof.

16. A method of inhibiting or relieving an HCV infection in a patient, comprising administering to the patient a therapeutically effective amount of a compound of claim 4, or a pharmaceutically acceptable salt thereof.

* * * * *